United States Patent
Hosoda et al.

[11] Patent Number: 6,117,870
[45] Date of Patent: Sep. 12, 2000

[54] CYCLIC AMIDE DERIVATIVES

[75] Inventors: Akihiko Hosoda; Nobuo Kobayashi; Naoko Tanabe; Tsuneo Koji; Masahiro Shibata; Akihiro Sekine; Masaharu Dozen, all of Tokyo, Japan

[73] Assignee: Fujirebio Kabushiki Kaisha, Tokyo, Japan

[21] Appl. No.: 09/437,438

[22] Filed: Nov. 10, 1999

[30] Foreign Application Priority Data

Nov. 12, 1998 [JP] Japan .................. 10-322283

[51] Int. Cl.⁷ .................. A61K 31/5375; C07D 295/215; A61P 19/02
[52] U.S. Cl. .................. 514/237.5; 544/159; 544/165; 544/58.4; 544/86; 544/131; 544/133; 544/148; 544/149; 544/139; 544/130; 544/137; 544/70; 544/152; 544/384; 544/388; 540/524; 540/575; 546/172; 546/226; 546/293; 549/436; 560/115
[58] Field of Search .................. 544/159, 165; 560/115; 514/237.5

[56] References Cited

U.S. PATENT DOCUMENTS 5,188,950  2/1993  Balani et al. .................. 544/165

*Primary Examiner*—Robert W. Ramsuer
*Attorney, Agent, or Firm*—Birch, Stewart, Kolasch & Birch, LLP

[57] ABSTRACT

A cyclic amide derivative of formula (I):

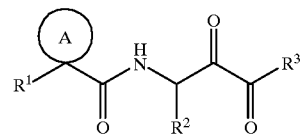

wherein $R^1$ represents a substituted alkyl group, a substituted alkenyl group, a substituted amino group, a substituted alkoxyl group, a substituted alkylthio group, a substituted carbamoyl group, a substituted sulfonamide group or a substituted amide group; the ring A represents a saturated cyclic alkyl group with 5 to 7 carbon atoms or a heteroatom-containing saturated heterocyclic group with 3 to 6 carbon atoms; $R^2$ represents a hydrogen atom, a substituted or unsubstituted alkyl group, a substituted or unsubstituted aromatic hydrocarbon group or a substituted or unsubstituted heterocyclic group; $R^3$ represents a hydrogen atom, a group represented by the general formula $R^4O$— or a group represented by the general formula $R^5(R^6)N$— wherein $R^4$ represents hydrogen atom, a substituted or unsubstituted alkyl group, a substituted or unsubstituted aromatic hydrocarbon group or a substituted or unsubstituted heterocyclic group; $R^5$ and $R^6$ may be the same or different and each represents a hydrogen atom, a substituted or unsubstituted alkyl group, a substituted or unsubstituted aromatic hydrocarbon group or a substituted or unsubstituted heterocyclic group.

The cyclic amide derivative of formula (I) have a strong and selective inhibitory action of a cathepsin K and a clinical efficacy when administered orally.

13 Claims, No Drawings

CYCLIC AMIDE DERIVATIVES

BACKGROUND OF THE INVENTION

1. Field of the Invention

The present invention relates to a cyclic amide derivative and a pharmaceutical agent containing the cyclic amide derivative as the effective ingredient. More specifically, the invention relates to a cyclic amide derivative useful as a therapeutic drug or preventive drug of arthritis and rheumatism due to the increase of bone resorption in addition to bone diseases such as osteoporosis, hypercalcemia, and Paget's disease.

2. Discussion of Background

Following the rapid progress of the phenomenon of aging society in recent years, the frequencies of senile diseases are increased due to the increase of aged people, causing a serious social problem. The number of patients with bone diseases in particular is increasingly elevated; among them, osteoporosis affects over 200 million people worldwide and postmenopausal osteoporosis affects 150 million people worldwide.

Postmenopausal osteoporosis is a serious problem; osteoporosis is observed in about 13% of females of age 40 years or older and in about 60% of females of age 60 years or older. The increase of bone resorption in menopausal female due to hormone imbalance or aging phenomenon is in close relation with the onset and progress of bone diseases, so bone resorption inhibitors are generally used for pharmaceutical treatment of such osteoporosis. However, pharmaceutical agents including calcitonin formulation, estrogen formulation, vitamin K formulation and bisphosphonate formulation and exerting an action to inhibit bone resorption have drawbacks in terms of the therapeutic effects, long lasting effects, side effects, drug compliance and the like. Hence, desirably, a bone resorption inhibitor functioning as a more highly effective therapeutic drug or preventive drug of osteoporosis will be developed.

Bone serves as a reservoir of an enormous amount of calcium in living organisms and calcium in bone is in equilibrium with calcium in blood; accordingly, calcium is consistently transferred from bone into blood or from blood into bone. Such calcium transfer between bone and blood is progressed in dynamic equilibrium between bone generation and bone resorption.

At the process of bone resorption, activated osteoclast dissolves inorganic bone materials such as calcium and concurrently degrades organic bone materials such as collagen. Recent research works indicate that cysteine protease secreted from osteoclast is responsible through collagen decomposition for bone resorption.

A report tells that in the lysosome of osteoclast are present cysteine proteases such as cathepsin B, cathepsin H, cathepsin L and cathepsin S and that inhibitors of these cysteine proteases exert an action to inhibit bone resorption (Biochem. J., 192, p.365 (1993); Biochem. Biophys. Res. Commun., 125, p.441 (1984); FEBS Lett., 321, p.247 (1993); JP-A-8-92193; JP-A-8-41043; JP-A-7-101924; JP-A-5-155764).

More recently, human cathepsin K locally present in osteoclast has been isolated. It has been elucidated that the expression thereof in osteoclast is greater than the expression of other cathepsins [Biochem. Biophys. Res. Commun., 206, p.89 (1995); J. Biol. Chem., 271, p.12511 (1996)]. Furthermore, it is suggested that patients with pycnodysostosis causing abnormality in bone resorption are mutant cathepsin K gene [Science, 273, p.1236 (1996)]. As has been described above, cathepsin K is drawing attention as a cysteine protease principally involved in bone resorption. Thus, it is expected that a cathepsin K inhibitor may function as a bone resorption inhibitor.

As compounds with cathepsin K inhibitory action, conventionally, aldehyde derivatives or epoxysuccinic acid derivatives [J. Biol. Chem., 271, p.2126 (1996); Biol. Pharm. Bull., 19, 1026(1996)] or vinylsulfone derivatives [Nature Structural Biology, 4, 105 (1997); J. Med. Chem., 38, 3193 (1995)] have been reported, but it is known that these derivatives are so poorly selective that these strongly inhibit cysteine proteases such as cathepsin B, cathepsin H, cathepsin L, cathepsin S and calpain, other than cathepsin K [J. Enzyme Inhibition, 3, p.195 (1990); Biochem. Biophys. Res. Commun., 153, p.1201(1988); J. Biochem., 87, 339 (1980); J. Biochem., 88, p.1805 (1980)].

While attention has been focused on cathepsin K as described above, furthermore, active research works have been carried out on X-ray crystallography of cathepsin K and inhibitors thereof [Nature Structural Biology, 4, 105 (1997); Nature Structural Biology, 4, 109 (1997)]. Consequently, a compound with an action selectively inhibiting cathepsin K has been known [Proc. Natl. Acad. Sci. USA, 94, 14249 (1997); WO 9801133; J. Am. Chem. Soc., 120, 9114 (1998); J. Med. Chem., 41, 3563 (1998)]. WO 9716177 describes the active site of cathepsin K and discloses the method for inhibiting cathepsin K by using a compound interactive with the active site.

While the compounds inhibiting cathepsin K have been drawing attention as bone resorption inhibitors as described above, numerous derivatives thereof have been reported, none of them has been practically applicable as a therapeutic drug of metabolic bone diseases.

Characteristic properties demanded for such therapeutic drug include therapeutic efficacy, long lasting effect, safety profile, and whether or not oral dosing is possible. Because the patients are older so therapeutic drugs therefor are possibly administered for a long term, significantly, these drugs should be clinically effective when dosed orally.

Thus, it is an object of the invention to provide a novel derivative functioning as a bone resorption inhibitor with a strong and selective inhibitory action of cathepsin K and with an efficacy when dosed orally.

SUMMARY OF THE INVENTION

The present inventors have made investigations to develop a compound with an action to selectively inhibit cathepsin K and with a clinical efficacy when administered orally. Consequently, the inventors have found a cyclic amide derivative with a non-natural amino acid moiety never found in the conventional inhibitors, as represented by the following general formula I. Thus, the invention has been achieved.

The inventive cyclic amide derivative represented by the general formula:

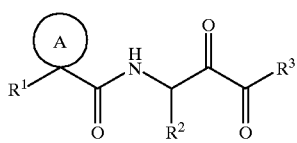

(I)

wherein $R^1$ represents a substituted alkyl group, a substituted alkenyl group, a substituted amino group, a substituted alkoxyl group, a substituted alkylthio group, a substituted carbamoyl group, a substituted sulfonamide group or a substituted amide group; the ring A represents a saturated cyclic alkyl group with 5 to 7 carbon atoms or a heteroatom-containing saturated heterocyclic group with 3 to 6 carbon atoms; $R^2$ represents a hydrogen atom, a substituted or unsubstituted alkyl group, a substituted or unsubstituted aromatic hydrocarbon group or a substituted or unsubstituted heterocyclic group; $R^3$ represents a hydrogen atom, a group represented by the general formula $R^4O$— or a group represented by the general formula $R^5(R^6)N$— wherein $R^4$ represents hydrogen atom, a substituted or unsubstituted alkyl group, a substituted or unsubstituted aromatic hydrocarbon group or a substituted or unsubstituted heterocyclic group; $R^5$ and $R^6$ may be the same or different and each represents a hydrogen atom, a substituted or unsubstituted alkyl group, a substituted or unsubstituted aromatic hydrocarbon group or a substituted or unsubstituted heterocyclic group;

DETAILED DESCRIPTION OF THE PREFERRED EMBODIMENTS

The inventive cyclic amide derivative represented by the general formula I is a compound produced by the following reaction scheme.

the general formula III. The cyclic carboxylic acid derivative represented by the general formula II as one raw material of the process is a compound readily produced from commercially available raw material compounds (see the reference example below). The amino alcohol represented by the general formula III can be produced from the corresponding aminoaldehyde derivative according to a method described in J. Med. Chem., 37, 2918–2929 (1994). The aminoaldehyde derivative can be produced by a known method [see Tetrahedron Letters, 33, 5029–5032 (1992); Chem. Pharm. Bull., 30, 1921–1924 (1989); Synthesis 1990, 1173–1176; Synthesis 1983, 676–678; Tetrahedron Letters, 33, 1347–1350 (1989); Chem. Rev., 89, 149–164 (1992)].

In the cyclic carboxylic acid derivative represented by the general formula II, $R^1$ represents a substituted alkyl group, a substituted alkenyl group, a substituted amino group, a substituted alkoxyl group, a substituted alkylthio group, a substituted carbamoyl group, a substituted sulfonamide group or a substituted amide group; the ring A represents a 5- to 7-membered saturated cyclic alkyl group or a 5- to 7-membered saturated heterocyclic group containing oxygen atom, sulfur atom or nitrogen atom; and the ring A may or may not contain a substituent.

The alkyl group as $R^1$ is any of alkyl groups with one to about 12 carbon atoms, linear, branched or cyclic, including for example methyl group, ethyl group, n-propyl group, 1-methylethyl group, cyclopropyl group, n-butyl group, 2-methylpropyl group, 1-methylpropyl group, 1,1-dimethylethyl group, cyclobutyl group, n-pentyl group, 3-methylbutyl group, cyclopentyl group, 2,2-dimethylpropyl group, 1-methylcyclobutyl group, cyclobutylmethyl group, n-hexyl group, 4-methylpentyl group, cyclohexyl group, 1-methylcyclopentyl group, cyclopentylmethyl group, (1-methylcyclobutyl)methyl group, n-heptyl group, 5-methylhexyl group, 4,4-dimethylpentyl group, cycloheptyl group, cyclohexylmethyl group, (1-methylcyclopentyl)methyl group, n-octyl group, 6-methyiheptyl group, 5,5-dimethylhexyl group, (1-methylcyclohexyl)methyl group, n-nonyl group, 7-methyloctyl group, 6,6-dimethylheptyl group, n-decyl group, 8-metbylnonyl group, 7,7-dimethyloctyl group, n-indecacyl group, 9-methyldecyl group, 8,8-dimethylnonyl group, n-dodecacyl group, 10-methylundecacyl group, and 9,9-dimethyldecacyl group.

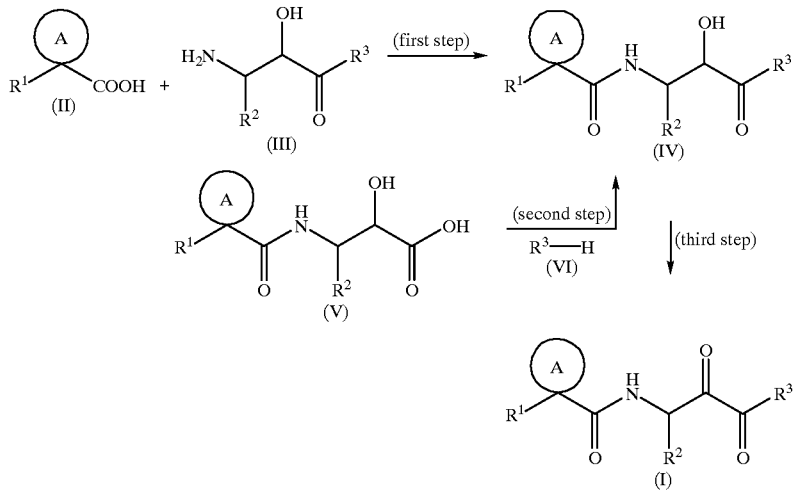

wherein A, $R^1$, $R^2$ and $R^3$ are the same as described above.

[First step]

The step is a process of producing an alcohol derivative represented by the general formula IV, comprising allowing a cyclic carboxylic acid derivative represented by the general formula II to react with an amino alcohol represented by The substituents for such alkyl group include for example hydroxyl group, oxo group, halogen atoms such as chlorine, bromine, iodine and fluorine; linear, branched or cyclic alkenyl groups with about 2 to 6 carbon atoms, substituted or unsubstituted; substituted or unsubstituted aromatic hydrocarbon groups; substituted or unsubstituted heterocyclic groups; nitro group; substituted or unsubstituted amino groups; trifluoromethyl group; substituted or unsubstituted sulfonyl groups; substituted alkoxyl groups; substituted alkylthio groups; substituted aryloxy groups; substituted arylthio groups; acyl groups; alkoxycarbonyl groups; substituted carbamoyl groups, mercapto group and cyano group.

Herein, the substituted or unsubstituted aromatic hydrocarbon groups illustrated as the substituents for the alkyl group include for example phenyl group, methylphenyl group, methoxyphenyl group, nitrophenyl group, fluorophenyl group, chlorophenyl group, bromophenyl group, 3,4-dimethoxyphenyl group, and 3,4-methylenedioxyphenyl group; the substituted or unsubstituted heterocyclic groups include for example tetrahydrofuran-2-yl group, 1,3-dioxolan-2-yl group, benzodioxolan-2-yl group, 1,3-dioxan-2-yl group, and 3,4-dihydro-2H-pyran-6-yl group; the substituted amino groups include for example methylamino group, N,N-dimethylamino group, butylamino group, N,N-dibutylamino group, 2,2-dimethylethylamino group, cyclohexylamino group, phenylamino group, methylphenylamino group, fluorophenylamino group, chlorophenylamino group, nitrophenylamino group, N,N-diphenylamino group, naphthylamino group, 3,4-dimethoxyphenylamino group, 3,4-methylenedioxyphenylamino group, N-methyl-N-phenylamino group, N-methyl-N-naphthylamino group, pyridylamino group, furylamino group, thienylamino group, quinolylamino group, isoquinolylamino group, phenylmethylamino group, fluorophenylmethylamino group, chlorophenylmetbylamino group, nitrophenylmetbylamino group, naphthylmethylamino group, 3,4-dimethoxyphenylmethylamino group, and 3,4-methylenedioxyphenylmethylamino group; the substituted sulfonyl groups include for example methylsulfonyl group, butylsulfonyl group, 2,2-dimethylethylsulfonyl group, cyclohexylsulfonyl group, phenylsulfonyl group, methylphenylsulfonyl group, fluorophenylsulfonyl group, chlorophenylsulfonyl group, nitrophenylsulfonyl group, naphthylsulfonyl group, 3,4-dimethoxylphenylsulfonyl group, 3,4-methylenedioxyphenylsulfonyl group, pyridylsulfonyl group, furylsulfonyl group, thienylsulfonyl group, quinolylsulfonyl group, isoquinolylsulfonyl group, phenylmethylsulfonyl group, fluorophenylmethylsulfonyl group, chlorophenylmethylsulfonyl group, nitrophenylmethylsulfonyl group, naphthylmethylsulfonyl group, 3,4-dimethoxyphenylmethylsulfonyl group and 3,4-methylenedioxyphenylmethyl-sulfonyl group; the substituted alkoxyl groups include for example methyloxy group, butyloxy group, 2,2-dimethylethyloxy group and cyclohexyloxy group; the substituted aryloxy groups include phenyloxy group, methylphenyloxy group, fluorophenyloxy group, chlorophenyloxy group, nitrophenyloxy group, naphthyloxy group, 3,4-dimethoxylphenyloxy group, 3,4-methylenedioxyphenyloxy group, pyridyloxy group, furyloxy group, thienyloxy group, quinolyloxy group, isoquinolyloxy group, phenylmetbyloxy group, fluorophenylmethyloxy group, chlorophenylmethyloxy group, nitrophenylmethyloxy group, naphthylmethyloxy group, 3,4-dimethoxyphenylmethyloxy group and 3,4-methylenedioxyphenylmethyloxy group; the substituted alkylthio groups include for example methylthio group, butylthio group, 2,2-dimethylethylthio group and cyclohexylthio group; the substituted arylthio groups include for example phenylthio group, methylphenylthio group, tluorophenylthio group, chlorophenylthio group, nitrophenylthio group, naphthylthio group, 3,4-dimethoxyphenylthio group, 3,4-methylenedioxyphenylthio group, pyridylthio group, furylthio group, thienylthio group, quinolylthio group, isoquinolylthio group, phenylmethylthio group, fluorophenylmethylthio group, chlorophenylmethylthio group, nitrophenylmethylthio group, naphthylmethylthio group, 3,4-dimethoxyphenylmethylthio group and 3,4-methylenedioxyphenylmethylthio group; the substituted carbamoyl groups include for example N-methylcarbamoyl group, N,N-dimethylcarbamoyl group, N-butylcarbamoyl group, N,N-dibutylcarbamoyl group, N-(2,2-dimethylethyl)carbamoyl group, N-cyclohexylcarbamoyl group, N-phenylcarbamoyl group, N-(methylphenyl)carbamoyl group, N-(fluorophenyl)carbamoyl group, N-(chlorophenyl)carbamoyl group, N-(nitrophenyl)carbamoyl group, N,N-diphenylcarbamoyl group, N-naphthylcarbamoyl group, N-(3,4-dimethoxyphenyl) carbamoyl group, N-(3,4-methylenedioxyphenyl)carbamoyl group, N-methyl-N-phenylcarbamoyl group, N-methyl-N-naphthylcarbamoyl group, N-pyridylcarbamoyl group, N-furylcarbamoyl group, N-thienylcarbamoyl group, N-quinolylcarbamoyl group, N-isoquinolylcarbamoyl group, N-(phenylmethyl) carbamoyl group, N-(tluorophenylmethyl)carbamoyl group, N-(chlorophenylmethyl) carbamoyl group, N-(nitrophenylmethyl)carbamoyl group, N-(naphthylmethyl) carbamoyl group, N-(3,4-dimethoxyphenylmethyl)carbamoyl group, and N-(3,4-methylenedioxyphenylmethyl)carbamoyl group.

The alkenyl group as $R^1$ is any of alkenyl groups with about 2 to 6 carbon atoms, linear, branched or cyclic, including for example 1-methyl-1-propenyl group, 1-methyl-2-propenyl group, 2-methyl-2-propenyl group, ethenyl group, 1-methylethenyl group, 1-propenyl group, 2-propenyl group, 1-butenyl group, 2-butenyl group, 2-pentenyl group, 1-pentenyl group, 1,3-butane dienyl group, 1-hexenyl group, 2-hexenyl group, 1,3-pentadienyl group, and 1,3-hexadienyl group.

The substituents for the alkenyl group include the same substituents as those for the alkyl group.

Additionally, the substituted amino group means a secondary amino group or tertiary amino group, which has been substituted with various substituents including substituted or unsubstituted alkyl groups, substituted or unsubstituted alkenyl groups, substituted or unsubstituted aromatic hydrocarbon groups, or substituted or unsubstituted heterocyclic groups.

The substituted or unsubstituted alkyl groups and the substituted or unsubstituted alkenyl groups include the same groups as those illustrated for $R^1$. Additionally, the substituted or unsubstituted aromatic hydrocarbon groups mean aromatic hydrocarbon groups, monocyclic or polycyclic, which may have a variety of one or more substituents on the rings thereof; the substituted or unsubstituted aromatic hydrocarbon groups include for example phenyl group, methylphenyl group, dimethylphenyl group, methoxyphenyl group, 2,3-dimethoxyphenyl group, 3,4-dimethoxyphenyl group, 3,5-dimetboxylphenyl group, 2,3-methylenedioxyphenyl group, 3,4-methylenedioxyphenyl group, nitrophenyl group, dinitrophenyl group, chlorophenyl group, dichlorophenyl group, bromophenyl group, dibromophenyl group, iodophenyl group, tluorophenyl group, 2,3-difluorophenyl group, 3,4-difluorophenyl group, 3,5-difluorophenyl group, trifluoromethylphenyl group, 3-phenoxyphenyl group, 4-phenoxyphenyl group, 4-(1- naphthoxy)phenyl group, 4-acetaminophenyl group, 1-naphthyl group and 2-naphthyl group.

Still additionally, the substituted or unsubstituted heterocyclic groups mean 5- or 6-membered rings containing at least one or more hetero atoms such as nitrogen atom, sulfur atom or oxygen atom as the ring-composing atoms, wherein the rings may satisfactorily be condensed with benzene ring and may have one or more substituents on the rings. The heterocyclic groups include for example pyridyl group, furyl group, thienyl group, indolyl group, quinolyl group, isoquinolyl group, benzofuranyl group, benzothienyl group, imidazolyl group, benzimidazolyl group, thiazolyl group, oxazolyl group, pyrazolyl group, pyrimidyl group, pyrimidinyl group, dioxanyl group, thiazolidinyl group, imidazolidinyl group, 2-oxotetrahydrofuran-3-yl group, benzothiazolyl group, quinazolyl group, hexahydro-2-azepinon-3-yl group, morpholino group, thiamorpholino group, pyrrolidino group, piperidino group, piperazino group, perhydroazepin-1-yl group, perhydro-4-azaazepin-1-yl group, 4-acetylpiperazino group, 4-propionylpiperazino group, 4-isobutyrylpiperazino group, 4-methoxycarbonylpiperazino group, 4-ethoxycarbonylpiperazino group, 4-(2-methyl-2-propyloxycarbonyl)piperazino group, 4-methylsulfonylpiperazino group, 4-methoxypiperidino group, 4-ethoxycarbonylpiperidino group, 4-(2-methyl-2-propyloxycarbonyl)piperidino group and 1-benzoylpiperidin-4-yl group.

The alkoxyl groups mean oxy groups substituted with an alkyl moiety with about one to 6 carbon atoms and include for example methoxy group, ethoxy group, n-propoxy group, 1-methylethoxy group, n-butoxy group, 2-methylpropoxy group, 1-methylpropoxy group, 2-methyl-2-propoxy group, n-pentyloxy group, 3-methylbutoxy group, n-hexyloxy group and 4-methylpentoxy group.

Furthermore, the substituted alkoxyl groups include the alkoxyl groups, additionally substituted with various substituents such as the same substituents for the alkyl group.

The alkylthio groups mean thio groups substituted with an alkyl moiety with one to about 6 carbon atoms and include for example methylthio group, ethylthio group, n-propylthio group, 1-methylethylthio group, n-butylthio group, 2-methylpropylthio group, 1-methylpropylthio group, 2-methyl-2-propylthio group, n-pentylthio group, 3-methylbutylthio group, n-hexylthio group, and 4-methylpentylthio group.

The substituted alkylthio groups mean alkylthio groups substituted with various substituents including the same groups as the substituents for the alkyl group.

The substituted carbamoyl groups include groups wherein various substituents are in substitution at the nitrogen atom in the carbamoyl-binding group, and the groups are represented by the formula $R^7$—NHCO— wherein the substituent $R^7$ includes the substituted or unsubstituted alkyl groups, the substituted or unsubstituted alkenyl groups, the substituted or unsubstituted amino groups, the substituted or unsubstituted aromatic hydrocarbon groups, and the substituted or unsubstituted heterocyclic groups.

The substituted sulfonamide groups include groups wherein various substituents are in substitution at the sulfur atom in the sulfonamide-binding group, and the groups are represented by the formula $R^8$—SO$_2$NH—. The substituent $R^8$ in substitution at the sulfur atom includes the substituted or unsubstituted alkyl groups, the substituted or unsubstituted alkenyl groups, the substituted or unsubstituted amino groups, the substituted or unsubstituted aromatic hydrocarbon groups, and the substituted or unsubstituted heterocyclic groups.

The substituted amide groups include groups wherein various substituents are in substitution at the carbon atom in the amide-binding group, and the groups are represented by the formula $R^9$—CO—NH—. The substituent $R^9$ in substitution at the carbon atom includes a substituted or unsubstituted alkyl group, a substituted alkoxyl group, phenoxy group, 1-naphthyloxy group, 2-naphthyloxy group, a substituted or unsubstituted alkenyl group, a substituted or unsubstituted amino group, a substituted or unsubstituted aromatic hydrocarbon group, and a substituted or unsubstituted heterocyclic group.

Still furthermore, the ring A represents a saturated cyclic alkyl group with 5 to 7 carbon atoms or a hetero-atom-containing saturated heterocyclic group with 3 to 6 cabon atoms. The saturated cyclic alkyl group with 5 to 7 carbon atoms includes for example groups derived from cyclopentane, cyclohexane, and cycloheptane. The hetero-atom-containing saturated heterocyclic group with 3 to 6 carbon atoms include groups deprived from for example pyrrolidine, piperidine, perhydroazepine, oxolane, oxane, oxepane, thiolane, and thiane and thiepane and the hetero-atom includes for example oxygen atom, sulfur atom and nitrogen atom. The 5- to 7-membered saturated heterocyclic group can be condensed with benzene ring and includes the saturated cyclic alkyl group with 5 to 7 carbon atoms or the hetero-atom-containing saturated heterocyclic group with 4 to 6 carbon atoms may contain substituents include groups derived from for example hydroxyl group, halogen atoms such as chlorine atom, bromine atom, iodine atom, and fluorine atom; substituted or unsubstituted alkyl groups, substituted or unsubstituted aromatic hydrocarbon groups such as phenyl group, methylphenyl group, and naphthyl group; substituted or unsubstituted heterocyclic groups such as thienyl group, furyl group, and pyridyl group; nitro group; substituted or unsubstituted amino groups; trifluoromethyl group; substituted or unsubstituted sulfonyl groups; substituted alkoxyl groups, substituted alkylthio groups, acyl groups, alkoxycarbonyl groups, substituted carbonyl groups, mercapto group and cyano group.

The cyclic carboxylic acid derivative represented by the general formula II includes the following compounds.

1-[N-(Phenylmethoxycarbonyl)amino]cyclohexane carboxylic acid

1-[N-(Phenyloxycarbonyl)aminol]cyclohexane carboxylic acid

1-[N-(2-Methylpropyloxycarbonyl)aminol]cyclohexane carboxylic acid

1-[N-(3,4-Methylenedioxyphenylcarbonyl)amino]cyclohexane carboxylic acid

1-[N-(Morpholine-4-carbonyl)amino]cyclohexane carboxylic acid

1-[N-[1-(Methoxycarbonyl)piperidine-4-carbonyl]amino]cyclohexane carboxylic acid 1-Phenylsulfonylmethylcyclohexane carboxylic acid 1-[N-[4-(2-Methyl-2-propyloxycarbonyl)piperazine-1-carbonyl]amino]cyclohexane carboxylic acid 1-[N-[4-(Methoxycarbonyl)piperazine-1-carbonyl]amino]cyclohexane carboxylic acid 1-[N-(4-Acetylpiperazine-1-carbonyl)amino]cyclohexane carboxylic acid 1-[N-(Phenylsulfonyl)amino]cyclohexane carboxylic acid 1-[N-(Piperazine-1-carbonyl)amino]cyclohexane carboxylic acid 1-[N-(Morpholine-4-sulfonyl)amino]cyclohexane carboxylic acid 1-[N-(4-Acetylpiperazine-1-sulfonyl)amino]cyclohexane carboxylic acid 1-[N-(Piperazine-1-sulfonyl)amino]cyclohexane carboxylic acid
1-[N-(4-Methylpiperazine-1-carbonyl)amino]cyclohexane carboxylic acid
1-[N-(4-Phenylpiperazine-1-carbonyl)amino]cyclohexane carboxylic acid
1-[N-(4-Methylpiperazine-1-sulfonyl)amino]cyclohexane carboxylic acid
1-[N-(4-Phenylpiperazine-1-sulfonyl)amino]cyclohexane carboxylic acid
1-[N-(4-Methoxyphenylsulfonyl)amino]cyclohexane carboxylic acid
1-[N-(4-Nitrophenylsulifonyl)amino]cyclohexane carboxylic acid
1-[N-(4-Acetaminophenylsulfonyl)amino]cyclohexane carboxylic acid
1-[N-(Pyridine-3-sulfonyl)amino]cyclohexane carboxylic acid
1-[N-(Quinoline-5-sulfonyl)amino]cyclohexane carboxylic acid
1-[N-(4-Dimethylaminophenylsulfonyl)amino]cyclohexane carboxylic acid
1-[N-(5-Acetaminonaphthyl-2-sulfonyl)amino]cyclohexane carboxylic acid
1-[N-(5-Dimethylaminonaphthyl-2-sulfonyl)amino]cyclohexane carboxylic acid
1-[(Morpholine-4-sulfonyl)methyl]cyclohexane carboxylic acid
1-[(4-Acetylpiperazine-1-sulfonyl)methyl]cyclohexane carboxylic acid
1-[N-[(4-Ethoxycarbonyl)piperazine-1-carbonyl]amino]cyclohexane carboxylic acid
1-[N-[(4-Methylsulfonyl)piperazine-1-carbonyl]amino]cyclohexane carboxylic acid
1-[N-[(4-Isobutyryl)piperazine-1-carbonyl]amino]cyclohexane carboxylic acid
1-[N-[(4-Thiamorpholine-4-carbonyl]amino]cyclohexane carboxylic acid
1-[N-[(4-Ethoxycarbonyl)piperidine-1-carbonyl]amino]cyclohexane carboxylic acid
1-[N-[(4-Acetyl)perhydro-4-azaazepine-1-carbonyl]amino]cyclohexane carboxylic acid
1-[N-[(4-Methoxy)piperidine-1-carbonyl]amino]cyclohexane carboxylic acid
1-[N-[N,N-Bis(2-Methoxyethyl)amino-1-carbonyl]amino]cyclohexane carboxylic acid
1-[N-[[N-(2-Methoxyethyl)-N-methyl]amino-1-carbonyl]amino]cyclohexane carboxylic acid In the amino alcohol derivative represented by the general formula III, $R^2$ represents a hydrogen atom, a substituted or unsubstituted alkyl group, a substituted or unsubstituted aromatic hydrocarbon group or a substituted or unsubstituted heterocyclic group; $R^3$ represents a hydrogen atom, a group represented by the general formula $R^4O$— or a group represented by the general formula $R^5(R^6)N$— wherein $R^4$ represents a hydrogen a atom, a substituted or unsubstituted alkyl group, a substituted or unsubstituted aromatic hydrocarbon group or a substituted or unsubstituted heterocyclic group; $R^5$ and $R^6$ may be the same or different and each represents a hydrogen atom, a substituted or unsubstituted alkyl group, a substituted or unsubstituted aromatic hydrocarbon group or a substituted or unsubstituted heterocyclic group. The alkyl group, aromatic hydrocarbon group and heterocyclic group in the amino alcohol derivative are the same groups as those illustrated for the cyclic carboxylate derivative represented by the general formula II.

The amino alcohol derivative represented by the general formula III includes for example the following compounds.

(2RS,3S)-N-Cyclopentyl-3-amino-2-hydroxyheptaneamide
(2RS,3S)-N-Cyclopentyl-3-amino-2-hydroxy-5-(methylthio)pentaneamide
(2RS,3S)-N-Cyclopentyl-3-amino-2-hydroxybutaneamide
(2RS,3S)-N-Cyclopentyl-3-amino-2-hydroxy-4-methylpentaneamide
(2RS,3S)-3-Amino-2-hydroxyheptaneamide
(2RS,3S)-N-Cyclopentylmethyl-3-amino-2-hydroxyheptaneamide
(2RS,3S)-N-(1-Methyl-cyclopentylmethyl)-3-amino-2-hydroxyheptaneamide
(2RS,3S)-N-2,2,-Dimethylpropyl-3-amino-2-hydroxyheptaneamide
(2RS,3S)-N-Cyclobutyl-3-amino-2-hydroxy-5-(methylthio)pentamide
(2RS,3S)-N-Cyclohexyl-3-amino-2-hydroxy-5-(methylthio)pentaneamide
(2RS,3S)-N-Cyclopentylmethyl-3-amino-2-hydroxy-5-(methylthio)pentaneamide
(2RS,3S)-N-(1-Methyl-cyclopentylmethyl)-3-amino-2-hydroxy-5-(methylthio)pentaneamide
(2RS,3S)-N-2,2-Dimethylpropyl-3-amino-2-hydroxy-5-(methylthio)pentaneamide
(2RS,3S)-N-Cyclopentylmethyl-3-amino-2-hydroxy-4-methylpentaneamide
(2RS,3S)-N-(1-Methyl-cyclopentylmethyl)-3-amino-2-hydroxy-4-methylpentaneamide
(2RS,3S)-N-2,2-Dimethylpropyl-3-amino-2-hydroxy-4-methylpentaneamide
(2RS,3S)-N-Cyclobutyl-3-amino-2-hydroxy-5-methylhexaneamide
(2RS,3S)-N-Cyclopentyl-3-amino-2-hydroxy-5-methylhexaneamide
(2RS,3S)-N-Cyclohexyl-3-amino-2-hydroxy-5-methylhexaneamide
(2RS,3S)-N-Cyclopentylmethyl-3-amino-2-hydroxy-5-methylhexaneamide
(2RS,3S)-N-(1-Methyl-cyclopentylmethyl)-3-amino-2-hydroxy-5-methylhexaneamide
(2RS,3S)-N-2,2-Dimethylpropyl-3-amino-2-hydroxy-5-methylhexaneamide
(2RS,3S)-N-Cyclobutyl-3-amino-2-hydroxy-4-phenylbutaneamide
(2RS,3S)-N-Cyclopentyl-3-amino-2-hydroxy-4-phenylbutaneamide
(2RS,3S)-N-Cyclohexyl-3-amino-2-hydroxy-4-phenylbutaneamide
(2RS,3S)-N-Cyclopentylmethyl-3-amino-2-hydroxy-4-phenylbutaneamide
(2RS,3S)-N-(1-Methyl-cyclopentylmethyl)-3-amino-2-hydroxy-4-phenylbutaneamide
(2RS,3S)-N-2,2-Dimethylpropyl-3-amino-2-hydroxy-4-phenylbutaneamide At the present process, the reaction of the amino alcohol derivative represented by the general formula III with the cyclic carboxylic acid derivative represented by the general formula II is preferably carried out in the presence of a condensing agent; as the condensing agent, use can be made of carbodiimide reagents, for example dicyclohexylcarbodiimide, 1-ethyl-3-(3-dimethylaminopropyl)carbodiimide, and isopropylcarbodiimide. At the process, the condensing agent is used at one to 3 equivalents to the cyclic carboxylic acid derivative represented by the general formula II or the amino alcohol derivative represented by the general formula III, preferably 1.5 to 2 equivalents thereto for the production at a higher yield. The reaction is preferably carried out in inactive solvents, singly or in combination, including for example, halogenated hydrocarbons such as dichloromethane, chloroform and dichloroethane; aromatic hydrocarbons such as benzene, toluene and xylene; ethers such as diethyl ether, dimethoxyethane, tetrahydrofuran, and dioxane; amides such as dimethylformamide and dimethylacetamide; dimethyl sulfoxide and acetonitrile. The reaction generally proceeds at atmospheric pressure and 50° C. to the reflux temperature, but for a higher yield, the reaction is facilitated at −10° C. to 30° C. Herein, the carboxyl group of the cyclic carboxylic acid derivative represented by the general formula II at the process may be converted to a variety of reactive derivatives, which are then subjected to this reaction.

[Second step]

At the present step, the alcohol derivative represented by the general formula IV can be produced via the reaction of the hydroxycarboxylic acid derivative represented by the general formula V with the compound represented by the general formula VI. The hydroxycarboxylic acid derivative represented by the general formula V as one raw material compound at this step is a compound readily prepared from commercially available raw material compounds (see the following reference example). The compound represented by the general formula VI as the other raw material is a compound represented by the general formula $R^4$—OH or $R^5(R^6)NH$ (wherein $R^4$, $R^5$ and $R^6$ are the same as described above). These alcohol compounds, phenol compounds and amine compounds are readily available compounds.

The step corresponds to a condensation reaction and can be progressed by using the same condensing agent as at the first step in the same reaction solvent under the same reaction conditions.

[Third step]

At this step, the cyclic amide derivative represented by the general formula I can be produced by oxidizing the alcohol derivative represented by the general formula IV as produced at the first or second step. As the oxidation reaction at this step, for example, active dimethyl sulfoxide oxidation process can be used. As the oxidizing agent, dimethyl sulfoxide is used, in combination with activating agents such as dicyclohexylcarbodiimide, phosphorus pentaoxide, pyridine-sulfur trioxide complex, oxalyl oxide, acetic anhydride, trifluoroacetic acid. Activated agents is used at an amount of one to 12 equivalents to the alcohol derivative represented by the general formula IV. Additionally, the reaction is preferably effected in solvents including halogenated hydrocarbons for example dichloromethane, chloroform, and dichloroethane. Dimethyl sulfoxide as the oxidizing agent can be used at an excess amount for allowing dimethyl sulfoxide to serve as a solvent. The reaction is carried out at −78° C. to 30° C.

The compound represented by the following general formula Ia as recovered at the third step, wherein $R^3$ is an alkoxyl group, can be further hydrolyzed to prepare a carboxylic acid derivative represented by the following general formula Ib to subsequently prepare various cyclic amide derivative compounds represented by the general formula I. The reaction scheme is shown below.

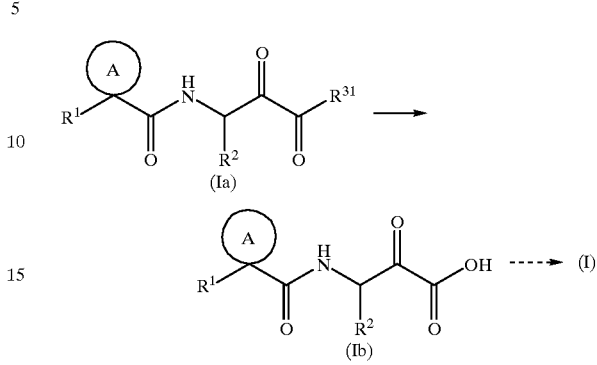

wherein $R^1$, $R^2$ and A are the same as described above; and $R^{31}$ is an alkoxyl group.

The cyclic amide derivative represented by the general formula I, which is produced by the method described above, can be prepared as known acid addition salts or basic salts, for example, for the administration as pharmaceutical agents for humans. The acid addition salts include inorganic salts (for example, with hydrochloric acid, sulfuric acid and phosphoric acid) or organic acid salts (for example, with acetic acid, propionic acid, citric acid, tartaric acid, malic acid, oxalic acid and methanesulfonic acid); and basic salts include pharmacologically acceptable salts such as sodium salt, potassium salt and ammonium salt.

[Function]

The inventive cyclic amide derivative represented by the general formula I exerted a strong inhibitory action at a test for assaying the activity to inhibit cathepsin K and was demonstrated to be highly effective when dosed orally. The effective doses of the compound or pharmacologically acceptable salts thereof to be administered as pharmaceutical agents to humans vary, depending on the levels of the effective activities and the age and subject disease of a patient, but generally, the doses are 0.01 to 100 mg, preferably 0.1 to 50 mg per 1 kg human body weight per day.

For dosing the cyclic amide derivative represented by the general formula I for therapeutic purpose, the cyclic amide derivative or one salt thereof is blended as the effective ingredient with pharmaceutically acceptable carriers such as organic or inorganic excipients in solid or liquid suitable for not only oral dosing but also parenteral dosing or external use or inhalation, to prepare a pharmaceutical composition. Such pharmaceutical composition may be in formulation of capsule, tablet, sugar-coated tablet, granule, liquid, suspension, or emulsion or the like. If necessary, auxiliary agents, stabilizers, lubricants, emulsifiers, buffers or other routine additives may be added to the resulting formulation.

EXAMPLES

The invention will now be described in more detail in the following reference examples, examples and test examples.

Reference Example 1

Synthesis of 1-[N-(phenylmethoxycarbonyl)amino]cyclohexanecarboxylic acid

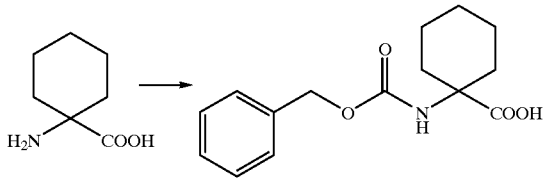

28.6 g (0.2 mol) of 1-aminocyclohexanecarboxylic acid was dissolved in 2N-aqueous sodium hydroxide solution (110 ml) and with stirring under an ice-cooled condition 2N-aqueous sodium hydroxide solution (120 ml) and 41 g (0.24 mol) of chloro carbonate phenylmethyl were slowly added dropwise to the above prepared mixture. After one hour, the reaction mixture was warmed to room temperature and then stirred overnight. The reaction mixture was put into a separatory funnel and washed with ethyl acetate so that excess chloro carbonic acid phenylmethyl was removed therefrom. The reaction mixture was made acid with the addition of 10% hydrochloric acid under an ice-cooled condition and extracted with ethyl acetate. The resultant organic extract layer was washed with saturated brine, and then, was dried over anhydrous sodium sulfate, and the solvent was distilled away under reduced pressure. Thus, the obtained crystal was washed with ether and 37.2 g of the captioned 1-[N-(phenylmethoxycarbonyl)amino]cyclohexanecarboxylic acid was obtained in a yield of 67%.

1H-NMR (CDCl$_3$, δ): 1.23–1.39 (7H, m), 1.39–1.51 (2H, m), 1.57–1.70 (3H, m), 1.79–1.97 (2H, m), 1.98–2.13 (2H, m), 5.01 (1H, s), 5.2 (2H, s), 7.26–7.39 (5H, m).

Reference Example 2

Synthesis of 1-[N-(phenyloxycarbonyl)amino]cyclohexanecarboxylic acid

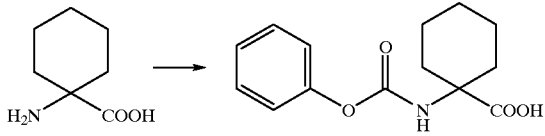

The same reaction procedure as in Reference Example 1 was repeated except that 3.29 g of 1-aminocyclobexanecarboxylic acid and 3.62 g of chloro carbonic acid phenylmethyl used in Reference Example 1 was replaced by chlorocarbonic acid phenyl, whereby 2.2 g of the captioned 1-[N-(phenyloxycarbonyl)amino]cyclohexanecarboxylic acid was obtained in a yield of 36%.

1H-NMR (CDCl$_3$, δ): 1.30–1.40 (1H, m), 1.40–1.60 (2H, m), 1.60–1.80 (3H, m), 1.90–2.00 (2H, m), 2.10–2.20 (2H, m), 5.20 (1H, br-s), 7.00–7.40 (5H, m).

Reference Example 3

Synthesis of 1-[N-(2-methylpropyloxycarbonyl)amino]cyclohexanecarboxylic acid

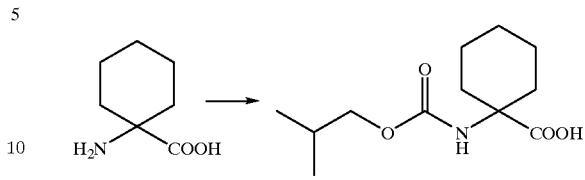

The same reaction procedure as in Reference Example 1 was repeated except that 3.93 g of 1-aminocyclobexanecarboxylic acid and chrolocarbonic acid phenylmethyl used in Reference Example 1 was replaced by 3.73 g of chlorocarbonic acid 2-methylpropyl, whereby 3.37 g of the cationed 1-[N-(2-methylpropyloxycarbonyl)amino]cyclohexanecarboxylic acid was obtained in a yield of 50%.

1H-NMR (CDCl$_3$, δ): 0.90 (6H, d, J=5 Hz), 1.20–1.40 (1H, m), 1.40–1.55 (2H, m), 1.60–1.70 (3H, m), 1.80–2.00 (3H, m), 2.00–2.10 (2H, m), 3.85 (2H, d, J=7 Hz), 5.90 (1H, br-s).

Reference Example 4

Synthesis of 1-[N-(3,4-methylenedioxyphenylcarbonyl)amino]cyclohexanecarboxylic acid

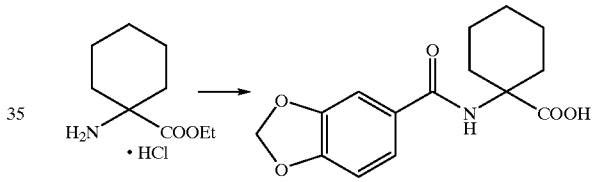

2.74 g (16.5 mmol) of 3,4-methylenedioxybenzoic acid was dissolved in anhydrous dichloromethane and then was ice cooled. 4.62 ml (33.0 mmol) of triethylamine, 2.53 g (16.5 mmol) of 1-hydroxybenzotriazole hydrate, 3.57 g (17.3 mmol) of N,N'-dicyclohexylcarbodiimide and 3.20 g (16.5 mmol) of ethyl 1-aminocyclohexanecarboxylate hydrochloride were successively added to the above reaction mixture and were stirred for 18 hours gradually rising the temperature up to the room temperature. The reaction mixture was concentrated under reduced pressure and was dissolved in ethyleacetate, and the insoluble components were removed therefrom by filtration. After the ethyl acetate solution was washed successively with 1N-hydrochloric acid, saturated brine, aqueous solution of saturated sodium hydrogen carbonate and saturated brine, the resultant organic layer was dried over anhydrous sodium sulfate, and concentrated under reduced pressure, whereby 5.21 g of ethyl 1-[N-(3,4-methylenedioxyphenylcarbonyl)amino]cyclohexanecarboxylate was obtained.

Subsequently, 5.21 g of ethyl 1-[N-(3,4-methylenedioxyphenylcarbonyl) amino] cyclohexanecarboxylate synthesized in the above was dissolved in ethanol, and then, 16 ml of aqueous solution of 1N-sodium hydroxide was added dropwise thereto. After making heat reflux for 18 hours, the reaction solution was concentrated under reduced pressure. The residue thus obtained was dissolved in water and was washed with ether. After the resulting water layer was made acid (pH=2) by addition of 4-hydrochloric acid thereto, said layer was extracted with ethylacetate and was washed with 1N-hydrochloric acid and saturated brine. The resultant organic layer was dried over anhydrous sodium sulfate, and concentrated under reduced pressure, whereby 3.18 g of the captioned 1-[N-(3,4-methylenedioxyphenylcarbonyl) amino]cyclohexanecarboxylic acid was obtained in a yield of 68%.

1H-NMR (δ, CD$_3$OD): 1.30–1.70 (6H, m), 1.85–1.98 (2H, m), 2.14–2.25 (2H, m), 6.02 (2H, s), 6.87 (1H, d, J=8 Hz), 7.28 (1H, d, J=2 Hz), 7.40 (1H, dd, J=8 Hz, 2 Hz).

Reference Example 5

Synthesis of 1-[N-(morpholine-4-carbonyl)amino] cyclohexanecarboxylic acid

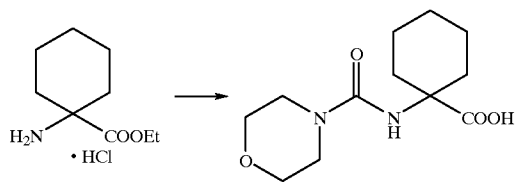

The same reaction procedure as used in Reference Example 4 was repeated by using 4.36 g (21 mmol) of ethyl 1-aminocyclohexanecarboxylate hydrochloride and 3.15 g (21 mmol) of morpholine carbonyl chloride, whereby 1.8 g of the captioned 1-[N-(morpholine-4-carbonyl)amino] cyclohexanecarboxylic acid was obtained in a yield of 33%.

1H-NMR (δ, CDCl$_3$): 1.30–1.50 (3H, m), 1.60–1.80 (3H, m), 1.90–2.15 (4H, m), 3.26–3.50 (4H, m), 3.60–3.80 (4H, m), 4.49 (1H, s).

Reference Example 6

Synthesis of 1-[N-[1-(2-methyl-2-propyloxycarbonyl) piperidine-4-carbonyl]amino]cyclohexanecarboxylic acid

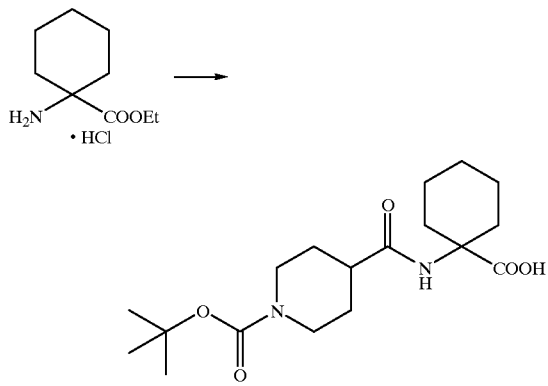

The same reaction procedure as in Reference Example 4 was repeated expect that 3,4-methylendioxybenzoic acid used in Reference Example 4 was replaced by 6.87 g of 1-(2-methyl-2-propyloxycarbonyl)piperidine-4-carboxylic acid, whereby 3.8 g of the captioned 1-[N-[1-(2-methyl-2-propyloxycarbonyl)piperidine-4-carbonyl]amino] cyclohexanecarboxylic acid was obtained in a yield of 70%.

1H-NMR (CDCl$_3$, δ): 1.30–1.40 (3H, m), 1.50 (9H, m), 1.55–1.88 (5H, m), 1.80–2.00 (4H, m), 2.00–2.10 (2H, m), 2.36 (1H, tt, J=11.3 Hz), 2.60–2.80 (2H, m), 4.00–4.30 (2H, m), 5.60 (1H, s).

Reference Example 7

Synthesis of 1-phenylsulfonylmethylcyclohexanecarboxylic acid

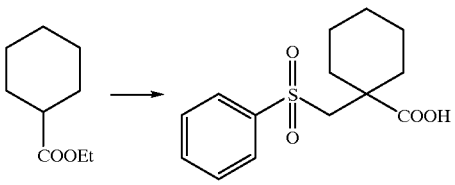

Under air current of nitrogen, anhydrous tetrahydrofuran solution of 1.85 ml (13.2 mmol) of diisopropylamine was cooled in a dry ice-acetone bath, and thereafter 7.23 ml (12 mmol) of hexane solution of n-butyllithium was added dropwise thereto. After the completion of dropping, the temperature of the reaction mixture was raised to room temperature and the reaction mixture was stirred for 1 hour and thereafter cooled again in the dry ice-acetone bath, and then, anhydrous tetrahydrofuran solution of 1.56 g (10.0 mmol) of cyclohexane carboxylic acid ethyl was added dropwise thereto. After stirring for 30 minutes, anhydrous tetrahydrofuran solution of 1.34 ml (10 mmol) of chloromethylphenylsulfide was added dropwise to the above reaction mixture and stirred for 18 hours gradually rising the temperature up to the room temperature. The reaction mixture was put into aqueous solution of saturated ammoniumchroride and extruded with ethyl acetate.

Further, ethyl acetate layer was washed successively with 1N-hydrochloric acid, saturated brine, aqueous solution of saturated sodium hydrogen carbonate and saturated brine. The resultant organic layer was dried over anhydrous sodiumsulfate and concentrated under reduced pressure, whereby 1.79 g of ethyl 1-phenylsulfonylmethylcyclohexanecarboxylate was obtained.

Subsequently, 1.28 g (4.60 mmol) of the ethyl 1-phenylsulfonylmethylcyclohexanecarboxylate was dissolved in 3 ml of acetic acid and 1.78 ml of 30% hydrogenperoxide water was gradually added dropwise thereto. After heating reflux for 30 minutes, the reaction mixture was put into iced water and extracted with ether and dried over anhydrous sodiumsulfate and concentrated under reduced pressure, whereby 1.43 g of ethyl 1-phenylsulfonylmethylcyclohexane carboxylate was obtained.

Further, 1.43 g (4.6 mmol) of the ethyl 1-phenylsulfonylmethylcyclohexanecarboxylate and 1.52 g (23.0 mmol) of potassium hydroxide were dissolved in aqueous solution of 90% ethanol. After heating reflux for 18 hours, the reaction mixture was concentrated under reduced pressure. The obtained residue was dissolved in water and washed with ether. The resulting water layer was made acid (pH=2) by the addition of 4N-hydrochloric acid thereto and then extracted with ethyl acetate and washed with 1N-hydrochloric acid and saturated brine. The obtained organic layer was dried over anhyrous sodiumsulfate and concentrated under reduced pressure, whereby 1.22 g of the captioned 1-phenylsulfonylmethylcyclohexane-carboxylic acid was obtained in a yield of 60%.

1H-NMR (δ, CDCl$_3$): 1.35–1.68 (4H, m), 1.68–1.80 (2H, m), 2.02–2.15 (2H, m), 3.56 (2H, s), 7.52–7.70 (3H, m), 7.90–8.00 (2H, m).

Reference Example 8

Synthesis of 1-[N-[4-(2-methyl-2-propyloxycarbonyl) piperazine-1-carbonyl]amino]cyclohexanecarboxylic acid

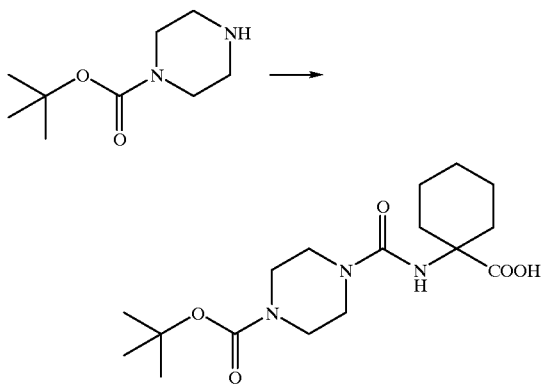

The same reaction procedure used in the reference of Tetrahedron Letters. Vol 35 839–842, 1994 was made. 15.78 g (84.7 mmol) of 1-(t-butoxycarbonylamino)piperazine, 6.85 ml (84.7 mmol) of pyridine and 15.1 ml (84.7 mmol) of diisopropylethylarine were dissolved in 200 ml of anhydrous toluene and then carbonic acid gas was intromitted for 1 hour under −10° C. The reaction solution was added to 80 ml of toluene solution of 10.6 ml (84.7 mmol) of thionylchloride being cooled under −10° C. and stirred for 1 hour. The reaction solution was added to 0.1 N hydrochloric acid and the toluene layer was separated out. The reaction mixture was dried over anhydride sodium sulfate and concentrated under reduced pressure. These crystals thus obtained were washed with hexane, whereby 13.7 g of 4-(2-methyl-2-propyloxycarbonyl)piperazine-1-carbonylchloride was obtained.

Subsequently, 6.39 g (25.71 mmol) of 4-(t-butoxycarboxylicamino)piperazinecarbonylchloride synthesized in the above, 5 g (21.43 mmol) of benzyl aminocyclohexanecarboxylate and 3.58 ml (25.71 mol) of triethylamine were dissolved in 100 ml of anhydrous teterahydrofuran and stirred for 18 hours under 50° C. After concentrating the reaction solution, the residue was dissolved in 1N hydrochloride-ethyl acetate solution and then the ethyl acetate layer was separated out. After completion of drying over anhydride sodium sulfate, the reaction mixture was concentrated under reduced pressure. The residue thus obtained was separated out by the column chromatography, whereby 7 g of phenylmethyl 1-[N-[4-(2-methyl-2-propyloxycarbonyl)piperazine-1-carbonyl]amino] cyclohexanecarboxylate was obtained.

Further, 4.3 g (9.65 mmol) of the above phenylmethyl 1-[N-[4-(2-methyl-2-propyloxycarbonyl)piperazine-1-carbonyl]amino]cyclohexanecarboxylate was dissolved in 200 ml of ethanol and 400 mg of 10% palladium carbon was suspended thereinto and under air current of hydrogen stirred for 15 hours. The insoluble components were removed from the reaction mixture by filtration. The filtrate was concentrated under reduced pressure, whereby 3.25 g of the captioned 1-[N-[4-(2-methyl-2-propyloxycarbonyl) piperazine-1-carbonyl]amino]cyclohexanecarboxylic acid was obtained in a yield of 45%.

1H-NMR (CD$_3$OD, δ): 1.30–1.40 (1H, m), 1.46 (9H, s), 1.50–1.70 (6H, m), 1.75–1.90 (2H, m), 2.00–2.10 (2H, m), 3.3–3.5 (8H, m).

Reference Example 9

Synthesis of 1-[N-[4-(methoxycarbonyl)piperazine-1-carbonyl]amino]cyclohexanecarboxylic acid

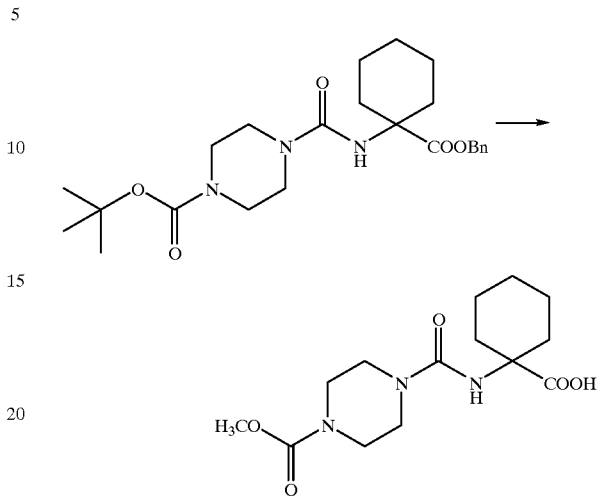

2.5 g (5.6 mmol) of phenylmethyl 1-[N-[4-(2-methyl-2-propyloxycarbonyl) piperazine-1-carbonyl]amino] cyclohexanecarboxylate synthesized in Reference Example 8 was dissolved in ethyl acetate and 14 ml (56 mmol) of 4N hydrogenchloride-ethyl acetate solution (56 mmol) was added to the above prepared mixture under 0° C. and stirred for 3 hours at the room temperature. After completion of concentration of the reaction solution, the reaction solution was dissolved in 1N hydrochloric acid and washed with ethyl acetate. The water layer was separated out and was made into pH 9 with the addition of sodium carbonate and extracted three times with chloroform. The chloroform layer was dried over anhydrous sodium sulfate and concentrated under reduced pressure, whereby 1.7 g of phenylmethyl 1-[N-(piperazine-1-carbonyl)amino] cyclohexanecarboxylate was obtained.

Subsequently, 0.98 ml (2.83 mmol) of the phenylmethyl 1-[N-(piperazine-1-carbonyl)amino] cyclohexanecarboxylate and 0.39 ml (2.83 mmol) of triethylamine were dissolved in 20 ml of anhydrous methylenechloride and then 0.21 ml (2.83 mmol) of chloromethylcarbonate was added to the above prepared mixture and stirred for 12 hours at the room temperature. The reaction solution was successively washed with 1N hydrochloric acid, saturated sodium hydrogen-carbonate solution and saturated brine, and dried over anhydrous sodium sulfate and concentrated under reduced pressure, whereby 1.12 g of phenylmethyl 1-[N-[4-(methoxycarbonyl)piperazine-1-carbonyl]amino] cyclohexanecarboxylate was obtained.

Further, the same reaction procedure as in Example 8 was repeated by using 1.12 g (2.77 mmol) of the phenylmethyl 1-[N-[4-(methoxycarbonyl)piperazine-1-carbonyl]amino9 cyclohexanecarboxylate, whereby 0.8 g of the captioned 1-[N-[4-(methoxycarbonyl)piperazine-1-carbonyl]amino] cyclohexanecarboxylic acid was obtained in a yield of 78%.

1H-NMR (CDCl$_3$, δ): 1.30–1.50 (3H, m), 1.60–1.70 (3H, m), 1.80–1.90 (2H, m), 2.00–2.10 (2H, m), 3.40–3.50 (4H, m), 3.50–3.60 (4H, m), 3.75 (3H, s), 5.15 (2H, s).

Reference Example 10

Synthesis of 1-[N-(4-acetylpiperazine-1-carbonyl)amino]cyclohexanecarboxylic acid

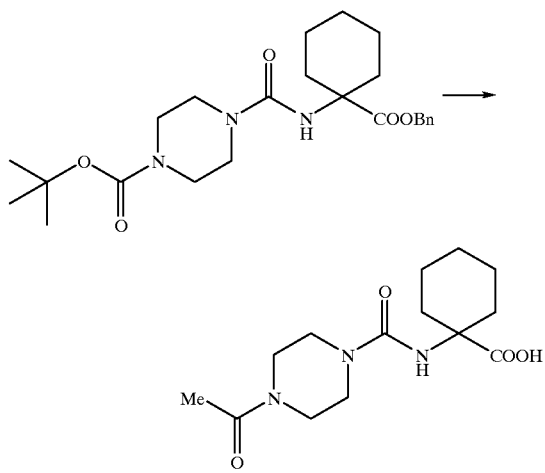

The same reaction procedure as in Reference Example 9 was repeated except that chlorocarbonic acid methyl used in Reference Example 9 was replaced by 1.32 g of acetic anhydride, whereby 2.3 g of the captioned 1-[N-(4-acetylpiperazine-1-carbonyl)amino]cyclohexanecarboxylic acid was obtained in a yield of 59%.

1H-NMR (CD$_3$SOCD$_3$, δ): 1.10–1.20 (1H, m), 1.40–1.70 (7H, m), 1.90–2.10 (5H, m), 3.20–3.50 (8H, m), 6.37 (1H, s).

Reference Example 11

Synthesis of (2RS,3S)-N-(2-methyl-2-propyl)-3-amino-2-hydroxy heptanamide

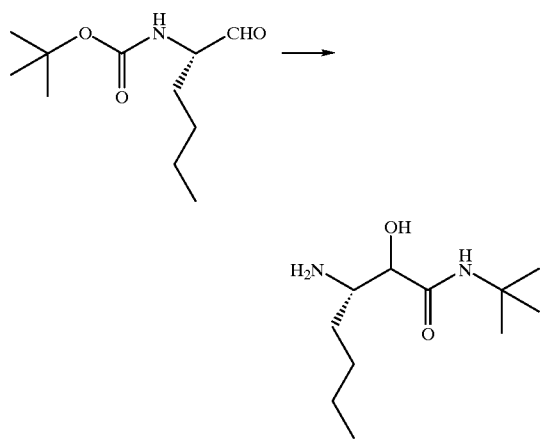

40 g (200 mmol) of (S)-2-[N-(2-methyl-2-propyloxycarbonyl)amino]hexanol was dissolved in 300 ml of anhydrous methylenechroride, 34 g (400 mmol) of acetone cyanhydrin and 12.1 g (120 mmol) of triethylamine were added to the above-prepared reaction solution, followed by stirring for one night. The reaction solution was concentrated under reduced pressure. The residue thus obtained was washed with 300 ml of ether in addition to distilled water and dried over anhydride sodium sulfate and concentrated under reduced pressure. The residue was separated out by silica gel column chromatography, whereby 38.7 g of (2RS,3S)-2-hydroxy-3-[N-(2-methyl-2-propyloxycarbonyl)amino]heptanenitrile was obtained.

Subsequently, to 260 ml of dioxane solution of 38.7 g (160 mmol) of the (2RS,3S)-2-hydroxy-3-[N-(2-methyl-2-propyloxycarbonyl)amino]heptanenitrile, 133 ml of concentrated hydrochloric acid was added thereto and was stirred under the reflux condition. After 3 hours, the reaction solution was concentrated under reduced pressure. 100 ml of distilled water and 100 ml of dioxane were added to the residue. 100 ml of dioxane of 70 g (319 mmol) of di-tert-butyl carboxylate was added dropwise to the above-prepared reaction mixture under 0° C. After completion of dropping, the reaction solution was warmed to the room temperature and then stirred overnight. The reaction solution was concentrated under reduced pressure. The residue thus obtained was washed with ether in addition to distilled water. The organic layer was extracted with aqueous solution of 1N sodium hydroxide and this water layer thus obtained was mixed with the water layer previously obtained. The mixed water layers was adjusted to be acid (pH 2 degree) with the addition of potassium hydrogensulfate and was extracted with ethyl acetate. The organic layer was washed with 50% brine and dried over anhydrous magnesium sulfate and concentrated under reduced pressure, whereby 36.2 g of (2RS,3S)-2-hydroxy- 3-[N-(2-methyl-2-propyloxycarbonyl)amino]heptanecarboxylic acid was obtained.

Further, 1.32 g (5 mmol) of the captioned (2RS,3S)-2-hydroxy-3-[N-(2-methyl-2-propyloxycarbonyl)amino]heptanecarboxylic acid, 0.37 g (5 mmol) of tert-butyl amine and 0.81 g (6 mmol) of 1-hydroxybenzotriazole hydrate were dissolved in 50 mol of anhydrous methylenechloride and then under air current of nitrogen, 1.15 g (6 mmol) of 1-ethyl-3-(3-dimethylaminopropyl)carbodiimide hydrochloride was added under 0° C. Thereafter, the reaction solution was warmed to the room temperature and stirred overnight. The reaction solution was concentrated under reduced pressure. The residue thus obtained was dissolved in 100 ml of ethyl acetate and washed successively with water, 10% aqueous solution of potassium hydrogensulfate, aqueous solution of saturated sodium hydrogen carbonate and saturated brine and then dried over anhydrous magnesium sulfate and concentrated under reduced pressure. The residue was separated out by silica gel column chromatography, whereby 0.74 g of (2RS,3S)-N-(2-methyl-2-propyl)-2-hydroxy-3-[N-(2-methyl-2-propyloxycarbonyl)amino]heptanamide was otained in a yield of 47%.

Furthermore, 0.74 g (2.33 mmol) of the (2RS,3S)-N-2-methyl-2-propyl)-2-hydroxy-3-[N-(2-methyl-2-propyloxycarbonyl)amino]heptanamide was dissolved in 50 ml of 4N hydrogen chloride-ethyle acetate solution and was left alone. After 2 hours, the reaction solution was concentrated under reduced pressure. The residue thus obtained was washed with ether in addition to 100 ml of distilled water thereto. The water layer was adjusted to be pH 9 degree with addition of potassium carbonate and extracted with ethyl acetate. The organic layer was dried over anhydrous magnesium sulfate and concentrated under reduced pressure, whereby 0.27 g of the captioned (2RS,3S)-N-(2-methyl-2-propyl)-3-amino-2-hydroxyheptanamide was obtained in a yield of 15%.

1H-NMR (CDCl$_3$, δ): 0.89–0.92 (3H, m), 1.21–1.44 (4H, m), 1.37 (9H, s), 1.58–1.63 (2H, m), 3.05 (1/2H, s), 3.31–3.34 (1/2H, m), 3.70 (1/2H, d, J=3 Hz), 3.76 (1/2H, d, J=5 Hz), 7.06 (1/2H, s), 7.35 (1/2H, s).

Reference Example 12

Synthesis of (2RS,3S)-N-cyclopentyl-3-amino-2-hydroxyheptanamide

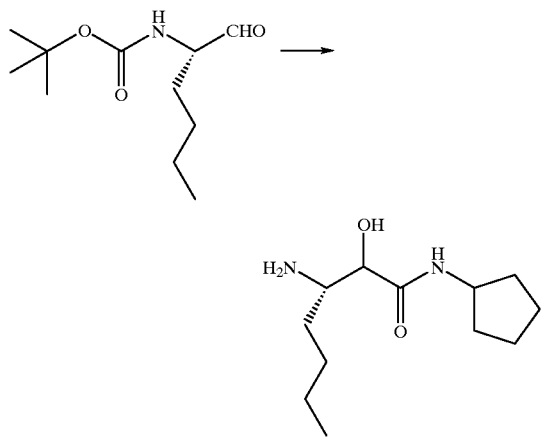

The same reaction procedure as in Reference Example 11 was repeated except that t-butylamine employed in Reference Example 11 was replaced by 2.70 g of the cyclopentylamine, whereby 6.22 g of the captioned (2RS,3S)-N-cyclopentyl-3-amino-2-hydroxyheptanamide was obtained in a yield of 55%.

1H-NMR (CDCl$_3$, δ): 0.90 (3/2H, t, J=7 Hz), 0.91 (3/2H, t, J=7 Hz), 1.22–1.48 (7H, m), 1.53–1.74 (5H, m), 1.92–2.03 (2H, m), 3.04–3.13 (1/2H, m), 3.30–3.35 (1/2H, m), 3.78 (1/2H, d, J=3 Hz), 3.88 (1/2H, d, J=5 Hz), 4.16–4.25 (1H, m), 7.11 (1/2H, d, J=7 Hz), 7.42 (1/2, d, J=7 Hz).

Reference Example 13

Synthesis of (2RS,3S)-N-cyclopentyl-3-amino-2-hydroxy-5-(methylthio) pentanamide

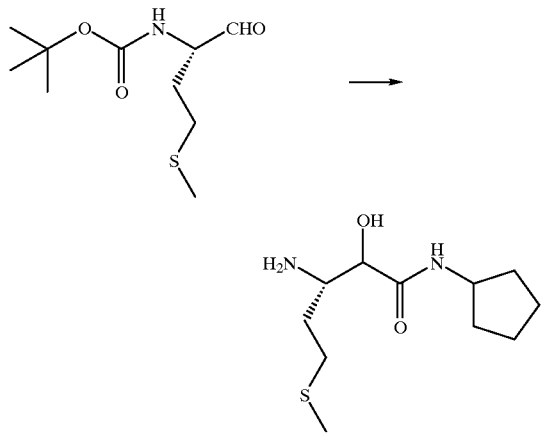

The same reaction procedure as in Reference Example 12 was repeated except that (S)-2-[N-(2-methyl-2-propyloxycarbonyl)amino]hexanol used in Reference Example 12 was replaced by 7.53 g of (S)-2-[N-(2-methyl-2-propyloxycarbonyl) amino]-4-(methylthio)butanol, whereby 3.22 g of the captioned (2RS,3S)-N-cyclopentyl-3-amino-2-hydroxy-5-(methylthio)pentanamide was obtained in a yield of 42%.

1H-NMR (CDCl$_3$, δ): 1.34–1.47 (2H, m), 1.54–1.75 (5H, m), 1.91–2.05 (3H, m), 2.10 (3/2H, s), 2.11 (3/2H, s), 2.52–2.69 (2H, m), 3.13–3.20 (1/2H, m), 3.40–3.46 (1/2H, m), 3.81 (1/2H, d, J=3 Hz), 3.83 (1/2H, d, J=5 Hz), 4.16–4.26 (1H, m), 7.09 (1/2H, d, J=7 Hz), 7.43 (1/2H, d, J=7 Hz).

Reference Example 14

Synthesis of (2RS,3S)-N-cyclopentyl-3-amino-2-hydroxybutanamide

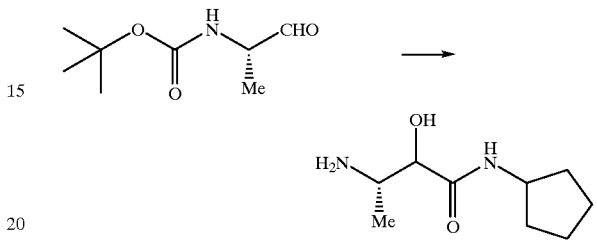

The same reaction procedure as in Reference Example 12 was repeated except that (S)-2-[N-(2-methyl-2-propyloxycarbonyl)amino]hexanol used in Reference Example 12 was replaced by 14.33 g of (S)-2-[N-(2-methyl-2-propyloxycarbonyl) amino]propanol, whereby 6.95 g of the captioned (2RS,3S)-N-cyclopentyl-3-amino-2-hydroxybutanamide was obtained in a yield of 45%.

1H-NMR (CDCl$_3$, δ): 1.05 (3/2H, d, J=7 Hz), 1.15 (3/2H, d, J=7 Hz), 1.35–1.50 (2H, m), 1.55–1.76 (4H, m), 1.90–2.10 (2H, m), 3.31–3.41 (1/2H, m), 3.48–3.52 (1/2H, m), 3.74 (1/2H, d, J=3 Hz), 3.87 (1/2H, d, J=5 Hz), 4.13–4.29 (1H, m), 7.18 (1/2H, d, J=8 Hz), 7.25 (1/2H, d, J=8 Hz).

Reference Example 15

Synthesis of (2RS,3S)-N-cyclopentyl-3-amino-2-hydoxy-4-methylpentanamide

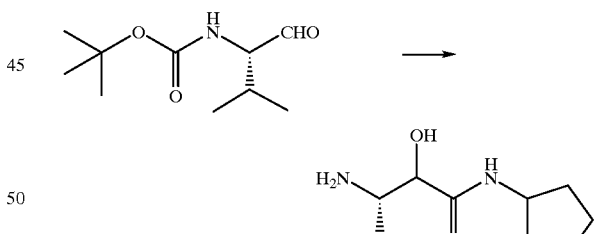

The same reaction procedure as in Reference Example 11 was repeated except that (S)-2-[N-(2-methyl-2-propyloxycarbonyl)amino]hexanal used in Reference Example 11 was replaced by 20.13 g of (S)-2-[N-(2-methyl-2-propyloxycarbonyl) amino]-4-methylbutanal, whereby 4.71 g of the captioned (2RS,3S)-N-cyclopentyl-3-amino-2-hydoxy-4-methylpentanamide was obtained in a yield of 22%. 1H-NMR (CDCl$_3$, δ): 0.87 (3H, d, J=7 Hz), 0.94 (3H, d, J=7 Hz), 1.30–2.10 (7H, m), 2.12–2.28 (1/2H, m), 2.60–2.67 (1/2H, m), 3.09 (1H, dd, J=7 Hz, 2 Hz), 3.70 (1/2H, d, J=8 Hz), 3.91 (1H, d, J=2 Hz), 4.15–4.28 (3/2H, m), 6.87 (1/2H, br-s), 8.37 (1/2H, br-s).

Reference Example 16

Synthesis of (2RS,3S)-3-amino-2-hydroxyheptanamide

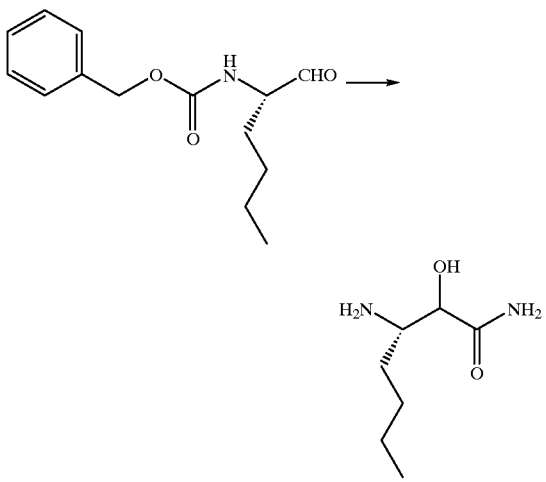

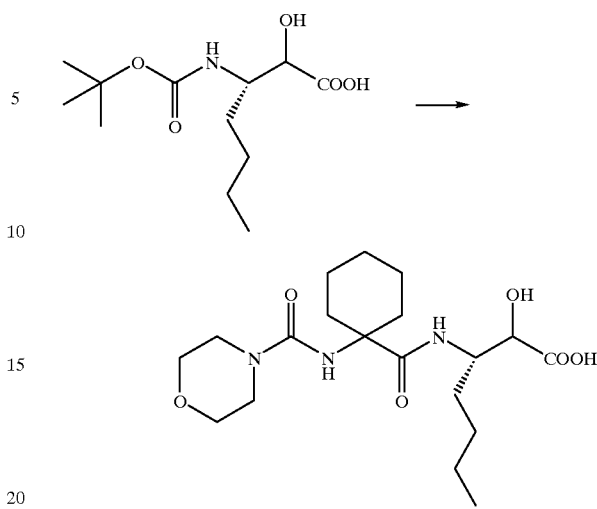

The same reaction procedure as in Reference Example 11 was repeated except that (S)-2-[N-(2-methyl-2-propyloxycarbonyl)amino]hexanal used in Reference Example 11 was replaced by 27.4 g of (S)-2-[N-(2-phenylmethoxycarbonyl)amino]hexanal, whereby 27.7 g of (2RS,3S)-[3-(N-phenylmehoxycarbonyl)amino]-2-hydroxyheptanenitrile was obtained.

Subsequently, 20.1 g (72.9 mmol) of the (2RS,3S)-[3-(N-phenylmethoxycarbony)amino]-2-hydroxyheptanenitrile was dissolved in mixed solvent containing of dimetbylsulfoxide and ethanol and then 73.6 ml of aqueous solution of 1N-sodium hydroxide and 15 ml of aqueous solution of 30% hydrogen peroxide were successively added dropwise under an ice-cooled condition and stirred for one hour. The reaction solution was put away to ethyl acetate and washed successively with 1N hyrochloric acid, saturated sodium haydrogen carbonate and saturated brine, and then was dried over anhydrous sodium sulfate and the residue was distilled away under reduced pressure. Thus obtained crystals were washed with mixed solvent containing ether-hexane, whereby 17.57 g of (2RS,3S)-[3-(N-phenylmethoxycarbonyl)amino]-2-hydroxyheptanamide was obtained.

Further, 17.6 g (59.7 mmol) of the (2RS,3S)-[3-(N-phenylmethoxycarbonyl)amino]-2-hydroxyheptanamide was dissolved in methanol and was stirred at 40° C. for two days under air current of hydrogen with addition of 1.7 g of 10% palladium-activated carbon. 10% palladium-activated carbon was removed by the sellite filteration and the filtrate was concentrated under reduced pressure, whereby 7.82 g of the captioned (2RS,3S)-3-amino-2-hydroxyheptanamide was obtained in a yield of 67%.

1H-NMR (CDCl$_3$, δ): 0.91 (3H, t, J=5 Hz), 1.10–1.82 (6H, m), 2.96–3.08 (1H, m), 3.87 (1H, d, J=6 Hz), 5.62 (1H, br-s), 7.50 (1H, br-s).

Reference Example 17

Synthesis of (2RS,3S)-2-hydroxy-3-[N-[1-[N-(morpholine-4-carbonyl)amino]cyclohexanecarbonyl]amino]heptanoic acid To 13.1 g (50 mmol) of (2RS,3S)-2-hydroxy-3-[N-(2-methyl-2-propyloxycarbonyl)amino]heptanoic acid synthesized in accordance with the method described in Reference Example 11 and 100 ml of suspension of dimethylfomiamide of 6.3 g (75 mmol) of sodium hydrogen carbonate, 20 ml of dimethylformamide solution of 9.4 g (55 mmol) of benzyl bromide was added and stirred at the room temperature for 18 hours. The reaction solution was added with ethyl acetate and washed with water twice and washed with saturated brine once. The resultant organic extracted layer was dried over anhyrous sodium sulfate and then the solvent was distilled away under reduced pressure, whereby the crude product of phenylmethyl (2RS,3S)-2-hydroxy-3-[N-(2-methyl-2-propyloxycarbonyl) amino]heptanoate was obtained. To the obtained phenylmethyl (2RS,3S)-2-hydroxy-3-[N-(2-methyl-2-propyloxycarbonyl)amino] heptanoate, 100 ml of 4N hydrogen chloride-ethyl acetate were added and was left alone at room temperature for one hour and thereafter the reaction solution was concentrated under reduced pressure. The residue was dissolved in water and washed with diethyl ether twice and the water layer was made basic with addition of sodium carbonate and was extracted with ethyl acetate three times. The organic layer was washed with saturated brine and dried over anhydrous sodium sulfate and, the solvent was distilled away from the reaction mixture under reduced pressure, whereby 9.3 g of phenylmethyl (2RS,3S)-3-amino-2-hydroxyheptanoate was obtained.

Subsequently, under ice-cooled condition, to 9.3 g (37 mmol) of phenylmethyl (2RS,3S)-3-amino-2-hydroxyheptanoate, 9.5 g (37 mmol) of 1-[N-(morpholine-4-carbonyl)amino]cyclohexanecarboxylic acid synthesized in Reference Example 5 and 6.0 g (45 mmol) of 1-hydroxybenzotriazole in 100 ml of dichloromethane, 8.5 g (45 mmol) of 1-ethyl-3-(3-dimethylaminopropyl) carbodiimide hydrochloride was added and then was stirred at the room temperature for 18 hours. The reaction solution was concentrated under reduced pressure. The residue was washed successively with water, aqueous solution of 10% of potassium hydrogensulfate, aqueous solution of saturated sodium hydrogen-carbonate and saturated brine in addition of ethyl acetate. The organic layer was dried over anhydrous sodium sulfate and the solvent was distilled away from the reaction mixture under reduced pressure. The residue was purified by the silicagel column chromatography, whereby 16.8 g of phenylmethyl (2RS,3S)-2-hydroxy-3-[N-[1-[N-(morpholine- 4-carbonyl)amino]cyclohexanecarbonyl]amino]heptanoate was obtained.

Further, to methanol 100 ml solution of 16.8 g (34 mmol) of the above phenylmethyl (2RS,3S)-2-hydroxy-3-[N-[1-[N-(morpholine-4-carbonyl)amino]cyclohexanecarbonyl]amino]heptanoate, 1.5 g of 10% palladium carbon was added under haydrogen atmosphere and was stirred at the room temperature for two hours. After insoluble components of the reaction solution were removed by filtration, the filtrate was concentrated under reduced pressure, whereby 13.6 g of the captioned (2RS,3S)-2-hydroxy-3-[N-[1-[N-(morpholine-4-carbonyl)amino]cyclohexanecarbonyl]amino]heptanoic acid was obtained in a yield of 68%.

1H-NMR (CDCl$_3$, δ): 0.90 (3H, t, J=7 Hz), 1.16–1.43 (8H, m), 1.51–2.19 (8H, m), 3.33–3.45 (4H, m), 3.64–3.74 (4H, m), 4.11–4.29 (1H, m), 4.30–4.40 (1H, m), 4.88 (1/2H, br-s), 5.07 (1/2H, br-s), 6.65 (1/2H, d, J=7 Hz), 7.31 (1/2H, d, J=7 Hz).

Reference Example 18

Synthesis of methyl (2RS,3S)-3-amino-2-hydroxyheptanoate

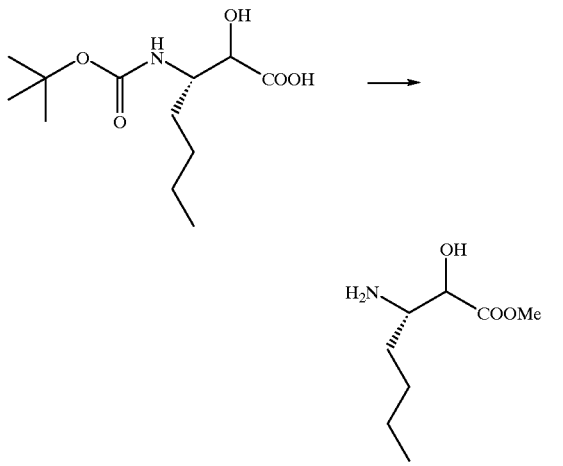

The same reaction procedure for synthesizing of phenylmethyl (2RS,3S)-3-amino-2-hydroxyheptanoate as in Reference Example 17 was repeated except that benzyl bromide used in Reference Example 17 was replaced by 579 mg of methyl iodide, whereby 683 mg of the captioned methyl (2RS,3S)-3-amino-2-hydroxyheptanoate was obtained in a yield of 91%.

1H-NMR (CDCl$_3$, δ): 0.85–0.96 (3H, m), 1.24–1.50 (6H, m), 3.01–3.09 (1H, m), 3.80 (3/2H, s), 3.81 (3/2H, s), 4.09 (1/2H, d, J=2 Hz), 4.17 (1/2H, d, J=4 Hz).

Reference Example 19

Synthesis of 1-[N-(phenylsulfonyl)amino]cyclohexanecarboxylic acid

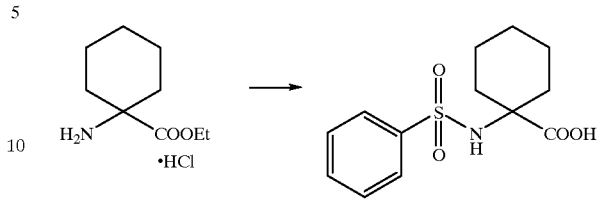

The same reaction procedure as in Reference Example 5 was repeated except that 4-morpholinecarbonyl chloride used in Reference Example 5 was replaced by 3.52 g of benzenesulfonyl chloride, whereby 3.04 g of the captioned 1-[N-(phenylsulfonyl)amino]cyclohexanecarboxylic acid was obtained in a yield of 54%.

1H-NMR (CDCl$_3$, δ): 1.09–1.49 (6H, m), 1.81–1.96 (4H, m), 4.97 (1H, s), 7.46–7.61 (3H, m), 7.90 (2H, dd, J=8 Hz, 2 Hz).

Example 1

Synthesis of N-[(S)-1,2-dioxo-1-N-(2-methyl-2-propyl)amino-3-heptyl]-1-[N-(morpholine-4-carbonyl)amino]cyclohexanecarboxamide

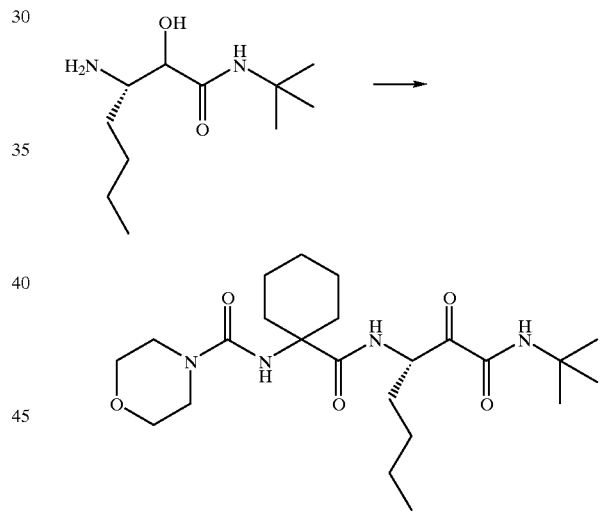

0.26 g (1.26 mmol) of 1-[N-(morpholine-4-carbonyl)amino]cyclohexanecarboxylic acid (1.26 mmol), 0.27 g (1.26 mmol) of (2RS,3S)-N-(2-methyl-2-propyl)-3-amino-2-hydroxyheptanamide and 0.24 g (1.5 mmol) of 1-hydroxybenzotriazole were dissolved in 15 ml of anhydrous methylen chloride and then, under air current of nitrogen, 0.29 g (1.5 mmol) of 1-ethyl-3-(3-dimethylaminopropyl)carbodiimide was added thereto at 0° C. Thereafter, the reaction solution was warmed to the room temperature and stirred overnight. The reaction solution was concentrated under reduced condition. The residue thus obtained was dissolved in 100 ml of ethyl acetate and washed successively with water, aqueous solution of 10% potassium hydrogensulfate, aqueous solution of saturated sodium hydrogencarbonte and saturated brine. After drying over anhydrous magnesium sulfate, the reaction mixture was concentrated under reduced pressure. The residue was separated out with the silicagel column chromatography, whereby 0.35 g of N-[(2RS,3S)-2-hydroxy-1-[N-(2-methyl-2-propyl)amino]-1-oxo-3-heptyl]-1-[N-(morpholine-4-carbonyl)amino]cyclohexanecarboxamide was obtained.

1H-NMR (CDCl₃, δ): 0.86–0.89 (3H, m), 1.24–1.31 (6H, m), 1.35 (9H, s), 1.50–2.11 (10H, m), 3.31–3.41 (4H, m), 3.69–3.71 (4H, m), 3.92–3.99 (1H, m), 4.09–4.16 (1H, m), 4.67 (1/2H, s), 4.79 (1/2H, s), 5.12 (1/2H, d, J=6 Hz), 5.27 (1/2H, s), 6.67 (1/2H, s), 6.82 (1H, s), 7.16 (1/2H, d, J=7 Hz).

Subsequently, to 0.35 g (0.78 mmol) of N-[(2RS,3S)-2-hydroxy-1-[N-( 2-methyl-2-propyl)amino]-1-oxo-3-heptyl]-1-[N-(morpholine-4-carbonyl)amino]cyclohexane carboxamide, 5 ml of anhydrous dimethylsulfoxide, 0.47 g (4.68 mmol) of triethylamine and 5 ml of anhydrous methylene chloride were added and then, under nitrogen air current, 3 ml of anhydrous dimethylsulfoxide (3 ml) solution of 0.75 g (4.6 mmol) of pyridine sulfurtrioxide complex salt was added dropwise thereto at 0° C. After completion of dropping, the reaction solution was warmed to the room temperature and stirred. 2 hours later, the reaction solution was extracted with ethyl acetate with addition of iced-water. The organic layer was washed successively with aqueous solution of 10% citric acid, aqueous solution of saturated sodium hydrogen carbonate and saturated brine and dried over anhydrous sodium sulfate and then was concentrated under reduced pressure. The residue thus obtained was stirred with addition of ether. 3 hours later, the crystals were separated from the reaction mixture by filtration, whereby 0.17 g of the captioned N-[(S)-1,2-dioxo-1-N-(2-methyl-2-propyl)amino-3-heptyl]-1-[N-(morpholine-4-carbonyl)amino]cyclohexanecarboxamide was obtained in a yield of 29%.

1H-NMR (CDCl₃, δ): 0.88 (3H, t, J=7 Hz), 1.26–1.42 (15H, m), 1.61–1.65 (5H, m), 1.86–2.13 (5H, m), 3.39 (4H, t, J=5 Hz), 3.72 (4H, t, J=5 Hz), 4.45 (1H, s), 5.18 (1H, ddd, J=4 Hz, 7 Hz, 9 Hz), 6.73 (1H, s), 7.88 (1H, d, J=7 Hz)

IR (ν, KBr, cm⁻¹): 3328, 2931, 1662, 1641, 1517.

Rf values: An analysis of the thin-layer chromatography was made under the condition mentioned below: Further, Rf value described in the following Examples was measured under the same condition.

Used TLC plates: HPTLC plates RP-18F254s of Merck Company.

Used Developing Solvent: Acetonitrile:Water=7:3

Rf: 0.52

Example 2

Synthesis of N-[(S)-1-(N-cyclopentylamino)-1,2-dioxo-3-heptyl]-1-[N-(morpholine-4-carbonyl)amino]cyclohexanecarboxamide

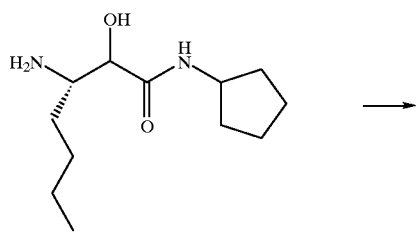

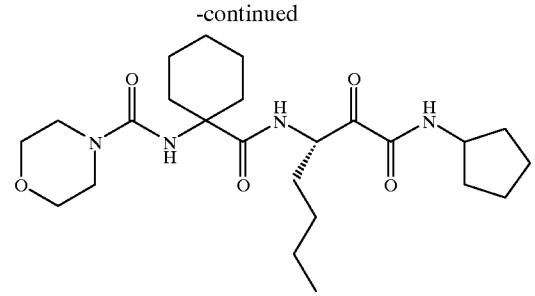

The same procedure as in Example 1 was repeated except that (2RS,3S)-N-(2-methyl-2-propyl)-3-amino-2-hydroxyheptanamide used in Example 1 was replaced by 0.45 g of (2RS,3S)-N-cyclopentyl-3-amino-2-hyroxyheptanamide synthesized in Reference Example 12, whereby 0.54 g of the captioned N-[(S)-1-(N-cyclopentylamino)-1,2-dioxo-3-heptyl]-1-[N-(morpholine-4-carbonyl)amino]cyclohexanecarboxamide was obtained in a yield of 58%.

1H-NMR (CDCl₃, δ): 0.88 (3H, t, J=7 Hz), 1.20–1.55 (9H, m), 1.55–1.80 (8H, m), 1.80–2.08 (5H, m), 2.08–2.18 (2H, m), 3.39 (4H, t, J=5 Hz), 3.72 (4H, t, J=5 Hz), 4.10–4.21 (1H, m), 4.46 (1H, s), 5.15–5.25 (1H, m), 6.81 (1H, d, J=7 Hz), 7.92 (1H, d, J=7 Hz)

IR (ν, KBr, cm⁻¹): 3340, 2864, 1840, 1812, 1364

Rf: 0.56.

Example 3

Synthesis of N-[(S)-1-(N-cyclopentylamino)-1,2-dioxo-3-heptyl]-1-[N-(phenylmethoxycarbonylamino)amino]cyclohexanecarboxamide

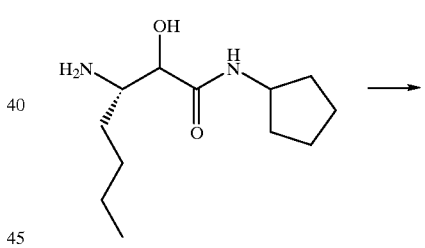

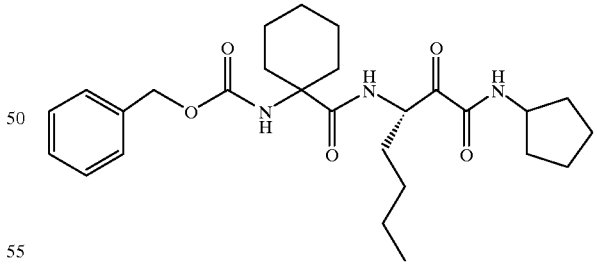

The same procedure as in Reference Example 2 was repeated except that 1-[N-(morphline-4-carbonyl)amino]cyclohexanecarboxylic acid used in Reference Example 2 was replaced by 555 mg of 1-[N-(phenylmethoxycarbonyl)amino]cyclohexanecarboxylic acid, whereby 721 mg of the captioned N-[(S)-1-(N-cyclopentylamino)-1,2-dioxo-3-heptyl]-1-[N-(phenylmethoxycarbonylamino)amino]cyclohexanecarboxamide was obtained in a yield of 74%.

1H-NMR (CDCl₃, δ): 0.87 (3H, t, J=7 Hz), 1.22–1.51 (9H, m), 1.52–1.76 (9H, m), 1.82–2.10 (6H, m), 4.10–4.22

(1H, m), 4.92 (1H, s), 5.11 (2H, s), 5.16–5.24 (1H, m), 6.79 (1H, br-s), 7.23–7.42 (6H, m)

IR (ν, KBr, cm$^{-1}$): 3344, 1648

Rf: 0.26.

Example 4

Synthesis of N-[(S)-1-(N-cyclopentylamino)-1,2-dioxo-3-heptyl]-1-[N-(3,4-methylenedioxyphenylcarbonyl)amino] cyclohexanecarboxamide

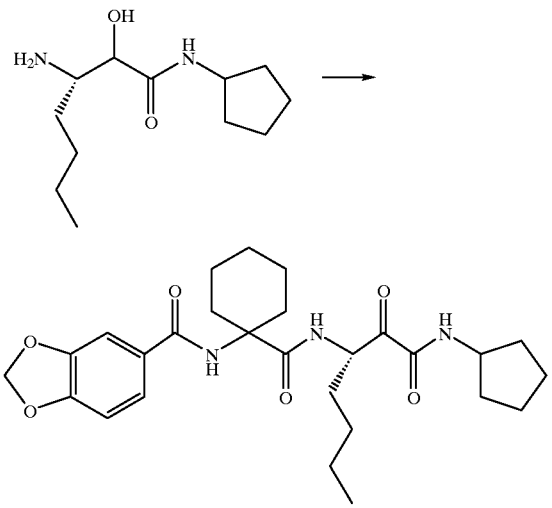

The same reaction procedure as in Example 2 was repeated except that the 1-[N-(morpholine-4-carbonyl) amino]cyclohexanecarboxylic acid used in Example 2 was replaced by 583 mg of 1-[N-(3,4-methylenedioxyphenylcarbonyl)amino]cyclohexane carboxylic acid shown in Reference Example 4, whereby 489 mg of the captioned N-[(S)-1-(N-cyclopentylamino)-1,2-dioxo-3-heptyl]-1-[N-(3,4-methylenedioxyphenylcarbonyl) amino]cyclohexanecarboxamide was obtained in a yield of 49%.

1H-NMR (CDCl$_3$, δ): 0.87 (3H, t, J=7 Hz), 1.23–1.54 (9H, m), 1.56–1.74 (9H, m), 1.92–2.05 (4H, m), 2.21–2.30 (2H, m), 4.08–4.17 (1H, m), 5.18–5.24 (1H, m), 5.95 (1H, s), 6.04 (2H, s), 6.79 (1H, d, J=8 Hz), 6.85 (1H, d, J=8 Hz), 7.26 (1H, d, J=2 Hz), 7.31 (1H, dd, J=8 Hz, 2 Hz), 7.82 (1H, d, J=7 Hz)

IR (ν, KBr, cm$^{-1}$): 3332, 1652

Rf: 0.38.

Example 5

Synthesis of N-[(S)-1-(N-cyclopentylamino)-1,2-dioxo-3-heptyl]-1-[N-[(4-methoxycarbonyl)piperazine-1-carbonyl]amino]cyclohexanecarboxamide

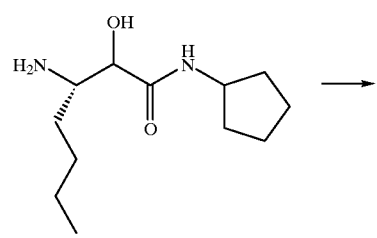

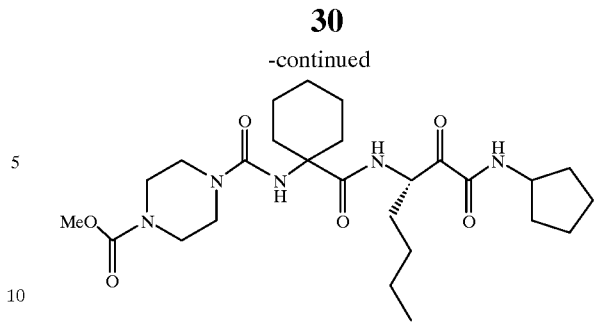

The same reaction procedure as in Example 1 was repeated except that the 1-[N-(morpholine-4-carbonyl) amino]cyclohexanecarboxylic acid used in Example 1 was replaced by 244 mg of 1-[N-[4-(methoxycarbonyl) piperazine-1-carbonyl]amino]cyclohexanecarboxylic acid synthesized in Reference Example 9, whereby 168 mg of the captioned N-[(S)-1-(N-cyclopentylamino)-1,2-dioxo-3-heptyl]-1-[N-[(4-methoxycarbonyl)piperazine-1-carbonyl] amino]cyclohexanecarboxamide was obtained in a yield of 32%.

1H-NMR (CDCl$_3$, δ): 0.88 (3H, t, J=7 Hz), 1.20–1.52 (8H, m), 1.52–1.80 (10H, m), 1.80–2.10 (6H, m), 3.30–3.45 (4H, m), 3.53 (4H, br-s), 3.73 (3H, s), 4.10–4.20 (1H, m), 4.49 (1H, s), 5.16–5.20 (1H, m), 6.81 (1H, d, J=8 Hz), 7.86 (1H, d, J=7 Hz)

IR (ν, KBr, cm$^{-1}$): 3684, 3300, 1656, 1374

Rf: 0.55.

Example 6

Synthesis of N-[(S)-1-(N-cyclopentylamino)-1,2-dioxo-3-heptyl]-1-[N-[(4-acetyl)piperazine-1-carbonyl]amino] cyclohexanecarboxamide

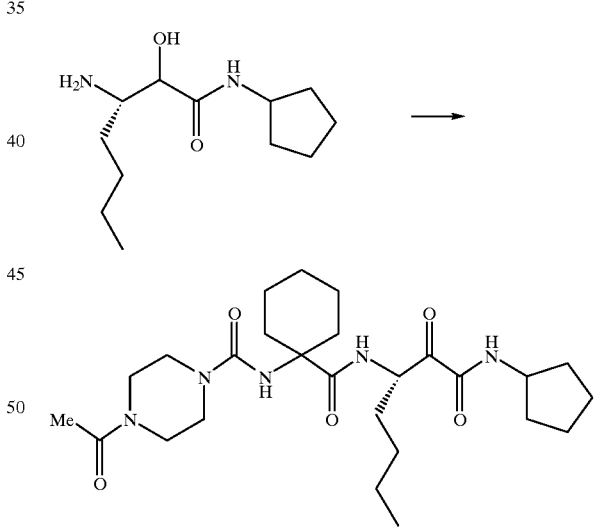

The same reaction procedure as in Example 2 was repeated except that the 1-[N-(morpholine-4-carbonyl) amino]cyclohexanecarboxylic acid used in Example 2 was replaced by 0.32 g of a 1-[N-(4-acetylpiperazine-1-carbonyl)amino]cyclohexanecarboxylic acid synthesized in Reference Example 10, whereby 0.26 g of the captioned N-[(S)-1-(N-cyclopentylamino)-1,2-dioxo-3-heptyl]-1-[N-[(4-acetyl)piperazine-1-carbonyl]amino] cyclohexanecarboxamide was obtained in a yield of 50%.

1H-NMR (CDCl$_3$, δ): 0.87 (3H, t, J=7 Hz), 1.20–2.10 (24H, m), 2.12 (3H, s), 3.35–3.45 (2H, m), 3.45–3.60 (4H, m), 3.62–3.72 (2H, m), 4.10–4.20 (1H, m), 4.50 (1H, s), 5.15–5.21 (1H, m), 6.81 (1H, d, J=7 Hz), 7.78 (1H, d, J=7 Hz)

Rf: 0.63.

Example 7

Synthesis of N-[(S)-1-(N-cyclopentylamino)-1,2-dioxo-5-(methylthio)-3-pentyl]-1-[N-[(4-methoxycarbonyl)piperazine-1-carbonyl]amino]cyclohexanecarboxamide

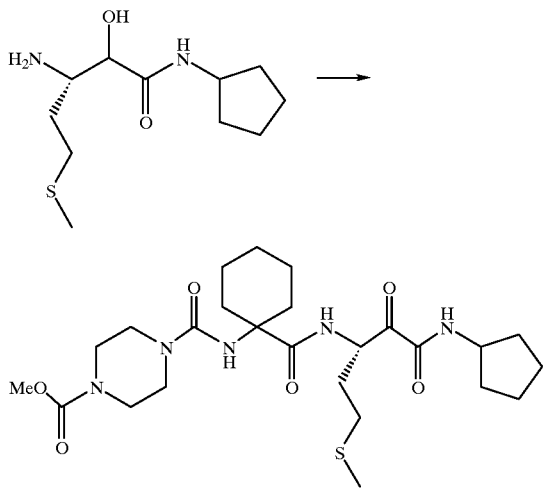

The same reaction procedure as in the Example 5 was repeated except that the (2RS,3S)-N-cyclopentyl-3-amino-2-hydroxyheptanamide used in Example 5 was replaced by 384 mg of the (2RS,3S)-N-cyclopentyl-3-amino-2-hydroxy-5-(methylthio)pentanamide synthesized in Reference Example 13, whereby 166 mg of the captioned N-[(S)-1-(N-cyclopentylamino)-1,2-dioxo-5-(methylthio)-3-pentyl]-1-[N-[(4-methoxycarbonyl)piperazine-1-carbonyl]amino]cyclohexanecarboxamide was obtained in a yield of 21%.

1H-NMR (CDCl$_3$, δ): 1.25–1.50 (6H, m), 1.55–1.78 (6H, m), 1.84–2.18 (7H, m), 2.04 (3H, s), 2.30–2.42 (1H, m), 2.50–2.60 (2H, m), 3.32–3.42 (4H, m), 3.53 (4H, br-s), 3.73 (3H, s), 4.10–4.21 (1H, m), 4.50 (1H, s), 5.20–5.28 (1H, m), 6.80 (1H, d, J=8 Hz), 7.93 (1H, d, J=7 Hz)

IR (ν, KBr, cm$^{-1}$): 3356, 2332, 1870, 1472, 1374

Rf: 0.60.

Example 8

Synthesis of N-[(S)-1-(N-cyclopentylamino)-1,2-dioxo-5-(methylthio)-3-pentyl]-1-[N-(morpholine-4-carbonyl]amino]cyclohexanecarboxamide

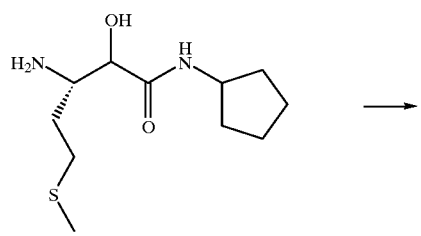

-continued

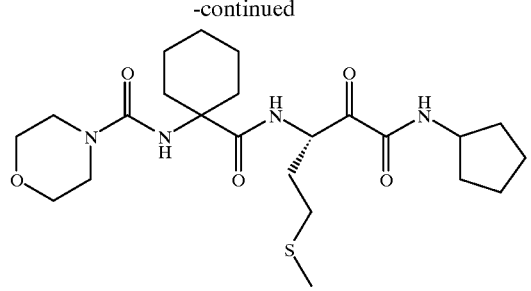

The same reaction procedure as in Example 2 was repeated except that the (2RS,3S)-N-cyclopentyl-3-amino-2-hydroxypentanamide used in Example 2 was replaced by 370 mg of (2RS,3S)-N-cyclopentyl-3-amino-hydorxy-5-(methylthio) pentanamide synthesized in Reference Example 13, whereby 360 mg of the captioned N-[(S)-1-(N-cyclopentylamino)-1,2-dioxo-5-(methylthio)-3-pentyl]-1-[N-(morpholine-4-carbonyl)amino]cyclohexanecarboxamide was obtained in a yield of 50%.

1H-NMR (CDCl$_3$, δ): 1.25–1.55 (6H, m), 1.55–1.82 (6H, m), 1.82–2.20 (7H, m), 2.05 (3H, s), 2.31–2.42 (1H, m), 2.52–2.61 (2H, m), 3.39 (4H, t, J=5 Hz), 3.72 (4H, t, J=5 Hz), 4.10–4.22 (1H, m), 4.52 (1H, s), 5.20–5.28 (1H, m), 6.81 (1H, d, J=8 Hz), 7.97 (1H, d, J=7 Hz)

IR (ν, KBr, cm$^{-1}$): 3728, 2332, 1730, 1338, 1224

Rf: 0.67.

Example 9

Synthesis of N-[(S)-1-(N-cyclopentylamino)-1,2-dioxo-5-methylthio-3-pentyl]-1-[N-(phenylmethoxycarbonyl)amino]cyclohexanecarboxamide

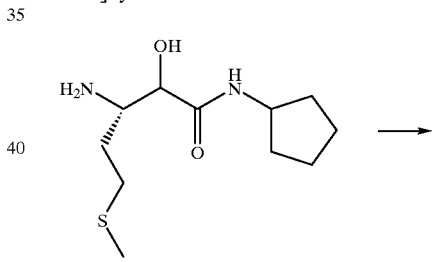

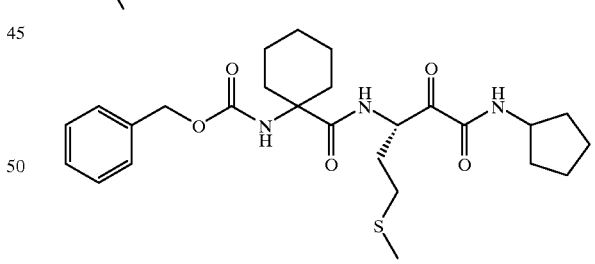

The same reaction procedure as in Example 7 was repeated except that the 1-[N-[4-(methoxycarbonyl)piperazine-1-carbonyl]amino]cyclohexanecarboxylic acid used in Example 7 was replaced by 832 mg of 1-[N-(phenylmethoxycarbonyl)amino]cyclohexanecarboxlic acid synthesized in Reference Example 1, whereby 200 mg of the captioned N-[(S)-1-(N-cyclopentylamino)-1,2-dioxo-5-methylthio-3-pentyl]-1-[N-(phenylmethoxycarbonyl)amino]cyclohexanecarboxamide was obtained in a yield of 29%.

1H-NMR (CDCl$_3$, δ): 1.31–1.48 (5H, m), 1.61–1.72 (7H, m), 1.86–2.10 (10H, m), 2.30–2.41 (1H, m), 2.51 (2H, s), 4.12–4.19 (1H, m), 4.96 (1H,s), 5.11 (2H, s), 5.24 (1H, d, J=5 Hz), 6.78 (1H, d, J=6 Hz), 7.33–7.45 (6H, m)

IR (ν, KBr, cm$^{-1}$): 3326, 1693, 1660, 1517

Rf: 0.36.

Example 10

Synthesis of N-[(S)-1-(N-cyclopentylamino)-1,2-dioxo-5-methylthio-3-pentyl]-1-[N-(3,4-methylenedioxyphenylcarbonyl)amino]cyclohexanecarboxamide

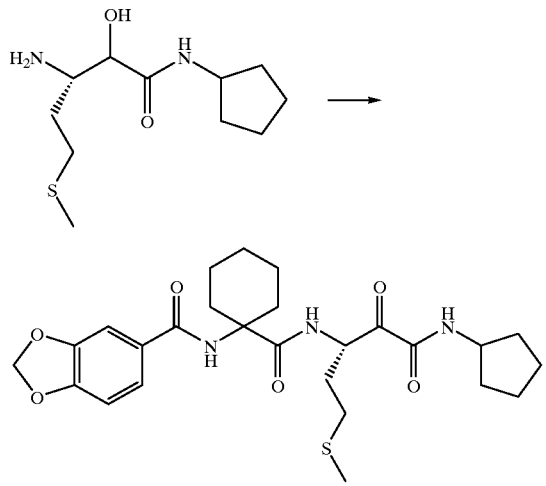

The same reaction procedure as in Example 4 was repeated except that the (2RS,3S)-N-cyclopentyl-3-amino-2-hydroxyheptanamide used in Example 4 was replaced by 246 mg of (2RS,3S)-N-cyclopentyl-3-amino-2-hydroxy-5-(methylthio) pentanamide synthesized in Reference Example 13, whereby 118 mg of the captioned N-[(S)-1-(N-cyclopentylamino)-1,2-dioxo-5-methylthio-3-pentyl]-1-[N-(3,4-methylenedioxyphenylcarbonyl)amino]cyclohexanecarboxamide was obtained in a yield of 23%.

1H-NMR (CDCl$_3$, δ): 1.31–1.76 (12H, m), 1.91–2.17 (5H, m), 2.03 (3H, s), 2.20–2.41 (3H, m), 2.56 (2H, t, J=7 Hz), 4.09–4.19 (1H, m), 5.24–5.31 (1H, m), 5.99 (1H, s), 6.05 (2H, s), 6.79 (1H, d, J=7 Hz), 6.85 (1H, d, J=8 Hz), 7.26 (1H, d, J=2 Hz), 7.31 (1H, dd, J=8 Hz, 2 Hz), 7.90 (1H, d, J=7 Hz)

IR (ν, KBr, cm$^{-1}$): 3320, 1660

Rf: 0.49.

Example 11

Synthesis of N-[(S)-1-[N-(cyclopentyl)amino]-1,2-dioxo-5-methylthio-3-pentyl]-1-[N-(phenyloxycarbonyl)amino]cyclohexanecarboxamide

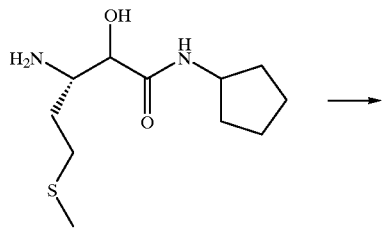

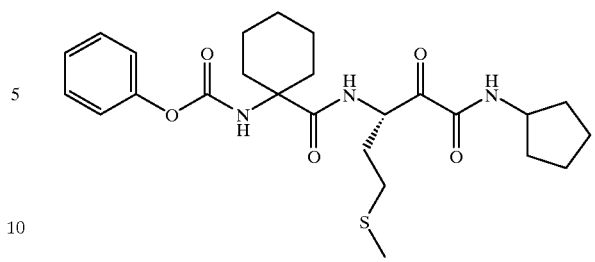

The same reaction procedure as in Example 7 was repeated except that the 1-[N-[4-(methoxycarbonyl)piperazine-1-carbonyl]amino]cyclohexane carboxylic acid used in Example 7 was replaced by 263 mg of 1-[N-(phenyloxycarbonyl)amino]cyclohexanecarboxylic acid synthesized in Reference Example 2, whereby 160 mg of the captioned N-[(S)-1-[N-(cyclopentyl)amino]-1,2-dioxo-5-methylthio-3-pentyl]-1-[N-(phenyloxycarbonyl)amino]cyclohexanecarboxamide was obtained in a yield of 34%.

1H-NMR (CDCl$_3$, δ): 1.34–1.70 (12H, m), 1.89–2.16 (10H, m), 2.35–2.39 (1H, m), 2.53 (2H, t, J=7 Hz), 4.12–4.17 (1H, m), 5.24–5.27 (2H, m), 6.79 (1H, d, J=8 Hz), 7.14–7.22 (3H, m), 7.34–7.38 (2H, m), 7.53 (1H, d, J=6 Hz)

IR (ν, KBr, cm$^{-1}$): 3305, 2937, 1727, 1658, 1530, 1490, 1454, 1251, 1201, 1162

Rf: 0.38.

Example 12

Synthesis of N-[(S)-1-(N-cyclopentylamino)-1,2-dioxo-5-methylthio-3-pentyl]-1-[N-(2-methylpropyloxycarbonyl)amino]cyclohexanecarboxamide

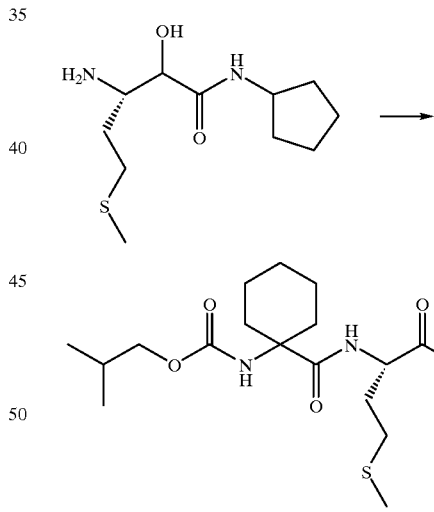

The same reaction procedure as in Example 10 was repeated except that the 1-[N-(3,4-methylenedioxyphenylcarbonyl)amino]cyclohexanecarboxylic acid used in Example 10 was replaced by 243 mg of 1-[N-(2-methylpropyloxycarbonyl)amino]cyclohexanecarboxylic acid synthesized in Reference Example 3, whereby 133 mg of the captioned N-[(S)-1-(N-cyclopentylamino)-1,2-dioxo-5-methylthio-3-pentyl]-1-[N-(2-methylpropyloxycarbonyl)amino]cyclohexanecarboxamide was obtained in a yield of 28%.

1H-NMR (CDCl$_3$, δ): 0.93 (6H, d, J=7 Hz), 1.13–1.51 (5H, m), 1.55–1.76 (7H, m), 1.81–2.17 (8H, m), 2.05 (3H, s), 2.31–2.42 (1H, m), 2.54 (2H, t, J=7 Hz), 3.85 (2H, d, J=7 Hz), 4.12–4.23 (1H, m), 4.85 (1H, s), 5.23–5.30 (1H, m), 6.79 (1H, d, J=7 Hz), 7.52 (1H, br-s)

IR (ν, KBr, cm$^{-1}$): 3344, 1658

Rf: 0.31.

Example 13

Synthesis of N-[(S)-1-(N-cyclopentylamino)-1,2-dioxo-3-butyl]-1-[N-(morpholine-4-carbonyl)amino]cyclohexanecarboxamide

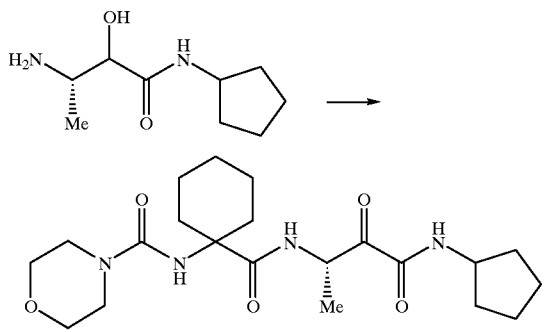

The same reaction procedure as in Example 2 was repeated except that the (2RS,3S)-N-cyclopentyl-3-amino-2-hydroxyheptanamide used in Example 2 was replaced by 373 mg of (2RS,3S)-N-cyclopentyl-3-amino-2-hydroxybutanamide synthesized in Reference Example 14, whereby 163 mg of the captioned N-[(S)-1-(N-cyclopentylamino)-1,2-dioxo-3-butyl]-1-[N-(morpholine-4-carbonyl)amino]cyclohexanecarboxamide was obtained in a yield of 39%.

1H-NMR (CDCl$_3$, δ): 1.14–1.50 (3H, m), 1.44 (3H, d, J=7 Hz), 1.45–1.80 (10H, m), 1.80–2.15 (5H, m), 3.33–3.42 (4H, m), 3.62–3.80 (4H, m), 4.07–4.23 (1H, m), 4.44 (1H, s), 5.16–5.27 (1H, m), 6.81 (1H, d, J=8 Hz), 7.81 (1H, d, J=7 Hz)

IR (ν, KBr, cm$^{-1}$): 3756, 3356, 2364, 1740, 1336

Rf: 0.76.

Example 14

Synthesis of N-[(S)-1-(N-cyclopentylamino)-1,2-dioxo-3-butyl]-1-[N-(3,4-methylenedioxycarbonyl)amino]cyclohexanecarboxamide

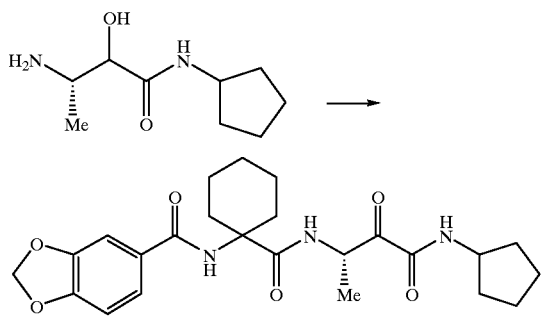

The same reaction procedure as in Example 4 was repeated except that the (2RS,3S)-N-cyclopentyl-3-amino-2-hydroxyheptanamido used in Example 4 was replaced by 373 mg of (2RS,3S)-N-cyclopentyl-3-amino-2-hydroxybutanamide synthesized in Reference Example 14, whereby 97 mg of the captioned N-[(S)-1-(N-cycopentylamino)-1,2-dioxo-3-butyl]-1-[N-(3,4-methylenedioxycarbonyl)amino]cyclohexanecarboxamide was obtained in a yield of 21%.

1H-NMR (CDCl$_3$, δ): 1.24–1.52 (4H, m), 1.45 (3H, d, J=7 Hz), 1.53–1.78 (8H, m), 1.90–2.05 (4H, m), 2.20–2.30 (2H, m), 4.09–4.20 (1H, m), 5.20–5.30 (1H, m), 5.94 (1H, s), 6.05 (2H, s), 6.79 (1H, d, J=8 Hz), 6.85 (1H, d, J=8 Hz), 7.28 (1H, d, J=2 Hz), 7.31 (1H, dd, J=8 Hz, 2 Hz), 7.76 (1H, d, J=7 Hz)

IR (ν, KBr, cm$^{-1}$): 3756, 3076, 2356, 1730, 1358

Rf: 0.60.

Example 15

Synthesis of N-[(S)-1-(N-cyclopentylamino)-1,2-dioxo-4-methyl-3-pentyl]-1-[N-(morpholine-4-carbonyl)amino]cyclohexanecarboxamide

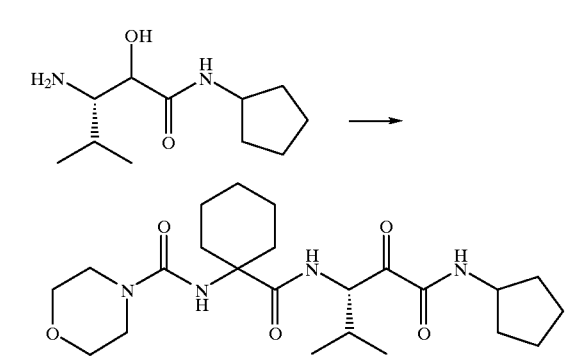

The same reaction procedure as in Example 1 was repeated except that the (2RS,3S)-N-(2-metyl-2-propyl)-3-amino-2-hydroxyheptanamide used in Example 1 was replaced by 268 mg of (2RS,3S)-N-cyclopentyl-3-amino-2-hydroxy-4-methylpentanamide synthesized in Reference Example 15, whereby 253 mg of the captioned N-[(S)-1-(N-cyclopentylamino)-1,2-dioxo-4-methyl-3-pentyl]-1-[N-(morpholine-4-carbonyl)amino]cyclohexanecarboxamide was obtained in a yield of 56%.

1H-NMR (CDCl$_3$, δ): 0.84 (3H, d, J=7 Hz), 1.01 (3H, d, J=7 Hz), 1.28–1.50 (5H, m), 1.55–1.76 (7H, m), 1.86–2.18 (6H, m), 2.35–2.48 (1H, m), 3.39 (4H, t, J=5 Hz), 3.72 (5H, t, J=5 Hz), 4.10–4.22 (1H, m), 4.45 (1H, s), 5.15 (1H, dd, J=8 Hz, 8 Hz), 6.82 (1H, d, J=8 Hz), 8.03 (1H, d, J=8 Hz)

IR (ν, KBr, cm$^{-1}$) 3808, 2860, 1730, 1454, 1394, 1338, 1300

Rf: 0.56.

Example 16

Synthesis of N-[(S)-1-(N-cyclopentylamino)-1,2-dioxo-4-methyl-3-pentyl]-1-[N-(3,4-methylenedioxyphenylcarbonyl)amino]cyclohexanecarboxamide

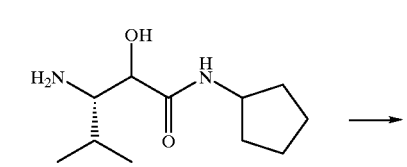

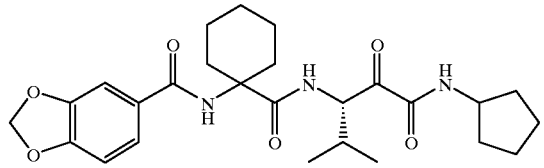

The same reaction procedure as in Example 4 was repeated except that the (2RS,3S)-N-cyclopentyl-3-amino-2-hydroxyheptaneamide used in Example 4 was replaced by 268 mg of (2RS,3S)-N-cyclopentyl-3-amino-2-hydroxy-4-methylpentanamide synthesized by Reference Example 15, whereby 82 mg of the captioned N-[(S)-1-(N-cyclopentylamino)-1,2-dioxo-4-methyl-3-pentyl]-1-[N-(3,4-methylenedioxyphenylcarbonyl)amino]cyclohexanecarboxamide was obtained in a yield of 17%.

1H-NMR (CDCl₃, δ): 0.83 (3H, d, J=7 Hz), 1.01 (3H, d, J=7 Hz), 1.30–1.52 (5H, m), 1.52–1.77 (7H, m), 1.90–2.05 (4H, m), 2.22–2.31 (2H, m), 2.38–2.48 (1H, m), 4.07–4.16 (1H, m), 5.18 (1H, dd, J=8 Hz, 8 Hz), 5.94 (1H, s), 6.05 (2H, s), 6.80 (1H, d, J=8 Hz), 6.86 (1H, d, J=8 Hz), 7.27 (1H, d, J=8 Hz), 7.31 (1H, dd, J=8 Hz, 2 Hz), 7.92 (1H, d, J=8 Hz)

IR (v, KBr, cm⁻¹) 3404, 2872, 2248, 1726, 1608, 1392, 1360

Rf: 0.37.

Example 17

Synthesis of N-[(S)-1-(N-cyclopentylamino)-1,2-dioxo-4-methyl-3-pentyl]-1-[N-[(4-methoxycarbonyl)piperazine-1-carbonyl]amino]cyclohexanecarboxamide

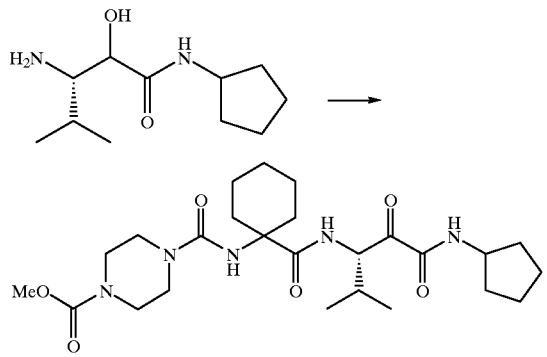

The same reaction procedure as in Example 5 was repeated except that the (2RS,3S)-N-cyclopentyl-3-amino-2-hydroxyheptanamide used in Example 5 was replaced by 268 mg of (2RS,3S)-N-cyclopentyl-3-amino-2-hydroxy-4-methylpentanamide synthesized in Reference Example 15, whereby 279 mg of the captioned N-[(S)-1-(N-cyclopentylamino)-1,2-dioxo-4-methyl-3-pentyl]-1-[N-[(4-methoxycarbonyl)piperazine-1-carbonyl]amino]cyclohexanecarboxamide was obtained in a yield of 55%.

1H-NMR (CDCl₃, δ): 0.83 (3H, d, J=7 Hz), 1.01 (3H, d, J=7 Hz), 1.25–1.48 (5H, m), 1.45–1.76 (7H, m), 1.87–2.20 (6H, m), 2.34–2.45 (1H, m), 3.34–3.47 (4H, m), 3.53 (4H, br-s), 3.73 (3H, s), 4.10–4.20 (1H, m), 4.46 (1H, s), 5.15 (1H, dd, J=8 Hz, 8 Hz), 6.81 (1H, d, J=8 Hz), 7.96 (1H, d, J=8 Hz)

IR (v, KBr, cm⁻¹): 3804, 3420, 2868, 1408, 1374, 1288, 1192

Rf: 0.53.

Example 18

Synthesis of N-[(S)-1-amino-1,2-dioxo-4-methyl-3-heptyl]-1-[N-(morpholine-4-carbonyl)amino]cyclohexanecarboxamide

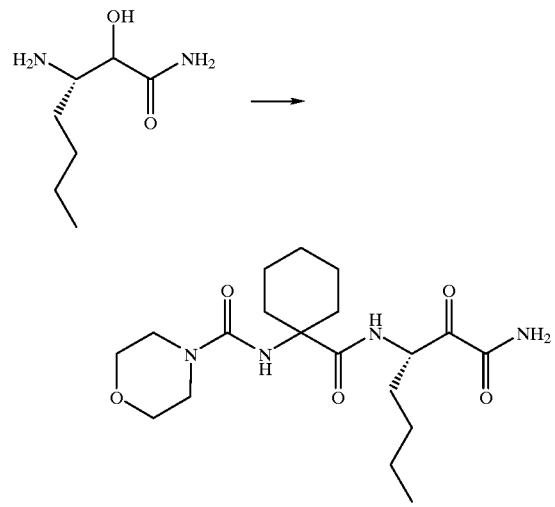

The same reaction procedure as in Example 1 was repeated except that the (2RS,3S)-N-(2-methyl-2-propyl)-3-amino-2-hydroxyheptanamide used in Example 1 was replaced by 0.77 g of (2RS,3S)-3-amino-2-hydroxyheptanamide synthesized in Reference Example 16, whereby 279 mg of N-[(S)-1-amino-1,2-dioxo-4-methyl-3-heptyl]-1-[N-(morpholine-4-carbonyl)amino]cyclohexanecarboxamide was obtained in a yield of 51%.

1H-NMR (CDCl₃, δ): 0.88 (3H, t, J=7 Hz), 1.20–1.45 (7H, m), 1.57–1.80 (4H, m), 1.80–2.00 (3H, m), 2.02–2.18 (2H, m), 3.39 (4H, t, J=5 Hz), 3.72 (4H, t, J=5 Hz), 4.49 (1H, s), 5.10–5.18 (1H, m), 5.54 (1H, s), 6.76 (1H, s), 7.98(1H, d, J=6 Hz)

IR (v, KBr, cm¹): 3356, 2936, 1696, 1670, 1650, 1524, 1258

Rf:0.87.

Example 19

Synthesis of N-[(S)-1-amino-1,2-dioxo-3-heptyl]-1-[N-(phenylmetoxycarbonyl)amino]cyclohexanecarboxamide

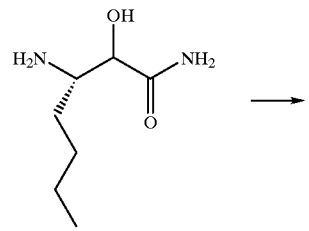

-continued

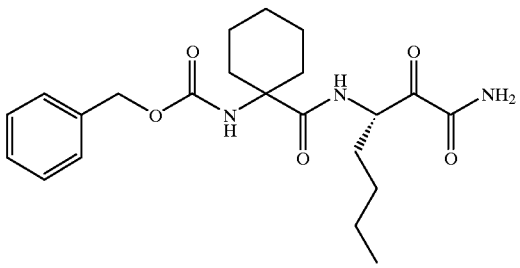

The same reaction procedure as in Example 3 was repeated except that the (2RS,3S)-N-cyclopentyl-3-amino-2-hydroxyheptanamide used in Example 3 was replaced by 0.64 g of (2RS,3S)-3-amino-2-hydroxyheptanamide synthesized in Reference Example 16, whereby 0.7 g of N-[(S N-[(S)-1-amino-1,2-dioxo-3-heptyl]-1-[N-(phenylmetoxycarbonyl)amino]cyclohexanecarboxamide was obtained in a yield of 66%.

1H-NMR (CDCl$_3$, δ): 0.87 (3H, t, J=7 Hz), 1.20–1.50 (7H, m), 1.50–1.70 (4H, m), 1.80–1.98 (3H, m), 1.98–2.12 (2H, m), 4.95 (1H, s), 5.11 (2H, s), 5.11–5.22 (1H, m), 5.45 (1H, s), 6.71 (1H, s), 7.20–7.45 (6H, m)

IR (ν, KBr, cm$^{-1}$): 3448, 3304, 2936, 1722, 1678, 1530, 1248

Rf: 0.57.

Example 20

Synthesis of N-[(S)-1-amino-1,2-dioxo-3-heptyl]-1-[N-(3,4-methylendioxyphenylcarbonyl)amino]cyclohexanecarboxamide

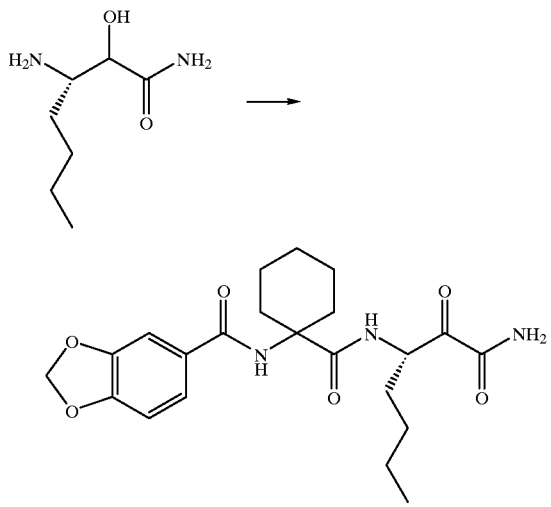

The same reaction procedure as in Example 4 was repeated except that the (2RS,3S)-N-cyclopentyl-3-amino-2-hydroxyheptanamide used in Example 4 was replaced by 0.64 g of (2RS,3S)-3-amino-2-hydroxyheptanamide synthesized in Reference Example 16, whereby 0.7 g of N-[(S)-1-amino-1,2-dioxo-3-heptyl]-1-[N-(3,4-methylendioxyphenylcarbonyl)amino] cyclobexanecarboxamide was obtained in a yield of 45%.

1H-NMR (CDCl$_3$, δ): 0.87 (3H, t, J=7 Hz), 1.20–1.55 (7H, m), 1.60–1.80 (4H, m), 1.85–2.10 (3H, m), 2.18–2.35 (2H, m), 5.12–5.22 (1H, m), 5.42 (1H, s), 5.96 (1H, s), 6.05 (2H, s), 6.72 (1H, s), 6.85 (1H, d, J=8 Hz), 7.27 (1H, s), 7.30 (1H, dd, J=8 Hz, 2 Hz), 7.89 (1H, d, J=6 Hz)

IR (ν, KBr, cm$^{-1}$): 3320, 2936, 1658, 1486, 1260, 1038

Rf: 0.70.

Example 21

Synthesis of N-[(S)-1-amino-1,2-dioxo-3-heptyl]-1-(phenylsulfonylmethyl) cyclohexanecarboxamide

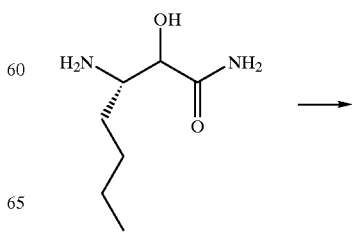

The same reaction procedure as in Example 18 was repeated except that the-1-[N-(3,4-methylendioxyphenylcarbonyl)amino]cyclohexanecarboxylic acid used in Example 18 was replaced by 1.12 g of 1-(phenylsulfonylmethyl) cyclohexanecarboxylic acid synthesized in Reference Example 7, whereby 1.05 g of N-[(S)-1-amino-1,2-dioxo-3-heptyl]-1-(phenylsulfonylmethyl) cyclohexanecarboxamide was obtained in a yield of 62%.

1H-NMR (CDCl$_3$, δ): 0.90 (3H, t, J=7 Hz), 1.20–1.70 (10H, m), 1.70–1.95 (3H, m), 1.95–2.10 (3H, m), 3.47 (2H, s), 5.15–5.25 (1H, m), 5.60 (1H, s), 6.80 (1H, s), 6.82 (1H, d, J=7 Hz), 7.53 (2H, t, J=8 Hz), 7.62 (1H, t, J=7 Hz), 7.89 (2H, d, J=7 Hz)

IR (ν, KBr, cm$^{-1}$): 3352, 2936, 1698, 1520, 1308, 1150, 600

Rf: 0.64.

Example 22

Synthesis of N-[(S)-1-amino-1,2-dioxo-3-heptyl]-1-[N-[(2-methyl-2-propyloxycarbonyl)piperidine-4-carbonyl]amino]cyclohexanecarboxamide -continued

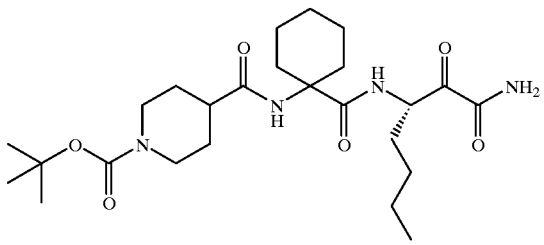

The same reaction procedure as in Example 1 was repeated except that the 1-[N-(morpholine-4-carbonyl) amino]cyclohexanecarboxylic acid used in Example 1 was replaced by 1.06 g of 1-[N-[1-[(2-methyl-2-propyloxycarbonyl)piperidine-4-carbonyl]amino] cyclohexanecarboxylic acid, and (2RS,3S)-N-(2-methyl-2-propyl)-3-amino-2-hydroxyheptanamide used in Example 1 was replaced by 0.48 g of (2RS, 3S)-3-amino-2-hydroxyheptanamide synthesized in Reference Example 16, whereby 0.73 g of N-[(S)-1-amino-1,2-dioxo-3-heptyl]-1-[N-[(2-methyl-2-propyloxycarbonyl)piperidine-4-carbonyl] amino]cyclobexanecarboxamide was obtained in a yield of 49%.

1H-NMR (CDCl$_3$, δ): 0.88 (3H, t, J=7 Hz), 1.20–1.50 (6H, m), 1.46 (9H, 1.60–1.80 (7H, m), 1.80–2.00 (5H, m), 2.10–2.20 (2H, m), 2.30 (1H, tt, J=11, 3 Hz), 2.70–2.90 (2H, m), 4.10–4.30 (2H, m), 5.10–5.20 (1H, m), 5.43 (1H, s), 5.47 (1H, br-s), 6.73 (1H, br-s), 7.77 (1H, d, J=5 Hz)

IR (ν, KBr, cm$^{-1}$): 3448, 3316, 2940, 2860, 1670, 1528, 1172

Rf: 0.62.

Example 23

Synthesis of N-[(S)-1-amino-1,2-dioxo-3-heptyl]-1-[N-[4-(2-methyl-2-propyloxycarbonyl)piperadine-1-carbonyl] amino]cyclohexanecarboxamide

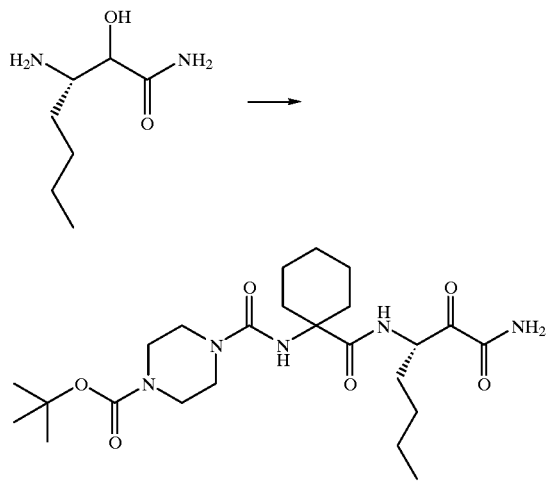

The same reaction procedure as in Example 1 was repeated except that the 1-[N-(morpholine-4-carbonyl) amino]cyclohexanecarboxylic acid used in Example 1 was replaced by 1.06 g of 1-[N-[4-(2-methy-2-propyloxycarbonyl)piperadine-4-carbonyl]amino] cyclohexanecarboxylic acid, and (2RS,3S)-N-(2-methyl-2-propyl)-3-amino-2-hydroxyheptanamide used in Example 1 was replaced by 0.43 g of (2RS, 3S)-3-amino-2-hydroxyheptanamide synthesized in Reference Example 16, whereby 0.92 g of N-[(S)-1-amino-1,2-dioxo-3-heptyl]-1-[N-[(2-methyl-2-propyloxycarbonyl)piperadine-4-carbonyl] amino]cyclohexanecarboxamide was obtained in a yield of 63%.

1H-NMR (CDCl$_3$, δ): 0.85 (3H, t, J=7 Hz), 1.20–1.50 (6H, m), 1.47 (9H, s), 1.58–1.70 (5H, m), 1.80–2.00 (3H, m), 2.00–2.20 (2H, m), 3.30–3.40 (4H, m), 3.40–3.60 (4H, m), 4.49 (1H, s), 5.09–5.14 (1H, m), 5.48 (1H, br-s), 6.75 (1H, br-s), 7.97 (1H, d, J=5 Hz)

IR (ν, KBr, cm$^{-1}$): 3330, 2936, 1686, 1522, 1464, 1254, 1234, 1170

Rf: 0.63.

Example 24

Synthesis of N-[(S)-1,2-dioxo-1-methoxy-3-heptyl]-1[N-(morpholine-4-carbonyl)amino] cyclohexanecarboxamide

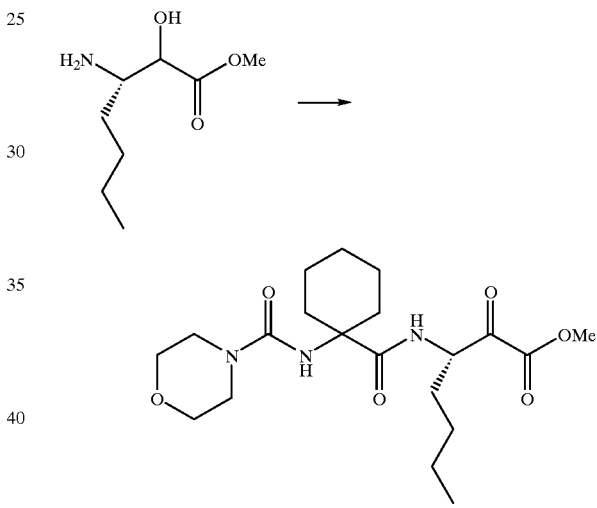

The same reaction procedure as in Example 1 was repeated except that the (2RS,3S)-N-(2-methyl-2-propyl)-3-amino-2-hydroxyheptanamide used in Example 1 was replaced by 1.02 g of methyl (2RS,3S)-3-amino-2-hydroxyheptanoate synthesized in Reference Example 18, whereby 0.83 g of N-[(S)-1,2-dioxo-1-methoxy-3-heptyl]-1-[N-(morpholine-4-carbonyl)amino] cyclohexanecarboxamide was obtained in a yield of 35%.

1H-NMR (CDCl$_3$, δ): 0.82–0.98 (3H, m), 1.20–1.45 (7H, m), 1.50–1.70 (4H, m), 1.80–2.00 (3H, m), 2.00–2.18 (2H, m), 3.38 (4H, t, J=5 Hz), 3.72 (4H, t, J=5 Hz), 3.88 (3H, s), 4.44 (1H, s), 4.95–5.04 (1H, m), 7.97 (1H, d, J=6 Hz)

IR (ν, KBr, cm$^{-1}$): 3312, 2928, 1736, 1650, 1630, 1536, 1260.

Example 25

Synthesis of N-[(S)-1-oxo-1-carboxy-2-hexyl]-1-[N-(morpholine-4-carbonyl)amino]cyclohexanecarboxamide

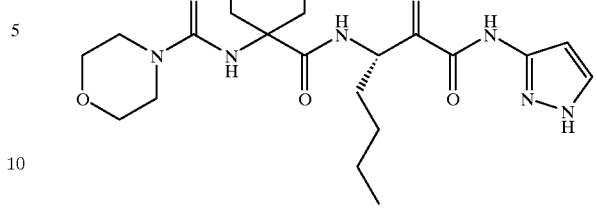

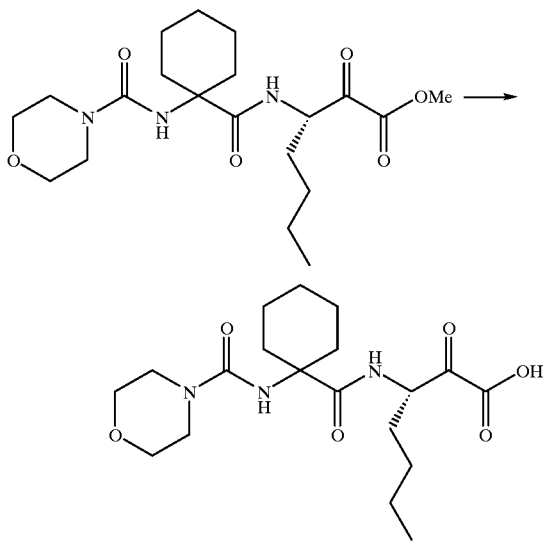

0.4 ml of 1 N sodium hydroxide solution was added to a methanol solution containing 77 mg (0.19 mmol) of N-[(S)-1,2-dioxy-1-methoxy-3-heptyl]-1-[N-(morpholine-4-carbonyl)amino]cyclohexanecarboxamide synthesized in Example 24. The reaction mixture was stirred at room temperature for 2 hours. The solvent was distilled away from the reaction mixture under reduced pressure. A 1N hydrochloric acid was added to the thus obtained residue. The resultant water layer was made neutral condition and extracted with chloroform. The resultant extract organic layer was washed with a saturated aqueous solution of sodium chloride and dried over anhydrous sodium sulfate. The solvent was distilled away under reduced pressure. The residue thus obtained was chromatographed on silica gel column for purification, whereby 52 mg of N-[(S)-1-oxo-1-carboxy-2-hexyl]-1-[N-(morpholine-4-carbonyl)amino]cyclohexanecarboxamide was obtained in a yield of 70%.

1H-NMR (CDCl$_3$, δ): 0.80–0.98 (3H, m), 1.20–1.50 (7H, m), 1.50–1.80 (4H, m), 1.80–2.00 (3H, m), 2.00–2.20 (2H, m), 3.40 (4H, t, J=5 Hz), 3.72 (4H, t, J=5 Hz), 4.00–5.00 (1H, br-s), 4.65 (1H, s), 4.85–5.00 (1H, m), 8.00 (1H, d, J=6 Hz)

IR (ν, KBr, cm$^{-1}$): 3388, 2932, 1644, 1528, 1260.

Example 26

Synthesis of N-[(S)-1,2-dioxo-1-[N-(3-pyrazolyl)amino-3-heptyl]-1-[N-(morpholine-4-carbonyl)amino]cyclohexanecarboxamide

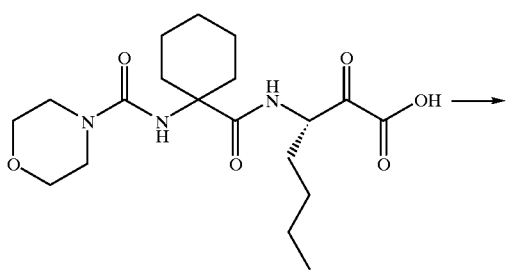

-continued

Under an ice-cooled condition, 460 mg (2.4 mmol) of 1-ethyl-3-(3-dimethylaminopropyl)carbodiimide hydrochloride was added to 20 ml of a dichloromethane solution containing 795 mg (2 mmol) of N-[(S)-1-carboxy-1-oxo-2-hexyl]-1-[N-(morpholine-4-carbonyl)amino]cyclohexanecarboxamide synthesized in Example 25, 166 mg (2 mmol) of 3-aminopyrazole and 324 mg (2.4 mmol) of 1-hydroxybenzotriazole hydrate. The reaction mixture was stirred overnight at room temperature. The solvent was distilled away from the reaction mixture under reduced pressure. The residue thus obtained was dissolved in ethyl acetate and washed with a water, a 10% aqueous solution of potassium hydrogen sulfate, a saturated aqueous solution of sodium hydrogencarbonate and a saturated solution of sodium chloride. The resultant extract organic layer was dried over anhydrous sodium sulfate. The solvent was distilled away under reduced pressure. The residue thus obtained was chromatographed on silica gel column for purification, whereby 218 mg of the captioned N-[(S)-1,2-dioxo-1-[N-(3-pyrazolyl)amino-3-heptyl]-1-[N-(morpholine-4-carbonyl)amino]cyclohexanecarboxamide was obtained in a yield of 26%.

1H-NMR (CDCl$_3$, δ): 0.89 (3H, t, J=7 Hz), 1.23–1.78 (10H, m), 1.82–2.17 (6H, m), 3.32–3.44 (4H, m), 3.62–3.76 (4H, m), 4.55–4.64 (1H, m), 4.75 (1H, s), 6.31 (1H, br-s), 6.64 (1H, br-s), 7.41 (1H, d, J=2 Hz), 10.220 (1H, s)

IR (ν, KBr, cm$^{-1}$): 3296, 1652

Rf: 0.78.

Example 27

Synthesis of N-[(S)-1-amino-1,2-dioxo-3-heptyl]-1-[N-(piperazine-1-carbonyl) amino]cyclohexanecarboxamide

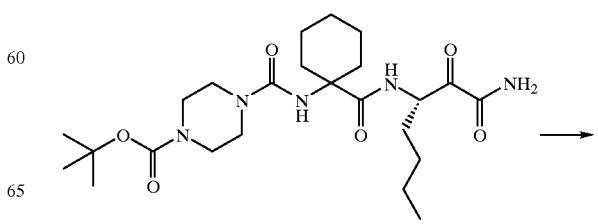

-continued

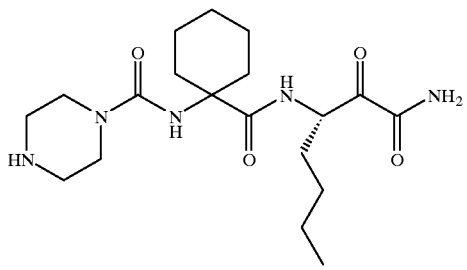

190 mg (1 mmol) of p-toluenesulfonic acid monohydrate was added 5 ml of a methanol solution containing 0.45 g (0.9 mmol) of N-[(3S)-1,2-dioxo-1-amino-3-heptyl]-1-[[4-(2-methyl-2-propyloxycarbonyl) piperazine-1-carbonyliamino]cyclohexanecarboxamide synthesized in Example 23. The reaction mixture stirred at 50° C. for 4 hours. After the reaction mixture was concentrated, the residue was dissolved in 1N hydrochloric acid and washed with ethyl acetate. The resulting water layer was made into acid (pH=10) with the addition of potassium carbonate thereto and then extracted with chloroform for three times. Chloroform layer was dried over anhydrous sodium sulfate and concentrated under reduce pressure, whereby 0.088 g the captioned N-[(S)-1-amino-1,2-dioxo-3-heptyl]-1-[N-(piperazine-1-carbonyl)amino]cyclohexanecarboxamide was obtained in a yield of 24%.

1H-NMR (CDCl$_3$, δ): 0.90 (3H, t, J=7 Hz), 1.20–2.20 (16H, m), 2.80–3.00 (4H, m), 3.30–3.40 (4H, m), 4.60–4.70 (1H, m), 4.76 (1H, s), 5.33 (1H, br-s), 5.56 (1H, br-s), 8.30 (1H, m)

IR (ν, KBr, cm$^{-1}$): 3396, 2936, 1680, 1654, 1539, 1260.

Example 28

Synthesis of N-[(S)-1-[N-(3-chlorophenylmethyl)amino]-1,2-dioxo-3-heptyl]-1-[N-(morpholine-4-carbonyl)amino]cyclohexanecarboxamide

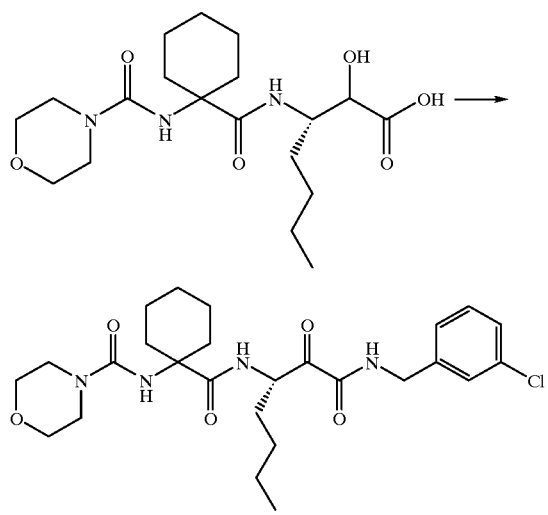

Under cooled condition, 460 mg (2.4 mmol) of 1-ethyl-3-(3-dimethylaminopropyl)carbodiimide hydrochloride was added to 20 ml of dichloromethane solution containing 799 mg (2 mmol) of (2RS,3S)-2-hydroxy-3-[N-[1-[N-(morpholine-4-carbonyl)amino]cyclohexanecarbonyl] amino]heptanoic acid obtained in Reference Example 17, 283 mg (2 mmol) of 3-chlorobenzylamine and 324 mg (2.4 mmol) of 1-hydroxybenzotriazole hydrate and the reaction mixture was stirred for 18 hours at room temperature. The reaction mixture was concentrated under reduced pressure and the residue was dissolved in ethyl acetate and washed with successive, water, 10% potassium hydrogensulfate solution, sodium hydrogencarbonate solution, and saturated brine. The obtained organic layer was dried over anhydrous sodium sulfate and concentrated under reduced pressure. The residue thus obtained was chromatographed on a silica gel column for purification, whereby 876 mg of N-1(2RS, 3S)-1-[N-(3-chlorophenylmethyl)amino]-2-hydroxy-1-oxo-3-heptyl]-1-[N-(morpholine-4-carbonyl)amino] cyclohexanecarboxamide was obtained.

1H-NMR (CDCl$_3$, δ): 0.88 (3H, t, J=7 Hz), 1.23–2.05 (16H, m), 3.28–3.38 (4H, m), 3.64–3.71 (4H, m), 3.92–4.01 (1/2H, m), 4.10–4.20 (1H, m), 4.33–4.49 (5/2H, m), 4.59 (1/2H, s), 4.66 (1/2H, s), 5.09 (1/2H, d, J=6 Hz), 5.23 (1/2H, d, J=6 Hz), 6.61 (1/2H, d, J=8 Hz), 6.75 (1/2H, d, J=8 Hz), 7.14–7.29 (4H, m), 7.33 (1/2H, t, J=7 Hz), 7.61 (1/2H, t, J=7 Hz).

Subsequently, under cooled condition, 5 ml of dimethyl sulfoxide solution containing 1.61 g (1.68 mmol) of sulfur trioxide-pyridine complex salt was added to the mixture 876 mg(1.68 mmol) of the N-[(2RS,3S)-2-hydroxyl-[N-(3-chlorophenylmethyl)amino]-1-oxo-3-heptyl]-1-[N-(morpholine-4-carbonyl)amino]cyclohexanecarboxamide, 1.02 g (10.1 mmol) of triethylamine in 10 ml of dimethyl-sulfoxide and 10 ml of dichloromethane, and then stirred for 2 hours. The reacton mixture was added to iced-water, and then ethyl acetate was added thereto. The obtained mixture was washed with successive, water for twice, 10% citric acid solution, saturated sodium hydrogencarbonate solution, and saturated brine. The thus obtained organic layer was dried over anhydrous sodium sulfate and concentrated under reduced pressure. The residue thus obtained was chromatographed on a silica gel column for purification, whereby 546 mg of the captioned N-[(S)-1-[N-(3-chlorophenylmethyl) amino]-1,2-dioxo-3-heptyl]-1-[N-(morpholine-4-carbonyl) amino]cyclohexanecarboxamide was obtained in a yield of 52%.

1H-NMR (CDCl$_3$, δ): 0.89 (3H, t, J=7 Hz), 1.21–1.42 (6H, m), 1.54–1.74 (5H, m), 1.82–2.18 (5H, m), 3.37 (4H, t, J=5 Hz), 3.65–3.74 (4H, m), 4.43 (1H, s), 4.45 (2H, d, J=6 Hz), 5.11–5.16(1H, m), 7.13–7.30 (5H, m), 8.01 (1H, d, J=7 Hz)

IR (ν, KBr, cm$^{-1}$): 3328, 1660

Rf: 0.56.

Example 29

Synthesis of N-[(S)-1,2-dioxo-1-[N-(3-fluorophenylmethyl)amino]-3-heptyl]-1-[N-(morpholine-4-carbonyl)amino]cyclohexanecarboxamide

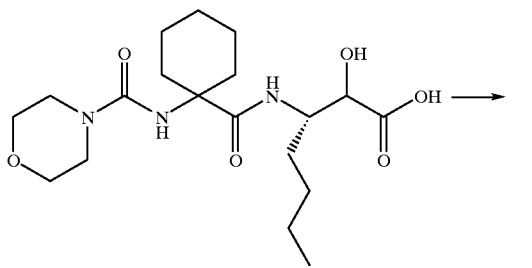

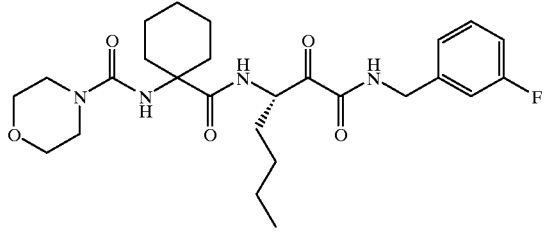

The same procedure as in Example 28 was repeated except that the 3-chlorobenzylamine was replaced by 250 mg of 3-tluorobenzylamine, whereby 597 mg of the captioned N-[(S)-1,2-dioxo-1-[N-(3-fluorophenylmethyl)amino]-3-heptyl]-1-[N-(morpholine-4-carbonyl)amino]cyclohexanecarboxamide was obtained in a yield of 59%.

1H-NMR (CDCl$_3$, δ): 0.89 (3H, t, J=7 Hz), 1.23–1.42 (6H, m), 1.57–1.74 (5H, m), 1.82–2.13 (5H, m), 3.37 (4H, t, J=5 Hz), 3.65–3.73 (4H, m), 4.43 (1H, s), 4.47 (2H, d, J=6 Hz), 5.09–5.16 (1H, m), 6.94–7.03 (2H, m), 7.05 (1H, d, J=7 Hz), 7.21 (1H, t, J=6 Hz), 7.25–7.34 (1H, m), 8.02 (1H, 6 Hz)

IR (v, KBr, cm$^{-1}$): 3320, 1658

Rf: 0.62.

Example 30

Synthesis of N-[(S)-1,2-dioxo-1-[N-(3-nitrophenylmethyl)amino]-3-heptyl]-1-[N-(morpholine-4-carbonyl)amino]cyclohexanecarboxamide

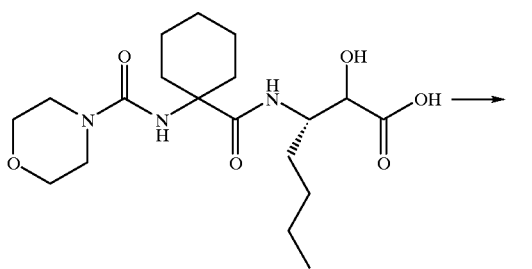

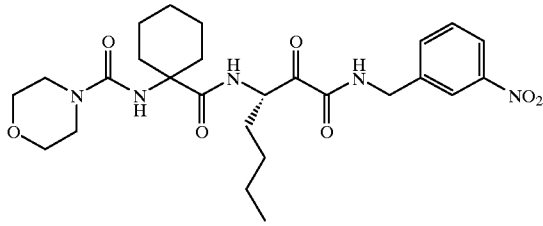

The same procedure as in Example 28 was repeated except that 377 mg of the 3-chlorobenzylamine was replaced by 3-nitrobenzylamine, whereby the captioned N-[(S)-1,2-dioxo-1-[N-(3-nitrophenylmethyl)amino]-3-heptyl]-1-[N-(morpholine-4-carbonyl)amino]cyclohexanecarboxamide 571 mg was obtained in a yield of 54%.

1H-NMR (CDCl$_3$, δ): 0.89 (3H, t, J=7 Hz), 1.22–1.42 (6H, m), 1.55–1.72 (5H, m), 1.82–2.13 (5H, m), 3.38 (4H, t, J=5 Hz), 3.64–3.73 (4H, m), 4.46 (1H, s), 4.58 (2H, d, J=6 Hz), 5.05–5.14 (1H, m), 7.38 (1H, t, J=6 Hz), 7.53 (1H, t, J=8 Hz), 7.64 (1H, d, J=8 Hz), 8.05 (1H, d, J=6 Hz), 8.12–8.18 (2H, m)

IR (v, KBr, cm$^{-1}$): 3340, 1658

Rf: 0.63.

Example 31

Synthesis of N-[(S)-1-(N-methylamino)-1,2-dioxo-3-heptyl]-1-[N-(morpholine-4-carbonyl)amino]cyclohexanecarboxamide

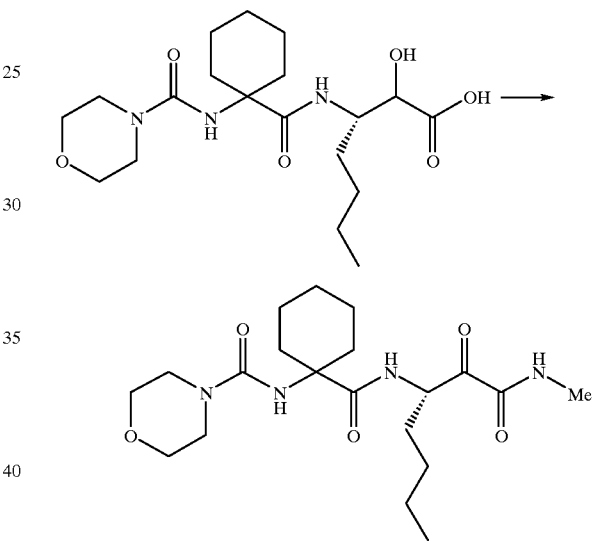

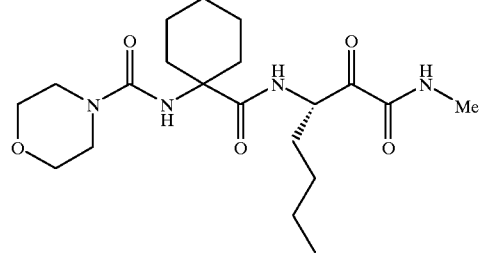

The same procedure as in Example 28 was repeated except that 0.06 g of the 3-chlorobenzylamine was replaced by methylamine, whereby 0.28 g the captioned N-[(S)-1-(N-methylamino)-1,2-dioxo3-heptyl]-1-[N-(morpholine-4-carbonyl)amino]cyclohexanecarboxamide was obtained in a yield of 38%.

1H-NMR (CDCl$_3$, δ): 0.88 (3H, t, J=7 Hz), 1.20–1.45 (7 Hz, m), 1.55–1.80 (4H, m), 1.80–2.02 (3H, m), 2.02–2.18 (2H, m), 2.88 (3H, d, J=5 Hz), 3.38 (3H, d, J=5 Hz), 3.72 (4H, t, J=5 Hz), 4.46 (1H, s), 5.12–5.22 (1H, m), 6.90 (1H, d, J=4 Hz), 7.95 (1H, d, J=7 Hz)

IR (v, KBr, cm$^{-1}$): 3352, 2936, 1664, 1532, 1258, 1116

Rf: 0.71.

Example 32

Synthesis of N-[(S)-1-(N-2-propylamino)-1,2-dioxo-3-heptyl]-1-[N-(morpholine-4-carbonyl)amino]cyclobexanecarboxamide

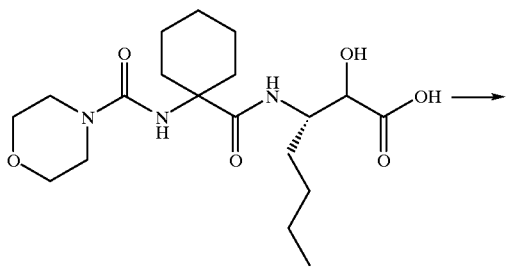

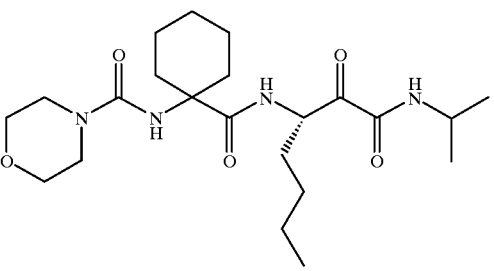

The procedure as in Example 28 was repeated except that the 3-chlorobenzylamine was replaced by 95 mg of isopropylamine, whereby 220 mg of the captioned N-[(S)-1-(N-2-propylamino)-1,2-dioxo-3-heptyl]-1-[N-(morpholine-4-carbonyl)amino]cyclohexanecarboxamide was obtained in a yield of 50%.

1H-NMR (CDCl$_3$, δ): 0.88 (3H, t, J=7 Hz), 1.20 (6H, d, J=7 Hz), 1.24–1.45 (6H, m), 1.58–1.70 (5H, m), 1.85–2.02 (2H, m), 3.39 (4H, t, J=5 Hz), 3.88–3.98 (4H, m), 3.98–4.10 (1H, m), 4.47(1H, s), 5.17–5.22 (1H, m), 6.70 (1H, d, J=8 Hz), 7.91 (1H, d, J=7 Hz)

IR (ν, KBr, cm$^{-1}$): 3760, 2324, 2232, 1730, 1336

Rf: 0.66.

Example 33

Synthesis of N-[(S)-1-(N-cyclohexylamino)-1,2-dioxo-3-heptyl]-1-[N-(morpholine-4-carbonyl)amino] cyclohexanecarboxamide

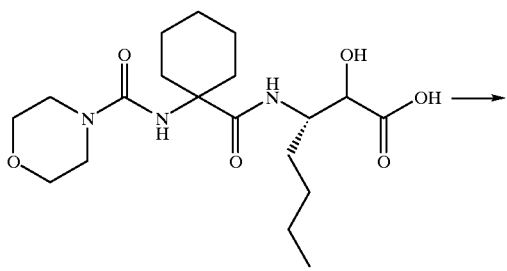

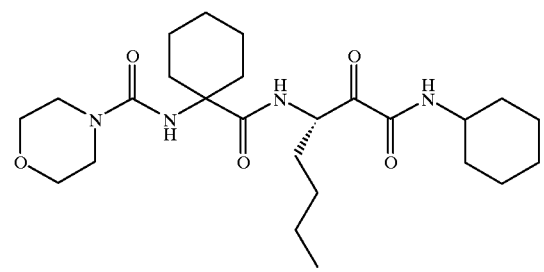

The same procedure as in Example 28 was repeated except that the 3-chlorobenzylamine was replaced by 157 mg of cyclohexylamine, whereby 199 mg of the captioned N-[(S)-1-(N-cyclohexylamino)-1,2-dioxo-3-heptyl]-1-[N-(morpholine-4-carbonyl)amino]cyclohexanecarboxamide was obtained in a yield of 42%.

1H-NMR (CDCl$_3$, δ): 0.88 (3H, t, J=7 Hz), 1.11–1.44 (12H, m), 1.56–1.78 (7H, m), 1.85–2.03 (5H, m), 2.06–2.16 (2H, m), 3.39 (4H, t, J=5 Hz), 3.66–3.80 (5H, m), 4.44 (1H, s), 5.19–5.23 (1H, m), 6.75 (1H, d, J=8 Hz), 7.91 (1H, d, J=7 Hz)

IR (ν, KBr, cm$^{-1}$): 3672, 3344, 1996, 1732, 1374

Rf:0.51.

Example 34

Synthesis of N-[(S)-1-(N-phenylamino)-1,2-dioxo-3-heptyl]-1-[N-(morpholine-4-carbonyl)amino] cyclohexanecarboxamide

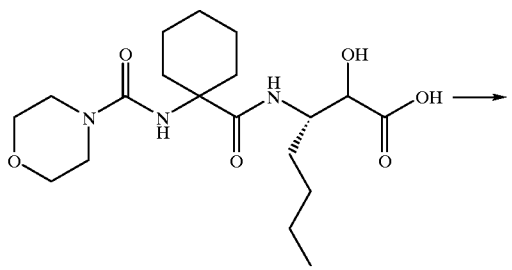

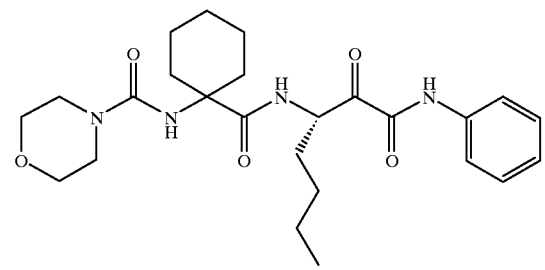

The same procedure as in Example 28 was repeated except that the 3-chlorobenzylamine was replaced by 0.17 g of aniline, whereby 0.33 g of the captioned N-[(S)-1-(N-phenylamino)-1,2-dioxo-3-heptyl]-1-[N-(morpholine-4-carbonyl)amino]cyclohexanecarboxamide was obtained in a yield of 37%.

1H-NMR (CDCl$_3$, δ): 0.82–0.98 (3H, m), 1.23–1.45 (7H, m), 1.50–1.80 (4H, m), 1.80–2.18 (5H, m), 3.36 (4H, t, J=5 Hz), 3.70 (4H, t, J=5 Hz), 4.44 (1H, s), 5.20–5.30 (1H, m), 7.17 (1H, t, J=8 Hz), 7.36 (2H, td, J=7 Hz, 2 Hz), 7.63 (2H, dd, J=8 Hz, 1Hz), 8.07 (1H, d, J=6 Hz), 8.64 (1H, s)

IR (ν, KBr, cm$^{-1}$): 3320, 2932, 1684, 1648, 1628, 1536, 1448, 1260, 1116, 760

Rf: 0.54.

Example 35

Synthesis of N-[(S)-1-(N-morpholine-4-amino)-1,2-dioxo-3-heptyl]-1-[N-(morpholine-4-carbonyl)amino] cyclohexanecarboxamide

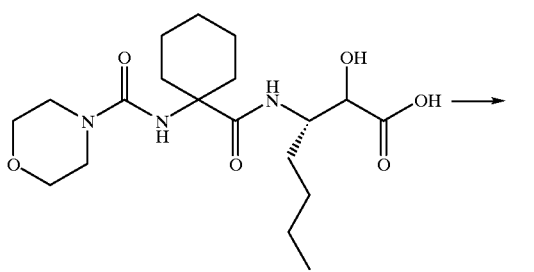

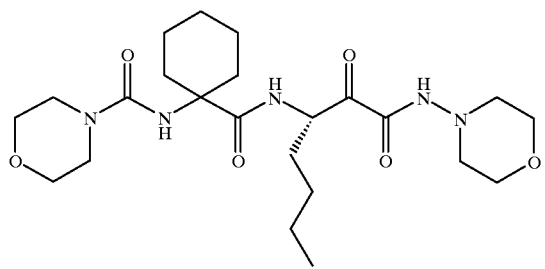

The same procedure as in Example 28 was repeated except that the 3-chlorobenzylamine was replaced by 163 mg of N-aminomorpholine, whereby 82 mg of the captioned N-[(S)-1-(N-morpholine-4-amino)-1,2-dioxo-3-heptyl]-1-[N-(morpholine-4-carbonyl)amino]cyclohexanecarboxamide was obtained in a yield of 17%.

1H-NMR (CDCl$_3$, δ): 0.88 (3H, t, J=7 Hz), 1.21–1.43 (7H, m), 1.51–1.70 (4H, m), 1.84–2.15 (5H.m), 2.80–2.92 (4H, m), 3.39 (4H, t, J=5 Hz), 3.72 (4H, t, J=5 Hz), 3.81 (4H, t, J=5 Hz), 4.43 (1H, s), 5.08–5.18 (1H, m), 7.61 (1H, s), 7.95 (1H, d, J=7 Hz)

IR (v, KBr, cm$^{-1}$): 3340, 2364, 1730, 1454, 1306, 1172
Rf: 0.77.

Example 36

Synthesis of N-[(S)-1,2-dioxo-1-[N-(3-methoxyphenylmethyl)amino]-3-heptyl]-1-[N-(morpholine-4-carbonyl)amino]cyclohexanecarboxamide

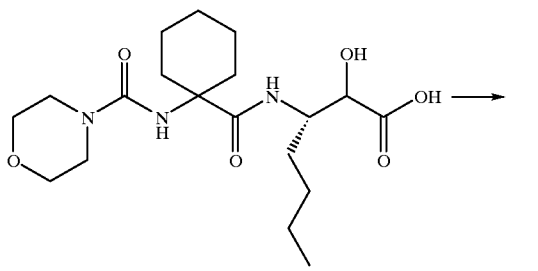

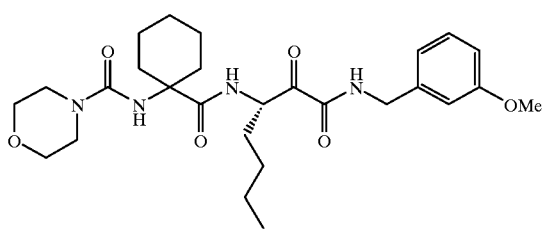

The same procedure as in Example 28 was repeated except that the 3-chlorobenzylamine was replaced by 1.1 g of 3-methoxyphenylmethylamine, whereby 735 mg of the captioned N-[(S)-1,2-dioxo-1-[N-(3-methoxyphenylmethyl)amino]-3-heptyl]-1-[N-(morpholine-4-carbonyl)amino]cyclohexanecarboxamide was obtained in a yield of 36%.

1H-NMR (CDCl$_3$, δ): 0.89 (3H, t, J=7 Hz), 1.26–1.40 (7H, m), 1.65–1.71 (4H, m), 1.85–2.11 (5H, m), 3.37 (4H, t, J=5 Hz), 370 (4H, t, J=5 Hz), 3.80 (3H, s), 4.45 (1H, s), 4.45 (2H, d, J=6 Hz), 5.14 (1H, ddd, J=5 Hz, 7 Hz, 8 Hz), 6.42–6.87 (3H, m), 7.15 (1H, t, J=6 Hz), 7.22–7.25 (1H, m), 7.99 (1H, d, J=7 Hz)

IR (v, KBr, cm$^{-1}$): 3322, 2931, 1685, 1648, 1529, 1454, 1257, 1112

Rf: 0.61.

Example 37

Synthesis of N-[(S)-1,2-dioxo-1-[N-(2-thiazolyl)amino]-3-heptyl]-1-[N-(morpholine-4-carbonyl)amino]cyclohexanecarboxamide

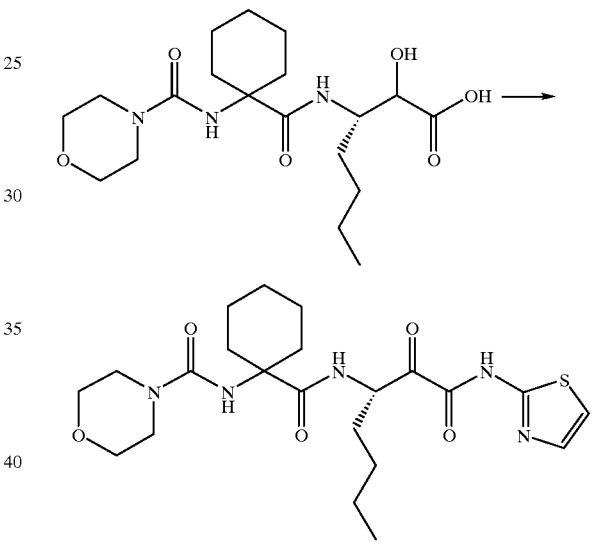

The same procedure as in Example 28 was repeated except that the 3-chlorobenzylamine used in Example 28 was replaced by 0.7 g of 2-aminothiazole, whereby 0.18 g of the captioned N-[(S)-1,2-dioxo-1-[N-(2-thiazolyl)amino]-3-heptyl]-1-[N-(morpholine-4-carbonyl)amino]cyclohexanecarboxamide was obtained in a yield of 13%.

1H-NMR (CDCl$_3$, δ): 0.89 (3H, t, J=6 Hz), 1.20–2.00 (16H, m), 3.30–3.50 (4H, m), 3.70–3.80 (4H, m), 4.40 (1H, s), 5.15–5.20 (1H, m), 7.08 (1H, d, J=3 Hz), 7.55 (1H, d, J=3 Hz), 8.22 (1H, d, J=5 Hz), 10.20–10.40 (1H, br-s)

IR (v, KBr, cm$^{-1}$) 3356, 2936, 2864, 1650, 1536, 1258, 1112

Rf: 0.64.

Example 38

Synthesis of N-[(S)-1,2-dioxo-1-[N-(phenylmethyl)amino]-3-heptyl]-1-[N-(morpholine-4-carbonyl)amino]cyclohexanecarboxamide

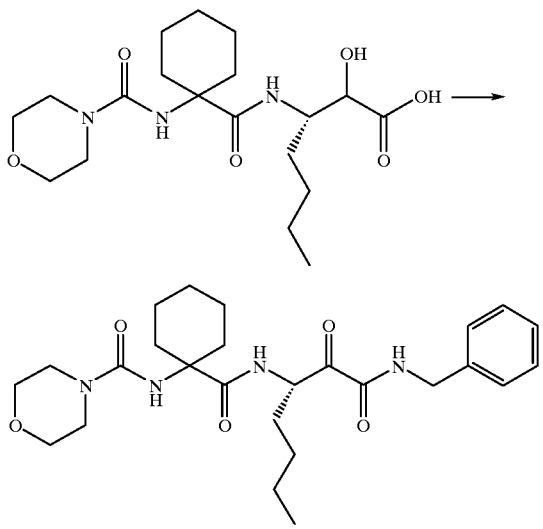

The same procedure as in Example 28 was repeated except that the 3-chlorobenzylamine was replaced by 536 mg of phenylmethylamine, whereby 900 mg of the captioned N-[(S)-1,2-dioxo-1-[N-(phenylmethyl)amino]-3-heptyl]-1-[N-(morpholine-4-carbonyl)amino]cyclohexanecarboxamide was obtained in a yield of 38%.

1H-NMR (CDCl$_3$, δ) 0.87–0.91 (3H, m), 1.24–1.42 (5H, m), 1.63–1.71 (7H, m), 1.85–2.17 (4H, m), 3.37 (4H, t, J=5 Hz), 3.70 (4H, t, J=5 Hz), 4.44 (1H, s), 4.46 (2H, dd, J=3 Hz, 6 Hz), 5.16 (1H, ddd, J=5 Hz, 7 Hz, 8 Hz), 7.16–7.20 (1H, m), 7.27–7.36 (5H, m), 7.96 (1H, d, J=7 Hz)

IR (ν, KBr, cm$^{-1}$): 3317, 2929, 2857, 1658, 1513, 1454, 1253

Rf: 0.58.

Example 39

Synthesis of N-[(S)-1,2-dioxo-1-[N-(tetrahydro-2-furylmethyl)amino]-3-heptyl]-1-[N-(morpholine-4-carbonyl)amino]cyclohexanecarboxamide

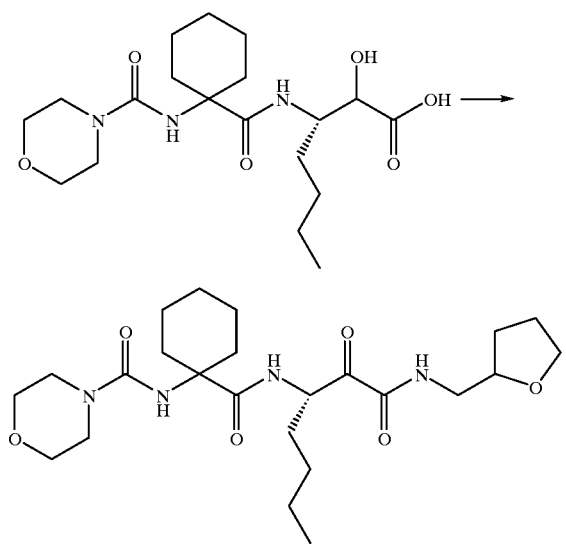

The same procedure as in Example 28 was repeated except that the 3-chlorobenzylamine was replaced by 202 mg of tetrahydrofurfurylamine, whereby 510 mg of the captioned N-[(S)-1,2-dioxo-1-[N-(tetrahydro-2-furylmethyl)amino]-3-heptyl]-1-[N-(morpholine-4-carbonyl)amino]cyclohexanecarboxamide was obtained in a yield of 53%.

1H-NMR (CDCl$_3$, δ): 0.87 (3H, t, J=7 Hz), 1.22–1.44 (7H, m), 1.47–1.70 (5H, m), 1.83–2.06 (8H, m), 3.21–3.28 (1H, m), 3.34–3.43 (4H, m), 3.49–3.58 (1H, m), 3.66–3.79 (5H, m), 3.83–3.90 (1H, m), 3.93–4.03 (1H, m), 4.46 (1H, s), 5.18–5.25 (1H, m), 7.17 (1H, br-s), 7.93 (1H, t, J=7 Hz)

IR (ν, KBr, cm$^{-1}$): 3324, 1670

Rf: 0.67

Example 40

Synthesis of N-[(S)-1,2-dioxo-1-[N-(2-oxotetrahydro-3-furyl)amino]-3-heptyl]-1-[N-(morpholine-4-carbonyl)amino]cyclohexanecarboxamide

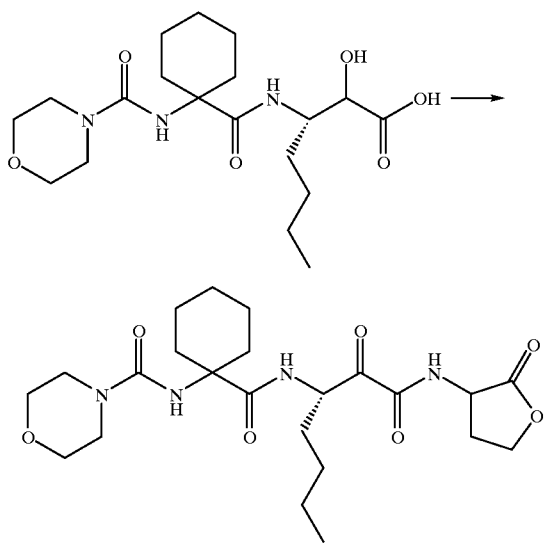

The same procedure as in Example 28 was repeated except that the 3-chlorobenzylamine was replaced by 364 mg of α-amino-γ-butyrolactone, whereby 341 mg of the captioned N-[(S)-1,2-dioxo-1-[N-(2-oxotetrahydro-3-furyl)amino]-3-heptyl]-1-[N-(morpholine-4-carbonyl)amino]cyclohexanecarboxamide was obtained in a yield of 36%.

1H-NMR (CDCl$_3$, δ): 0.89 (3H, t, J=7 Hz), 1.22–1.46 (6H, m), 1.53–1.67 (4H, m), 1.77–1.98 (4H, m), 2.03–2.39 (3H, m), 2.71–2.83 (1H, m), 3.32–3.42 (4H, m), 3.66–3.74 (4H, m), 4.26–4.35 (1H, m), 4.42–4.63 (3H, m), 4.88–5.04 (1H, m), 7.23–7.33 (1H, m), 8.21 (1/2H, d, J=7 Hz), 8.31 (1/2H, d, J=7 Hz)

IR (ν, KBr, cm$^{-1}$): 3360, 1666

Rf: 0.80.

Example 41

Synthesis of N-[(S)-1-[N-(cyclopentylmethyl)amino]-1,2-dioxo-3-heptyl]-1-[N-(morpholine-4-carbonyl)amino]cyclohexanecarboxamide

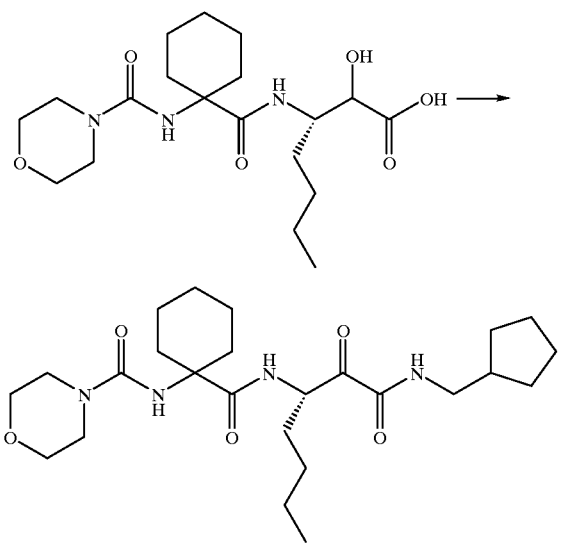

The same procedure as in Example 28 was repeated except that the 3-chlorobenzylamine was replaced by 399 mg of cyclopentylmethylamine, whereby 190 mg of the captioned N-[(S)-1-[N-(cyclopentyl methyl)amino]-1,2-dioxo-3-heptyl]-1-[N-(morpholine-4-carbonyl)amino] cyclohexanecarboxamide was obtained in a yield of 20%.
1H-NMR(CDCl$_3$, δ): 0.88(3H,t,J=5 Hz), 1.17–1.42(10H, m), 1.50–1.80 (8H, m), 1.86–2.12 (7H, m), 3.22 (2H, dd, J=6 Hz, 7 Hz), 3.39 (4H, t, J=5 Hz), 3.72 (4H, t, J=5 Hz), 4.45 (1H, s), 5.17 (1H, ddd, J=5 Hz, 7 Hz, 8 Hz), 6.91 (1H, br-s), 7.92 (1H, d, J=7 Hz)

IR (v, KBr, cm$^{-1}$): 3328, 2953, 1656, 1525

Rf: 0.46.

Example 42

Synthesis of N-[(S)-1-[N-(1-methylcyclopentyl)amino]-1,2-dioxo-3-heptyl]- 1-[N-(morpholine-4-carbonyl)amino] cyclohexanecarboxamide

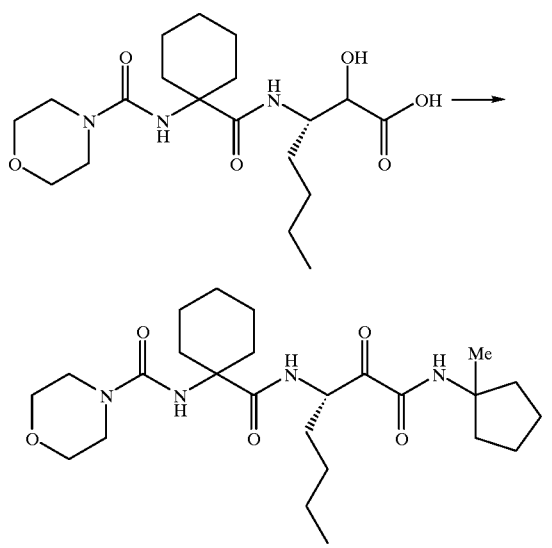

The same procedure as in Example 28 was repeated except that the 3-chlorobenzylamine was replaced by 452.8 mg of 1-methylcyclopentylamnine, whereby 228 mg of the captioned N-[(S)-1-[N-(1-methylcyclopentyl)amino]-1,2-dioxo-3-heptyl]-1-[N-(morpholine-4-carbonyl)amino] cyclohexanecarboxamide was obtained in a yield of 23%.

1H-NMR (CDCl$_3$, δ): 0.88 (3H, t, J=5 Hz), 1.26–1.41 (9H, m), 1.42 (3H, s), 1.60–1.72 (9H, s), 1.86–2.12 (6H, m), 3.39 (4H, t, J=5 Hz), 3.72 (4H, t, J=5 Hz), 4.46 (1H, s), 5.17 (1H, ddd, J=5 Hz, 7 Hz, 8 Hz), 6.79 (1H, s), 7.89 (1H, d, J=7 Hz)

IR (v, KBr, cm$^{-1}$): 3313, 2958, 2933, 1656, 1521, 1255

Rf: 0.42.

Example 43

Synthesis of N-[(S)-1,2-dioxo-1-[N-(1-indanyl)amino]-3-heptyl]-1-[N-(morpholine-4-carbonyl)amino] cyclohexanecarboxamide

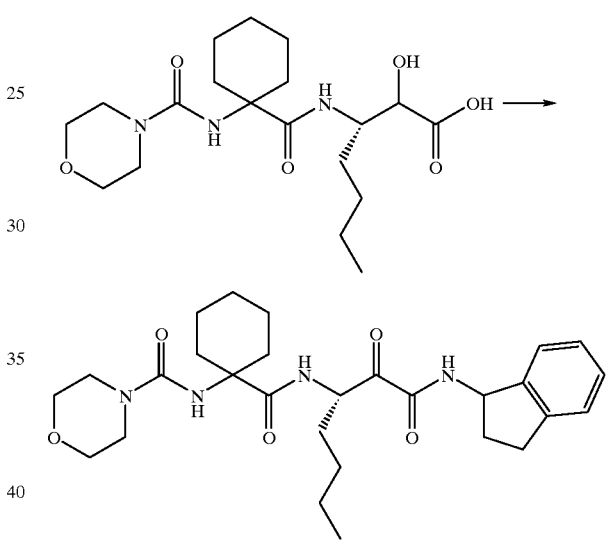

The same procedure as in Example 28 was repeated except that the 3-chlorobenzylamine was replaced by 533 mg of 1-aminoindane, whereby 556 mg of the captioned N-[(S)-1,2-dioxo-1-[N-(1-indanyl)amino]-3-heptyl]-1-[N-(morpholine-4-carbonyl)amino]cyclohexanecarboxamide was obtained in a yield of 28%.

1H-NMR (CDCl$_3$, δ): 0.88–0.92 (3H, m), 1.21–1.42 (7H, m), 1.62–1.73 (5H, m), 1.84–2.09 (5H, m), 2.56–2.65 (1H, m), 2.86–3.00 (1H, m), 3.01–3.06 (1H, m), 3.37–3.40 (4H, m), 3.68–3.72 (4H, m), 4.46 (1H, s), 5.22–5.29 (1H, m), 5.39–5.47 (1H, m), 7.07 (1H, d, J=8 Hz), 7.19–7.31 (4H, m), 7.94 (1H, d, J=7 Hz)

IR (v, KBr, cm$^{-1}$): 3317, 2929, 1654, 1525, 1255

Rf: 0.46.

Example 44

Synthesis of N-[(S)-1,2-dioxo-1-[N-(2-indanyl)amino]-3-heptyl]-1-[N-(morpholine-4-carbonyl)amino] cyclohexanecarboxamide

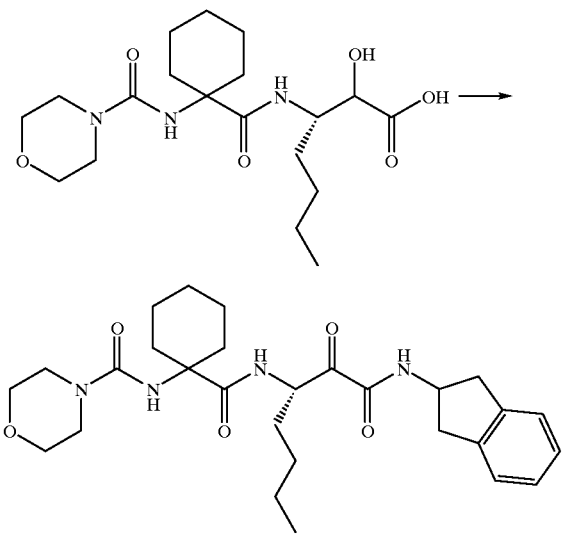

The same procedure as in Example 28 was repeated except that the 3-chlorobenzylamine was replaced by 533 mg of 2-aminoindane, whereby 650 mg of the captioned N-[(S)-1,2-dioxo-1-[N-(2-indanyl)amino]-3-heptyl]-1-[N-(morpholine-4-carbonyl)amino]cyclohexanecarboxamide was obtained in a yield of 33%.

1H-NMR (CDCl$_3$, δ): 0.89 (3H, t, J=7 Hz), 1.25–1.66 (11H, m), 1.85–2.21 (5H, m), 2.85 (2H, dt, J=5 Hz, 16 Hz), 3.29–3.39 (6H, m), 3.71 (4H, t, J=5 Hz), 4.44 (1H, s), 4.68–4.72 (1H, m), 5.18 (1H, ddd, J=5 Hz, 7 Hz, 9 Hz), 7.07 (1H, d, J=9 Hz), 7.16–7.23 (4H, m), 7.92 (1H, d, J=7 Hz)

IR (ν, KBr, cm$^{-1}$): 3311, 2933, 1652

Rf: 0.47.

Example 45

Synthesis of N-[(S)-1-[N-(cyclobutyl)amino]-1,2-dioxo-3-heptyl]-1-[N-(morpholine-4-carbonyl)amino]cyclohexanecarboxamide

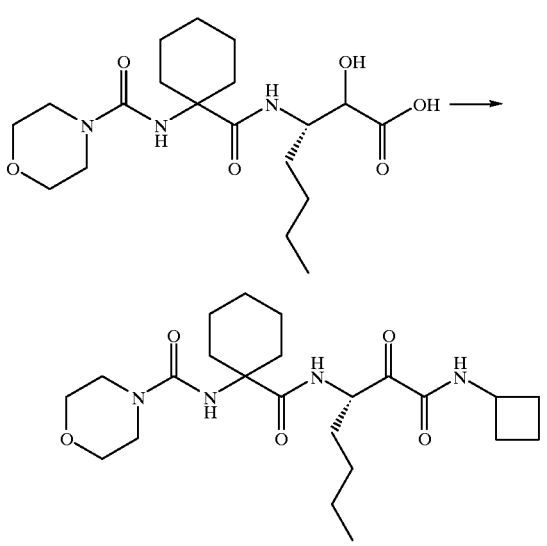

The same procedure as in Example 28 was repeated except that the 3-chlorobenzylamine was replaced by 284 mg of cyclobutylamine, whereby 440 mg of the captioned N-[(S)-1-[N-(cyclobutyl)amino]-1,2-dioxo-3-heptyl]-1-[N-(morpholine-4-carbonyl)amino]cyclohexanecarboxamide was obtained in a yield of 24%.

1H-NMR (CDCl$_3$, δ): 0.88 (3H, t, J=7 Hz), 1.21–1.54 (7H, m), 1.62–1.81 (7H, m), 1.86–2.11 (6H, m), 2.31–2.39 (2H, m), 3.37–3.42 (4H, m), 3.71–3.73 (4H, m), 4.30–4.39 (1H, m), 4.45 (1H, s), 5.14 (1H, ddd, J=5 Hz, 7 Hz, 8 Hz), 7.00 (1H, d, J=7 Hz), 7.91 (1H, d, J=7 Hz)

IR (ν, KBr, cm$^{-1}$): 3330, 2933, 1649, 1527, 1257

Rf: 0.60.

Example 46

Synthesis of N-[(S)-1,2-dioxo-1-[N-(3-pyridyl)amino]-3-heptyl]-1-[N-(morpholine-4-carbonyl)amino]cyclohexanecarboxamide

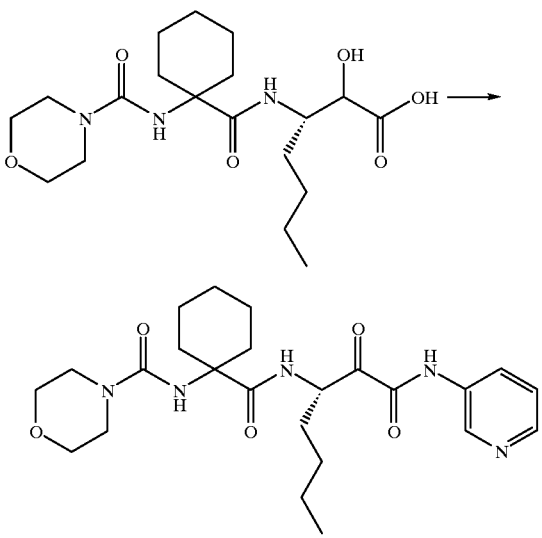

The same procedure as in Example 28 was repeated except that the 3-chlorobenzylamine was replaced by 376 mg of 3-aminopyridine, whereby 30 mg of the captioned N-[(S)-1,2-dioxo-1-[N-(3-pyridyl)amino]-3-heptyl]-1-[N-(morpholine-4-carbonyl)amino]cyclohexanecarboxamide was obtained in a yield of 2%.

1H-NMR (CDCl$_3$, δ): 0.90 (3H, t, J=7 Hz), 1.24–1.30 (5H, m), 1.32–1.74 (6H, m), 1.85–2.11 (5H, m), 3.36–3.38 (4H, m), 3.69–3.72 (4H, m), 4.51 (1H, s), 5.17 (1H, ddd, J=5 Hz, 6 Hz, 9 Hz), 7.32 (1H, dd, J=5 Hz, 8 Hz), 8.15 (1H, d, J=6 Hz), 8.21 (1H, ddd, J=1 Hz, 3 Hz, 8 Hz), 8.41 (1H, dd, J=1 Hz, 5 Hz), 8.72 (1H, d, J=3 Hz), 8.79 (1H, s)

IR (ν, KBr, cm$^{-1}$): 3052, 2300, 1674, 1628, 1276

Rf: 0.67.

Example 47

Synthesis of N-[(S)-1,2-dioxo-1-[N-(furylmethyl)amino]-3-heptyl]-1-[N-(morpholine-4-carbonyl)amino]cyclohexanecarboxamide

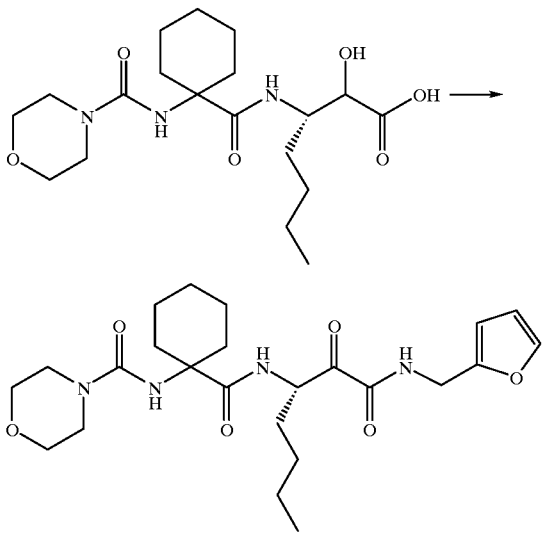

The same procedure as in Example 28 was repeated except that the 3-chlorobenzylamine was replaced by 389 mg of furylmethylamine, whereby 375 mg of the captioned N-[(S)-1,2-dioxo-1-[N-(furylmethyl)amino]-3-heptyl]-1-[N-(morpholine-4-carbonyl)amino]cyclohexanecarboxamide was obtained in a yield of 20%.

1H-NMR (CDCl$_3$, δ): 0.86–0.90 (3H, m), 1.24–1.42 (6H, m), 1.63–1.71 (3H, m), 1.83–2.11 (7H, m), 3.38 (4H, t, J=5 Hz), 3.71 (4H, t, J=5 Hz), 4.46 (2H, dd, J=1 Hz, 6 Hz), 4.52 (1H, s), 5.15 (1H, ddd, J=5 Hz, 7 Hz, 9 Hz), 6.26 (1H, dd, J=1 Hz, 3 Hz), 6.32 (1H, dd, J=2 Hz, 3 Hz), 7.20 (1H, t, J=6 Hz), 7.35 (1H, dd, J=1 Hz, 2 Hz), 7.93 (1H, d, J=7 Hz)

IR (ν, KBr, cm$^{-1}$): 3376, 1658

Rf: 0.67.

Example 48

Synthesis of N-[(S)-1-(N,N-dimethylamino)-1,2-dioxo-3-heptyl]-1-[N-(morpholine-4-carbonyl)amino]cyclohexanecarboxamide

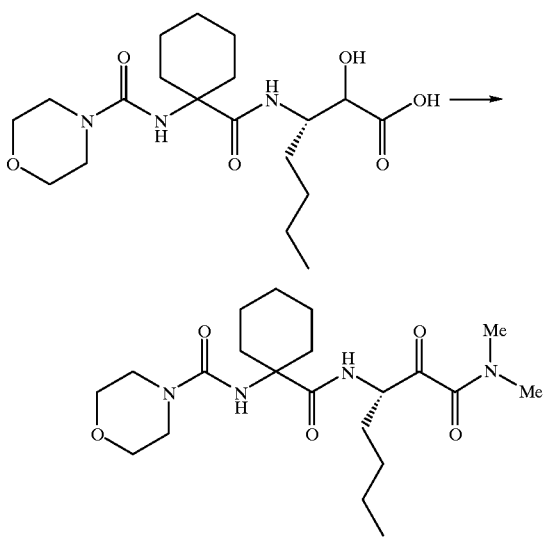

The same procedure as in Example 28 was repeated except that the 3-chlorobenzylamine was replaced by 0.009 g of dimethylamine, whereby 0.33 g of the captioned N-[(S)-1-(N,N-dimethylamino)-1,2-dioxo-3-heptyl]-1-[N-(morpholine-4-carbonyl)amino]cyclohexanecarboxamide was obtained in a yield of 39%.

1H-NMR (CDCl$_3$, δ): 0.89 (3H, t, J=7 Hz), 1.25–1.45 (7H, m), 1.59–1.73 (3H, m), 1.73–1.95 (3H, m), 1.98–2.15 (3H, m), 2.94 (3H, s), 3.00 (3H, s), 3.37 (4H, t, J=5 Hz), 3.71 (4H, t, J=5 Hz), 4.48 (1H, s), 4.50–4.58 (1H, s), 7.53 (1H, d, J=7 Hz)

IR (ν, KBr, cm$^{-1}$): 2932, 1666, 1642, 1522, 1260, 1124

Rf: 0.69.

Example 49

Synthesis of N-[(S)-1,2-dioxo-1-[N-(1-methylcyclopentylmethyl)amino]-3-heptyl]-1-[N-(morpholine-4-carbonyl)amino]cyclohexanecarboxamide

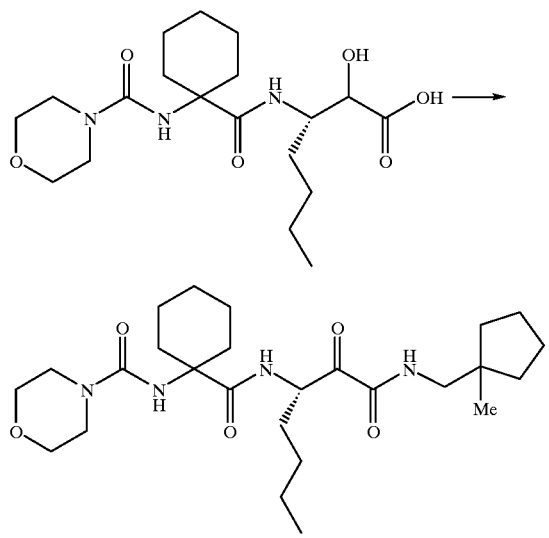

The same procedure as in Example 28 was repeated except that the 3-chlorobenzylamine was replaced by 453 mg of 1-methylcyclopentylmethylamine, whereby 430 mg of the captioned N-[(S)-1,2-dioxo-1-[N-(1-methylcyclopentylmethyl)amino]-3-heptyl]-1-[N-(morpholine-4-carbonyl) amino]cyclohexanecarboxamide was obtained in a yield of 22%.

1H-NMR (CDCl$_3$, δ): 0.86–0.90 (3H, m), 0.98 (3H, s), 1.31–1.45 (12H, m), 1.59–1.70 (7H, m), 1.86–1.97 (3H, m), 2.09–2.12 (2H, m), 3.19 (2H, dd, J=5 Hz, 6 Hz), 3.39 (4H, t, J=5 Hz), 4.45 (1H, s), 5.18 (1H, ddd, J=5 Hz, 7 Hz, 8 Hz), 6.94 (1H, br-s), 7.94 (1H, d, J=7 Hz)

IR (ν, KBr, cm$^{-1}$): 3368, 2932, 1676, 1662, 1612, 1538

Rf: 0.36.

Example 50

Synthesis of N-[(S)-1-(N-cyclopentylamino)-1,2-dioxo-3-heptyl]-1-[N-(phenylsulfonyl)amino]cyclohexanecarboxamide

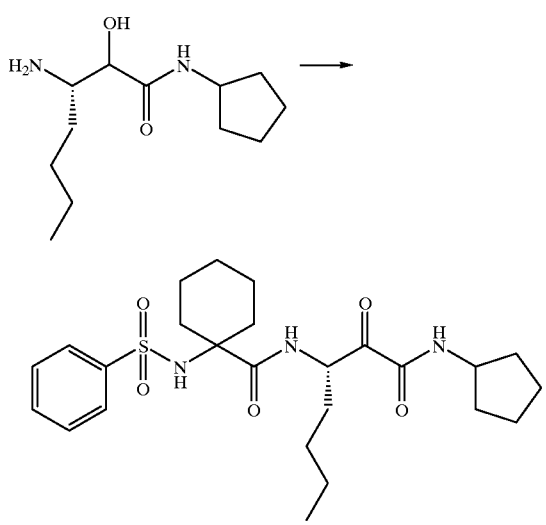

The same procedure as in Example 2 was repeated except that the 1-[N-(morpholine-4-carbonyl)amino] cyclohexanecarboxylic acid was replaced by 567 mg of 1-[N-(phenylsulfonyl)amino]cyclohexanecarboxylic acid obtained in Reference Example 19, whereby 786 mg of the captioned N-[(S)-1-(N-cyclopentylamino)-1,2-dioxo-3-heptyl]-1 [N-(phenylsulfonyl)amino] cyclohexanecarboxamide was obtained in a yield of 80%. 1H-NMR (CDCl$_3$, δ): 0.89 (3H, t, J=7 Hz), 1.09–1.53 (12H, m), 1.57–1.77 (5H, m), 1.78–2.05 (7H, m), 4.13–4.23 (1H, m), 5.10 (1H, dt, J=8 Hz, 5 Hz), 5.17 (1H, s), 6.86 (1H, d, J=8 Hz), 7.06 (1H, d, J=7 Hz), 7.45–7.58 (3H, m), 7.88 (2H, dd, J=8 Hz, 2 Hz)

IR (ν, KBr, cm$^{-1}$): 3360, 1666

Rf: 0.32.

Reference Example 20

Synthesis of (2RS,3S)-N-cyclopentyl-3-amino-2-hydroxy-5-methylhexaneamide

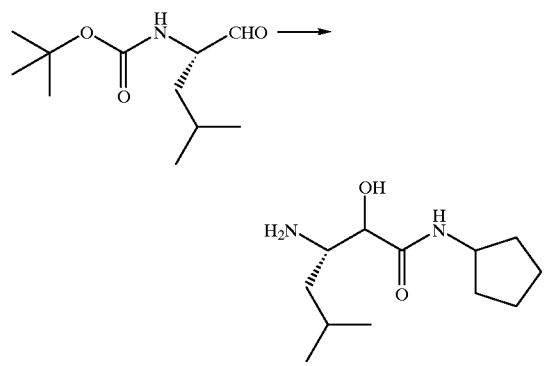

The same procedure as in Reference Example 11 was repeated except that the (S)-2-[N-(2-methyl-2-propyloxycarbonyl)amino]hexanal was replaced by 18.64 g of (S)-2-[N-(2-methyl-2-propyloxycarbonyl)amino]-4-methylpentanal, whereby 6.72 g of the captioned (2RS,3S)-N-cyclopentyl-3-amino-2-hydroxy-5-methylhexanamide was obtained in a yield of 34%.

1H-NMR (CDCl$_3$, δ): 0.88 (1.5H, d, J=7 Hz), 0.93 (4H, d, J=7 Hz), 0.96 (0.5H, d, J=7 Hz), 1.20–1.48 (4H, m), 1.65–1.73 (5H, m), 1.93–2.04 (2H, m), 3.19–3.25 (0.4H, m), 3.22–3.29 (0.6H, m), 3.76 (0.6H, d, J=3 Hz), 3.93 (0.4H, d, J=5 Hz), 4.16–4.25 (1H, m), 7.11 (0.6H, d, J=8 Hz), 7.29 (0.4H, d, J=8 Hz).

Reference Example 21

Synthesis of 1-[N-(4-methoxybenzenesulfonyl)amino] cyclohexanecarboxylic acid

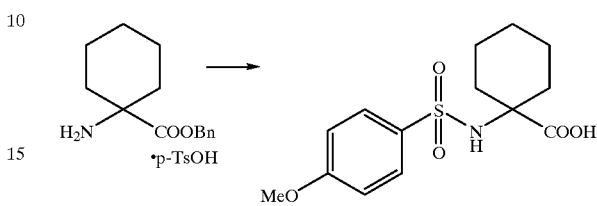

8.1 g (20 mmol) of phenylmethyl 1-aminocyclohexanecarboxylate ·p-toluenesulfonate was added to 50 nm of water, and then 4.1 g (20 mmol) of 4-methoxybenzenesulfonylchloride and 50 ml of ethyl acetate was added to the mixture with stirring. After stirring at room temperature, the reaction mixture was put into a separatory funnel and water layer was removed therefrom. Subsequently, organic layer was washed with successive, 10% potassium hydrogensulfate solution, and saturated brine, and then, was dried over anhydrous magnesium sulfate, and the solvent was concentrated under reduced pressure. The obtained crystal was stirred overnight in ether, whereby 4.36 g of phenylmethyl 1-[N-(4-methoxybenzenesulfonyl)amino]cyclohexanecarboxylate was obtained.

Subsequently, the same procedure as in Reference Example 4 was repeated except that the ethyl 1-[N-(3,4-methylenedioxyphenylcarbonyl)amino] cyclohexanecarboxylate was replaced by 1.0 g (2.5 mmol) of phenylmethyl 1-[N-(4-methoxybenzenesulfonyl)amino] cyclohexanecarboxylate, whereby 450 mg of the captioned 1-[N-(4-methoxybenzenesulfonyl)amino] cyclohexanecarboxylic acid was obtained in a yield of 26%.

1H-NMR (CDCl$_3$, δ): 1.26–1.89 (10H, m), 3.88 (3H, s), 4.78 (1H, s), 6.95–7.00 (2H, m), 7.82–7.89 (2H, m).

Reference Example 22

Synthesis of 1-[N-(4-nitrobenzenesulfonyl)amino] cyclohexanecarboxylic acid

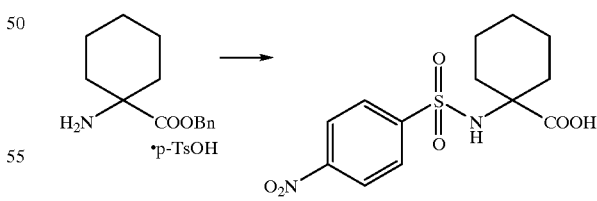

The same procedure as in Reference Example 21 was repeated except that the 4-methoxybenzenesulfonylchloride was replaced by 4.4 g of 4-nitrobenzenesulfonylchloride, whereby 6.1 g of the captioned 1-[N-(4-nitrobenzenesulfonyl)amino]cyclohexanecarboxylic acid was obtained in a yield of 72.9%.

1H-NMR (CDCl$_3$, δ): 1.23–1.35 (4H, m), 1.47–1.49 (2H, m), 1.80–2.05 (4H, m), 8.06–8.08 (2H, m), 8.32–8.36 (2H, m);

Reference Example 23

Synthesis of (2RS,3S)-N-cyclopentylmethyl-3-amino-2-hydroxy-5-methylhexanamide

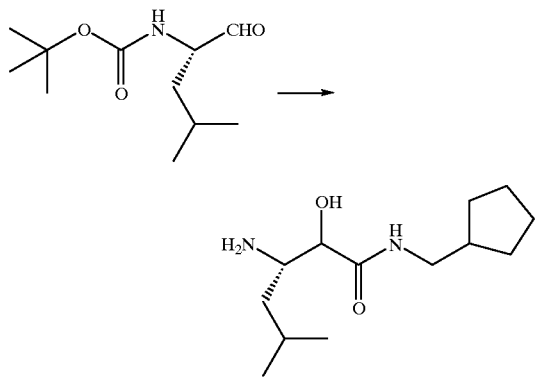

The same procedure as in Reference Example 20 was repeated except that the cyclopentylamnine was replaced by 496 mg of cyclopentylmethylamine, whereby 603 mg of the captioned (2RS,3S)-N-cyclopentylmethyl-3-amino-2-hydroxy-5-methylhexanamide was obtained in a yield of 58%.

1H-NMR (CDCl$_3$, δ): 0.89–0.96 (6H, m), 1.15–1.37 (3H, m), 1.49–1.79 (8H, m), 2.00–2.07 (1H, m), 3.10–3.32 (2H, m), 3.84 (1H, br-s), 4.06–4.81 (1/2H, m), 4.15–4.18 (1/2H, m), 5.16 (1/2H, d, J=6 Hz), 5.23 (1/2H, br-s), 6.89 (1/2H, br-s), 6.95 (1/2H, br-s).

Reference Example 24

Synthesis of 1-[N-(quinoline-8-sulfonyl)amino]cyclohexanecarboxylic acid

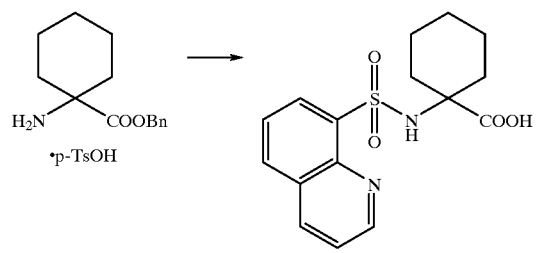

The same procedure as in Reference Example 21 was repeated except that the 4-nitrobenzenesulfonylchloride was replaced by 4.5 g of quinoline-8-sulfonylchloride, whereby 4.9 g of the captioned 1-[N-(quinoline-8-sulfonyl)amino]cyclohexanecarboxylic acid was obtained in a yield of 57.7%.

1H-NMR (CDCl$_3$, δ): 1.08–1.24 (4H, m), 1.33–1.37 (2H, m), 1.85–1.86 (4H, m), 7.54 (1H, dd, J=4 Hz, 8 Hz), 7.69 (1H, d, J=8 Hz), 8.01 (1H, dd, J=2 Hz, 8 Hz), 8.26 (1H, dd, J=1 Hz, 8 Hz), 8.31 (1H, dd, J=1 Hz, 8 Hz), 9.01 (1H, dd, J=2 Hz, 4 Hz).

Reference Example 25

Synthesis of 1-[N-(morpholine-4-sulfonyl)amino]cyclohexanecarboxylic acid

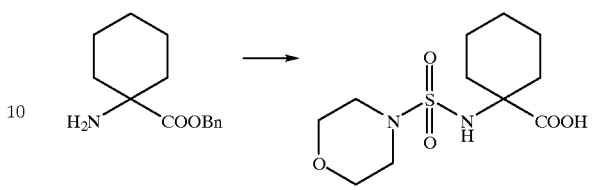

Under an ice-cooled, dichloromethane solution containing 12 ml (0.15 mol) of sulfurylchloride was cooled, dichloromethane solution containing 21 ml (0.15 mol) of triethylamine and 13 ml (0.15 mol) of morpholine was added dropwise over a period one hour. After stirring for 2 hour, the reaction mixture was washed cooled-0.1N hydrochloric acid and saturated brine and then was dried over anhydrous sodium sulfate, and concentrated under reduced pressure. The residue thus obtained was chromatographed on silica gel column for purification, whereby 20.54 g of morpholine-4-sulfonylchloride was obtained.

Subsequently, the same procedure as in Reference Example 8 was repeated except that the 4-(t-butoxycarbonylamino)piperazine-1-carbonylchloride was replaced by 3.65 g of said morpholine-4-sulfonylchloride, whereby 0.98 g of the captioned 1-[N-(morpholine-4-sulfonyl)amino]cyclohexanecarboxylic acid was obtained in a yield of 16%.

1H-NMR(CDCl$_3$, δ): 1.30–1.42(1H,m), 1.58–1.62(5H, m), 1.90–2.00 (4H, m), 3.23 (4H, t, J=5 Hz), 3.73 (4H, t, J=5 Hz), 4.62 (1H, s).

Reference Example 26

Synthesis of 1-[N-[(4-acetylpiperazine-1-sulfonyl)]amino]cyclohexanecarboxylic acid

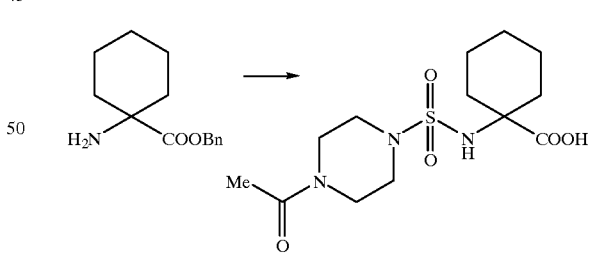

The same procedure as in Reference Example 25 was repeated except that the morpholine was replaced by 5.53 g of 1-acetylpiperazinesulfonylchloride, whereby 1.99 g of the captioned 1-[N-[(4-acetylpiperazine-1-sulfonyl)]amino]cyclohexanecarboxylic acid was obtained in a yield of 23%.

1H-NMR (CDCl$_3$, δ): 1.30–1.40 (1H, m), 1.48–1.70 (5H, m), 1.80–2.00 (4H, m), 2.10 (3H, s), 3.18 (2H, t, J=7 Hz), 3.23 (2H, t, J=7 Hz), 3.52 (2H, t, J=7 Hz), 3.66 (2H, t, J=7 Hz), 6.14 (1H, s).

Reference Example 27

Synthesis of 1-[N-(pyridine-3-sulfonyl)amino]cyclohexanecarboxylic acid

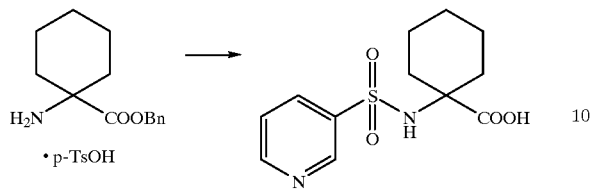

The same procedure as in Reference Example 21 was repeated except that the 4-nitrobenzenesulfonylchloride was replaced by 2.74 g of pyridine-3-sulfonylchloride, whereby 1.60 g of the captioned 1-[N-(pyridine-3-sulfonyl)amino]cyclohexanecarboxylic acid was obtained in a yield of 28%.

1H-NMR (DMSO-d6, δ): 1.18–1.40 (4H, m), 1.44–1.54 (2H, m), 1.70–1.72 (4H, m), 7.54 (1H, dd, J=5 Hz, 8 Hz), 8.16 (1H, dd, J=2 Hz, 8 Hz), 8.75 (1H, dd, J=1 Hz, 5 Hz), 8.94 (1H, d, J=2 Hz).

Reference Example 28

Synthesis of (2RS,3S)-2-hydroxy-3-[N-[1-[N-(4-acetylpiperazine-1-carbonyl)amino]cyclohexanecarbonyl]amino]heptanoic acid

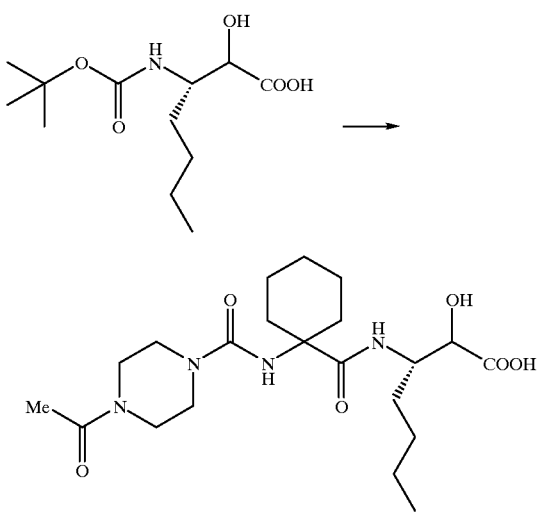

The same procedure as in Reference Example 17 was repeated except that the 1-[N-(morpholine-4-carbonyl)amino]cyclohexanecarboxylic acid was replaced by 595 mg of 1-[N-(4-acetylpiperazine-1-carbonyl)amino]cyclohexanecarboxylic acid synthesized in Reference Example 10, whereby 1.0 g of the captioned (2RS,3S)-2-hydroxy-3-[N-[1-[N-(4-acetylpiperazine-1-carbonyl)amino]cyclohexanecarbonyl]amino]heptanoic acid was obtained in a yield of 99%.

1H-NMR (d-DMSO, δ): 0.80–0.89 (3H, m), 1.18–1.72 (16H, m), 1.92–2.03 (3H, s), 3.29–4.19 (1 1H, m), 6.29 (1/2H, s), 6.31 (1/2H, s), 7.15–7.50 (1H, m).

Reference Example 29

Synthesis of 1-[N-(4-acetylaminobenzenesulfonyl)amino]cyclohexanecarboxylic acid

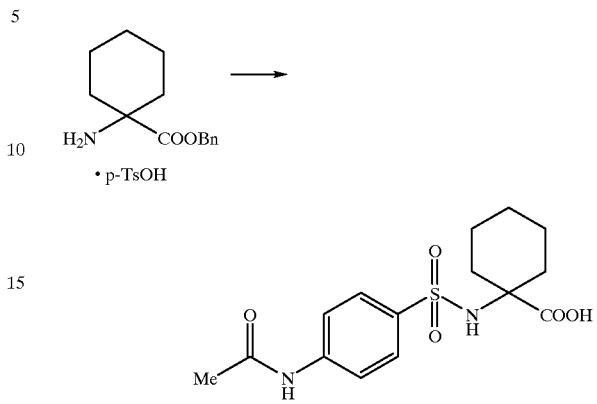

The same procedure as in Reference Example 21 was repeated except that the 4-methoxybenzenesulfonylchloride was replaced by 11.7 g of 4-acetylaminobenzenesulfonylchloride, whereby 11.5 g of phenylmethyl 1-[N-(4-acetylaminobenzenesulfonyl)amino]cyclohexanecarboxylate was synthesized.

The same procedure as in Reference Example 8 was repeated except that the phenylmethyl 1-[N-[4-(2-methyl-2-propyloxycarbonyl)piperazine-1-carbonyl]amino]cyclohexanecarboxylate was replaced by 11.5 g of said phenylmethyl 1-[N-(4-acetylaminobenzenesulfonyl)amino]cyclohexanecarboxylate, whereby 8.7 g of the captioned 1-[N-(4-acetylaminobenzenesulfonyl)amino]cyclohexanecarboxylic acid was obtained in a yield of 97%.

1H-NMR (CDCl₃, δ): 1.13–1.31 (6H, m), 1.61–1.66 (2H, m), 1.76–1.80 (2H, m), 2.08 (3H, s), 7.68–7.73 (5H, m), 10.29 (1H, s).

Example 51

Synthesis of N-[(S)-1-(N-cyclopentylamino)-1,2-dioxo-5-methyl-3-hexyl]-1-[N-(morpholine-4-carbonyl)amino]cyclohexanecarboxamide

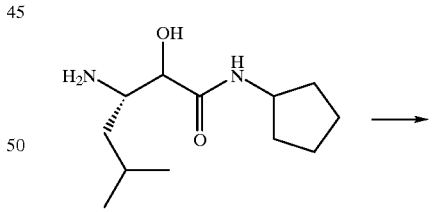

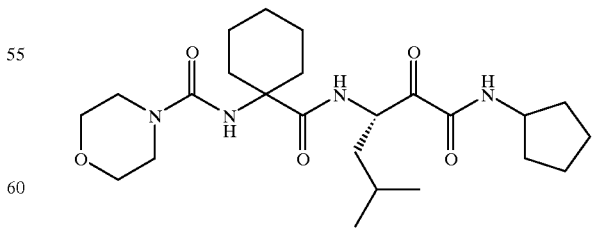

The same procedure as in Example 1 was repeated except that the (2RS,3S)-N-(2-methyl-2-propyl)-3-amino-2-hydroxyheptanamide was replaced by 571 mg of (2RS,3S)-N-cyclopentyl-3-amino-2-hydroxy-5-methylhexanamide synthesized in Reference Example 20, whereby 689 mg of the captioned N-[(S)-1-(N-cyclopentylamino)-1,2-dioxo-5-methyl-3-hexyl]-1-[N-(morpholine-4-carbonyl) amino] cyclohexanecarboxamide was obtained in a yield of 59%.

1H-NMR (CDCl$_3$, δ): 0.94 (3H, d, J=7 Hz), 0.99 (3H, d, J=7 Hz), 1.28–1.80 (14H, m), 1.86–2.15 (7H, m), 3.38 (4H, t, J=5 Hz), 3.72 (4H, t, J=5 Hz), 4.10–4.21 (1H, m), 4.42 (1H, s), 5.19–5.25 (1H, m), 6.80 (1H, d, J=8 Hz), 7.90 (1H, d, J=7 Hz)

IR (ν, KBr, cm$^{-1}$): 3840, 2360, 1732, 1334, 1150, 1072, 1016

Rf: 0.54.

Example 52

Synthesis of N-[(S)-1-(N-cyclopentylamino)-1,2-dioxo-5-methyl-3-hexyl]-1-[N-1(4-methoxycarbonyl) piperazine-1-carbonyl]amino] cyclohexanecarboxamide

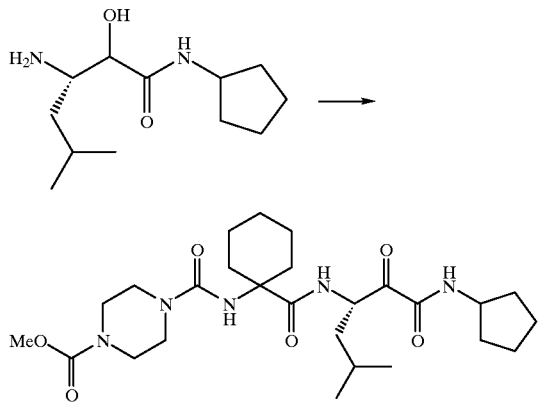

The same procedure as in Example 5 was repeated except that the (2RS,3S)-N-cyclopentyl-3-amino-2-hydroxyheptanamide was replaced by 343 mg of (2RS,3S)-N-cyclopentyl-3-amino-2-hydroxy-5-methylhexanamide synthesized in Reference Example 20, whereby 416 mg of the captioned N-[(S)-1-(N-cyclopentylamino)-1,2-dioxo-5-methyl-3-hexane]-1-[N-(4-methoxycarbonyl) piperazine-1-carbonyl]amino] cyclohexanecarboxamide was obtained in a yield of 53%.

1H-NMR (CDCl$_3$, δ): 0.93 (3H, d, J=7 Hz), 0.99 (3H, d, J=7 Hz), 1.23–1.50 (6H, m), 1.55–1.78 (8H, m), 1.83–2.14 (7H, m), 3.37–3.45 (4H, m), 3.53 (4H, br-s), 3.73 (3H, s), 4.10–4.21 (1H, m), 4.44 (1H, s), 5.19–5.25(1H, m), 6.80 (1H, d, J=8 Hz), 7.84 (1H, d, J=7 Hz)

IR (ν, KBr, cm$^{-1}$): 3392, 2872, 1372, 1286, 1192, 1172, 1118

Rf: 0.54.

Example 53

Synthesis of N-[(S)-1-(N-cyclopentylamino)-1,2-dioxo-3-heptyl]-1-[N-(4-methoxybenzenesulfonyl)amino] cyclobexanecarboxamide

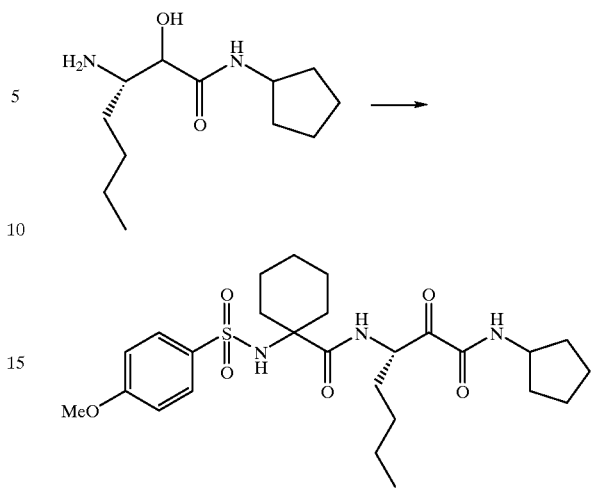

The same procedure as in Example 2 was repeated except that the 1-[N-(morpholine-4-carbonyl)amino]cyclohexane carboxylic acid was replaced 450 mg of 1-[N-(4-methoxybenzenesulfonyl)amino]cyclohexane carboxylic acid synthesized in Reference Example 21, whereby 407 mg of captioned N-[(S)-1-(N-cyclopentylamino)-1,2-dioxo-3-heptyl]-1-[N-(4-methoxybenzenesulfonyl)amino] cyclohexanecarboxamide was obtained in a yield 56%.

1H-NMR (CDCl$_3$, δ): 0.87–0.92 (3H, m), 1.24–1.52 (13H, m), 1.65–1.76 (4H, m), 1.85–2.05 (7H, m), 4.23 (3H, s), 4.98 (1H, s), 4.16–4.21 (1H, m), 5.08 (1H, ddd, J=5 Hz, 8 Hz, 13 Hz), 6.85 (1H, d, J=8 Hz), 6.93 (2H, dd, J=2 Hz, 7 Hz), 7.04 (1H, d, J=7 Hz), 7.80 (2H, dd, J=2 Hz, 7 Hz)

IR (ν, KBr, cm$^{-1}$): 3330, 2954, 1664, 1498, 1455, 1328, 1259, 1149

Rf: 0.34.

Example 54

Synthesis of N-[(S)-1-(N-cyclopentylamino)-1,2-dioxo-3-heptyl]-1-[N-(4-nitrobenzenesulfonyl)amino] cyclohexanecarboxamide

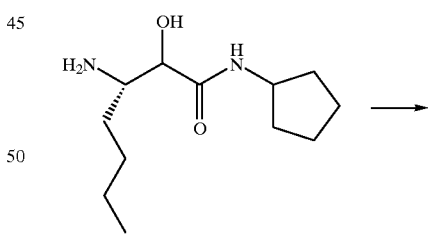

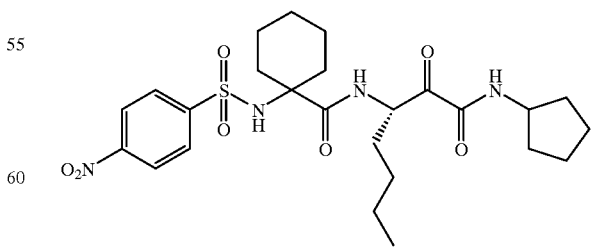

The same procedure as in Example 53 was repeated except that the 1-[N-(4-methoxybenzenesulfonyl)amino] cyclohexane carboxylic acid was replaced by 463 mg of 1-[N-(4-nitrobenzenesulfonyl)aminocyclohexane carboxylic acid synthesized in Reference Example 22, whereby 266 mg of the captioned N-[(S)-1-(N-cyclopentylamino)-1,2-dioxo-3-heptyl]-1-[N-(4-nitrobenzenesulfonyl)amino]cyclohexanecarboxamide was obtained in a yield of 30%.

1H-NMR (CDCl$_3$, δ): 0.88 (3H, t, J=7 Hz), 1.22–1.39 (6H, m), 1.44–1.51 (5H, m), 1.62–1.72 (5H, m), 1.85–2.05 (8H, m), 4.15–4.24 (1H, m), 5.11 (1H, ddd, J=5 Hz, 8 Hz, 13 Hz), 6.10 (1H, s), 6.92 (1H, d, J=8 Hz), 7.13 (1H, d, J=8 Hz), 8.10 (2H, d, J=9 Hz), 8.33 (2H, d, J=9 Hz)

IR (ν, KBr, cm$^{-1}$): 3347, 2954, 1664, 1531, 1349, 1168

Rf: 0.34.

Example 55

Synthesis of N-[(S)-1-(N-cyclopentylamino)-1,2-dioxo-4-methy]-3-pentyl]-1-[N-[(4-acetyl)piperazine-1-carbonyl]amino]cyclohexanecarboxamide

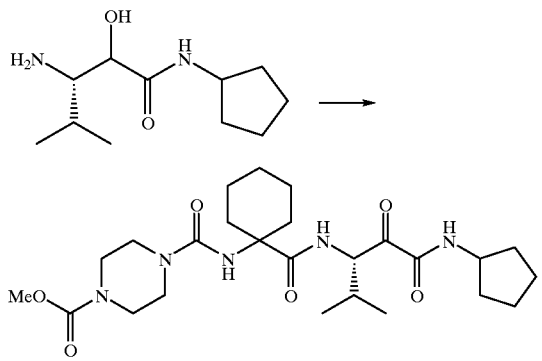

The same procedure as in Example 6 was repeated except that the (2RS,3S)-N-cyclopentyl-3-amino-2-hydroxyheptanamide was replaced by 321 mg of (2RS, 3S)-N-cyclopentyl-3-amino-2-hydroxy-4-methylpentanamide synthesized in Reference Example 15, whereby 190 mg of the captioned N-[(S)-1-(N-cyclopentylamino)-1,2-dioxo-4-methyl-3-pentyl]-1-[N-[(4-acetyl)piperazine-1-carbonyl]amino]cyclohexanecarboxamide was obtained in a yield of 26%.

1H-NMR (CDCl$_3$, δ): 0.84 (3H, d, J=7 Hz), 1.01 (3H, d, J=7 Hz), 1.28–1.50 (6H, m), 1.66–1.75 (5H, m), 1.86–2.20 (7H, m), 2.13 (3H, s), 2.35–2.45 (1H, m), 3.37–3.51 (2H, m), 3.47–3.53 (4H, m), 3.65–3.71 (2H, m), 4.08–4.20 (1H, m), 4.51 (1H, s), 5.15 (1H, dd, J=8 Hz, 8 Hz), 6.82 (1H, d, J=8 Hz), 7.90 (1H, d, J=8 Hz)

IR (ν, KBr, cm$^{-1}$): 3856, 3760, 2108, 1730, 1468, 1374, 1200

Rf: 0.67.

Example 56

Synthesis of N-[(S)-1-(N-cyclopentylmethylamino)-1,2-dioxo-5-methyl-3-hexyl]-1-[N-(4-acetylpiperazine-1-carbonyl)amino]cyclohexanecarboxamide

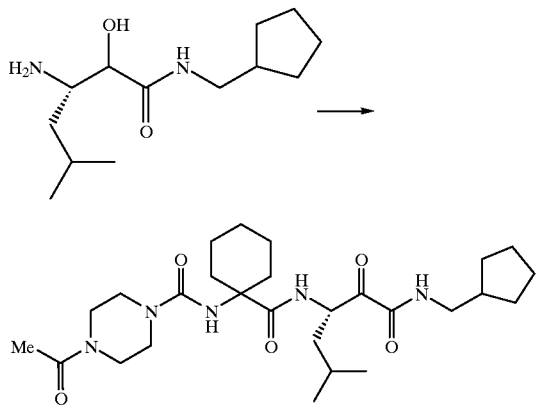

The same procedure as in Example 6 was repeated except that the (2RS,3S)-N-cyclopentyl-3-amino-2-hydroxyheptanamide was replaced by 343 mg of the (2RS, 3S)-N-cyclopentylmethyl-3-amino-2-hydroxy-5-methylhexanamide synthesized in Reference Example 23, whereby 304 mg of captioned N-[(S)-1-(N-cyclopentylmethylamino)-1,2-dioxo-5-methyl-3-hexyl]-1-[N-(4-acetylpiperazine-1-carbonyl) amino]cyclohexanecarboxamide was obtained in a yield 47%.

1H-NMR (CDCl$_3$, δ): 0.93 (3H, d, J=6 Hz), 0.98 (3H, d, J=6 Hz), 1.15–1.43 (6H, m), 1.52–1.77 (10H, m), 1.84–1.92 (2H, m), 2.02–2.10 (3H, m), 2.13 (3H, s), 3.10–3.16 (1H, m), 3.20–3.24 (2H, m), 3.38–3.40 (2H, m), 3.50 (4H, d, J=2 Hz), 3.67–3.70 (2H, m), 4.53 (1H, s), 5.19–5.24 (1H, m), 6.93 (1H, t, J=5 Hz), 7.78 (1H, d, J=7 Hz)

IR (ν, KBr, cm$^{-1}$): 3343, 2950, 1654, 1631, 1251

Rf: 0.56.

Example 57

Synthesis of N-[(S)-1-(N-cyclopentylamino)-1,2-dioxo-3-heptyl]-1-[N-(quinoline-8-sulfonyl)amino]cyclohexanecarboxamide

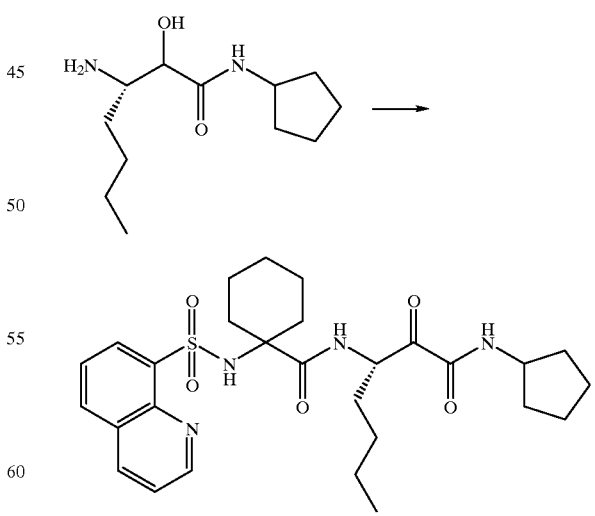

The same procedure as in Example 53 was repeated except that the 1-[N-(4-methoxybenzenesulfonyl)amino]cyclohexane carboxylic acid was replaced by 669 mg of 1-[N-(quinoline-8-sulfonyl)amino]cyclohexane carboxylic acid synthesized in Reference Example 24, whereby 520 mg of the captioned N-[(S)-1-(N-cyclopentylamino)-1,2-dioxo-3-heptyl]-1-[N-(quinoline-8-sulfonyl)amino] cyclohexanecarboxamide was obtained in a yield of 48%.

1H-NMR (CDCl$_3$, δ): 0.91 (3H, t, J=7 Hz), 1.24–1.49 (9H, m), 1.58–1.74 (7H, m), 1.86–2.08 (8H, m), 4.17–4.22 (1H, m), 5.24–5.30 (1H, m), 6.86 (1H, d, J=8 Hz), 7.09 (1H, s), 7.32 (1H, d, J=7 Hz), 7.59–7.66 (2H, m), 8.05 (1H, d, J=7 Hz), 8.31–8.36 (2H, m), 9.09 (1H, dd, J=2 Hz, 4 Hz)

IR (ν, KBr, cm$^{-1}$): 3340, 3266, 2954, 2935, 2857, 1679, 1644, 1508, 1324, 1170,1143

Rf: 0.53.

Example 58

Synthesis of N-[(S)-1-(N-cyclopentylamino)-1,2-dioxo-5-methyl-3-hexyl]-1-[N-[(4-acetyl)piperazine-1-carbonyl]amino]cyclohexanecarboxamide

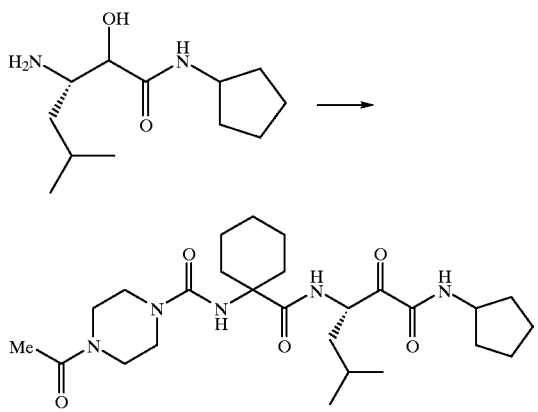

The same procedure as in Example 6 was repeated except that the (2RS,3S)-N-cyclopentyl-3-amino-2-hydroxyheptanamide was replaced by 343 mg of (2RS,3S)-N-cyclopentyl-3-amino-2-hydroxy-5-methylhexanarmide synthesized in Reference Example 20, whereby 345 mg of the captioned N-[(S)-1-(N-cyclopentylamino)-1,2-dioxo-5-methyl-3-hexyl1-1-[N-[(4-acetyl)piperazine-1-carbonyl]amino]cyclohexanecarboxamide was obtained in a yield of 44%.

1H-NMR (CDCl$_3$, δ): 0.94 (3H, d, J=7 Hz), 0.97 (3H, d, J=7 Hz), 1.25–1.57 (6H, m), 1.58–1.80 (8H, m), 1.85–2.20 (7H, m), 2.13 (3H, s), 3.37–3.41 (2H, m), 3.47–3.51 (4H, m), 3.66–3.70 (2H, m), 4.10–4.20 (1H, m), 4.52 (1H, s), 5.19–5.25 (1H, m), 6.82 (1H, d, J=8 Hz), 7.78 (1H, d, J=7 Hz)

IR (ν, KBr, cm$^{-1}$): 3904, 1730, 1370, 1286, 1202, 1172, 1104

Rf: 0.62.

Example 59

Synthesis of N-[(S)-1-(N-cyclopentylamino)-1,2-dioxo-3-heptyl]-1-[N-(morpholine-4-sulfonyl)amino]cyclohexanecarboxamide

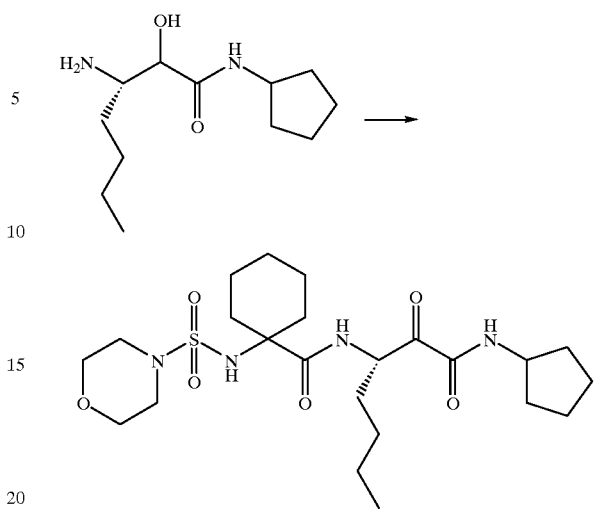

The same procedure as in Example 2 was repeated except that the 1-[N-[4-(morpholine-4-carbonyl)]amino] cyclohexane carboxylic acid was replaced by 0.49 g of 1-[N-(morpholine-4-sulfonyl)amino]cyclohexane carboxylic acid synthesized in Reference Example 25, whereby 0.64 g of the captioned N-[(S)-1-(N-cyclopentylamino)-1,2-dioxo-3-heptyl]-1-[N-(morpholine-4-sulfonyl)amino]cyclohexanecarboxamide was obtained in a yield of 76%.

1H-NMR (CDCl$_3$, δ): 0.88 (3H, t, J=7H), 1.20–1.50 (8H, m), 1.58–1.80 (9H, m), 1.90–2.10 (7H, m), 3.22 (4H, t, J=4 Hz), 3.72 (4H, t, J=4 Hz), 4.14–4.20 (1H, m), 4.54 (1H, s), 5.21–5.26 (1H, m), 6.82 (1H, d, J=8 Hz), 6.93 (1H, d, J=8 Hz)

IR (ν, KBr, cm$^{-1}$): 3336, 3270, 2956, 2931, 2861, 1725, 1671, 1521, 1454

Rf: 0.47.

Example 60

Synthesis of N-[(S)-1-(N-cyclopentylamino)-1,2-dioxo-5-methyl-3-hexyl]-1-[N-(morpholine-4-sulfonyl)amino]cyclohexanecarboxamide

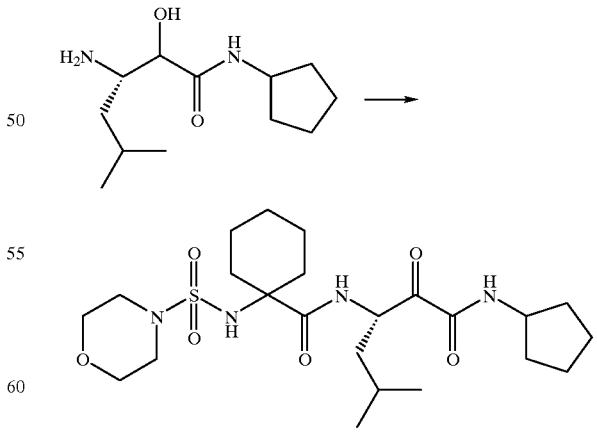

The same procedure as in Example 51 was repeated except that the 1-[N-(morpholine-4-carbonyl)amino] cyclohexane carboxylic acid was replaced by 0.49 g of 1-[N-(morpholine-4-sulfonyl)amino]cyclohexane carboxylic acid synthesized in Reference Example 25, whereby 0.63 g of the captioned N-[(S)-1-(N-cyclopentylamino)-1,2-dioxo-5-methyl-3-hexyl]-1-[N-(morpholine-4-sulfonyl)amino]cyclohexanecarboxamide was obtained in a yield of 74%.

1H-NMR (CDCl₃, δ): 0.95 (3H, d, J=6H), 1.01 (3H, d, J=6H), 1.20–1.80 (15H, m), 1.90–2.10 (6H, m), 3.22 (4H, t, J=5 Hz), 3.72 (4H, t, J=5 Hz), 4.10–4.20 (1H, m), 4.51 (1H, s), 5.20–5.30 (1H, m), 6.82 (1H, d, J=7 Hz), 6.86 (1H, d, J=7 Hz)

IR (ν, KBr, cm⁻¹): 3394, 3340, 3261, 2958, 2865, 1725, 1671, 1523, 1454

Rf: 0.48.

Example 61

Synthesis of N-[(S)-1-(N-cyclopentylamino)-1,2-dioxo-3-heptyl]-1-[N-(4-acetylpiperazine-1-sulfonyl)amino]cyclohexanecarboxamide

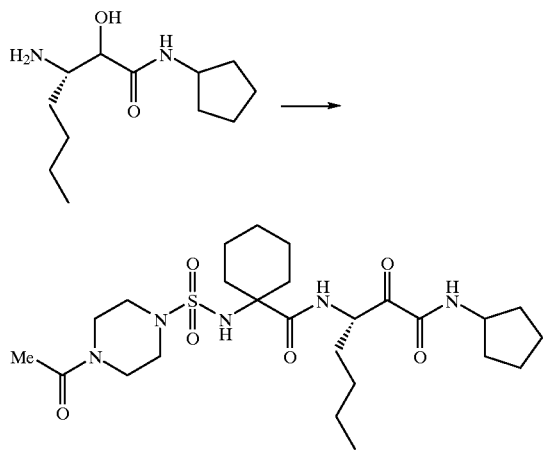

The same procedure as in Example 59 was repeated except that the 1-[N-(morpholine-4-sulfonyl)amino]cyclohexane carboxylic acid was replaced by 0.5 g of 1-[N-(4-acetylpiperazine-1-sulfonyl)aminocyclohexane carboxylic acid synthesized in Reference Example 26, whereby 0.35 g of the captioned N-[(S)-1-(N-cyclopentylamino)-1,2-dioxo-3-heptyl]-1-[N-(4-acetylpiperazine-1-sulfonyl)amino]cyclohexanecarboxamide was obtained in a yield of 43%.

1H-NMR (CDCl₃, δ): 0.88 (3H, t, J=7H), 1.31–1.80 (17H, m), 1.88–2.10 (7H, m), 2.11 (3H, s), 3.20–3.30 (4H, m), 3.50–3.57 (2H, m), 3.60–3.70 (2H, m), 4.10–4.20 (1H, m), 4.70 (1H, s), 5.20–5.25 (1H, m), 6.86 (1H, d, J=8 Hz), 6.91 (1H, d, J=8 Hz)

IR (ν, KBr, cm⁻¹): 3334, 3266, 2956, 2933, 2867, 1727, 1668, 1646, 1525, 1450

Rf: 0.60.

Example 62

Synthesis of N-[(S)-1-(N-cyclopentylamino)-1,2-dioxo-5-methy]-3-hexyl]-1-[N-(4-acetylpiperazine-1-sulfonyl)amino]cyclohexanecarboxamide

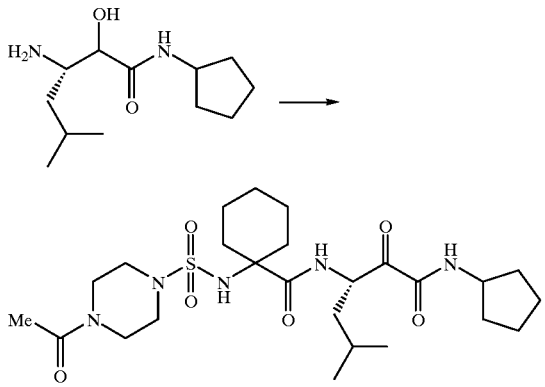

The same procedure as in Example 60 was repeated except that the 1-[N-[4-(morpholine-4-sulfonyl)]amino]cyclohexane carboxylic acid was replaced by 0.5 g of 1-[N-(4-acetylpiperazine-1-sulfonyl)amino]cyclohexane carboxylic acid synthesized in Reference Example 26, whereby 0.4 g of the captioned N-[(S)-1-(N-cyclopentylamino)-1,2-dioxo-5-methyl-3-hexyl-1-[N-(4-acetylpiperazine-1-sulfonyl)amino]cyclohexanecarboxamide was obtained in a yield of 50%.

1H-NMR (CDCl₃, δ): 0.95 (3H, d, J=6H), 1.00 (3H, d, J=6H), 1.30–2.10 (21H, m), 2.11 (3H, s), 3.20–3.30 (4H, m), 3.50–3.57 (2H, m), 3.60–3.70 (2H, m), 4.10–4.20 (1H, m), 4.51 (1H, s), 5.20–5.30 (1H, m), 6.84 (1H, d, J=8 Hz), 6.87 (1H, d, J=8 Hz)

IR (ν, KBr, cm⁻¹): 3340, 3266, 2956, 2869, 1727, 1671, 1641, 1521, 1430

Rf: 0.61.

Example 63

Synthesis of N-[(S)-1-(N-cyclopentylamino)-1,2-dioxo-4-methyl-3-pentyl]-1-[N-(4-acetylpiperazine-1-sulfonyl)amino]cyclohexanecarboxamide

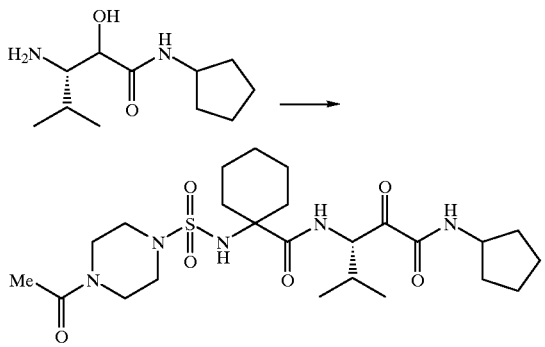

The same procedure as in Example 15 was repeated except that the 1-[N-[4-(morpholine-4-carbonyl)]amino]cyclohexane carboxylic acid was replaced by 0.5 g of 1-[N-(4-acetylpiperazine-1-sulfonyl)amino]cyclohexane carboxylic acid synthesized in Reference Example 26, whereby 0.41 g of the captioned N-[(S)-1-(N-cyclopentylamino)-1,2-dioxo-4-methyl-3-pentyl]-1-[N-(4-acetylpiperazine-1-sulfonyl)amino]cyclohexanecarboxamide was obtained in a yield of 50%.

1H-NMR (CDCl₃, δ): 0.88 (3H, d, J=7H), 1.01 (3H, d, J=7H), 1.30–1.80 (12H, m), 1.90–2.05 (6H, m), 2.11 (3H, s), 2.36–2.43 (1H, m), 3.20–3.25 (4H, m), 3.46–3.51 (2H, m), 3.60–3.70 (2H, m), 4.13–4.18 (1H, m), 4.64 (1H, s), 5.12–5.15 (1H, m), 6.86 (1H, d, J=8 Hz), 7.00 (1H, d, J=8 Hz)

IR (ν, KBr, cm$^{-1}$): 3384, 3261, 2958, 2865, 1737, 1670, 1633, 1536, 1508, 1450

Rf: 0.63.

Example 64

Synthesis of N-[(S)-1-[N-(2,2-dimethylpropyl)amino]-1,2-dioxo-3-heptyl]-1-[N-(morpholine-4-carbonyl)amino]cyclohexanecarboxamide

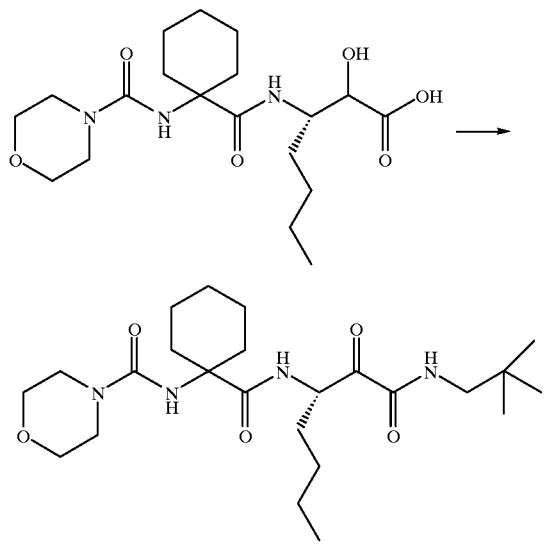

The same procedure as in Example 28 was repeated except that the 3-chlorobenzylamine was replaced by 174 mg of neopentylamine, whereby 367 mg of the captioned N-[(S)-1-[N-(2,2-dimethyl-propyl)amino]-1,2-dioxo-3-heptyl]-1-[N-(morpholine-4-carbonyl)amino]cyclohexanecarboxamide was obtained in a yield of 38%.

1H-NMR (CDCl$_3$, δ): 0.88–0.90 (3H, m), 0.92 (9H, s), 1.08–1.42 (7H, m), 1.65–1.71 (4H, m), 1.86–1.99 (3H, m), 2.00–2.12 (2H, m), 3.04–3.15 (2H, m), 3.39 (4H, t, J=5 Hz), 3.72 (4H, t, J=5 Hz), 4.46 (1H, s), 5.18 (1H, ddd, J=5 Hz, 7 Hz, 8 Hz), 6.96 (1H, t, J=6 Hz), 7.95 (1H, d, J=7 Hz)

IR (ν, KBr, cm$^{-1}$): 3340, 2958, 2929, 1677, 1608, 1531, 1261, 1116

Rf: 0.48.

Example 65

Synthesis of N-[(S)-1-(N-cyclopentylamino)-1,2-dioxo-3-heptyl]-1-[N-(pyridine-3-sulfonyl)amino]cyclohexanecarboxamide

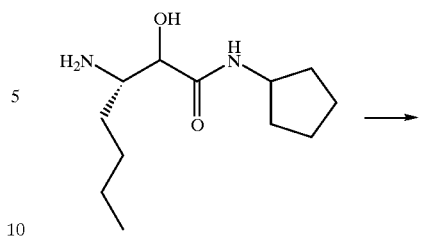

The same procedure as in Example 53 was repeated except that the 1-[N-(4-methoxybenzenesulfonyl)amino]cyclohexane carboxylic acid was replaced by 1.1 g of 1-[N-(pyridine-3-sulfonyl)amino]cyclohexane carboxylic acid synthesized in Reference Example 27, whereby 248 mg of the captioned N-[(S)-1-(N-cyclopentylamino)-1,2-dioxo-3-heptyl]-1-[N-(pyridine-3-sulfonyl)amino]cyclohexanecarboxamide was obtained in a yield of 13%.

1H-NMR (CDCl$_3$, δ): 0.86–0.93 (3H, m), 1.26–1.36 (7H, m), 1.47–1.51 (5H, m), 1.60–1.72 (5H, m), 1.84–2.06 (7H, m), 4.19–4.23 (1H, m), 4.98–5.04 (1H, m), 5.50 (1H, s), 6.93 (1H, d, J=8 Hz), 7.01 (1H, dt, J=2 Hz, 8 Hz), 7.43 (1H, ddd, J=1 Hz, 5 Hz, 8 Hz), 8.15 (1H, dt, J=2 Hz, 8 Hz), 8.75 (1H, dt, J=2 Hz, 5 Hz), 9.06 (1H, d, J=2 Hz)

IR (ν, KBr, cm$^{-1}$): 3355, 2956, 1668, 1525, 1170

Rf: 0.48.

Example 66

Synthesis of N-[(S)-1-(N-cyclopentylmethylamino)-1,2-dioxo-3-heptyl]-1-[N-(4-acetylpiperazine-1-carbonyl)amino]cyclohexanecarboxamide

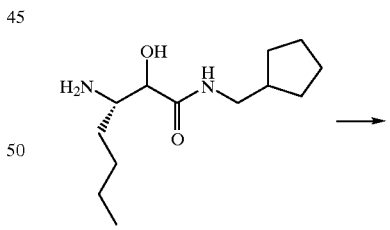

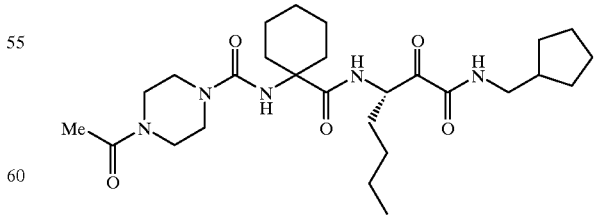

The same procedure as in Example 28 was repeated except that the (2RS,3S)-2-hydroxy-3-[1-[N-[N-(morpholine-4-carbonyl)amino]cyclohexanecarbonyl]amino]heptanoic acid was replaced by 881 mg of (2RS,3S)-

2-hydroxy-3-[N-[1-[N-(4-acetylpiperazine-1-carbonyl) amino]cyclohexanecarbonyl]amino]heptanoic acid synthesized in Reference Example 28 and the 3-chlorobenzylamine was replaced by 496 mg of cyclopentylmethylamine, whereby 64 mg of the captioned N-[(S)-1-(N-cyclopentylmethylamino)-1,2-dioxo-3-heptyl]-1-[N-(4-acetylpiperazine-1-carbonyl) amino] cyclohexanecarboxamide was obtained in a yield of 11%.

1H-NMR (CDCl₃, δ): 0.86–0.90 (3H, m), 1.17–1.44 (9H, m), 1.53–1.77 (8H, m), 1.86–2.14 (10H, m), 3.22 (2H, dd, J=6 Hz, 7 Hz), 3.34–3.41 (2H, m), 3.45–3.51 (5H, m), 3.67–3.70 (2H, m), 4.52 (1H, s), 5.17–5.22 (1H, m), 6.90 (1H, t, J=6 Hz), 7.79 (1H, d, J=7 Hz)

IR (ν, KBr, cm⁻¹): 3353, 2952, 1629, 1529, 1444, 1250

Rf: 0.51.

Example 67

Synthesis of N-[(S)-1-(N-cyclopentylamino)-1,2-dioxo-3-heptyl]-1-[N-( 4-acetylaminobenzene-1-sulfonyl)amino] cyclohexanecarboxamide

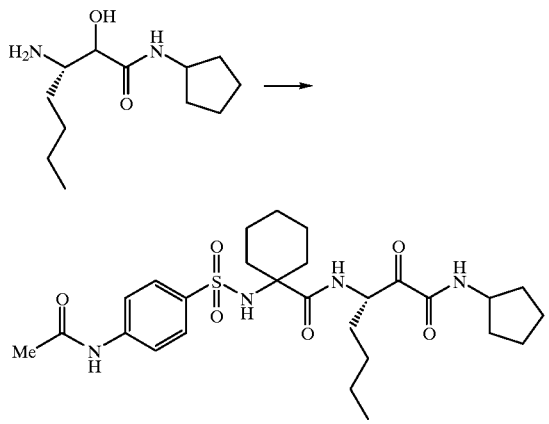

The same procedure as in Example 53 was repeated except that the 1-[N-(4-methoxybenzenesulfonyl)amino] cyclohexane carboxylic acid was replaced by 511 mg of 1-[N-(4-acetylaminobenzenesulfonyl)amino]cyclohexane carboxylic acid synthesized in Reference Example 29, whereby 526 mg of the captioned N-[(S)-1-(N-cyclopentylamino)-1,2-dioxo-3-heptyl]-1-[N-(4-acetylaminobenzene-1-sulfonyl) amino] cyclohexanecarboxamide was obtained in a yield of 63%.

1H-NMR (CDCl₃, δ): 0.85–0.87 (3H, m), 1.24–1.35 (7H, m), 1.46–1.60 (5H, m), 1.63–2.05 (12H, m), 2.23 (3H, s), 4.11–4.21 (1H, m), 4.90–4.95 (1H, m), 5.00 (1H, s), 6.98 (1H, d, J=8 Hz), 7.08 (1H, d, J=8 Hz), 7.55 (1H, s), 7.61 (2H, d, J=9 Hz), 7.78 (2H, dd, J=2 Hz, 7 Hz)

IR (ν, KBr, cm⁻¹): 3334, 2952, 1656, 1592, 1531, 1402, 1324, 1151, 1095

Rf: 0.58.

Example 68

Synthesis of N-[(S)-1,2-dioxo-1-[N-(1-hydroxycyclohexylmethyl)amino]-3-heptyl]-1-[N-(morpholine-4-carbonyl)amino]cyclohexanecarboxamide

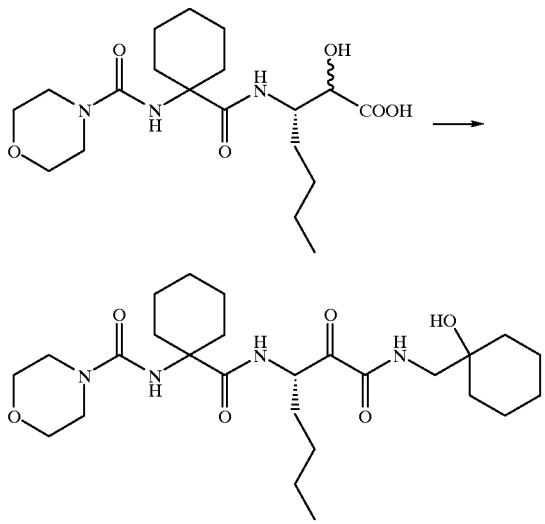

The same procedure as in Example 28 was repeated except that the 3-chlorobenzylamine was replaced by 258 mg of 1-hydroxycyclohexylmethylamine, whereby 140 mg of the captioned N-[(S)-1,2-dioxo-1-[N-(1-hydroxycyclohexylmethyl)amino]-3-heptyl]-1-[N-(morpholine-4-carbonyl)amino]cyclohexanecarboxamide was obtained in a yield of 18%.

1H-NMR (CDCl₃, δ): 0.88 (3H, t, J=7 Hz), 1.26–1.44 (11H, m), 1.52–1.71 (9H, m), 1.84–1.97 (3H, m), 2.04–2.11 (3H, m), 3.30 (2H, d, J=6 Hz), 3.38 (4H, t, J=5 Hz), 3.71 (4H, t, J=5 Hz), 4.48 (1H, s), 5.06–5.11 (1H, m), 7.18 (1H, bs), 7.90 (1H, d, J=7 Hz)

IR (ν, KBr, cm⁻¹): 2931, 1664, 1631, 1529

Rf: 0.65.

Example 69

Synthesis of N-[(S)-1-(N-cyclopentylamino)-1,2-dioxo-3-heptyl]-1-[N-[(4-ethoxycarbonyl)piperazine-1-carbonyl] amino]cyclohexanecarboxamide

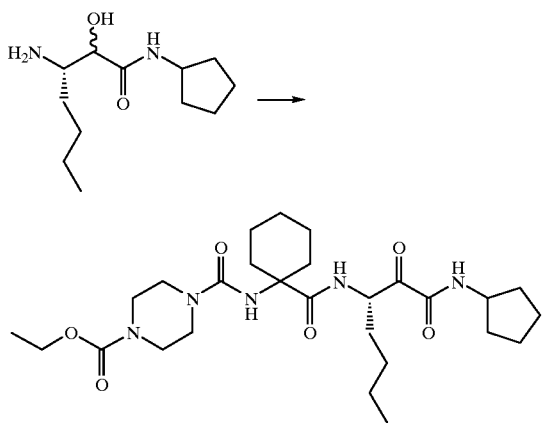

The same procedure as in Example 2 was repeated except that the 1-[N-(morpholine-4-carbonyl)amino] cyclohexanecarboxylic acid was replaced 982 mg of 1-[N-[(4-ethoxycarbonyl)piperazine-1-carbonyl]amino] cyclohexanecarboxylic acid synthesized by the same procedure as in Reference Example 8, whereby 767 mg of the captioned N-[(S)-1-(N-cyclopentylamino)-1,2-dioxo-3-heptyl]-1-[N-[( 4-ethoxycarbonyl)piperazine-1-carbonyl] amino]cyclohexanecarboxamide was obtained in a yield of 48%.

1H-NMR (CDCl₃, δ): 0.88 (3H, t, J=7 Hz), 1.20–1.51 (12H, m), 1.55–1.73 (8H, m), 1.82–2.04 (5H, m), 2.05–2.14 (2H, m), 3.37–3.42 (4H, m), 3.51–3.53 (4H, m), 4.13–4.19 (3H, m), 4.48 (1H, s), 5.18 (1H, ddd, J=12 Hz, 7 Hz, 5 Hz), 6.81 (1H, d, J=8 Hz), 7.88 (1H, d, J=7 Hz)

IR (ν, KBr, cm⁻¹): 3299, 2931, 1650, 1523

Rf: 0.49.

Example 70

Synthesis of N-[(S)-1-(N-cyclopentylamino)-1,2-dioxo-3-heptyl]-1-[N-[(4-methylsulfonyl)piperazine-1-carbonyl] amino]cyclohexanecarboxamide

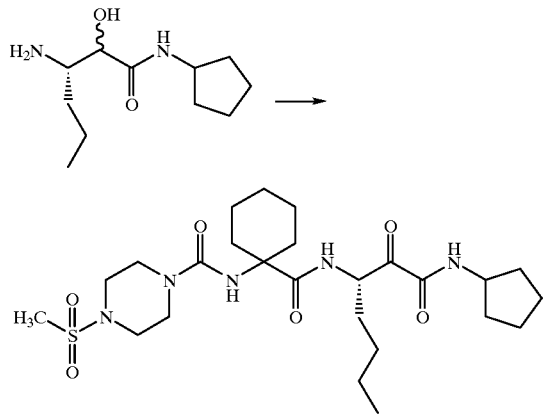

The same procedure as in Example 2 was repeated except that the 1-[N-(morpholine-4-carbonyl)amino] cyclohexanecarboxylic acid was replaced by the 667 mg of 1-[N-[(4-methylsulfonyl)piperazine-1-carbonyl]amino] cyclohexanecarboxylic acid synthesized by same procedure as in Reference Example 8, whereby 791 mg of the captioned N-[(S)-1-(N-cyclopentylamino)-1,2-dioxo-3-heptyl]-1-[N-[(4-methylsulfonyl)piperazine-1-carbonyl]amino] cyclohexanecarboxamide was obtained in a yield of 73%.

1H-NMR (CDCl₃, δ): 0.88 (3H, t, J=7 Hz), 1.23–1.50 (8H, m), 1.58–1.80 (9H, m), 1.83–2.18 (7H, m), 3.10 (3H, s), 3.26 (4H, t, J=5 Hz), 3.54 (4H, t, J=5 Hz), 4.11–4.21 (1H, m), 4.54 (1H, s), 5.19 (1H, ddd, J=12 Hz, 7 Hz, 5 Hz), 6.80(1H, d, J=8 Hz), 7.71 (1H, d, J=7 Hz)

IR (ν, KBr, cm⁻¹): 3318, 2954, 2933, 1654, 1529

Rf: 0.62.

Example 71

Synthesis of N-[(S)-1-(N-cyclopentylamino)-1,2-dioxo-3-heptyl]-1-[N-[(4-isobutyryl)piperazine-1-carbonyl] amino]cyclohexanecarboxamide

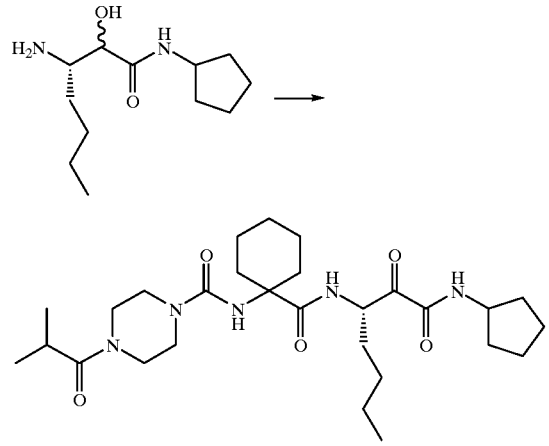

The same procedure as in Example 2 was repeated except that the 1-[N-(morpholine-4-carbonyl)amino] cyclohexanecarboxylic acid was replaced by the 416 mg of 1-[N-[(4-isobutyryl)piperazine-1-carbonyl]amino] cyclohexanecarboxylic acid synthesized by the same procedure as in Reference Example 8, whereby 349 mg of the captioned N-[(S)-1-(N-cyclopentylamino)-1,2-dioxo-3-heptyl]-1-[N-[(4-isobutyryl)piperazine-1-carbonyl]amino] cyclohexanecarboxamide was obtained in a yield of 51%.

1H-NMR (CDCl₃, δ): 0.88 (3H, t, J=7 Hz), 1.14 (6H, d, J=9 Hz), 1.21–2.18 (24H, m), 2.78–2.82 (1H, m), 3.30–3.70 (8H, m), 4.10–4.20 (1H, m), 4.48 (1H, s), 5.18 (1H, ddd, J=12 Hz, 7 Hz, 5 Hz), 6.79 (1H, d, J=8 Hz), 7.81 (1H, d, J=7 Hz)

IR (ν, KBr, cm⁻¹): 3332, 3266, 2960, 2861, 1733, 1666, 1614

Rf: 0.54.

Example 72

Synthesis of N-[(S)-1-(N-cyclopentylamino)-1,2-dioxo-3-heptyl]-1-[N-(thiamorpholine-4-carbonyl)amino] cyclohexanecarboxamide

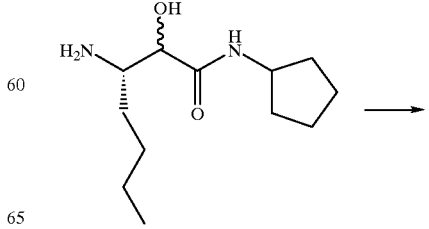

81

-continued

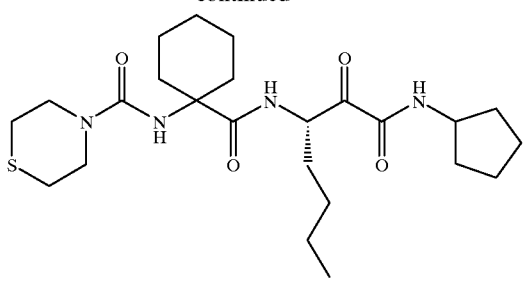

The same procedure as in Example 2 was repeated except that the 1-[N-(morpholine-4-carbonyl)amino]cyclohexanecarboxylic acid was replaced by 348 mg of 1-[N-(thiamorpholine-4-carbonyl)amino]cyclohexanecarboxylic acid synthesized by the same procedure as in Reference Example 5, wherby 333 mg of the captioned N-[(S)-1-(N-cyclopentylamino)-1,2-dioxo3-heptyl]-1-[N-(thiamorpholine-4-carbonyl)amino]cyclohexanecarboxamide was obtained in a yield of 53%.

1H-NMR (CDCl$_3$, δ): 0.88 (3H, t, J=7 Hz), 1.20–2.20 (24H, m), 2.60–2.70 (4H, m), 3.65–3.80 (4H, m), 4.05–4.10 (1H, m), 4.42 (1H, s), 5.18 (1H, ddd, J=12 Hz, 7 Hz, 5 Hz), 6.79 (1H, d, J=8 Hz), 7.94 (1H, d, J=7 Hz)

IR (v, KBr, cm$^{-1}$): 3320, 2952, 2933, 2856, 1727, 1648, 1623, 1517

Rf: 0.41.

Example 73

Synthesis of N-[(S)-1-(N-cyclopentylamino)-1,2-dioxo-3-heptyl]-1-[N-[( 4-ethoxycarbonyl)piperidine-1-carbonyl]amino]cyclohexanecarboxamide

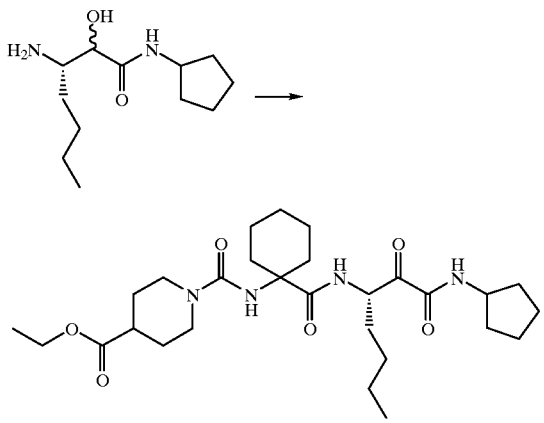

The same procedure as in Example 2 was repeated except that the 1-[N-(morpholine-4-carbonyl)amino]cyclohexanecarboxylic acid was replaced by 979 mg of 1-[N-[(4-ethoxycarbonyl)piperidine-1-carbonyl]amino]cyclohexanecarboxylic acid synthesized by the same procedure as in Reference Example 8, whereby 815 mg of the captioned N-[(S)-1-(N-cyclopentylamino)-1,2-dioxo-3-heptyl]-1-[N-[(4-ethoxycarbonyl)piperidine-1-carbonyl]amino] cyclohexanecarboxamide was obtained in a yield of 50%.

1H-NMR (CDCl$_3$, δ): 0.88 (3H, t, J=7 Hz), 1.26 (3H, t, J=7 Hz), 1.21–2.18 (28H, m), 2.50 (1H, tt, J=10 Hz, 4 Hz), 2.90–3.05 (2H, m), 3.80–3.95 (2H, m), 4.05–4.12 (3H, m), 4.44 (1H, s), 5.19 (1H, ddd, J=12 Hz, 7 Hz, 5 Hz), 6.85 (1H, d, J=9 Hz), 8.04 (1H, d, J=7 Hz)

IR (v, KBr, cm$^{-1}$): 3372, 2954, 2859, 1731, 1656, 1544

Rf: 0.38.

Example 74

Synthesis of N-[(S)-1,2-dioxo-1-[N-(2-oxo-2-phenylethyl)amino]-3-heptyl]-1-[N-(morpholine-4-carbonyl)amino]cyclohexanecarboxamide

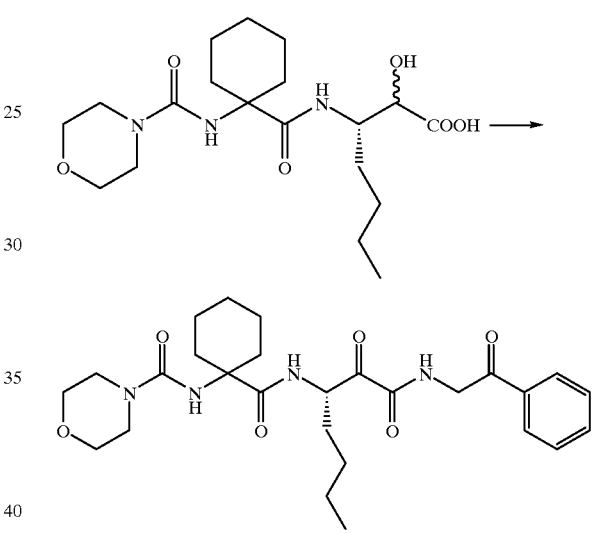

The same procedure as in Example 28 was repeated except that the 3-chlorobenzylamine was replaced by 257 mg of 2-aminoacetophenone hydrochloride and 304 mg of triethylamine, whereby 364 mg of the captioned N-[(S)-1,2-dioxo-1-[N-(2-oxo-2-phenylethyl)amino]-3-heptyl]-1-[N-(morpholine-4-carbonyl)amino]cyclohexanecarboxamide was obtained in a yield of 47%.

1H-NMR (CDCl$_3$, δ): 0.89 (3H, t, J=7 Hz), 1.26–1.43 (6H, m), 1.57–1.71 (5H, m), 1.85–2.18 (5H, m), 3.36–3.42 (4H, m), 3.68–3.74 (4H, m), 4.46 (1H, s), 4.73 (1H, dd, J=16 Hz, 5 Hz), 4.84 (1H, dd, J=16 Hz, 5 Hz), 5.22–5.28 (1H, m), 7.52 (2H, t, J=8 Hz), 7.64 (1H, t, J=8 Hz), 7.87 (1H, t, J=5 Hz), 7.97 (2H, d, J=8 Hz), 7.98 (1H, d, J=6 Hz)

IR (v, KBr, cm$^{-1}$): 3288, 2929, 2857, 1677, 1629

Rf: 0.61.

Example 75

Synthesis of N-[(S)-1,2-dioxo-1-[N-[(2-methyl-1,3-benzodioxolane-2-yl)methyl]amino]-3-heptyl]-1-[N-(morpholine-4-carbonyl)amino]cyclobexanecarboxamide

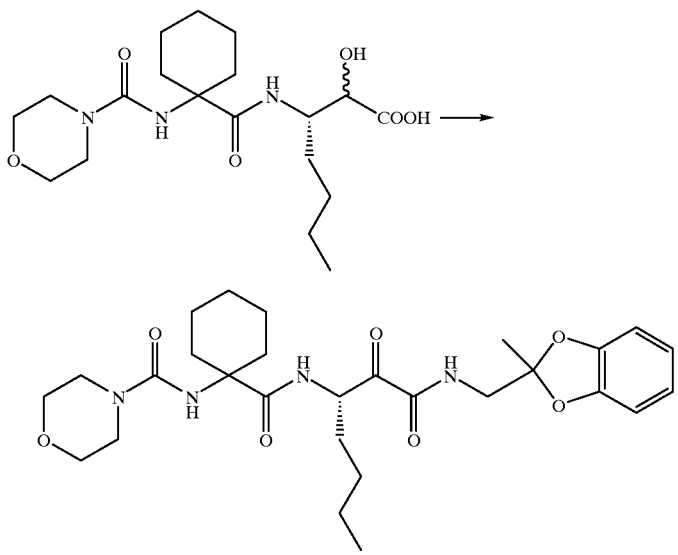

The same procedure as in Example 28 was repeated except that the 3-chlorobenzylamine was replaced by 248 mg of 1-(2-methyl-1,3-benzodioxolane-2-yl)methanamine, whereby 464 mg of the captioned N-[(S)-1,2-dioxo-1-[N-[(2-methyl-1,3-benzodioxolane-2-yl)methyl]amino-3-heptyl]-1-[N-(morpholine-4-carbonyl)amino]cyclohexanecarboxamide was obtained in a yield of 57%.

1H-NMR (CDCl$_3$, δ): 0.87 (3H, t, J=7 Hz), 1.22–1.42 (6H, m), 1.56–1.68 (5H, m), 1.65 (3H, s), 1.61–1.94 (3H, m), 2.03–2.13 (2H, m), 3.37 (4H, t, J=5 Hz), 3.64 (1H, dd, J=12 Hz, 6 Hz), 3.71 (4H, t, J=5 Hz), 3.78 (1H, dd, J=12 Hz, 6 Hz), 4.41 (1H, s), 5.15–5.22 (1H, m), 6.73–6.82 (4H, m), 7.54 (1H, t, J=5 Hz), 7.94 (1H, d, J=6 Hz)

IR (ν, KBr, cm$^{-1}$): 3315, 2931, 2857, 1666, 1639

Rf: 0.50.

Example 76

Synthesis of N-[(S)-1,2-dioxo-1-[N-[(2-phenyl-1,3-dioxolane-2-yl)methyl]amino]-3-heptyl]-1-[N-(morpholine-4-carbonyl)amino]cyclohexanecarboxamide

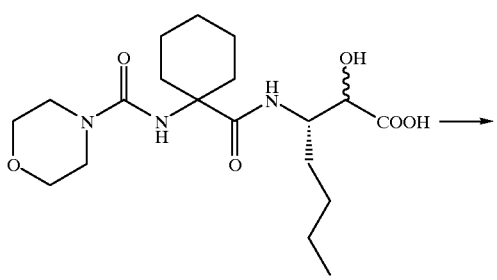

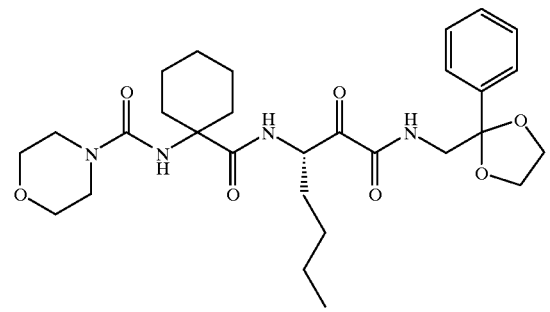

The same procedure as in Example 28 was repeated except that the 3-chlorobenzylamine was replaced by 269 mg of 1-(2-phenyl-1,3-dioxolane-2-yl)methanamine, whereby 553 mg of the captioned N-[(S)-1,2-dioxo-1-[N-[(2-phenyl-1,3-dioxolane-2-yl)methyl]amino]-3-heptyl]-1-[N-(morpholine-4-carbonyl)amino]cyclohexanecarboxamide was obtained in a yield of 66%.

1H-NMR (CDCl$_3$, δ): 0.88 (3H, t, J=7 Hz), 1.21–1.42 (6H, m), 1.55–1.71 (5H, m), 1.83–1.97 (3H, m), 2.04–2.15 (2H, m), 3.38 (4H, t, J=5 Hz), 3.61 (1H, dd, J=14 Hz, 6 Hz), 3.70 (1H, dd, J=14 Hz, 6 Hz), 3.72 (4H, t, J=5 Hz), 3.79–3.89 (2H, m), 4.00–4.10 (2H, m), 4.44 (1H, s), 5.12–5.18 (1H, m), 7.15 (1H, t, J=5 Hz), 7.31–7.38 (3H, m), 7.45–7.56 (2H, m), 7.93 (1H, d, J=7 Hz)

IR (ν, KBr, cm$^{-1}$): 3313, 2954, 2931, 1689, 1650

Rf: 0.50.

Example 77

Synthesis of N-[(S)-1-[N-(2,2-dimethoxyethyl)amino]-1,2-dioxo-3-heptyl]-1-N-(morpholine-4-carbonyl)amino]cyclohexanecarboxamide

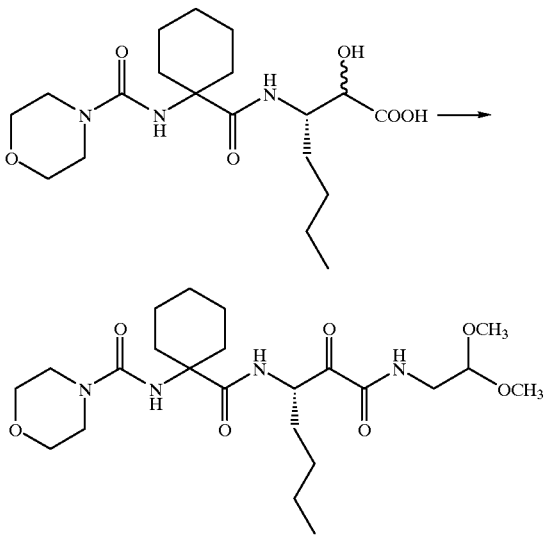

The same procedure as in Example 28 was repeated except that the 3-chlorobenzylamine was replaced by 158 mg of 2,2-dimethoxyethanamine, whereby 391 mg of the captioned N-[(S)-1-[N-(2,2-dimethoxyethyl)amino]-1,2-dioxo-3-heptyl]-1-[N-(morpholine-4-carbonyl)amino]cyclohexanecarboxamide was obtained in a yield of 54%.

1H-NMR (CDCl$_3$, δ): 0.88 (3H, t, J=7 Hz), 1.23–1.42 (6H, m), 1.57–1.69 (5H, m), 1.83–2.15 (5H, m), 3.35–3.51 (2H, m), 3.39 (4H, t, J=5 Hz), 3.40 (6H, s), 3.72 (4H, t, J=5 Hz), 4.40 (1H, t, J=6 Hz), 4.44 (1H, s), 5.16–5.24 (1H, m), 7.03 (1H, t, J=5 Hz), 7.94 (1H, d, J=6 Hz)

IR (ν, KBr, cm$^{-1}$): 3332, 2931, 2857, 1675, 1631

Rf: 0.74.

Example 78

Synthesis of N-[(S)-1,2-dioxo-1-[N-[(1,3-dioxolane-2-yl)methyl]amino]-3-heptyl]-1-[N-(morpholine-4-carbonyl)amino]cyclohexanecarboxamide

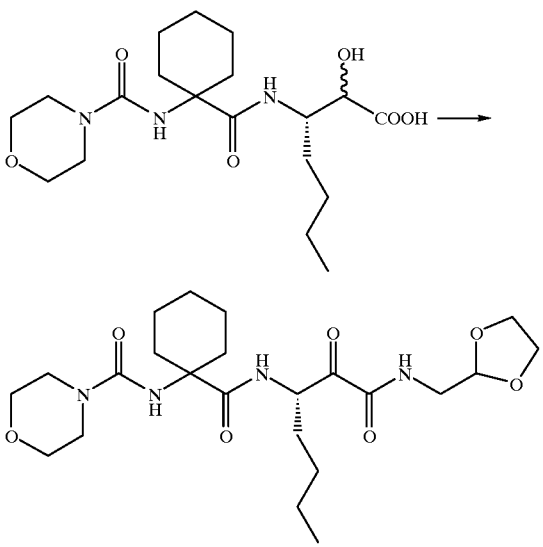

The same procedure as in Example 28 was repeated except that the 3-chlorobenzylamine was replaced by 155 mg of 1-(1,3-dioxolane-2-yl)methanamine, whereby 352 mg of the captioned N-[(S)-1,2-dioxo-1-[N-[(1,3-dioxolane-2-yl)methyl]amino]-3-heptyl]-1-[N-(morpholine-4-carbonyl)amino]cyclohexanecarboxamide was obtained in a yield of 49%.

1H-NMR (CDCl$_3$, δ): 0.88 (3H, t, J=7 Hz), 1.22–1.44 (6H, m), 1.57–1.69 (5H, m), 1.82–2.15 (5H, m), 3.39 (4H, t, J=5 Hz), 3.52 (2H, dd, J=6 Hz, 4 Hz), 3.72 (4H, t, J=5 Hz), 3.85–4.04 (4H, m), 4.45 (1H, s), 5.00 (1H, t, J=4 Hz), 5.13–5.20 (1H, m), 7.06 (1H, t, J=6 Hz), 7.95 (1H, d, J=6 Hz)

IR (ν, KBr, cm$^{-1}$): 3320, 2931, 2857, 1677, 1648

Rf: 0.77.

Example 79

Synthesis of N-[(S)-1-[N-[(2-methyl-1,3-dioxolane-2-yl)methyl]amino]-1,2-dioxo-3-heptyl]-1-[N-(morpholine-4-carbonyl)amino]cyclohexanecarboxamide

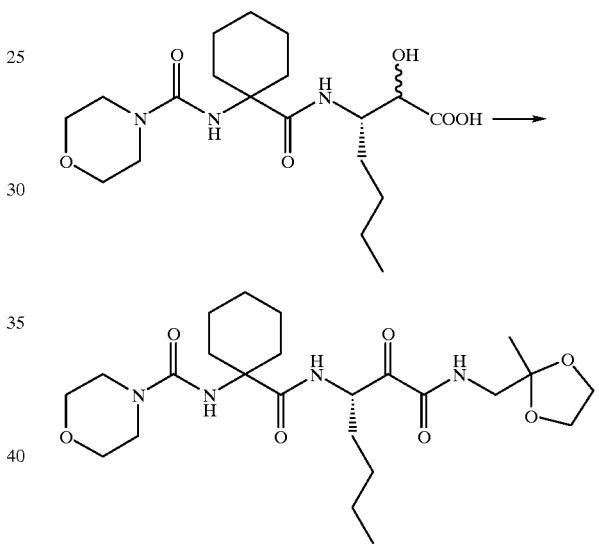

The same procedure as in Example 28 was repeated except that the 3-chlorobenzylamine was replaced by 179 mg of 1-(2-methyl-1,3-dioxolane-2-yl)methanamine, whereby 447 mg of the captioned N-[(S)-1-[N-[(2-methyl-1,3-dioxolane-2-yl)methyl]amino]-1,2-dioxo-3-heptyl]-1-[N-(morpholine-4-carbonyl)amino]cyclohexanecarboxamide was obtained in a yield of 60%.

1H-NMR (CDCl$_3$, δ): 0.88 (3H, t, J=7 Hz), 1.22–1.42 (6H, m), 1.33 (3H, s), 1.50–1.71 (5H, m), 1.82–2.15 (5H, m), 3.39 (4H, t, J=5 Hz), 3.39–3.49 (2H, m), 3.72 (4H, t, J=5 Hz), 3.93–4.02 (4H, m), 4.43 (1H, s), 5.15–5.22 (1H, m), 7.06 (1H, t, J=5 Hz), 7.96 (1H, d, J=6 Hz)

IR (ν, KBr, cm$^{-1}$): 3428, 2929, 2857, 1660

Rf: 0.72.

Example 80

Synthesis of N-[(S)-1,2-dioxo-1-N-[(S)-(1-phenylethyl)amino]-3-heptyl]-1-[N-(morpholine-4-carbonyl)amino]cyclohexanecarboxamide

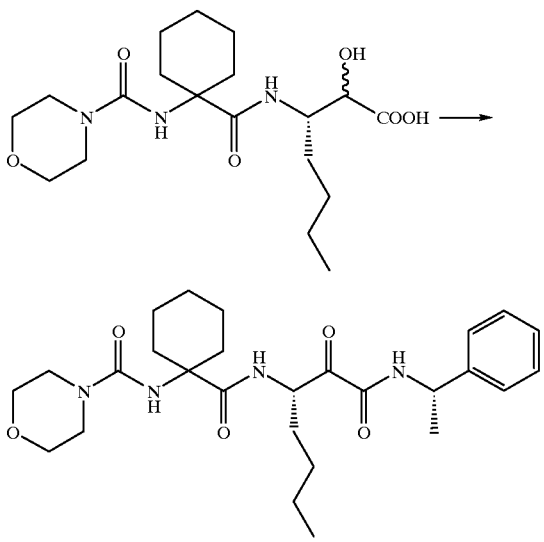

The same procedure as in Example 28 was repeated except that the 3-chlorobenzylamine was replaced by 164 mg of (S)-1-phenylethylamine, whereby 601 mg of the captioned N-[(S)-1,2-dioxo-1-N-[(S)-(1-phenylethyl) amino]-3-heptyl]-1-[N-(morpholine-4-carbonyl)amino] cyclohexanecarboxamide was obtained in a yield of 80%.

1H-NMR (CDCl₃, δ): 0.88 (3H, t, J=7 Hz), 1.24–1.45 (8H, m), 1.53 (3H, d, J=7 Hz), 1.58–1.70 (4H, m), 1.80–1.91 (2H, m), 2.02–2.14 (2H, m), 3.22–3.38 (4H, m), 3.68–3.72 (4H, m), 4.47 (1H, s), 5.03–5.07 (1H, m), 5.12 (1H, ddd, J=12 Hz, 8 Hz, 5 Hz), 7.10 (1H, d, J=8 Hz), 7.27–7.35 (5H, m), 7.95 (1H, d, J=8 Hz)

IR (ν, KBr, cm⁻¹): 3376, 2931, 1654, 1546, 1511

Rf: 0.54.

Example 81

Synthesis of N-[(S)-1,2-dioxo-1-N-[(R)-(1-phenylethyl) amino]-3-heptyl]-1-N-(morpholine-4-carbonyl)amino] cyclohexanecarboxamide

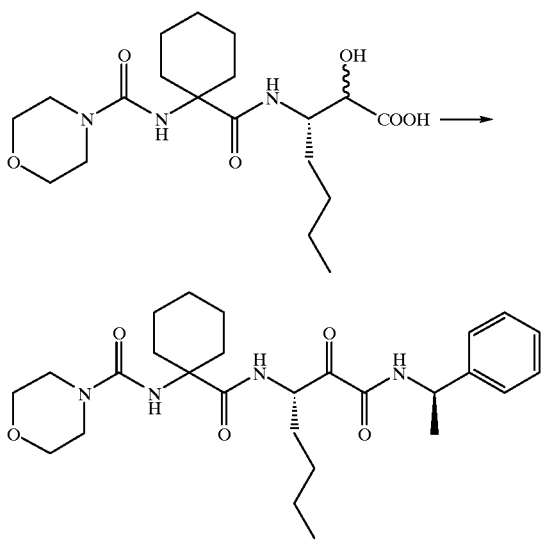

The same procedure as in Example 28 was repeated except that the 3-chlorobenzylamine was replaced by 164 mg of (R)-1-phenylethylamine, whereby 587 mg of the captioned N-[(S)-1,2-dioxo-1-N-[(R)-(1-phenylethyl) amino]-3-heptyl]-1-[N-(morpholine-4-carbonyl)amino] cyclohexanecarboxamide was obtained in a yield of 78%.

1H-NMR (CDCl₃, δ): 0.86 (3H, t, J=7 Hz), 1.13–1.45 (8H, m), 1.53 (3H, d, J=7 Hz), 1.55 (4H, m), 1.80–2.00 (2H, m), 2.02–2.18 (2H, m), 3.35–3.38 (4H, m), 3.68–3.72 (4H, m), 4.47 (1H, s), 5.04–5.08 (1H, m), 5.12 (1H, ddd, J=12 Hz, 7 Hz, 5 Hz), 7.11 (1H, d, J=8 Hz), 7.25–7.37 (5H, m), 7.93 (1H, d, J=7 Hz)

IR (ν, KBr, cm⁻¹): 3367, 3307, 1650, 1550, 1511

Rf: 0.54.

Example 82

Synthesis of N-[(S)-1,2-dioxo-1-[N-3-pentylamino]-3-heptyl]-1-[N-(morpholine-4-carbonyl)amino] cyclohexanecarboxamide

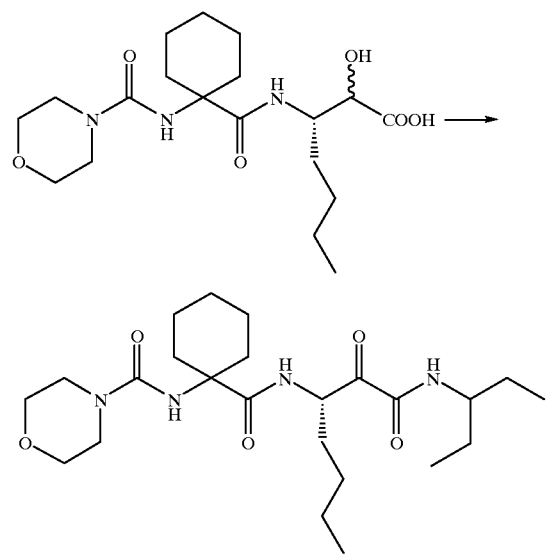

The same procedure as in Example 28 was repeated except that the 3-chlorobenzylamine was replaced by 131 mg of 3-pentylamine, whereby 330 mg of the captioned N-[(S)-1,2-dioxo-1-[N-3-pentylamino]-3-heptyl-1-[N-(morpholine-4-carbonyl)amino]cyclohexanecarboxamide was obtained in a yield of 46%.

1H-NMR (CDCl₃, δ): 0.86–0.91 (9H, m), 1.20–1.57 (13H, m), 1.64–1.74 (2H, m), 1.80–2.02 (3H, m), 2.16–2.17 (2H, m), 3.34 (4H, t, J=5 Hz), 3.72 (4H, t, J=5 Hz), 4.45 (1H, m), 5.19–5.24 (1H, m), 6.59 (1H, d, J=9 Hz), 7.93 (1H, d, J=7 Hz)

IR (ν, KBr, cm⁻¹): 3316, 1654, 1513

Rf: 0.51.

Example 83

Synthesis N-[(S)-1,2-dioxo-1-[N-(2-methylphenyl) amino]-3-heptyl]-1-[N-(morpholine-4-carbonyl)amino] cyclohexanecarboxamide

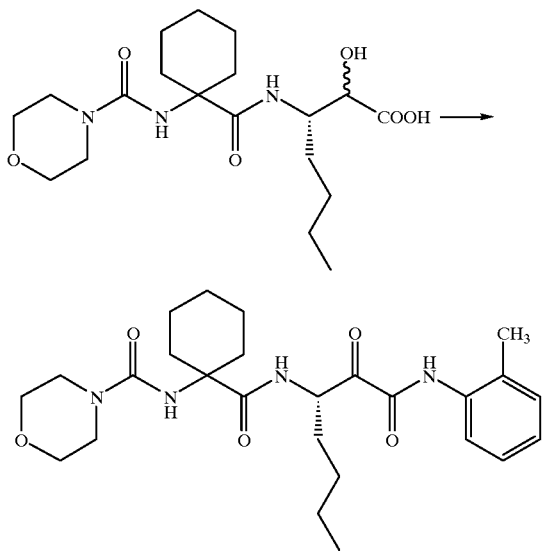

The same procedure as in Example 28 was repeated except that the 3-chlorobenzylamine was replaced by 161 mg of 2-methylaniline, whereby 445 mg of the captioned N-[(S)-1,2-dioxo-1-[N-(2-methylphenyl)amino-3-heptyl]-1-[N-(morpholine-4-carbonyl)amino]cyclohexanecarboxamide was obtained in a yield of 59%.

1H-NMR (CDCl$_3$, δ): 0.90 (3H, t, J=7 Hz), 1.30–1.42 (6H, m), 1.62–1.76 (6H, m), 1.87–2.17 (5H, m), 2.32 (3H, s), 3.37 (4H, t, J=5 Hz), 3.69 (4H, t, J=5 Hz), 5.24–5.29 (1H, m), 7.10 (1H, dt, J=7 Hz, 1 Hz), 7.20 (1H, d, J=7 Hz), 7.23 (1H, d, J=8 Hz), 8.07 (2H, d, J=8 Hz), 8.64 (1H, s)

IR (ν, KBr, cm$^{-1}$): 3386, 2929, 1685, 1643, 1527, 1457, 1255

Rf: 0.52.

Example 84

Synthesis of N-[(S)-1-(N-cyclopentylamino)-1,2-dioxo-3-heptyl]-1-[N-[(4-acetyl)perhydro-4-azaazepine-1-carbonyl]amino]cyclohexanecarboxamide

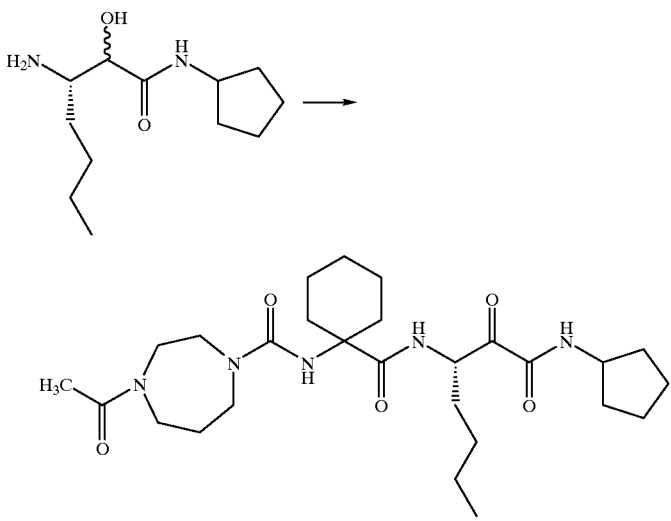

The same procedure as in Example 2 was repeated except that the 1-[N-(morpholine-4-carbonyl)amino]cyclohexanecarboxylic acid was replaced by 622 mg of 1-[N-[(4-acetyl)perhydro-4-azaazepine-1-carbonyl]amino]cyclohexanecarboxylic acid synthesized by the same procedure as in Reference Example 8, whereby 502 mg of the captioned N-[(S)-1-(N-cyclopentylamino)-1,2-dioxo-3-heptyl]-1-[N-[(4-acetyl)perhydro-4-azaazepine-1-carbonyl]amino]cyclohexanecarboxamide was obtained in a yield of 47%.

1H-NMR (CDCl$_3$, δ): 0.88 (3H, t, J=7 Hz), 1.20–2.20 (29H, m), 3.40–3.80 (8H, m), 4.10–4.20 (1H, m), 4.44 (1H, s), 5.18–5.23 (1H, m), 6.85 (1/2H, d, J=8 Hz), 6.88 (1/2H, d, J=8 Hz), 7.86 (1/2H, d, J=7 Hz), 7.95 (1/2H, d, J=7 Hz)

IR (ν, KBr, cm$^{-1}$): 3397, 3363, 2954, 2935, 1664, 1629, 1527

Rf: 0.62.

Example 85

Synthesis of N-[(S)-1-(N-cyclopentylamino)-1,2-dioxo-3-heptyl]-1-[N-[(4-methoxy)piperidine-1-carbonyl]amino]cyclohexanecarboxamide

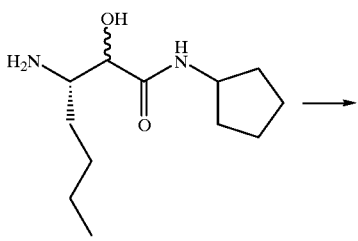

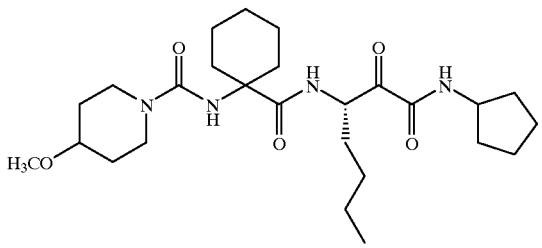

The same procedure as in Example 2 was repeated except that the 1-[N-(morpholine-4-carbonyl)amino]cyclohexanecarboxylic acid was replaced by 568 mg of 1-[N-[(4-methoxy)piperidine-1-carbonyl]amino]cyclohexanecarboxylic acid synthesized by the same procedure as in Reference Example 8, whereby 512 mg of the captioned N-[(S)-1-(N-cyclopentylamino)-1,2-dioxo-3-heptyl]-1-[N-[(4-methoxy)piperidine-1-carbonyl]amino]cyclohexanecarboxamide was obtained in a yield of 51%.

1H-NMR (CDCl$_3$, δ): 0.87 (3H, t, J=7 Hz), 1.20–2.18 (28H, m), 3.10–3.25 (2H, m), 3.36 (3H, s), 3.34–3.42 (1H, m), 3.60–3.70 (2H, m), 4.10–4.20 (1H, m), 4.45 (1H, s), 5.18 (1H, ddd, J=11 Hz, 7 Hz, 4 Hz), 6.80 (1H, d, J=7 Hz), 8.10 (1H, d, J=7 Hz)

IR (v, KBr, cm$^{-1}$): 3330, 2935, 1658, 1625, 1517

Rf: 0.47.

Example 86

Synthesis of N-[(S)-1-(N-cyclopentylamino)-1,2-dioxo-3-heptyl]-1-[N-[N,N-bis(2-methoxyethyl)aminocarbonyl]amino]cyclohexanecarboxamide

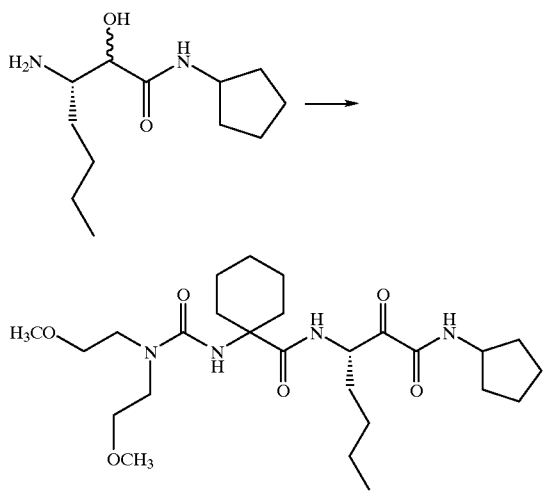

The same procedure as in Example 2 was repeated except that the 604 mg of 1-[N-(morpholine-4-carbonyl)amino]cyclohexanecarboxylic acid was replaced by 1-[N-[N,N-bis(2-methoxyethyl)aminocarbonyl]amino]cyclohexanecarboxylic acid synthesized by the same procedure as in Reference Example 5, whereby 456 mg of the captioned N-[(S)-1-(N-cyclopentylamino)-1,2-dioxo-3-heptyl]-1-[N-[N,N-bis(2-methoxyethyl)aminocarbonyl]amino]cyclohexanecarboxamide was obtained in a yield of 43%.

1H-NMR (CDCl$_3$, δ): 0.87 (3H, t, J=7 Hz), 1.20–2.10 (24H, m), 3.63 (3H, s), 3.69 (3H, s), 3.50–3.60 (8H, m), 4.10–4.20 (1H, m), 5.19 (1H, ddd, J=11 Hz, 7 Hz, 4 Hz), 6.23 (1H, s), 6.80 (1H, d, J=8 Hz), 7.97 (1H, d, J=7 Hz)

IR (v, KBr,cm$^{-1}$) 3361, 3257, 2952, 2859, 1724, 1646, 1517

Rf: 0.36.

Example 87

Synthesis of N-[(S)-1-(N-cyclopentylamino)-1,2-dioxo-3-heptyl]-1-[N-[[N-(2-methoxyethyl)-N-methyl]aminocarbonyl]amino]cyclohexanecarboxamide

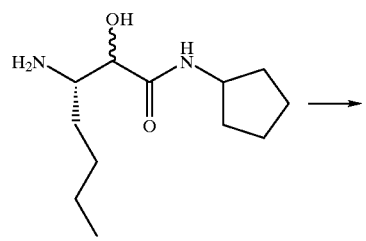

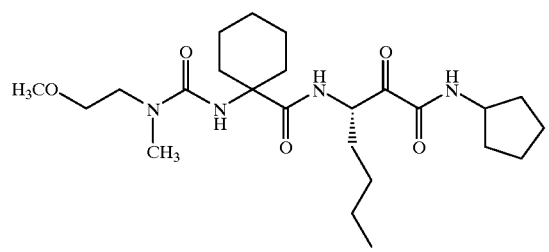

The same procedure as in Example 2 was repeated except that the 1-[N-(morpholine-4-carbonyl)amino]cyclohexanecarboxylic acid was replaced by 516 mg of 1-[N-[[N-(2-methoxyethyl)-N-methyl]aminocarbonyl]amino]cyclohexanecarboxylic acid synthesized by the same procedure as in Example was repeated except that the in Reference Example 5, whereby 496 mg of the captioned N-[(S)-1-(N-cyclopentylamino)-1,2-dioxo-3-heptyl]-1-[N-[[N-(2-methoxyethyl)-N-methyl]aminocarbonyl]amino]cyclohexanecarboxamide was obtained in a yield of 52%.

1H-NMR (CDCl$_3$, δ): 0.88 (3H, t, J=7 Hz), 1.20–2.20 (24H, m), 2.93 (3H, s), 3.40 (3H, s), 3.45 (2H, t, J=4 Hz), 3.56 (2H, t, J=4 Hz), 4.10–4.20 (1H, m), 5.17 (1H, ddd, J=12 Hz, 7 Hz, 4 Hz), 5.72 (3H, br-s), 6.82 (1H, d, J=8 Hz), 8.03 (1H, d, J=7 Hz)

IR (v, KBr, cm$^{-1}$): 3347, 3257, 2952, 2857, 1725, 1646, 1523

Rf: 0.43.

Example 88

Synthesis of N-[(S)-1,2-dioxo-1-[N-[(S)-1-oxo-1-methoxy-3-methyl-2-butyl]amino]-3-heptyl]-1-[N-(morpholine-4-carbonyl)amino]cyclohexanecarboxamide

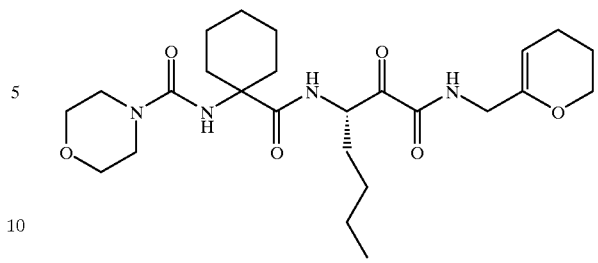

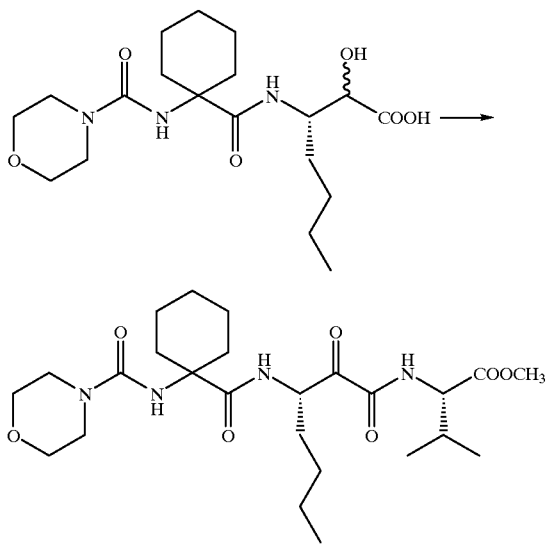

The same procedure as in Example 28 was repeated except that the 3-chlorobenzylamine was replaced by 251 mg of L-valinemethylester hydrochloride and 304 mg of triethylamine, whereby 325 mg of the captioned N-[(S)-1,2-dioxo- 1-[N-[(S)-1-oxo-1-methoxy-3-methyl-2-butyl]amino]-3-heptyl]-1-[N-(morpholine-4-carbonyl)amino]cyclohexanecarboxamide was obtained in a yield of 43%.

1H-NMR (CDCl₃, δ): 0.87 (3H, t, J=7 Hz), 0.92 (3H, d, J=7 Hz), 0.94 (3H, d, J=7 Hz), 1.23–1.43 (6H, m), 1.56–1.69 (5H, m), 1.84–2.27 (6H, m), 3.38(4H, t, J=5 Hz), 3.72 (4H, t, J=5 Hz), 3.76 (3H, s), 4.43 (1H, s), 4.49 (1H, dd, J=9 Hz, 5 Hz), 5.18–5.24 (1H, m), 7.33 (1H, d, J=9 Hz), 8.00 (1H, d, J=7 Hz)

IR (ν, KBr, cm⁻¹): 3332, 2958, 2933, 1685, 1648

Rf: 0.57.

Example 89

Synthesis of N-[(S)-1-[N-[(3,4-dihydro-2H-pyrane-6-yl)methyl]amino]-1,2-dioxo-3-heptyl]-1-[N-(morpholine-4-carbonyl)amino]cyclohexanecarboxamide

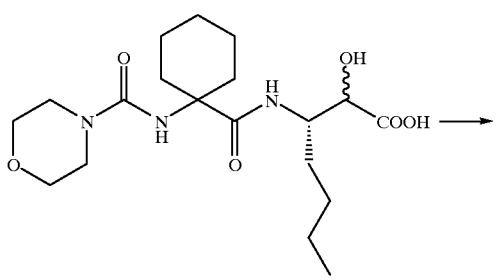

-continued

The same procedure as in Example 28 was repeated except that the 3-chlorobenzylamine was replaced by 170 mg of 1-(3,4-dihydro-2H-pyrane-6-yl)methanamine, whereby 256 mg of the captioned N-[(S)-1-[N-[(3,4-dihydro-2H-pyrane-6-yl)methyl]amino]-1,2-dioxo-3-heptyl]-1-[N-(morpholine-4-carbonyl) amino]cyclohexanecarboxamide was obtained in a yield of 29%.

1H-NMR (CDCl₃, δ): 0.88 (3H, t, J=7 Hz), 1.22–1.44 (6H, m), 1.54–1.70 (5H, m), 1.75–2.15 (9H, m), 3.38 (4H, t, J=5 Hz), 3.72 (4H, t, J=5 Hz), 3.80 (2H, d, J=5 Hz), 4.00 (2H, t, J=5 Hz), 4.43 (1H, s), 4.72 (1H, t, J=4 Hz), 5.14–5.21 (1H, m), 7.05 (1H, t, J=5 Hz), 7.94 (1H, d, J=6 Hz)

IR(ν, KBr, cm⁻¹):3318, 2931, 2856, 1668

Rf: 0.58.

Example 90

Synthesis of N-[(S)-1-[N-[(2-cyclohexyl-2-oxo)ethyl]amino]-1,2-dioxo-3-heptyl]-1-[N-(morpholine-4-carbonyl)amino]cyclohexanecarboxamide

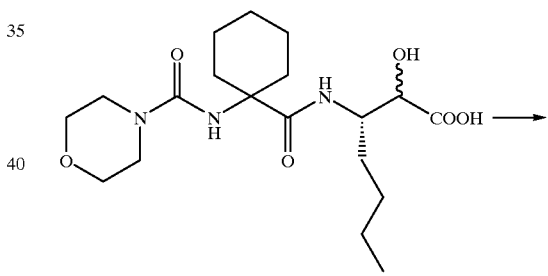

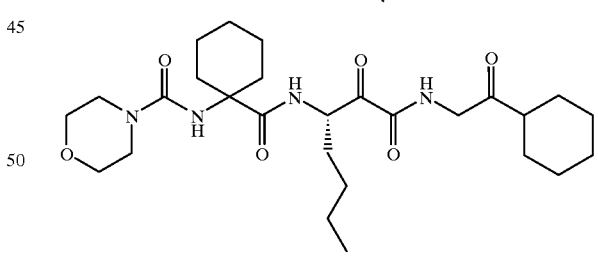

The same procedure as in Example 28 was repeated except that the 3-chlorobenzylamine was replaced by 215 mg of 2-amino-1-cyclohexylethanol, whereby 470 mg of the captioned N-[(S)-1-[N-[(2-cyclohexyl-2-oxo)ethyl]amino]-1,2-dioxo-3-heptyl]-1-[N-(morpholine-4-carbonyl)amino]cyclohexanecarboxamide was obtained in a yield of 60%.

1H-NMR (CDCl₃, δ): 0.88 (3H, t, J=7 Hz), 1.08–1.45 (12H, m), 1.54–1.71 (5H, m), 1.74–1.98 (7H, m), 2.02–2.17 (2H, m), 2.37–2.46 (1H, m), 3.39 (4H, t, J=5 Hz), 3.72 (4H, t, J=5 Hz), 4.16 (1H, dd, J=20 Hz, 5 Hz), 4.24 (1H, dd, J=20 Hz, 5 Hz), 4.27 (1H, s), 5.18–5.25 (1H, m), 7.57 (1H, t, J=5 Hz), 7.96 (1H, d, J=6 Hz)

IR (ν, KBr, cm⁻¹): 3320, 2931, 2856, 1685, 1648
Rf: 0.49.

Example 91

Synthesis of N-[(S)-1,2-dioxo-1-[N-(1-methoxycyclohexylmethyl)amino]-3-heptyl]-1-[N-(morpholine-4-carbonyl)amino]cyclohexanecarboxamide

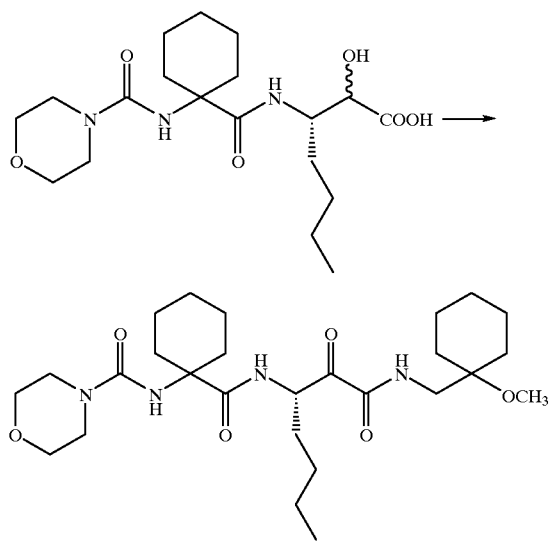

The same procedure as in Example 28 was repeated except that the 3-chlorobenzylamine was replaced by 340 mg of 1-methoxycyclohexylmethylamnine, whereby 310 mg of the captioned N-[(S)-1,2-dioxo-1-[N-(1-methoxycyclohexylmethyl)amino]-3-heptyl]-1-N-(morpholine-4-carbonyl)amino]cyclohexanecarboxamide was obtained in a yield of 39%.

1H-NMR (CDCl₃, δ): 0.87 (3H, t, J=7 Hz), 1.24–1.34 (16H, m), 1.48–1.55 (3H, m), 1.64–1.67 (5H, m), 1.89–1.97 (2H, m), 2.04–2.13 (2H, m), 3.17 (3H, s), 3.38 (4H, t, J=5 Hz), 3.72 (4H, t, J=5 Hz), 4.42 (1H, s), 5.22–5.27 (1H, m), 7.03 (1H, bs), 7.91 (1H, d, J=7 Hz)

IR (ν, KBr, cm⁻¹): 3413, 2933, 1675, 1629, 1523
Rf: 0.68.

Example 92

Synthesis of N-[(S)-1,2-dioxo-1-[N-[(RS)-2-oxocyclohexyl]amino]-3-heptyl]-1-[N-(morpholine-4-carbonyl)amino]cyclohexanecarboxamide

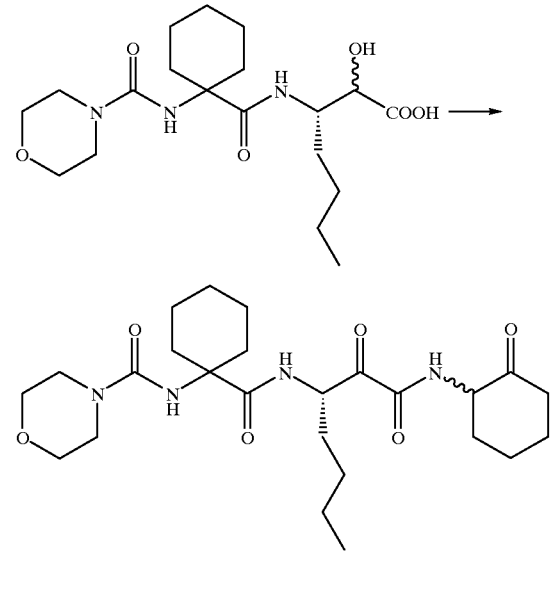

The same procedure as in Example 28 was repeated except that the 3-chlorobenzylamine was replaced by 173 mg of trans-2-amino]cyclohexanol, whereby 508 mg of the captioned N-[(S)-1,2-dioxo-1-[N-[(RS)-2-oxocyclohexyl]amino]-3-heptyl]-1-[N-(morpholine-4-carbonyl)amino]cyclohexanecarboxamide was obtained in a yield of 69%.

1H-NMR (CDCl₃, δ): 0.88 (3H, t, J=7 Hz), 1.22–1.47 (8H, m), 1.55–2.00 (10H, m), 2.03–2.20 (3H, m), 2.35–2.70 (3H, m), 3.39 (4H, t, J=5 Hz), 3.72 (4H, t, J=5 Hz), 4.36–4.47 (1H, m), 4.46 (1H, s), 5.20–5.29 (1H, m), 7.69 (1/2H, d, J=7 Hz), 7.76 (1/2H, d, J=6 Hz), 7.89 (1/2H, d, J=7 Hz), 7.93 (1/2H, d, J=7 Hz)

IR (ν, KBr, cm⁻¹): 3332, 2931, 2859, 1675, 1643

Rf: 0.68.

Example 93

Synthesis of N-[(S)-1,2-dioxo-1-N-[[(RS)-4-methyl-1-oxo-1-[N-(phenylmethyl)amino]-2-pentyl]amino]-3-pentyl]-1-[N-(morpholine-4-carbonyl) amino] cyclohexaneccarboxamide

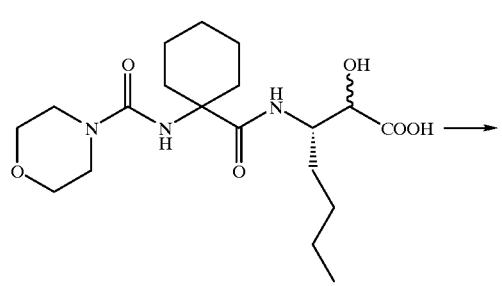

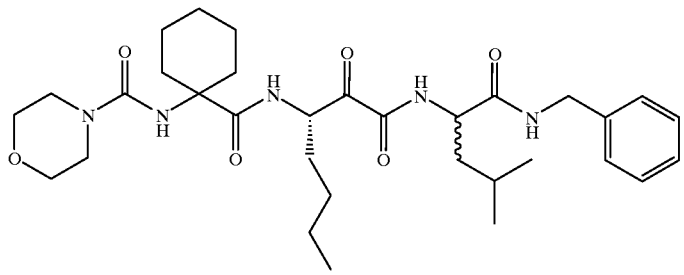

The same procedure as in Example 28 was repeated except that the 3-chlorobenzylamine was replaced by 330 mg of DL-N-benzyl-leucinamide, whereby 503 mg of the captioned N-[(S)-1,2-dioxo-1-N-[[(RS)-4-methyl-1-oxo-1-[N-(phenylmethyl)amino]-2-pentyl]amino-3-pentyl]-1-[N-(morpholine-4-carbonyl) amino] cyclohexanecarboxamide was obtained in a yield of 56%.

1H-NMR (CDCl$_3$, δ): 0.87 (3H, t, J=7 Hz), 0.92 (3/2H, d, J=6 Jz), 0.94 (3/2H, d, J=6 Hz), 1.21–1.42 (8H, m), 1.53–1.97 (9H, m), 1.98–2.16 (2H, m), 3.36 (4H, t, J=5 Hz), 3.69 (4H, t, J=5 Hz), 4.20–4.51 (1H, m), 4.42 (2H, d, J=6 Hz), 4.61 (1/2H, s), 4.66 (1/2H, s), 5.00–5.03 (1H, m), 5.92–6.10 (1H, m), 7.10 (1/2H, dd, J=6 Hz, 6 Hz), 7.12 (1/2H, dd, J=6 Hz, 6 Hz), 7.87 (1/2H, d, J=6 Hz), 8.07 (1/2H, d, J=6 Hz)

IR (ν, KBr, cm$^{-1}$): 3315, 2956, 2933, 1654, 1527

Rf: 0.53.

Example 94

Synthesis of N-[(S)-1,2-dioxo-1-N-[(RS)-1-phenylsulfonyl-5-methylthio-1-pentene-3-yl]amino-3-heptyl]-1-[N-(morpholine-4-carbonyl)amino] cyclohexanecarboxamide The same procedure as in Example 28 was repeated except that the 3-chlorobenzylamine was replaced by 407 mg of (2RS)-1-phenylsulfonyl-3-amino-5-methylthio-3-pentene, whereby 478 mg of the captioned N-[(S)-1,2-dioxo-1-N-[(RS)-1-phenylsulfonyl-5-methylthio-1-pentene-3-yl]amino-3-heptyl]-1-[N-(morpholine-4-carbonyl)amino] cyclohexanecarboxamide was obtained in a yield of 49%.

1H-NMR (CDCl$_3$, δ): 0.88 (3/2H, t, J=7 Hz), 0.90 (3/2H, t, J=7 Hz), 1.22–1.51 (9H, m), 1.52–1.78 (6H, m), 1.80–2.28 (3H, m), 2.05 (3/2H, s), 2.09 (3/2H, s), 2.43–2.60 (2H, m), 3.41 (4H, t, J=5 Hz), 3.71 (4H, t, J=5 Hz), 4.62–4.69 (1H, m), 4.73–4.85 (1H, m), 4.78 (1H, s), 6.48 (1/2H, d, J=15 Hz), 6.59 (1/2H, d, J=15 Hz), 6.89–6.98 (2H, m), 7.52–7.70 (3H, m), 7.59 (1/2H, d, J=8 Hz), 7.85 (1/2H, d, J=8 Hz), 7.86 (1H, d, J=8 Hz), 8.38 (1/2H, d, J=6 Hz), 8.54 (1/2H, d, J=6 Hz)

IR (ν, KBr, cm$^{-1}$): 3384, 2954, 2927, 1671, 1634, 1523

Rf: 0.57.

Example 95

Synthesis of N-[(S)-1,2-dioxo-1-N-[[(RS)-4-methyl-1-oxo-1-(phenylmethyl) oxy-2-pentyl]amino]-3-pentyl]-1-[N-(morpholine-4-carbonyl)amino]cyclohexanecarboxamide

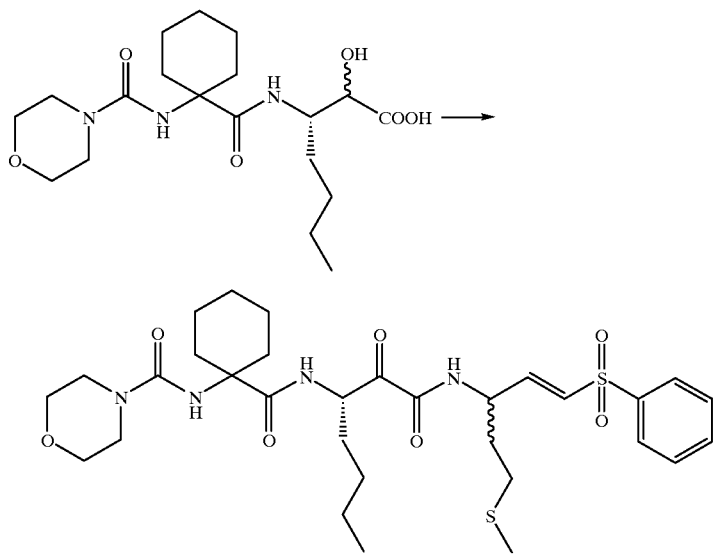

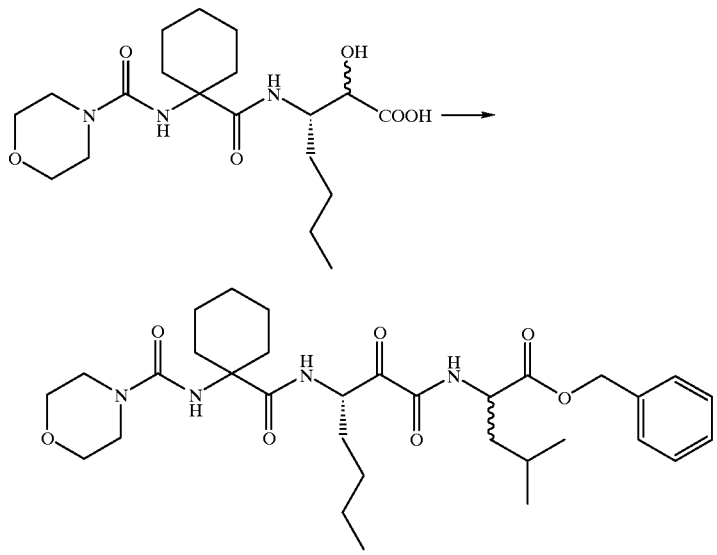

The same procedure as in Example 28 was repeated except that the 3-chlorobenzylamine was replaced by 332 mg of DL-leucinebenzylester, whereby 550 mg of the captioned N-[(S)-1,2-dioxo-1-N-[[(RS)-4-methyl-1-oxo-1-(phenylmethyl)oxy-2-pentyllamino-3-pentyl]-1-[N-(morpholine-4-carbonyl)amino]cyclohexanecarboxamide was obtained in a yield of 61%.

1H-NMR (CDCl$_3$, δ): 0.87 (3H, t, J=7 Hz), 0.91 (3H, d, J=6 Hz), 0.92 (3H, d, J=6 Hz), 1.21–1.42 (8H, m), 1.52–1.72 (6H, m), 1.83–2.00 (3H, m), 2.02–2.18 (2H, m), 3.38 (4H, t, J=5 Hz), 3.71 (4H, t, J=5 Hz), 4.43 (1H, s), 4.60–4.68 (1H, m), 5.14–5.22 (1H, m), 5.17 (2H, s), 7.21 (1/2H, d, J=9 Hz), 7.23 (1/2H, d, J=9 Hz), 7.31–7.40 (5H, m), 7.96 (1/2H, d, J=6 Hz), 7.97 (1/2H, d, J=6 Hz)

IR(ν, KBr, cm ):3357, 2958, 1675, 1631, 1523

Rf: 0.34.

Example 96

Synthesis of N-[(S)-1-[N-[(2-methyl-1,3-dioxane-2-yl)methyl]amino]-1,2-dioxo-3-heptyl]-1-[N-(morpholine-4-carbonyl)amino]cyclohexanecarboxamide The same procedure as in Example 28 was repeated except that the 3-chlorobenzylamine was replaced by 197 mg of 1-(2-methyl-1,3-dioxane-2-yl) methanamine, whereby 450 mg of the captioned N-[(S)-1-[N-[(2-methyl-1,3-dioxane- 2-yl)methyl]amino]-1,2-dioxo-3-heptyl]-1-[N-(morpholine-4-carbonyl)amino]cyclohexanecarboxamide was obtained in a yield of 59%.

1H-NMR (CDCl$_3$, δ): 0.87 (3H, t, J=7 Hz), 1.22–1.41 (6H, m), 1.43–1.70 (6H, m), 1.83–2.16 (6H, m), 3.39 (4H, t, J=5 Hz), 3.44 (2H, d, J=5 Hz), 3.72 (4H, t, J=5 Hz), 3.83–3.99 (4H, m), 4.44 (1H, s), 5.20–5.25 (1H, m), 7.15 (1H, t, J=6 Hz), 7.94 (1H, d, J=6 Hz)

IR (ν, KBr, cm$^{-1}$): 3351, 2933, 2861, 1677

Rf: 0.74.

Example 97

Synthesis of N-[(S)-1-[N-[[2-(1,1-dimethylethyl)-1,3-dioxolane-2-yl]methyl]amino]-1,2-dioxo-3-heptyl]-1-[N-(morpholine-4-carbonyl)amino]cyclohexanecarboxamide

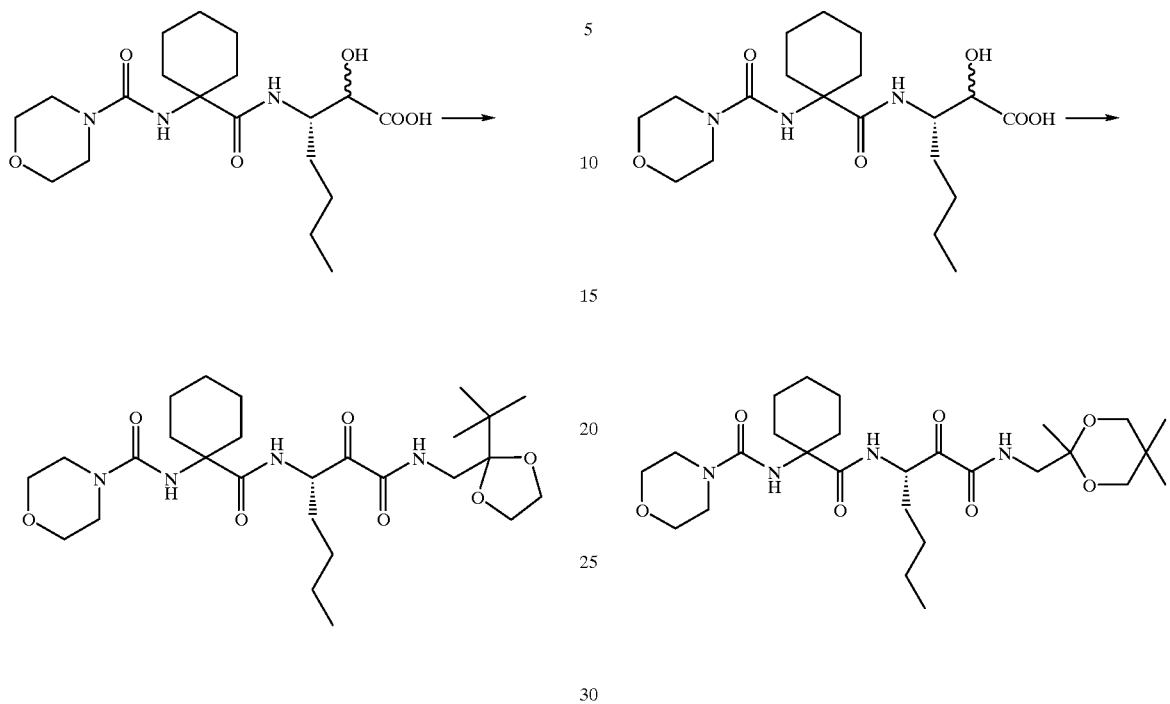

The same procedure as in Example 28 was repeated except that the 3-chlorobenzylamine was replaced by 239 mg of 1-[2-(1,1-dimethylethyl)-1,3-dioxolane-2-yl] methanamine, whereby 603 mg of the captioned N-[(S)-1-[N-[[2-(1,1-dimethylethyl)-1,3-dioxolane-2-yl]methyl]amino]-1,2-dioxo-3-heptyl]-1-[N-(morpholine-4-carbonyl) amino] cyclohexanecarboxamide was obtained in a yield of 75%.

1H-NMR (CDCl$_3$, δ): 0.88 (3H, t, J=7 Hz), 0.98 (9H, s), 1.23–1.42 (6H, m), 1.56–1.70 (5H, m), 1.83–2.17 (5H, m), 3.38 (4H, t, J=5 Hz), 3.53 (1H, dd, J=14 Hz, 6 Hz), 3.61 (1H, dd, J=14 Hz, 6 Hz), 3.71 (4H, t, J=5 Hz), 3.94–4.04 (4H, m), 4.43 (1H, s), 5.12–5.19 (1H, m), 7.00 (1H, t, J=5 Hz), 7.97 (1H, d, J=7 Hz)

IR (ν, KBr, cm$^{-1}$): 3311, 2952, 2933, 1660

Rf: 0.45.

Example 98

Synthesis of N-[(S)-1-[N-[(2,5,5-trimethyl-1,3-dioxane-2-yl)methyl]amino]-1,2-dioxo-3-heptyl]-1-[N-(morpholine-4-carbonyl)amino]cyclohexanecarboxamide The same procedure as in Example 28 was repeated except that the 3-chlorobenzylamine was replaced by 251 mg of 1-(2,5,5-trimethyl-1,3-dioxane-2-yl) methanamine, whereby 546 mg of the captioned N-[(S)-1-[N-[(2,5,5-trimethyl-1,3-dioxane-2-yl)methyl]amino]-1,2-dioxo-3-heptyl]-1-[N-(morpholine-4-carbonyl) amino] cyclohexanecarboxamide was obtained in a yield of 68%.

1H-NMR (CDCl$_3$, δ): 0.82 (3H, s), 0.88 (3H, t, J=7 Hz), 1.23–1.43 (6H, m), 1.38 (3H, s), 1.57–1.70 (5H, m), 1.83–2.16 (5H, m), 3.36–3.51 (4H, m), 3.38 (4H, t, J=5 Hz), 3.61 (2H, d, J=11 Hz), 3.72 (4H, t, J=7 Hz), 4.45 (1H, s), 5.21–5.27 (1H, m), 7.21 (1H, t, J=5 Hz), 7.91 (1H, d, J=6 Hz)

IR (ν, KBr, cm$^{-1}$): 3347, 2954, 2857, 1677

Rf: 0.51.

Example 99

Synthesis of N-[(S)-1,2-dioxo-1-[N-(4-phenoxyphenyl) amino]-3-heptyl]-1-[N-(morpholine-4-carbonyl)amino] cyclohexanecarboxamide

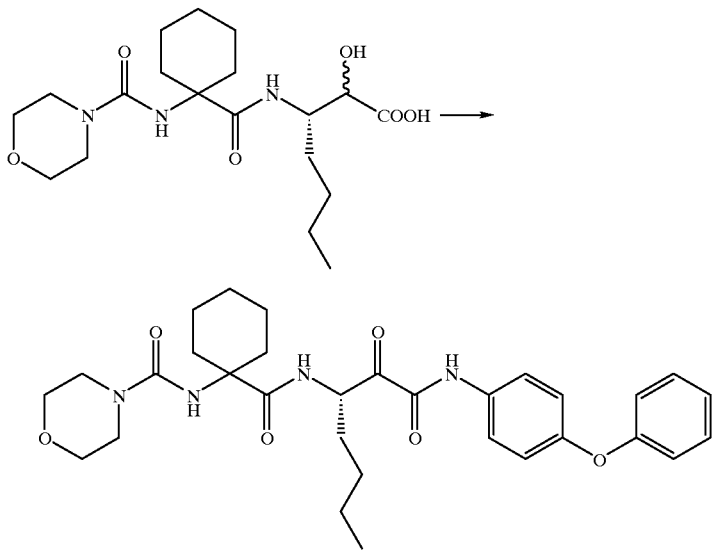

The same procedure as in Example 28 was repeated except that the 3-chlorobenzylamine was replaced by 277 mg of 4-phenoxyaniline, whereby 170 mg of the captioned N-[(S)-1,2-dioxo-1-[N-(4-phenoxyphenyl)amino]-3-heptyl]-1-[N-(morpholine-4-carbonyl)amino]cyclohexanecarboxamide was obtained in a yield of 19%.

1H-NMR (CDCl$_3$, δ): 0.89 (3H, t, J=7 Hz), 1.20–2.20 (16H, m), 3.35–3.42 (4H, m), 3.60–3.80 (4H, m), 4.43 (1H, s), 5.25 (1H, ddd, J=12 Hz, 7 Hz, 5 Hz), 6.95–7.05 (4H, m), 7.06–7.15 (1H, m), 7.30–7.40 (2H, m), 7.55–7.65 (2H, m), 8.07 (1H, d, J=7 Hz), 8.64 (1H, s)

IR (ν, KBr, cm$^{-1}$): 3318, 3264, 2929, 2856, 1666, 1637, 1508

Rf: 0.31.

Example 100

Synthesis of N-[(S)-1,2-dioxo-1-[N-(1-benzoyl-piperidine-4-yl)amino]-3-heptyl]-1-[N-(morpholine-4-carbonyl)amino]cyclohexanecarboxamide

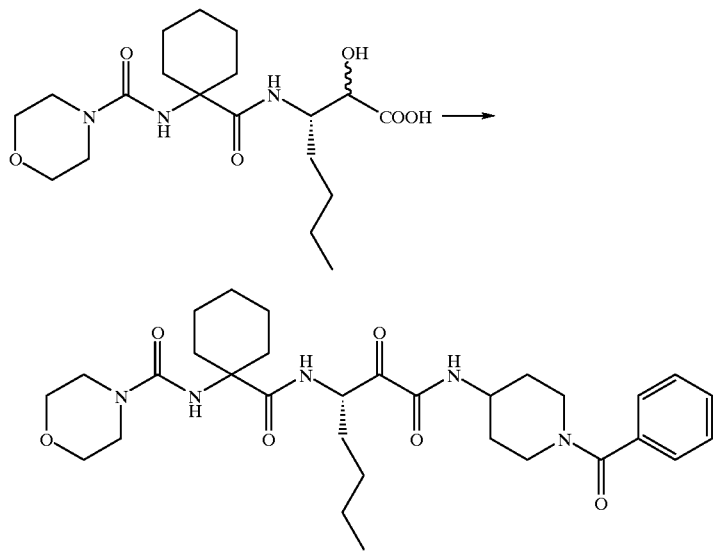

The same procedure as in Example 28 was repeated except that the 3-chlorobenzylamine was replaced by 306 mg of 4-amino]-benzoylpiperidine, whereby 356 mg of the captioned N-[(S)-1,2-dioxol-[N-(1-benzoyl-piperidine-4-yl)amino]-3-heptyl]-1-[N-(morpholine-4-carbonyl)amino] cyclohexanecarboxamide was obtained in a yield of 40%.

1H-NMR (CDCl$_3$, δ): 0.88 (3H, t, J=7 Hz), 1.20–2.20 (20H, m), 2.90–3.30 (2H, m), 3.30–3.42 (4H, m), 3.60–3.90 (5H, m), 3.95–4.05 (1H, m), 4.44 (1H, s), 4.50–4.80 (1H, m), 5.18 (1H, ddd, J=12 Hz, 7 Hz, 5 Hz), 6.85 (1H, d, J=8 Hz), 7.30–7.42 (5H, m), 7.96 (1H, d, J=6 Hz)

IR (ν, KBr, cm$^{-1}$): 3355, 2929, 2857, 1670, 1619, 1527

Rf: 0.66.

Example 101

Synthesis of N-[(S)-1,2-dioxo-1-[N-(4-oxo-1-cyclohexyl)amino]-3-heptyl]-1-[N-(morpholine-4-carbonyl)amino]cyclohexanecarboxamide

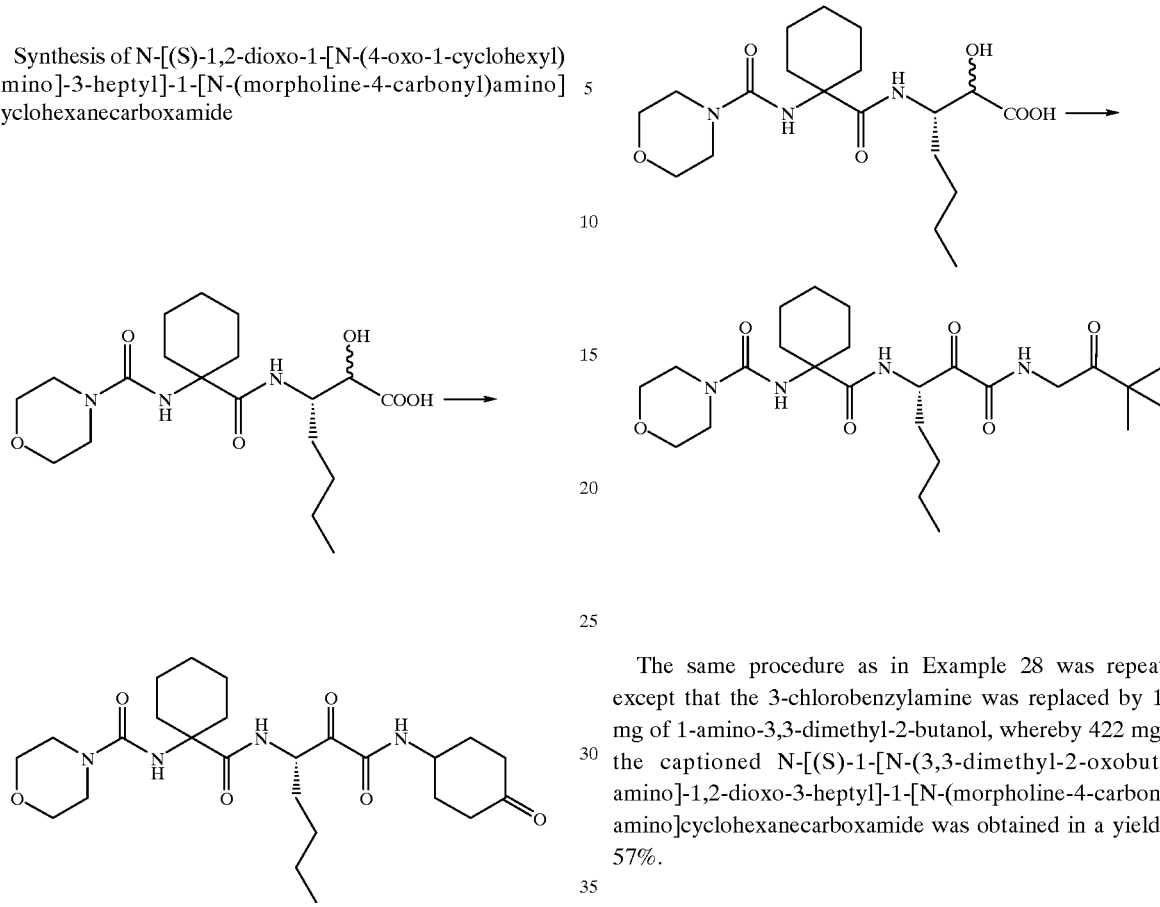

The same procedure as in Example 28 was repeated except that the 3-chlorobenzylamine was replaced by 230 mg of 4-amino]cyclohexanole, whereby 101 mg of the captioned N-[(S)-1,2-dioxo-1-[N-(4-oxo-1-cyclohexyl)amino]-3-heptyl]-1-[N-(morpholine-4-carbonyl)amino]cyclohexanecarboxamide was obtained in a yield 13%.

1H-NMR (CDCl$_3$, δ): 0.85–1.00 (3H, m), 1.30–1.42 (7H, m), 1.60–2.00 (10H, m), 2.00–2.30 (3H, m), 2.40–2.55 (4H, m), 3.30–3.45 (4H, m), 3.65–3.80 (4H, m), 4.10–4.20 (1H, m), 4.47 (1H, s), 5.18 (1H, ddd, J=12 Hz, 7 Hz, 5 Hz), 6.92 (1H, d, J=8 Hz), 7.99 (1H, d, J=6 Hz)

IR (ν, KBr, cm$^{-1}$): 3332, 2934, 2857, 1718, 1662, 1629, 1529

Rf: 0.75.

Example 102

Synthesis of N-[(S)-1-[N-(3,3-dimethyl-2-oxobutyl)amino]-1,2-dioxo-3-heptyl]-1-[N-(morpholine-4-carbonyl)amino]cyclohexanecarboxamide The same procedure as in Example 28 was repeated except that the 3-chlorobenzylamine was replaced by 176 mg of 1-amino-3,3-dimethyl-2-butanol, whereby 422 mg of the captioned N-[(S)-1-[N-(3,3-dimethyl-2-oxobutyl)amino]-1,2-dioxo-3-heptyl]-1-[N-(morpholine-4-carbonyl)amino]cyclohexanecarboxamide was obtained in a yield of 57%.

1H-NMR (CDCl$_3$, δ): 0.88 (3H, t, J=7 Hz), 1.21 (9H, s), 1.22–1.43 (6H, m), 1.55–1.69 (5H, m), 1.82–2.15 (5H, m), 3.39 (4H, t, J=5 Hz), 3.72 (4H, t, J=5 Hz), 4.26 (1H, dd, J=16 Hz, 5 Hz), 4.35 (1H, dd, J=16 Hz, 5 Hz), 4.45 (1H, s), 5.21–5.27 (1H, m), 7.62 (1H, t, J=5 Hz), 7.95 (1H, d, J=6 Hz)

IR (ν, KBr, cm$^{-1}$): 3374, 2933, 2857, 1683, 1643

Rf: 0.60.

Example 103

Synthesis of N-[(S)-1,2-dioxo-1-[N-[2-(phenylsulfonyl)ethyl]amino]-3-beptyl]-1-[N-(morpholine-4-carbonyl)amino]cyclohexanecarboxamide

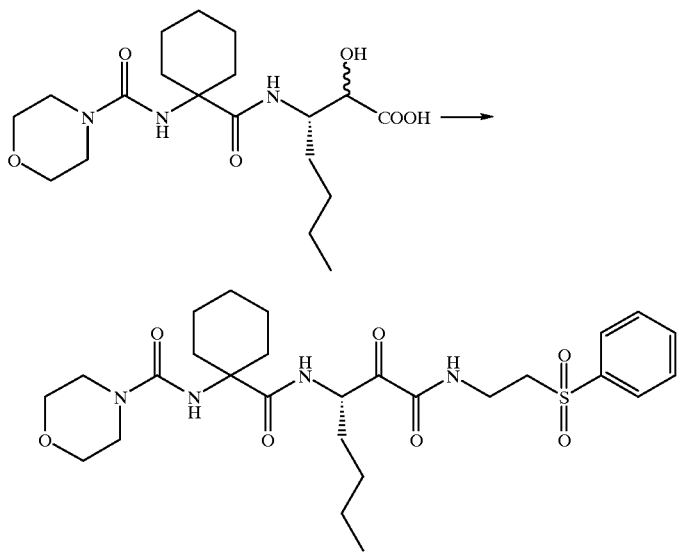

The same procedure as in Example 28 was repeated except that the 3-chlorobenzylamine was replaced by 278 mg of 2-(phenylsulfonyl)ethanamine, whereby 256 mg of the captioned N-[(S)-1,2-dioxo-1-[N-[2-(phenylsulfonyl) ethyl]amino]-3-heptyl]-1-[N-(morpholine-4-carbonyl) amino]cyclohexanecarboxamide was obtained in a yield of 30%.

1H-NMR (CDCl$_3$, δ): 0.88 (3H, t, J=7 Hz), 1.21–1.43 (7H, m), 1.53–1.69 (4H, m), 1.83–2.16 (5H, m), 3.29–3.41 (6H, m), 3.69–3.77 (6H, m), 4.44 (1H, s), 5.11–5.17 (1H, m), 7.45 (1H, t, J=5 Hz), 7.60 (2H, t, J=8 Hz), 7.69 (1H, t, J=8 Hz), 7.89–7.97 (3H, m)

IR (v, KBr, cm$^{-1}$): 3394, 2929, 2857, 1675, 1643

Rf: 0.68.

Example 104

Synthesis of N-[(S)-1,2-dioxo-1-[N-(2-oxo-3-phenylpropyl)amino]-3-heptyl]-1-[N-morpholine-4-carbonyl)amino]cyclohexanecarboxamide

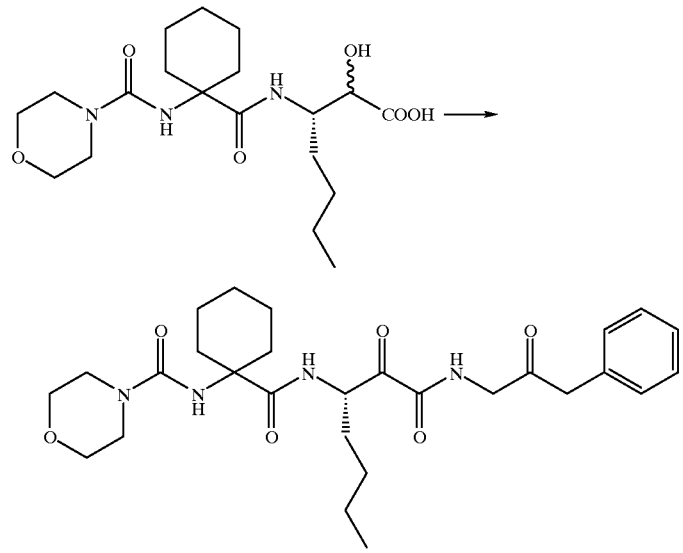

The same procedure as in Example 28 was repeated except that the 3-chlorobenzylamine was replaced by 454 mg of (2RS)-2-hydroxy-3-phenylpropylamine, whereby 200 mg of the captioned N-[(S)-1,2-dioxo-1-[N-(2-oxo-3-phenylpropyl)amino]-3-heptyl]-1-[N-(morpholine-4-carbonyl)amino]cyclohexanecarboxamide was obtained in a yield of 25%.

1H-NMR (CDCl$_3$, δ): 0.87 (3H, t, J=7 Hz), 1.24–1.38 (7H, m), 1.60–1.64 (4H, m), 1.83–1.93 (3H, m), 2.05–2.12 (2H, m), 3.36 (4H, t, J=5 Hz), 3.69 (4H, t, J=5 Hz), 3.76 (2H, s), 4.17 (2H, ddd, J=5 Hz, 20 Hz, 25 Hz), 4.43 (1H, s), 5.12–5.18 (1H, m), 7.21–7.32 (5H, m), 7.49 (1H, t, J=5 Hz), 7.79 (1H, d, J=6 Hz)

IR (ν, KBr, cm⁻¹): 3318, 2931, 1685, 1644, 1529
Rf: 0.63.

Example 105

Synthesis of N-[(S)-1,2-dioxo-1-[N-(2-oxo-4-phenylbutyl)amino]-3-heptyl]-1-[N-(morpholine-4-carbonyl)amino]cyclohexanecarboxamide

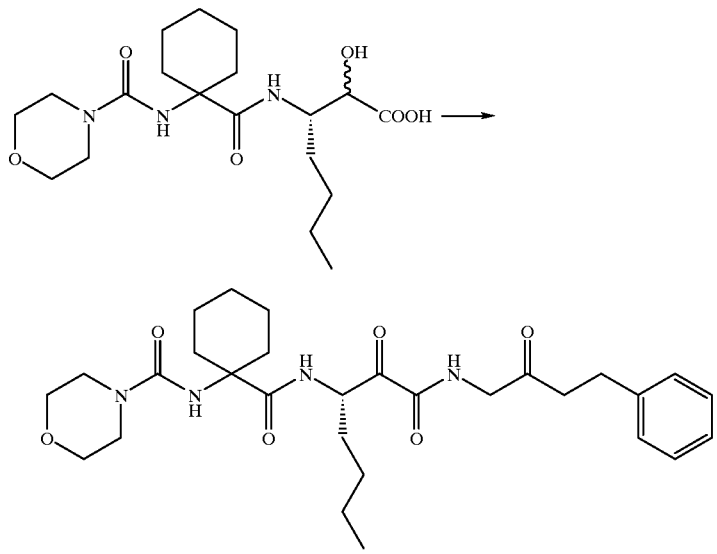

The same procedure as in Example 28 was repeated except that the 3-chlorobenzylamine was replaced by 496 mg of (2RS)-2-hydroxy-4-phenylbutylamine, whereby 235 mg of the captioned N-[(S)-1,2-dioxo-1-[N-(2-oxo-4-phenylbutyl) amino]-3-heptyl]-1-[N-(morpholine-4-carbonyl)amino]cyclohexanecarboxamide was obtained in a yield of 29%.

1H-NMR (CDCl₃, δ): 0.87 (3H, t, J=7 Hz), 1.29–1.45 (8H, m), 1.60–1.65 (3H, m), 1.86–1.94 (3H, m), 2.03–2.13 (2H, m), 2.80 (2H, t, J=7), 2.95 (2H, t, J=7 Hz), 3.38 (4H, t, J=5 Hz), 3.71 (4H, t, J=5 Hz), 4.07 (2H, ddd, J=5 Hz, 20 Hz, 35 Hz), 4.43 (1H, s), 5.16–5.21 (1H, m), 7.16–7.29 (5H, m), 7.52 (1H, t, J=5 Hz), 7.97 (1H, d, J=6 Hz)

IR (ν, KBr, cm⁻¹): 3382, 2927, 1675, 1527
Rf: 0.59.

Example 106

Synthesis of N-[(S)-1,2-dioxo-1-[N-(2-methyl-2-phenoxypropyl)amino-3-heptyl]-1-[N-(morpholine-4-carbonyl)amino]cyclohexanecarboxamide

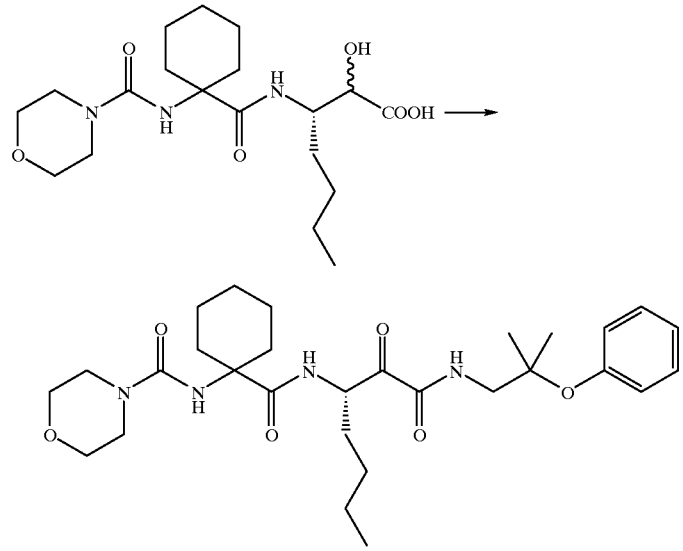

The same procedure as in Example 28 was repeated except that the 3-chlorobenzylamine was replaced by 600 mg of 2-methyl-2-phenoxypropylamine, whereby 241 mg of the captioned N-[(S)-1,2-dioxo-1-[N-(2-methyl-2-phenoxypropyl)amino]-3-heptyl]-1-[N-(morpholine-4-carbonyl)amino]cyclohexanecarboxamide was obtained in a yield of 22%.

1H-NMR (CDCl$_3$, δ): 0.86 (3H, t, J=7 Hz), 1.26 (6H, d, J=2 Hz), 1.30–1.43 (7H, m), 1.64–1.72 (4H, m), 1.86–2.01 (3H, m), 2.09–2.11 (2H, m), 3.39 (4H, t, J=5 Hz), 3.49 (2H, dd, J=2 Hz, 6 Hz), 3.72 (4H, t, J=5Hz), 4.44 (1H, s), 5.23–5.28 (1H, m), 6.94–6.96 (2H, m), 7.09–7.12 (1H, s), 7.27–7.30 (2H, m), 7.41 (1H, t, J=6 Hz), 7.97 (1H, d, J=7 Hz)

IR (ν, KBr, cm$^{-1}$): 3330, 2931, 1689, 1648, 1527

Rf: 0.44.

Example 107

Synthesis of N-[(S)-1,2-dioxo-1-[N-[(R)-2-oxocyclohexyl]amino]-3-heptyl]-1-[N-(morpholine-4-carbonyl)amino]cyclohexanecarboxamide

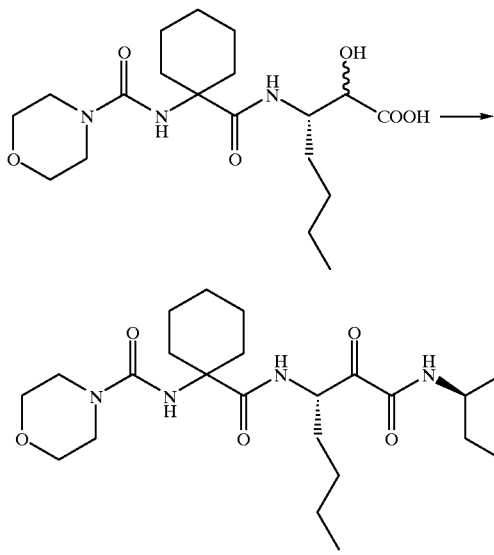

The same procedure as in Example 28 was repeated except that the 3-chlorobenzylamine was replaced by 173 mg of (1R,2R)-2-amino]cyclohexanol, whereby 280 mg of the captioned N-[(S)-1,2-dioxo-1-[N-[(R)-2-oxocyclohexyl]amino]-3-heptyl]-1-[N-(morpholine-4-carbonyl)amino]cyclohexanecarboxamide was obtained in a yield of 38%.

1H-NMR (CDCl$_3$, δ): 0.88 (3H, t, J=7 Hz), 1.22–1.47 (8H,m), 1.55–1.99 (10H, m), 2.03–2.20 (3H, m), 2.35–2.69 (3H, m), 3.39 (4H, t, J=5 Hz), 3.72 (4H, t, J=5 Hz), 4.40–4.46 (1H,m), 4.46 (1H s), 5.22–5.29 (1H, m), 7.69 (1H, d, J=7 Hz), 7.89 (1H, d, J=7 Hz)

IR (ν, KBr, cm$^{-1}$): 3392, 2931, 2859, 1675, 1629

Rf: 0.68.

Example 108

Synthesis of N-[(S)-1,2-dioxo-1-[N-[(S)-2-oxocyclohexyl]amino]-3-heptyl]-1-[N-(morpholine-4-carbonyl)amino]cyclohexanecarboxamide

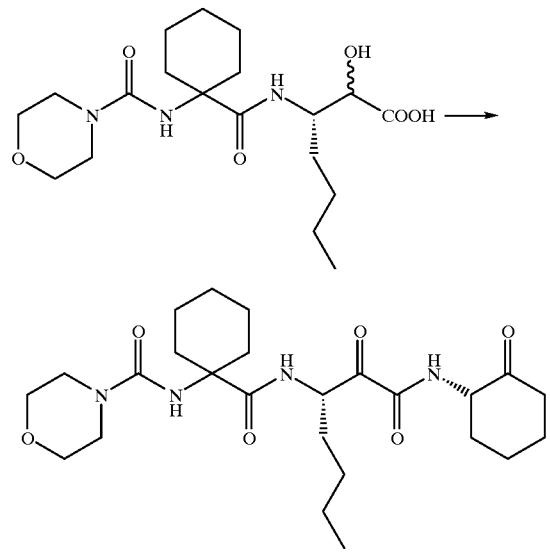

The same procedure as in Example 28 was repeated except that the 3-chlorobenzylamine was replaced by 173 mg of (1S,2S)-2-amino]cyclohexanol, whereby 236 mg of the captioned N-[(S)-1,2-dioxo-1-[N-[(S)-2-oxocyclohexyl amino]-3-heptyl]-1-[N-(morpholine-4-carbonyl)amino] cyclohexanecarboxamide was obtained in a yield of 32%.

1H-NMR (CDCl$_3$, δ): 0.88 (3H, t, J=7 Hz), 1.23–1.46 (8H,m), 1.56–2.00 (10H, m), 2.03–2.20 (3H, m), 2.36–2.70 (3H, m), 3.39 (4H, t, J=5 Hz), 3.72 (4H, t, J=5 Hz), 4.36–4.47 (1H, m), 4.46 (1H, s), 5.20–5.25 (1H, m), 7.76 (1H, d, J=6 Hz), 7.93 (1H, d, J=7 Hz)

IR (ν, KBr, cm$^{-1}$): 3380, 2931, 2859, 1675, 1629

Rf: 0.66.

Example 109

Synthesis of N-[(S)-1,2-dioxo-1-[N-[(1RS)-2-oxo-1-cyclohexyl]amino]-5-methyl-3-hexyl]-1-[N-(morpholine-4-carbonyl)amino]cyclohexanecarboxamide

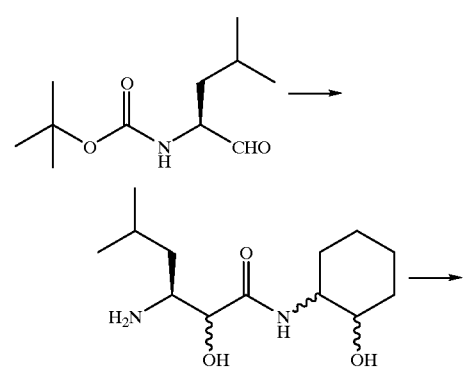

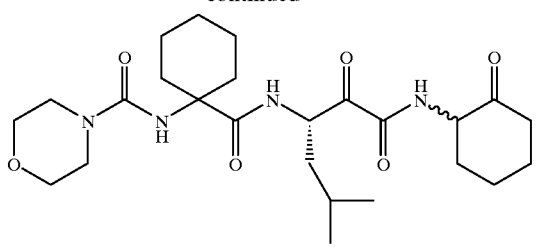

The same procedure as in Reference Example 20 was repeated except that the cyclopentylamine was replaced by 3.7 g of (1R2R,1S2S)-2-amino]cyclohexanol, whereby 910 mg of (2RS,3S)-N-[(1R2R,1S2S)-2-hydroxycyclohexyl]-3-amino-2-hydoroxy-5-methylhexanamide was obtained in a yield of 7%. Next the same procedure as in Example 1 was repeated except that the (3S)-N-(2-methyl2-propyl)-3-amino2-hydroxyheputanamide was replaced by 910 mg of said(2RS,3S)-N-[(1R2R, 1S2S)-2-hydroxycyclohexyl]-3-amino2-hydroxy-5-methylhexanamide, whereby 395 mg of the captioned N-[(3S)-1,2-dioxol-[N-[(1RS)-2-oxo1-cyclohexyl]amino]-5-methyl-3-hexyl]-1-[N-(morpholine-4-carbonyl)amino]cyclohexanecarboxamide was obtained in a yield of 22%.

1H-NMR (CDCl$_3$, δ): 0.93 (3H, t, J=8 Hz), 0.98 (3H, t, J=8 Hz), 1.20–2.20 (19H, m), 2.30–2.45 (1H, m), 2.50–2.70 (1H, m), 3.38 (4H, t, J=5 Hz), 3.71 (4H, t, J=5 Hz), 4.19–4.30 (2H, m), 5.20–5.35 (1H, m), 7.69 (1/2H, d, J=6 Hz), 7.76 (1/2H, d, J=6 Hz), 7.90 (1/2H, d, J=7 Hz), 7.94 (1/2H, d, J=7 Hz)

IR (ν, KBr, cm$^{-1}$): 3378, 2937, 2861, 1725, 1675, 1648, 1523

Rf: 0.68.

Example 110

Synthesis of N-[(S)-1,2-dioxo-1-[N-[(S)-3-methyl-1-oxo-1-(phenylmethoxy)-2-butyl]amino]-3-heptyl]-1-[N-(morpholine-4-carbonyl)amino]cyclohexanecarboxamide The same procedure as in Example 28 was repeated except that the 3-chlorobenzylamine was replaced by 223 mg of L-valinebenzylester, whereby 217 mg of the captioned N-[(S)-1,2-dioxo-1-[N-[(S)-3-methyl-1-oxo-1-(phenylmethoxy)-2-butyl]amino]-3-heptyl]-1-[N-(morpholine-4-carbonyl)amino]cyclohexanecarboxamide was obtained in a yield of 34%.

1H-NMR (CDCl$_3$, δ): 0.87 (3H, t, J=7 Hz), 0.88 (6H, dd, J=14 Hz, 7 Hz), 1.30–1.41 (8H, m), 1.52–1.67 (4H, m), 1.82–2.00 (3H, m), 2.04–2.13 (2H, m), 2.14–2.26 (1H, m), 3.38 (4H, t, J=5 Hz), 3.72 (4H, t, J=5 Hz), 4.43 (1H, s), 4.52 (1H, dd, J=9 Hz, 5 Hz), 5.14–5.24 (3H, m), 7.32–7.39 (6H, m), 7.98 (1H, d, J=7 Hz)

IR (ν, KBr, cm$^{-1}$): 3332, 2960, 2931, 1741, 1675, 1629, 1523

Rf: 0.39.

Example 111

Synthesis of N-[(S)-1,2-dioxo-1-[N-[(R)-1-methoxy-3-methyl-1-oxo-2-butyl]amino]-3-heptyl]-1-[N-(morpholine-4-carbonyl)amino]cyclohexanecarboxamide

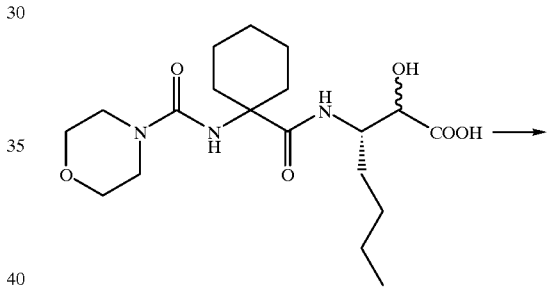

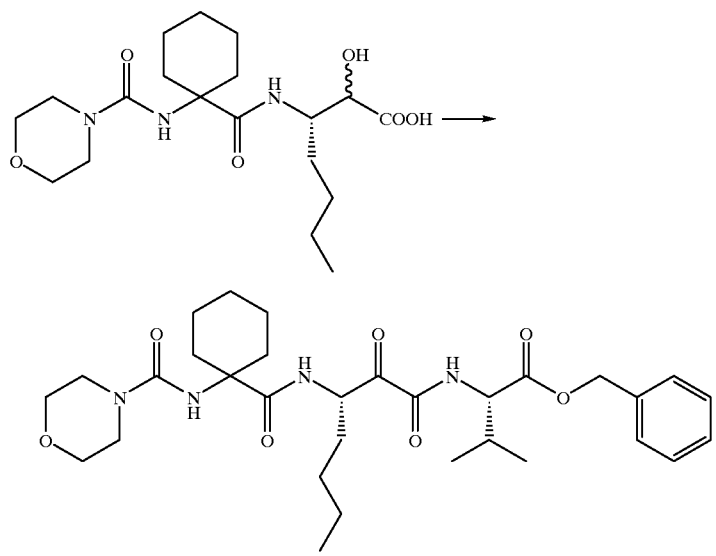

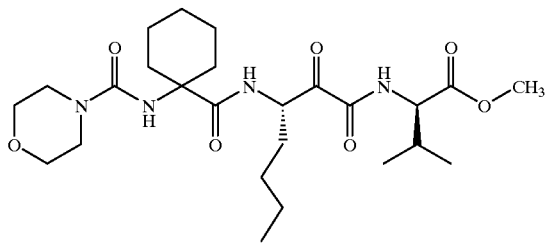

The same procedure as in Example 28 was repeated except that the 3-chlorobenzylamine was replaced by 262 mg of D-valinemethylester, whereby 472 mg of the captioned N-[(S)-1,2-dioxo-1-[N-[(R)-1-methoxy-3-methyl-1-oxo-2-butyl]amino]-3-heptyl]-1-[N-(morpholine-4-carbonyl)amino]cyclohexanecarboxamide was obtained in a yield of 46%.

1H-NMR (CDCl$_3$, δ): 0.88 (3H, t, J=7 Hz), 0.90–0.96 (6H, m), 1.21–1.39 (7H, m), 1.57–1.65 (5H, m), 1.89–1.97 (2H, m), 2.11–2.16 (2H, m), 2.17–2.24 (1H, m), 3.39 (4H, t, J=5 Hz), 3.72 (4H, t, J=5 Hz), 3.76 (3H, s), 4.44 (1H, s), 4.49 (1H, dd, J=9 Hz, 5 Hz), 5.18–5.23 (1H, m), 7.31 (1H, d, J=10 Hz), 7.96 (1H, d, J=7 Hz)

IR (ν, KBr, cm$^{-1}$): 3355, 2960, 2933, 1745, 1677, 1643, 1517, 1257

Rf: 0.60.

Example 112

Synthesis of N-[(S)-1,2-dioxo-1-[N-[(R)-2-methoxy-2-oxo-1-phenylethyl]amino]-3-heptyl]-1-[N-(morpholine-4-carbonyl)amino]cyclohexanecarboxamide

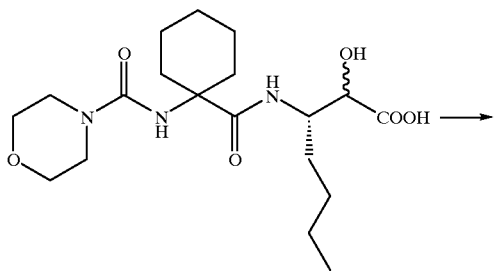

The same procedure as in Example 28 was repeated except that the 3-chlorobenzylamine was replaced by 323 mg of D-phenylglycinemethylester, whereby 490 mg of the captioned N-[(S)-1,2-dioxo-1-[N-[(R)-2-methoxy-2-oxo-1-phenylethyl]amino]-3-heptyl]-1-[N-(morpholine-4-carbonyl)amino]cyclohexanecarboxamide was obtained in a yield of 45%.

1H-NMR (CDCl$_3$, δ): 0.88 (3H, t, J=8 Hz), 1.30–1.38 (7H, m), 1.61–1.66 (3H, m), 1.81–2.09 (6H, m), 3.36 (4H, t, J=5 Hz), 3.70 (4H, t, J=5 Hz), 3.74 (3H, s), 4.40 (1H, s), 5.08–5.15 (1H, m), 5.50 (1H, d, J=8 Hz), 7.34–7.36 (5H, m), 7.76 (1H, d, J=7 Hz), 7.97 (1H, d, J=7 Hz)

IR (ν, KBr, cm$^{-1}$): 3430, 3293, 2954, 2931, 1735, 1666, 1525

Rf: 0.60.

Example 113

Synthesis of N-[(S)-1,2-dioxo-1-[N-[(R)-2-oxocyclopentyl]amino]-3-heptyl]-1-[N-(morpholine-4-carbonyl)amino]cyclohexanecarboxamide

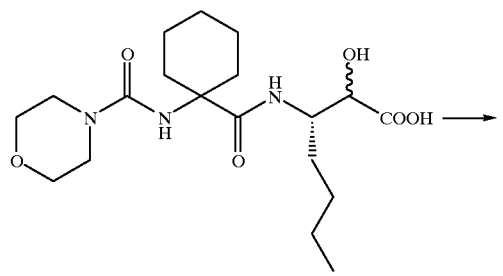

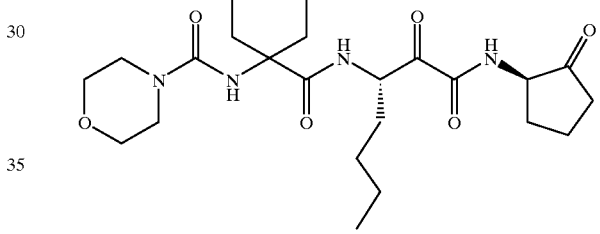

The same procedure as in Example 28 was repeated except that the 3-chlorobenzylamine was replaced by 152 mg of (1R,2R)-2-amino]cyclopentanol, whereby 266 mg of the captioned N-[(S)-1,2-dioxo-1-[N-[(R)-2-oxocyclopentyl]amino]-3-heptyl]-1-[N-(morpholine-4-carbonyl)amino]cyclohexanecarboxamide was obtained in a yield of 37%.

1H-NMR (CDCl$_3$, δ): 0.88 (3H, t, J=7 Hz), 1.23–1.45 (7H, m), 1.58–1.72 (5H, m), 1.82–1.99 (4H, m), 2.03–2.31 (4H, m), 2.39–2.49 (1H, m), 2.60–2.68 (1H, m), 3.38 (4H, t, J=5 Hz), 3.71 (4H, t, J=5 Hz), 4.12–4.21 (1H, m), 4.50 (1H, s), 5.12–5.17 (1H, m), 7.14 (1H, d, J=7 Hz), 8.02 (1H, d, J=6 Hz)

IR (ν, KBr, cm$^{-1}$): 3332, 2929, 2857, 1675, 1648

Rf: 0.71.

Example 114

Synthesis of N-[(S)-1,2-dioxo-1-[N-[(S)-2-oxocyclopentyl]amino]-3-heptyl]-1-[N-(morpholine-4-carbonyl)amino]cyclohexanecarboxamide

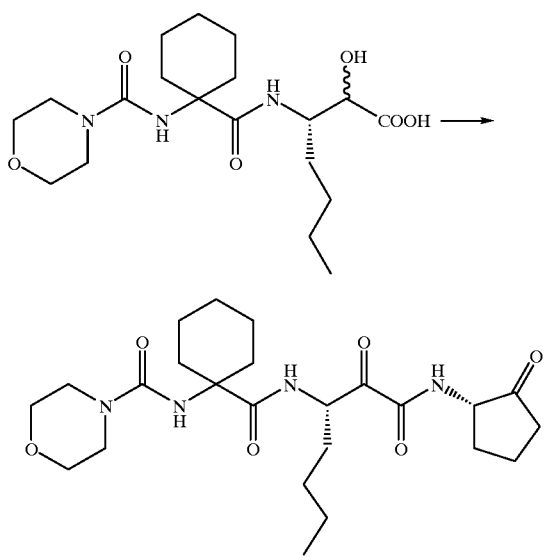

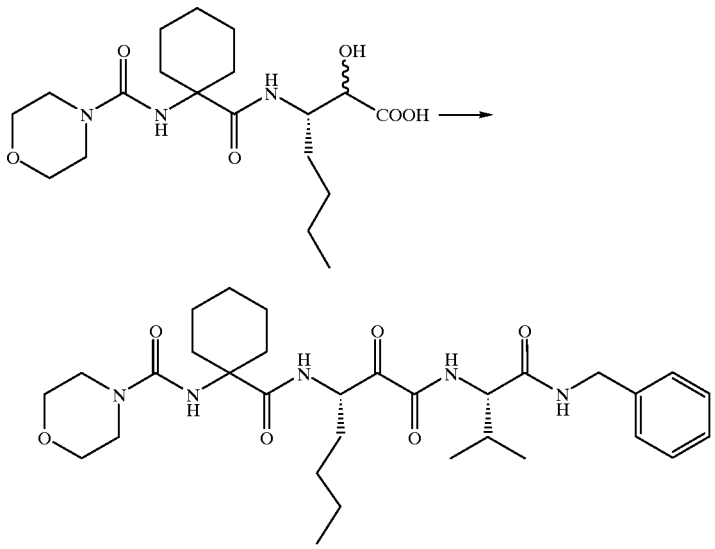

The same procedure as in Example 28 was repeated except that the 3-chlorobenzylamine was replaced by 152 mg of (1S,2S)-2-amino]cyclopentanol, whereby 230 mg of the captioned N-[(S)-1,2-dioxo-1-[N-[(S)-2-oxocyclopentyl]amino]-3-heptyl]-1-[N-(morpholine-4-carbonyl)amino]cyclohexanecarboxamide was obtained in a yield of 32%.

1H-NMR (CDCl$_3$, δ): 0.88 (3H, t, J=7 Hz), 1.23–1.46 (7H, m), 1.54–1.99 (9H, m), 2.03–2.33 (4H, m), 2.40–2.49 (1H, m), 2.57–2.64 (1H, m), 3.89 (4H, t, J=5 Hz), 3.72 (4H, t, J=5 Hz), 4.01–4.09 (1H, m), 4.51 (1H, s), 5.08–5.15 (1H, m), 7.18 (1H, d, J=7 Hz), 8.05 (1H, d, J=6 Hz)

IR (ν, KBr, cm$^{-1}$) 3316, 2931, 2857, 1677, 1648

Rf: 0.70.

Example 115

Synthesis of N-[(S)-1,2-dioxo-1-[N-[(S)-3-methyl-1-oxo-1-[N-(phenylmethyl) amino]-2-butyl]amino]-3-heptyl]-1-[N-(morpholine-4-carbonyl)amino] cyclohexanecarboxamide The same procedure as in Example 28 was repeated except that the 3-chlorobenzylamine was replaced by 128 mg of N-[(S)-1,2-dioxo-1-[N-[(S)-3-methyl-1-oxo-1-[N-(phenylmethyl)amino]-2-butyl]amino]-3-heptyl]-1-[N-(morpholine-4-carbonyl)amino]cyclohexanecarboxamide was obtained in a yield of 45%.

1H-NMR (CDCl$_3$, δ): 0.88 (3H, t, J=7 Hz), 0.94 (6H, dd, J=19 Hz, 7 Hz), 1.24–1.33 (7H, m), 1.60–1.80 (5H, m), 1.81–2.11 (4H, m), 2.42 (1H, dt, J=19 Hz, 7 Hz), 3.36 (4H, t, J=5 Hz), 3.71 (4H, t, J=5 Hz), 4.27 (1H, dd, J=9 Hz, 5 Hz), 4.38 (1H, s), 4.43 (2H, d, J=6 Hz), 5.06–5.11 (1H, m), 6.73 (1H, t, J=6 Hz), 7.22–7.35 (6H, m), 8.06 (1H, d, J=6 Hz)

IR (ν, KBr, cm$^{-1}$): 3399, 1648, 1529

Rf: 0.57.

Example 116

Synthesis of N-[(S)-1,2-dioxo-1-[N-[(S)-3-methyl-1-oxo-1-[N-(1,1-dimethylethyl)amino]-2-butyl]amino]-3-heptyl]-

1-[N-(morpholine-4-carbonyl)amino]cyclohexanecarboxamide

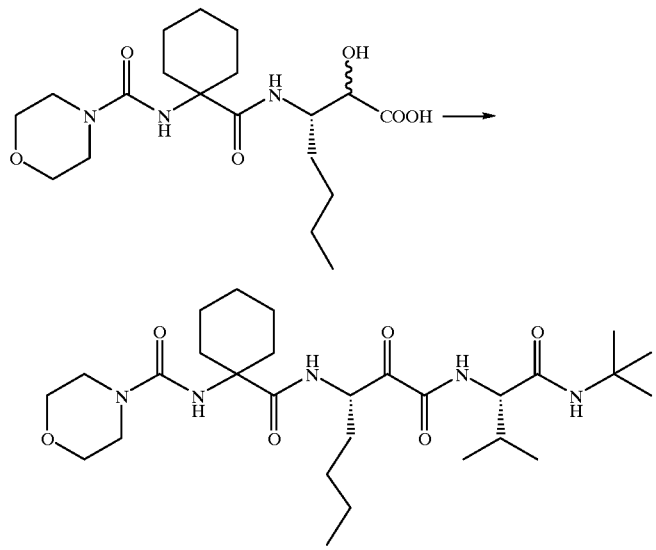

The same procedure as in Example 28 was repeated except that the 3-chlorobenzylamine was replaced by 143 mg of L-N-tert-butylvalinamide, whereby 154 mg of the captioned N-[(S)-1,2-dioxo-1-[N-[(S)-3-methyl-1-oxo-1-[N-(1,1-dimethylethyl)amino]-2-butyl]amino]-3-heptyl]-1-[N-(morpholine-4-carbonyl) amino] cyclohexanecarboxamide was obtained in a yield of 34%.

1H-NMR (CDCl₃, δ): 0.87 (3H, t, J=7 Hz), 0.92 (6H, dd, J=12 Hz, 7 Hz), 1.24–1.34 (7H, m), 1.35 (9H, s), 1.58–1.70 (3H, m), 1.87–2.00 (3H, m), 2.04–2.22 (3H, m), 3.39 (4H, t, J=5 Hz), 3.72 (4H, t, J=5 Hz), 4.02 (1H, dd, J=9 Hz, 6 Hz), 4.43(1H, s), 5.20–5.26 (1H, m), 5.61 (1H, s), 7.35 (1H, d, J=9 Hz), 7.94 (1H, d, J=6 Hz)

IR (ν, KBr, cm⁻¹): 3322, 2962, 2933, 1677, 1643, 1531, 1255

Rf: 0.55.

Example 117

Synthesis of N-[(S)-1,2-dioxo-1-[N-[4-(ethoxycarbonylmethylene) cyclohexane-1-yl]amino]-3-heptyl]-1-[N-(morpholine-4-carbonyl)amino] cyclohexanecarboxamide

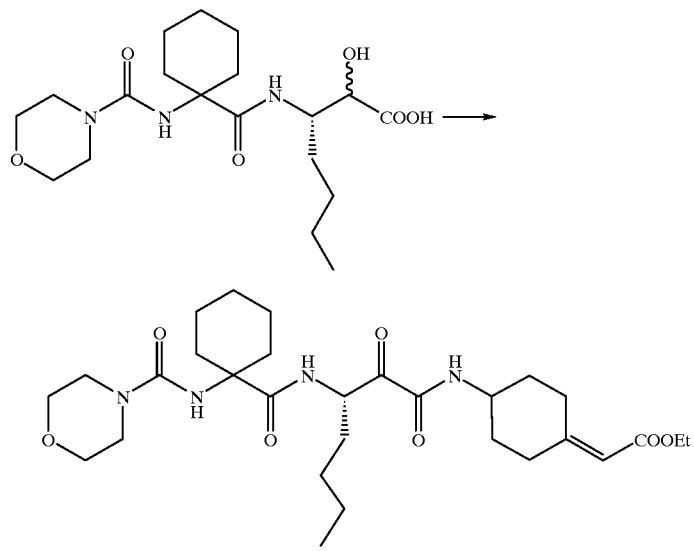

The same procedure as in Example 28 was repeated except that the 3-chlorobenzylamine was replaced by 361 mg of 4-(ethoxycarbonylmethylene) cyclohexylamine, whereby 250 mg of the captioned N-[(S)-1,2-dioxo-1-[N-[4-(ethoxycarbonylmethylene)cyclohexane-1-yl]amino]-3-heptyl]-1-[N-(morpholine-4-carbonyl)amino] cyclohexanecarboxamide was obtained in a yield of 22%.

1H-NMR (CDCl₃, δ): 0.88 (3H, t, J=7 Hz), 1.27 (3H, t, J=7 Hz), 1.20–2.40 (21H, m), 3.38 (4H, t, J=5 Hz), 3.71 (4H, t, J=5 Hz), 3.90–4.10 (1H, m), 4.15 (2H, qd, J=12 Hz, 7 Hz), 4.43 (1H, s), 5.19 (1H, ddd, J=13 Hz, 9 Hz, 4 Hz), 5.66 (1H, s), 6.78 (1H, d, J=8 Hz), 7.95 (1 H, d, J=6 Hz)

IR (ν, KBr, cm$^{-1}$): 3328, 2935, 2856, 1712, 1681, 1646, 1527

Rf: 0.51.

Example 118

Synthesis of N-[(S)-1,2-dioxo-1-[N-(1,4-dioxaspiro[4,5] decane-8-yl)amino]-3-heptyl]-1-[N-(morpholine-4-carbonyl)amino]cyclohexanecarboxamide

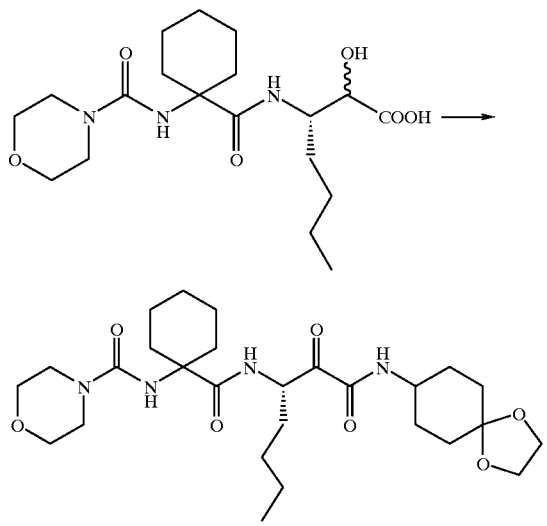

The same procedure as in Example 28 was repeated except that the 3-chlorobenzylamine was replaced by 314 mg of 8-amino1,4-dioxaspiro[4,5]decane, whereby 360 mg of the captioned N-[(S)-1,2-dioxo-1-[N-(1,4-dioxaspiro[4,5] decane-8-yl)amino]-3-heptyl]-1-[N-(morpholine-4-carbonyl)amino]cyclohexanecarboxamide was obtained in a yield of 33%.

1H-NMR (CDCl$_3$, δ): 0.87 (3H, t, J=7 Hz), 1.20–2.20 (24H, m), 3.38 (4H, t, J=5 Hz), 3.71 (4H, t, J=5 Hz), 3.94 (4H, s), 4.45 (1H, s), 5.20 (1H, ddd, J=12 Hz, 7 Hz, 4 Hz), 6.78 (1H, d, J=8 Hz), 7.92(1H, d, J=7 Hz)

IR (ν, KBr, cm$^{-1}$): 3345, 2937, 2857, 1729, 1685, 1648, 1525

Rf: 0.68.

Example 119

Synthesis of N-[(S)-1-[N-[(S)-hexahydro-2-azepinone-3-yl]amino]-1,2-dioxo-3-heptyl]-1-[N-(morpholine-4-carbonyl)amino]cyclohexanecarboxamide

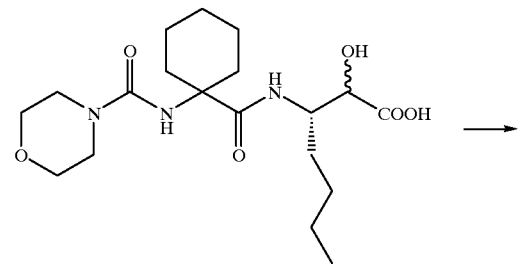

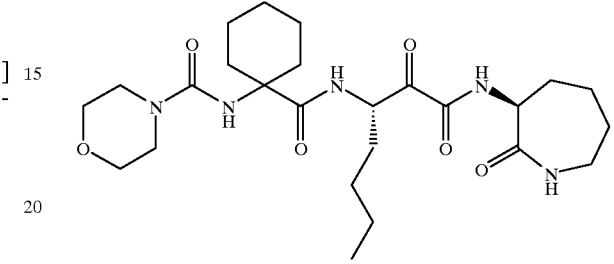

The same procedure as in Example 28 was repeated except that the 3-chlorobenzylamine was replaced by 192 mg of (S)-3-aminohexahydro-2-azepinone, whereby 88 mg of the captioned N-[(S)-1-[N-[(S)-hexahydro-2-azepinone-3-yl]amino]-1,2-dioxo-3-heptyl]-1-[N-(morpholine-4-carbonyl)amino]cyclohexanecarboxamide was obtained in a yield of 12%.

1H-NMR (CDCl$_3$, δ): 0.87 (3H, t, J=7 Hz), 1.22–1.73 (13H, m), 1.75–2.18 (9H, m), 3.20–3.31 (2H, m), 3.39 (4H, t, J=5 Hz), 3.72 (4H, t, J=5 Hz), 4.43–4.50 (1H, m), 4.48 (1H, s), 5.24–5.31 (1H, m), 6.02 (1H, t, J=5 Hz), 7.86 (1H, d, J=7 Hz), 8.16 (1H, d, J=6 Hz)

IR (ν, KBr, cm$^{-1}$): 3355, 2931, 2857, 1658

Rf: 0.76.

Example 120

Synthesis of N-[(S)-1,2-dioxo-1-[N-[(2S,3S)-1-methoxy-3-methyl-1-oxo-2-hexyl]amino]-3-heptyl]-1-[N-(morpholine-4-carbonyl)amino]cyclohexanecarboxamide The same procedure as in Example 28 was repeated except that the 3-chlorobenzylamine was replaced by 363 mg of L-isoleucinemethylester hydrochloride and 403 mg of triethylamine, whereby 377 mg of the captioned N-[(S)-1,2-dioxo-1-[N-[(2S,3S)-1-methoxy-3-methyl-1-oxo-2-hexyl]amino]-3-heptyl]-1-[N-(morpholine-4-carbonyl) amino] cyclohexanecarboxamide was obtained in a yield of 36%.

1H-NMR (CDCl₃, δ): 0.87 (3H, t, J=7 Hz), 0.91 (3H, d, J=7 Hz), 0.92 (3H, t, J=7 Hz), 1.20–1.50 (9H, m), 1.62–1.70 (3H, m), 1.85–2.00 (4H, m), 2.07–2.13 (3H, m), 3.39 (4H, t, J=5 Hz), 3.72 (4H, t, J=5 Hz), 3.75 (3H, s), 4.44 (1H, s), 4.52 (1H, dd, J=9 Hz, 5 Hz), 5.18–5.23 (1H, m), 7.33 (1H, d, J=9 Hz), 7.99 (1H, d, J=7 Hz)

IR (ν, KBr, cm⁻¹): 3332, 2958, 2931, 1743, 1648, 1525

Rf: 0.55.

Example 121

Synthesis of N-[(S)-1,2-dioxo-1-[N-[(S)-2-methoxy-2-oxo-1-phenylethyl]amino]-3-heptyl]-1-[N-(morpholine-4-carbonyl)amino]cyclohexanecarboxamide

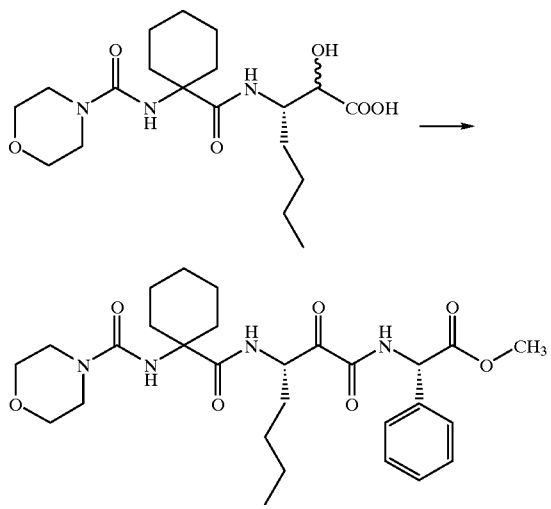

The same procedure as in Example 28 was repeated except that the 3-chlorobenzylamine was replaced by 330 mg of L-phenylglycinemethylester, whereby 531 mg of the captioned N-[(S)-1,2-dioxo-1-[N-[(S)-2-methoxy-2-oxo-1-phenylethyl]amino]-3-heptyl]-1-[N-(morpholine-4-carbonyl)amino]cyclohexanecarboxamide was obtained in a yield of 49%.

1H-NMR (CDCl₃, δ): 0.84 (3H, t, J=7 Hz), 1.21–1.42 (8H, m), 1.50–1.68 (3H, m), 1.81–1.95 (3H, m), 2.01–2.16 (2H, m), 3.35 (4H, t, J=5 Hz), 3.70 (4H, t, J=5 Hz), 3.74 (3H, s), 4.40 (1H, s), 5.07–5.15 (1H, m), 5.50 (1H, d, J=7 Hz), 7.34–7.38 (5H, m), 7.83 (1H, d, J=8 Hz), 7.96 (1H, d, J=6 Hz)

IR (ν, KBr, cm⁻¹): 3380, 1654, 1511

Rf: 0.61.

Example 122

Synthesis of N-[(S)-1,2-dioxo-1-[N-[(S)-3,3-dimethyl-1-methoxy-1-oxo-2-butyl]amino]-3-heptyl]-1-[N-(morpholine-4-carbonyl)amino]cyclohexanecarboxamide

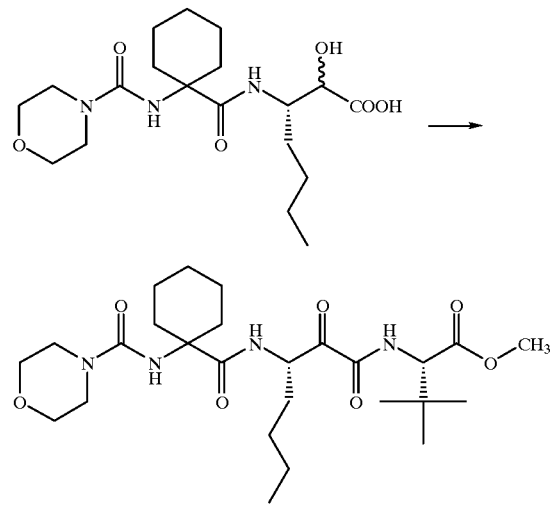

The same procedure as in Example 28 was repeated except that the 3-chlorobenzylamine was replaced by 400 mg of L-tert-leucinemethylester, whereby 445 mg of the captioned N-[(S)-1-[N-[(S)-3,3-dimethyl-1-methoxy-1-oxo-2-butyl]amino]-1,2-dioxo-3-heptyl]-1-[N-(morpholine-4-carbonyl)amino]cyclohexanecarboxamide was obtained in a yield of 43%.

1H-NMR (CDCl₃, δ): 0.87 (3H, t, J=7 Hz), 0.98 (9H, s), 1.22–1.42 (7H, m), 1.62–1.69 (4H, m), 1.86–1.95 (3H, m), 2.06–2.10 (2H, m), 3.39 (4H, t, J=5 Hz), 3.72 (4H, t, J=5 Hz), 3.74 (3H, s), 4.40 (1H, d, J=10 Hz), 4.44 (1H, s), 5.20–5.25 (1H, m), 7.39 (1H, d, J=10 Hz), 8.00 (1H, d, J=7 Hz)

IR (ν, KBr, cm⁻¹) 3332, 2956, 2933, 1741, 1691, 1648, 1521

Rf: 0.55.

Example 123

Synthesis of N-8 (S)-1-[N-[(S)-3-methyl-1-oxo-1-phenyl-2-butyl]amino]-1,2-dioxo-3-heptyl]-1-[N-(morpholine-4-carbonyl)amino]cyclohexanecarboxamide

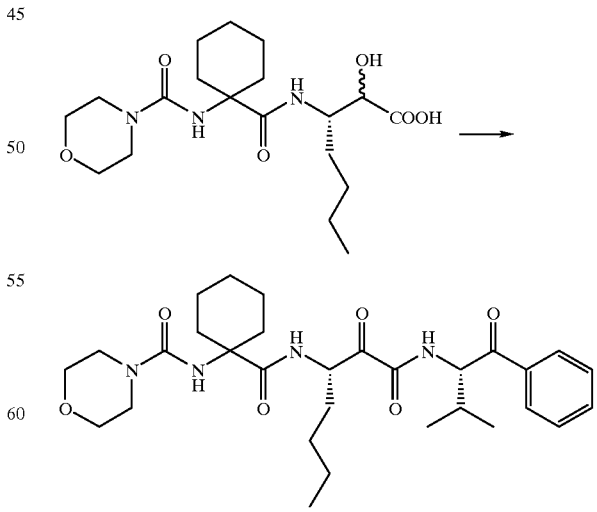

The same procedure as in Example 28 was repeated except that the 3-chlorobenzylamine was replaced by 269 mg of (1RS,2S)-2-amino-3-methyl-1-phenyl-1-butanol, whereby 400 mg of the captioned N-[(S)-1-[N-[(S)-3-methyl-1-oxo-1-phenyl-2-butyl]amino]-1,2-dioxo-3-heptyl]-1-[N-(morpholine-4-carbonyl) amino] cyclohexanecarboxamide was obtained in a yield of 48%.

1H-NMR (CDCl₃, δ): 0.79 (3H, d, J=7 Hz), 0.88 (3H, t, J=7 Hz), 1.01 (3H, d, J=7 Hz), 1.23–1.44 (6H, m), 1.54–1.73 (5H, m), 1.83–2.30 (6H, m), 3.39 (4H, t, J=5 Hz), 3.72 (4H, t, J=5 Hz), 4.43 (1H, s), 5.23–5.30 (1H, m), 5.51 (1H, dd, J=9 Hz, 4 Hz), 7.49 (2H, t, J=8 Hz), 7.62 (1H, t, J=8 Hz), 7.69 (1H, d, J=8 Hz), 7.95–8.03 (3H, m)

IR (ν, KBr, cm⁻¹): 3332, 2931, 2857, 1675, 1648

Rf: 0.43.

Example 124

Synthesis of N-[(S)-1,2-dioxo-1-[N-[[2-(2-propyl)-1,3-dioxolane-2-yl]methyl]amino]-3-heptyl]-1-[N-(morpholine-4-carbonyl)amino]cyclohexanecarboxamide

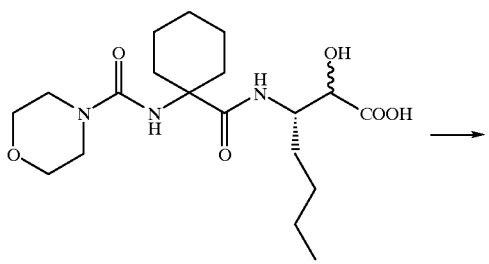

The same procedure as in Example 28 was repeated except that the 3-chlorobenzylamine was replaced by 194 mg of 1-[2-(2-propyl)-1,3-dioxolane-2-yl]methanamine, whereby 368 mg of the captioned N-[(S)-1,2-dioxo-1-[N-[[2-(2-propyl)-1,3-dioxolane-2-yl ]methyl]amino]-3-heptyl]-1-[N-(morpholine-4-carbonyl) amino] cyclohexanecarboxamide was obtained in a yield of 47%.

1H-NMR (CDCl₃, δ): 0.87 (3H, t, J=7 Hz), 0.95 (6H, d, J=7 Hz), 1.24–1.42 (6H, m), 1.53–1.70 (5H, m), 1.83–2.15 (6H, m), 3.39 (4H, t, J=5 Hz), 3.41–3.53 (2H, m), 3.72 (4H, t, J=5 Hz), 3.94–4.03 (4H, m), 4.43 (1H, s), 5.14–5.21 (1H, m), 6.99 (1H, t, J=5 Hz), 7.95 (1H, d, J=7 Hz)

IR (ν, KBr, cm⁻¹): 3320, 2952, 2857, 1658

Rf: 0.57.

Example 125

Synthesis of N-[(S)-1-[N-[(S)-4-methyl-2-oxo-3-pentyl] amino]-1,2-dioxo-3-heptyl]-1-[N-(morpholine-4-carbonyl) amino]cyclohexanecarboxamide

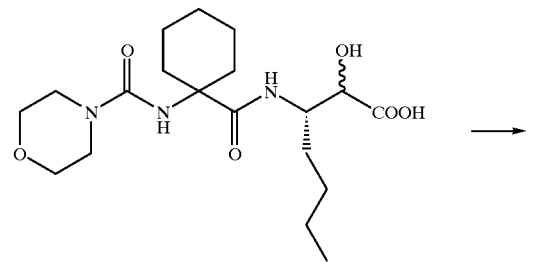

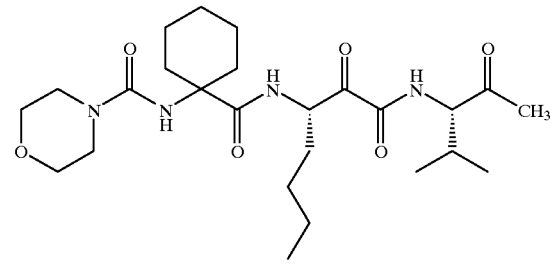

The same procedure as in Example 28 was repeated except that the 3-chlorobenzylamine was replaced by 176 mg of (2RS,3S)-3-amino-4-methyl-2-pentanol, whereby 448 mg of the captioned N-[(S)-1-[N-[(S)-4-methyl-2-oxo-3-pentyl]amino]-1,2-dioxo-3-heptyl]-1-[N-(morpholine-4-carbonyl)amino]cyclohexanecarboxamide was obtained in a yield of 62%.

1H-NMR (CDCl₃, δ): 0.83 (3H, d, J=7 Hz), 0.87 (3H, t, J=7 Hz), 0.99 (3H, d, J=7 Hz), 1.21–1.43 (6H, m), 1.50–1.72 (5H, m), 1.82–2.33 (6H, m), 2.23 (3H, s), 3.39 (4H, t, J=5 Hz), 3.72 (4H, t, J=5 Hz), 4.45 (1H, s), 4.56 (1H, dd, J=9 Hz, 5 Hz), 5.19–5.24 (1H, m), 7.42 (1H, d, J=9 Hz), 7.99 (1H, d, J=7 Hz)

IR (ν, KBr, cm⁻¹): 3336, 2932, 2860, 1668

Rf: 0.64.

Example 126

Synthesis of N-[(S)-1-[N-[(S)-2-methyl-1-(2-methyl-1,3-dioxolane-2-yl) propyl]amino]-1,2-dioxo-3-heptyl]-1-[N-(morpholine-4-carbonyl)amino]cyclohexanecarboxamide

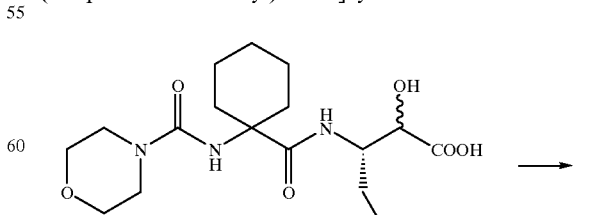
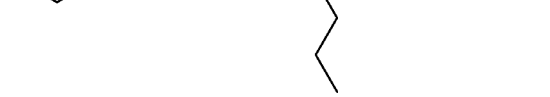

-continued

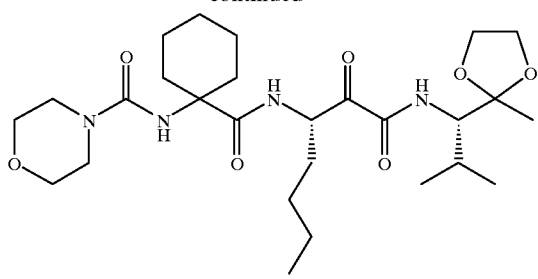

The same procedure as in Example 28 was repeated except that the 3-chlorobenzylamine was replaced by 239 mg of (S)-2-methyl-1-(2-methyl-1,3-dioxolane-2-yl)propanamine, whereby 478 mg of the captioned N-[(S)-1-[N-[(S)-2-methyl-1-(2-methyl-1,3-dioxolane-2-yl)propyl]amino]-1,2-dioxo-3-heptyl]-1-[N-(morpholine-4-carbonyl)amino]cyclohexanecarboxamide was obtained in a yield of 59%.

1H-NMR (CDCl$_3$, δ): 0.83–0.96 (9H, m), 1.22–1.43 (6H, m), 1.32 (3H, s), 1.56–1.75 (5H, m), 1.82–2.17 (6H, m), 3.38 (4H, t, J=5 Hz), 3.72 (4H, t, J=5 Hz), 3.84–4.07 (5H, m), 4.44 (1H, s), 5.17–5.26 (1H, m), 6.97 (1H, d, J=6 Hz), 7.96 (1H, d, J=7 Hz)

IR (ν, KBr, cm$^{-1}$): 3424, 2936, 2864, 1664

Rf: 0.51.

Example 127

Synthesis of N-[(S)-1,2-dioxo-1-[N-(4-methoxyphenyl)amino]-3-heptyl]-1-[N-(morpholine-4-carbonyl)amino]cyclohexanecarboxamide

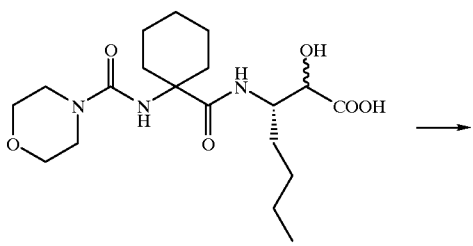

The same procedure as in Example 28 was repeated except that the 3-chlorobenzylamine was replaced by 369 mg of 4-methoxyaniline, whereby 493 mg of the captioned N-[(S)-1,2-dioxo-1-[N-(4-methoxyphenyl)amino]-3-heptyl]-1-[N-(morpholine-4-carbonyl)amino]cyclohexanecarboxamide was obtained in a yield of 49%.

1H-NMR(CDCl$_3$, δ): 0.89 (3H, t, J=7 Hz), 1.20–2.20 (16H, m), 3.35–3.40 (4H, m), 3.70–3.80 (4H, m), 3.80 (3H, s), 4.44 (1H, s), 5.25 (1H, ddd, J=12 Hz, 7 Hz, 5 Hz), 6.89 (2H, ddd, J=9 Hz, 6 Hz, 3 Hz), 7.53 (2H, ddd, J=9 Hz, 6 Hz, 3 Hz), 8.04 (1H, d, J=7 Hz), 8.57 (1H, s)

IR (ν, KBr, cm$^{-1}$): 3320, 2936, 2860, 1728, 1666, 1642, 1514

Rf: 0.59.

Example 128

Synthesis of N-[(S)-1-[N-(4-fluorophenyl)amino]-1,2-dioxo-3-heptyl]-1-[N-(morpholine-4-carbonyl)amino]cyclohexanecarboxamide

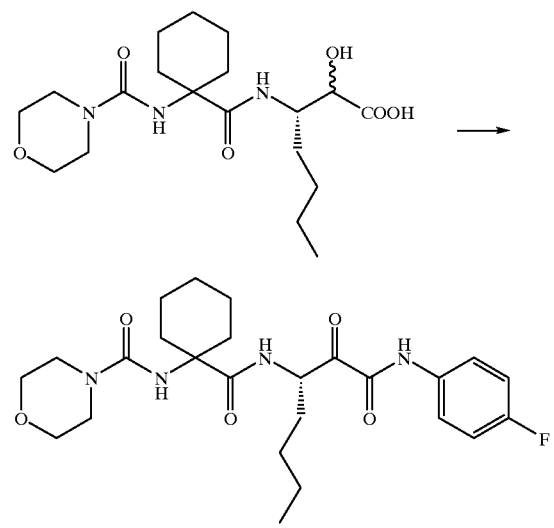

The same procedure as in Example 28 was repeated except that the 3-chlorobenzylamine was replaced by 167 mg of 4-fluoroaniline, whereby 363 mg of the captioned N-[(S)-1-[N-(4-tluorophenyl)amino]-1,2-dioxo-3-heptyl]-1-[N-(morpholine-4-carbonyl)amino]cyclohexanecarboxamide was obtained in a yield of 49%.

1H-NMR (CDCl$_3$, δ): 0.90 (3H, t, J=7 Hz), 1.25–1.44 (6H, m), 1.53–1.77 (5H, m), 1.83–2.15 (5H, m), 3.37 (4H, t, J=5 Hz), 3.70 (4H, t, J=5 Hz), 4.43 (1H, s), 5.19–5.26 (1H, m), 7.01–7.08 (2H, m), 7.56–7.64 (2H, m), 8.09 (1H, d, J=6 Hz), 8.64 (1H, s)

IR (ν, KBr, cm$^{-1}$): 3332, 2936, 2864, 1668, 1644

Rf: 0.53.

Example 129

Synthesis of N-[(S)-1-[N-(3,5-difluorophenyl)amino]-1,2-dioxo-3-heptyl]-1-[N-(morpholine-4-carbonyl)amino]cyclohexanecarboxamide

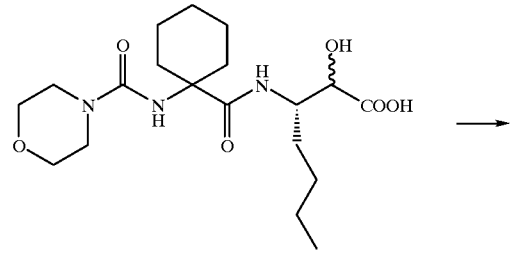

-continued

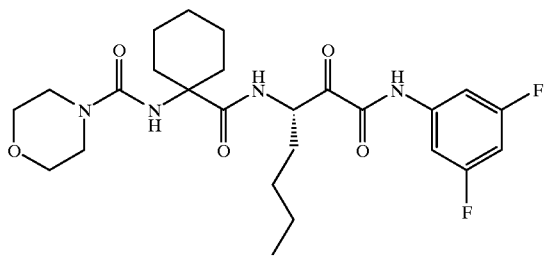

The same procedure as in Example 28 was repeated except that the 3-chlorobenzylamine was replaced by 194 mg of 3,5-difluoroaniline, whereby 328 mg of the captioned N-[(S)-1-[N-(3,5-difluorophenyl)amino]-1,2-dioxo-3-heptyl]-1-[N-(morpholine-4-carbonyl)amino]cyclohexanecarboxamide was obtained in a yield of 43%.

1H-NMR (CDCl$_3$, δ): 0.90 (3H, t, J=7 Hz), 1.28–1.44 (6H, m), 1.58–1.78 (5H, m), 1.83–2.17 (5H, m), 3.37 (4H, t, J=5 Hz), 3.71 (4H, t, J=5 Hz), 4.42 (1H, s), 5.12–5.19 (1H, m), 6.58–6.66 (1H, m), 7.21–7.30 (2H, m), 8.17 (1H, d, J=6 Hz), 8.73 (1H, s)

IR (ν, KBr, cm$^{-1}$): 3336, 2932, 2864, 1678, 1642
Rf: 0.44.

Example 130

Synthesis of N-[(S)-1,2-dioxo-1-[N-[(S)-2-methyl-1-oxo-1-(N-phenylamino)-2-butyl]amino]-3-heptyl]-1-[N-(morpholine-4-carbonyl)amino]cyclohexanecarboxamide

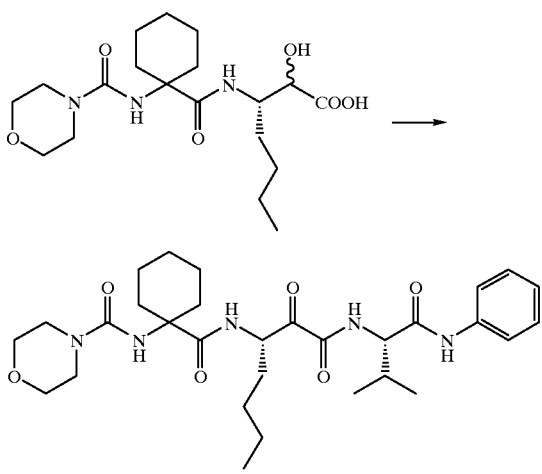

The same procedure as in Example 28 was repeated except that the 3-chlorobenzylamine was replaced by 461 mg of L-N-phenyl-valinamide, whereby 291 mg of the captioned N-[(S)-1,2-dioxo-1-[N-[(S)-2-methyl-1-oxo-1-(N-phenylamino)-2-butyl]amino]-3-heptyl]-1-[N-(morpholine-4-carbonyl)amino]cyclohexanecarboxamide was obtained in a yield of 25%.

1H-NMR (CDCl$_3$, δ): 0.89 (3H, t, J=7 Hz), 1.01 (6H, dd, J=16 Hz, 7 Hz), 1.06–1.35 (7H, m), 1.58–1.75 (4H, m), 1.78–2.10 (4H, m), 2.48 (1H, q, J=6 Hz), 3.34 (4H, t, J=5 Hz), 3.67 (4H, t, J=5 Hz), 4.37 (1H, dd, J=9 Hz, 6 Hz), 4.41 (1H, s), 4.98–5.03 (1H, s), 7.09 (1H, t, J=8 Hz), 7.25–7.28 (5H, m), 7.57 (1H, d, J=8 Hz), 8.04 (1H, d, J=6 Hz), 8.14 (1H, s)

IR (ν, KBr, cm$^{-1}$): 3320, 2936, 1604, 1448
Rf: 0.53.

Example 131

Synthesis of N-[(S)-1,2-dioxo-1-[N-(3,4-methylenedioxyphenylmethyl) amino]-3-heptyl]-1-[N-(morpholine-4-carbonyl)amino]cyclohexanecarboxamide

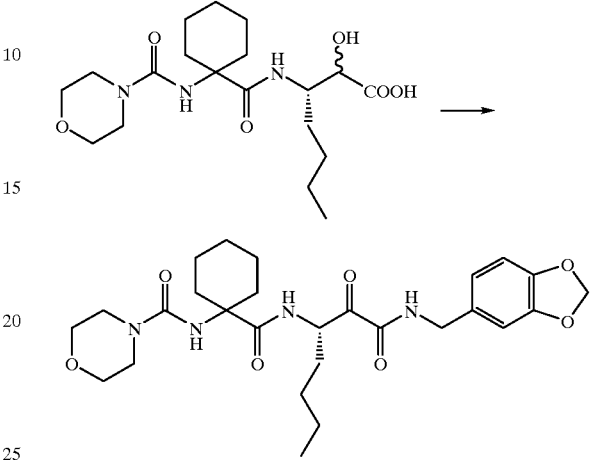

The same procedure as in Example 28 was repeated except that the 3-chlorobenzylamine was replaced by 1.13 g of 3,4-methylenedioxyphenylmethylamine, whereby 1.1 g of the captioned N-[(S)-1,2-dioxo-1-[N-(3,4-methylenedioxyphenylmethyl)amino]-3-heptyl]-1-[N-(morpholine-4-carbonyl) amino]cyclohexanecarboxamide was obtained in a yield of 42%.

1H-NMR (CDCl$_3$, δ): 0.88 (3H, t, J=7 Hz), 1.23–1.42 (7H, m), 1.58–1.75 (4H, m), 1.81–2.06 (3H, m), 2.08–2.11 (2H, m), 3.37 (4H, t, J=5 Hz), 3.71 (4H, t, J=5 Hz), 4.36 (2H, d, J=6 Hz), 4.44 (1H, s), 5.13–5.21 (1H, m), 5.94 (2H, s), 6.74–6.76 (3H, m), 7.11 (1H, bs), 7.99 (1H, d, J=7 Hz)

IR (ν, KBr, cm$^{-1}$): 3076, 2860, 1724, 1516, 1494

Rf: 0.63.

Example 132

Synthesis of N-[(S)-1,2-dioxo-1-[N-[(S)-1-methylamino-2-methyl-1-oxo-2-butyl]amino]-3-heptyl]-1-[N-(morpholine-4-carbonyl)amino]cyclohexanecarboxamide

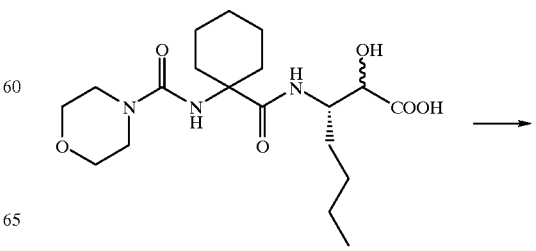

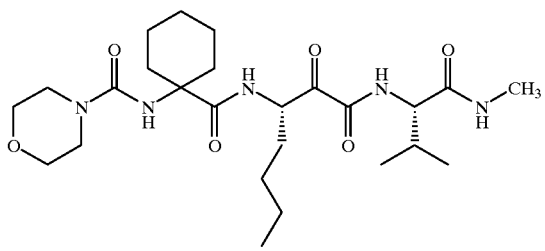

The same procedure as in Example 28 was repeated except that the 3-chlorobenzylamine was replaced by 867 mg of L-N-methyl-valinamide hydrochloride and 607 mg of triethylamine, whereby 158 mg of the captioned N-[(S)-1,2-dioxo-1-[N-[(S)-1-methylamino-2-methyl-1-oxo-2-butyl]amino]-3-heptyl]-1-[N-(morpholine-4-carbonyl)amino]cyclohexanecarboxamide was obtained in a yield of 10%.

1H-NMR (CDCl$_3$, δ): 0.88 (3H, t, J=7 Hz), 0.91 (3H, d, J=7 Hz), 0.95 (3H, d, J=7 Hz), 1.34–1.38 (7H, m), 1.64–1.73 (6H, m), 1.80–1.93 (3H, m), 2.04–2.15 (2H, m), 2.39 (1H, dq, J=7 Hz, 6 Hz), 2.78–2.84 (1H, m), 3.39 (4H, t, J=5 Hz), 3.72 (4H, t, J=5 Hz), 4.24 (1H, dd, J=10 Hz, 6 Hz), 4.54 (1H, s), 5.08 (1H, dt, J=8 Hz, 6 Hz), 6.49 (1H, d, J=5 Hz), 7.25 (1H, d, J=10 Hz), 8.06 (1H, d, J=6 Hz)

IR (ν, KBr, cm$^{-1}$): 3311, 2960, 2931, 1654, 1517

Rf: 0.78.

Example 133

Synthesis of N-[(3S)-1,2-dioxo-1-[N-[(1RS)-1-methoxy-3-methyl-2-butyl]amino]-3-heptyl]-1-[N-(morpholine-4-carbonyl)amino]cyclohexanecarboxamide

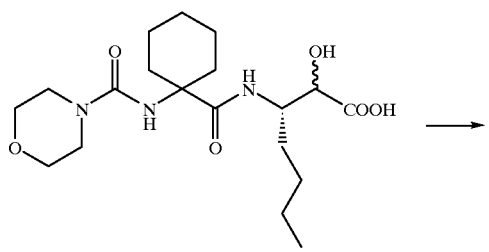

The same procedure as in Example 28 was repeated except that the 3-chlorobenzylamine was replaced by 569 mg of (1RS)-1-(methoxymethyl)-2-methylpropyl]amine, whereby 314 mg of the captioned N-[(3S)-1,2-dioxo-1-[N-[(1RS)-1-methoxy-3-methyl-2-butyl]amino]-3-heptyl]-1-[N-(morpholine-4-carbonyl)amino]cyclohexanecarboxamide was obtained in a yield of 33%.

1H-NMR (CDCl$_3$, δ): 0.80–1.10 (9H, m), 1.20–2.20 (17H, m), 3.15–3.25 (1H, m), 3.32 (3H, s), 3.30–3.50 (4H, m), 3.50–3.60 (1H, m), 3.70–3.85 (5H, m), 4.49 (1H, s), 5.18–5.22 (1/2H, m), 5.23–5.28 (1/2H, m), 7.01 (1/2H, d, J=6 Hz), 7.04 (1/2H, d, J=6 Hz), 7.91 (1/2H, d, J=7 Hz), 7.94 (1/2H, d, J=7 Hz)

IR (ν, KBr, cm$^{-1}$): 3328, 2964, 2864, 1728, 1664, 1532

Rf: 0.56.

Example 134

Synthesis of N-[(3S)-1,2-dioxo-1-[N-[(1RS)-1-phenoxy-3-methyl-2-butyl]amino]-3-heptyl]-1-[N-(morpholine-4-carbonyl)amino]cyclohexanecarboxamide

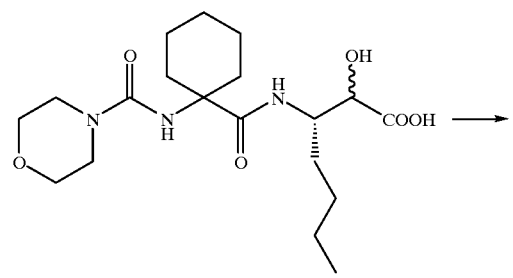

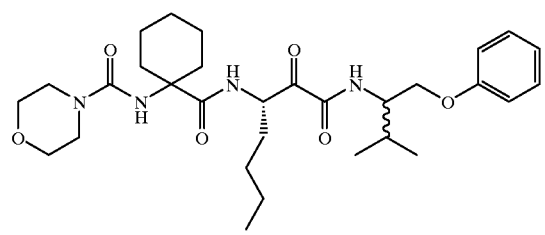

The same procedure as in Example 28 was repeated except that the 3-chlorobenzylamine was replaced by 520 mg of (1RS)-1-(phenoxymethyl)-2-methylpropyl]amine, whereby 368 mg of the captioned N-[(3S)-1,2-dioxo-1-[N-[(1RS)-1-phenoxy-3-methyl-2-butyl]amino]-3-heptyl]-1-[N-(morpholine-4-carbonyl)amino]cyclohexanecarboxamide was obtained in a yield of 27%.

1H-NMR (CDCl$_3$, δ): 0.80–1.00 (9H, m), 1.20–2.20 (17H, m), 3.36–3.40 (4H, m), 3.70 (4H, t, J=4 Hz), 3.90–4.05 (2H, m), 4.05–4.15 (1H, m), 4.18 (1/2H, s), 4.29 (1/2H, s), 5.19–5.27 (1H, m), 6.88 (2H, t, J=6 Hz), 6.89 (1H, t, J=7 Hz), 7.15 (1/2H, d, J=9 Hz), 7.17 (1/2H, d, J=9 Hz), 7.29 (2H, d, J=7 Hz), 7.94 (1/2H, d, J=7 Hz), 7.96 (1/2H, d, J=7 Hz)

IR (ν, KBr, cm$^{-1}$): 3316, 2960, 2864, 1726, 1658, 1602, 1588

Rf: 0.36.

Example 135

Synthesis of N-[(S)-1,2-dioxo-1-[N-(3,4-methylenedioxyphenyl)amino]-3-heptyl]-1-[N-(morpholine-4-carbonyl)amino]cyclohexanecarboxamide

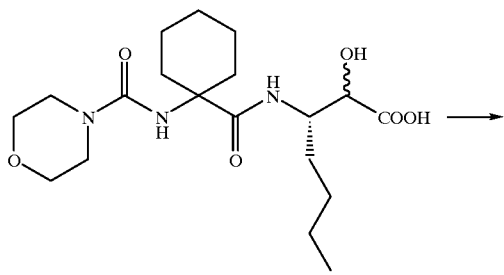

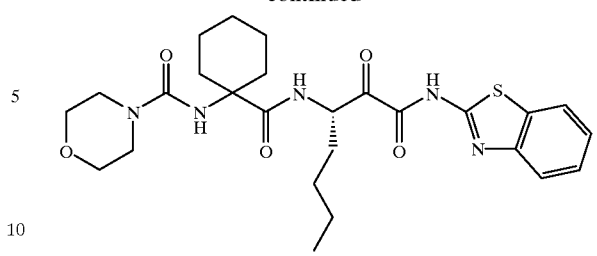

The same procedure as in Example 28 was repeated except that the 3-chlorobenzylamine was replaced by 600 mg of 2-aminobenzothiazole, whereby 192 mg of the captioned N-[(S)-1,2-dioxo-1-[N-(2-benzothiazolyl)amino]-3-heptyl]-1-[N-(morpholine-4-carbonyl)amino]cyclohexanecarboxamide was obtained in a yield of 18%.

1H-NMR (CDCl$_3$, δ): 0.82 (3H, t, J=7 Hz), 1.110–2.20 (16H, m), 3.20–3.40 (4H, m), 3.50–3.80 (4H, m), 4.75 (1/2H, s), 4.82 (1/2H, s), 5.05–5.15 (1/2H, m), 6.10–6.20 (1/2H, m), 7.20–7.42 (2H, m), 7.70–7.80 (2H, m), 8.20 (1H, d, J=8 Hz)

IR (ν, KBr, cm$^{-1}$): 3388, 2936, 2860, 1642, 1604, 1536

Rf: 0.53.

Example 137

Synthesis of N-[(3S)-1,2-dioxo-1-[N-[(1 S)-1-oxo-1-methoxy-3-phenyl-2-propyl]amino]-3-heptyl]-1-[N-(morpholine-4-carbonyl)amino]cyclohexanecarboxamide

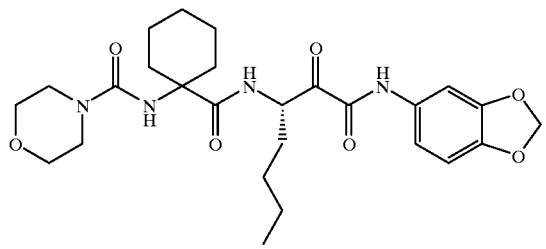

The same procedure as in Example 28 was repeated except that the 3-chlorobenzylamine was replaced by 548 mg of 3,4-methylenedioxyaniline, whereby 447 mg of the captioned N-[(S)-1,2-dioxo-1-[N-(3,4-methylenedioxyphenyl)amino]- 3-heptyl]-1-[N-(morpholine-4-carbonyl)amino]cyclohexanecarboxamide was obtained in a yield of 43%.

1H-NMR (CDCl$_3$, δ): 0.89 (3H, t, J=7 Hz), 1.20–2.20 (16H, m), 3.30–3.40 (4H, m), 3.70 (4H, t, J=5 Hz), 4.44 (1H, s), 5.22 (1H, ddd, J=12 Hz, 7 Hz, 5 Hz), 5.97 (2H, s), 6.77 (1H, d, J=8 Hz), 6.94 (1H, dd, J=8 Hz, 2 Hz), 7.34 (1H, d, J=2 Hz), 8.06 (1H, d, J=6 Hz), 8.56 (1H, s)

IR (ν, KBr, cm$^{-1}$): 3324, 2932, 2864, 1728, 1668, 1644, 1506

Rf: 0.60.

Example 136

Synthesis of N-[(S)-1,2-dioxo-1-[N-(2-benzothiazolyl)amino]-3-heptyl]-1-[N-(morpholine-4-carbonyl)amino]cyclohexanecarboxamide

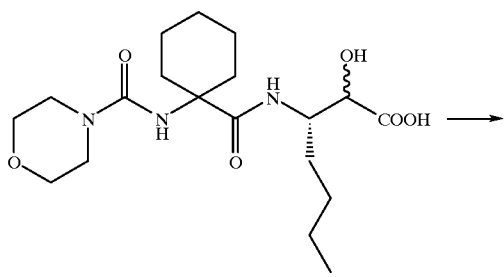

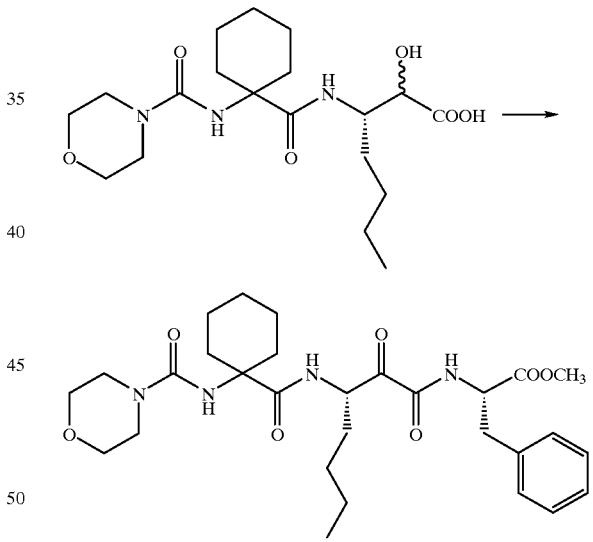

The same procedure as in Example 28 was repeated except that the 3-chlorobenzylamine was replaced by 862 mg of L-phenylalaninemethylester hydrochloride and 404 mg of triethylamine, whereby 513 mg of the captioned N-[(3S)-1,2-dioxo-1-[N-[(1S)-1-oxo-1-methoxy-3-phenyl-2-propyl]amino]-3-heptyl]-1-[N-(morpholine-4-carbonyl)amino]cyclohexanecarboxamide was obtained in a yield of 46%.

1H-NMR (CDCl$_3$, δ): 0.80–0.95 (3H, m), 1.20–2.10 (16H, m), 3.08 (1H, dd, J=14 Hz, 7 Hz), 3.20 (1H, dd, J=14 Hz, 6 Hz), 3.37 (4H, t, J=4 Hz), 3.70 (4H, t, J=4 Hz), 3.73 (3H, s), 4.42 (1H, s), 4.80–4.86 (1H, m), 5.16–5.20 (1H, m), 7.08 (1H, d, J=8 Hz), 7.20–7.35 (5H, m), 7.96 (1H, d, J=7 Hz)

IR (ν, KBr, cm⁻¹): 3400, 2936, 2860, 1748, 1672, 1530

Rf: 0.53.

Example 138

Synthesis of N-[(3S)-1,2-dioxo-1-[N-[(R)-1-oxo-1-methoxy-3-methylthio-2-propyl]amino]-3-heptyl]-1-[N-(morpholine-4-carbonyl)amino]cyclohexanecarboxamide

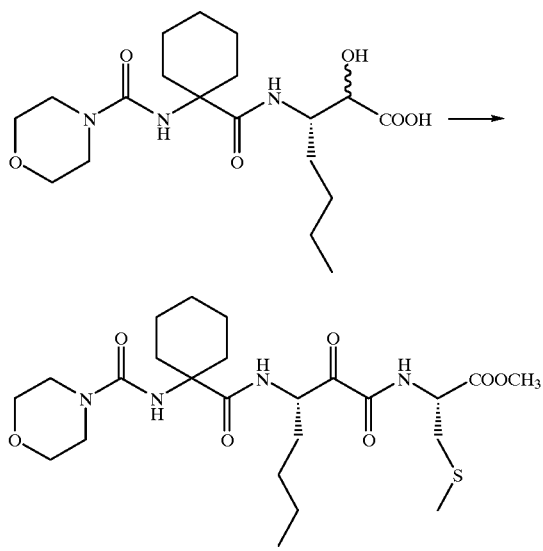

The same procedure as in Example 28 was repeated except that the 3-chlorobenzylamine was replaced by 742 mg of L-S-methylcysteinemethylester hydrochloride and 404 mg of triethylamine, whereby 378 mg of the captioned N-[(3S)-1,2-dioxo-1-[N-[(R)-1-oxo-1-methoxy-3-methylthio-2-propyl]amino]-3-heptyl]-1-[N-(morpholine-4-carbonyl)amino]cyclohexanecarboxamide was obtained in a yield of 35%.

1H-NMR (CDCl₃, δ): 0.87 (3H, t, J=7 Hz), 1.20–2.20 (16H, m), 2.11 (3H, s), 2.94 (1H, dd, J=14 Hz, 6 Hz), 3.02 (1H, dd, J=14 Hz, 5 Hz), 3.39 (4H, t, J=5 Hz), 3.72 (4H, t, J=5 Hz), 3.79 (3H, s), 4.43 (1H, s), 4.75–4.79 (1H, m), 5.19–5.24 (1H, m), 7.56 (1H, d, J=8 Hz), 7.99 (1H, d, J=6 Hz)

IR (ν, KBr, cm⁻¹): 3352, 2932, 2864, 1748, 1662, 1524

Rf: 0.66.

Example 139

Synthesis of N-[(3S)-1,2-dioxo-1-[N-[(S)-1,4-dioxo-1,4-dimethoxy-2-butyl]amino]-3-heptyl]-1-[N-(morpholine-4-carbonyl)amino]cyclohexanecarboxamide

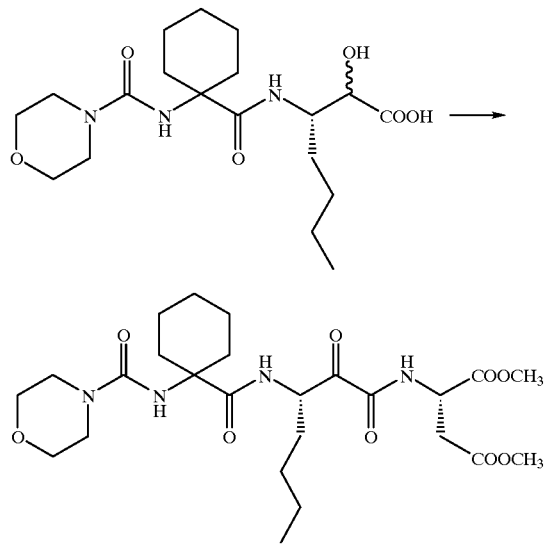

The same procedure as in Example 28 was repeated except that the 3-chlorobenzylamine was replaced by 988 mg of L-aspartic acid dimethylester hydrochloride and 505 mg of triethylamine, whereby 469 mg of the captioned N-[(3S)-1,2-dioxo-1-[N-[(S)-1,4-dioxo-1,4-dimethoxy-2-butyl]amino]-3-heptyl]-1-[(morpholine-4-carbonyl)amino]cyclohexanecarboxamide was obtained in a yield of 43%.

1H-NMR (CDCl₃, δ): 0.80–0.90 (3H, m), 1.20–2.20 (16H, m), 2.87 (1H, dd, J=17 Hz, 5 Hz), 3.06 (1H, dd, J=17 Hz, 5 Hz), 3.39 (4H, t, J=5 Hz), 3.65–3.80 (4H, m), 3.69 (3H, s), 3.77 (3H, s), 4.84 (1H, s), 4.75–4.92 (1H, m), 5.15–5.26 (1H, m), 7.72 (1H, d, J=8 Hz), 7.99 (1H, d, J=6 Hz)

IR (ν, KBr, cm⁻¹): 3380, 2965, 2859, 1741, 1675, 1629, 1523

Rf: 0.73.

Example 140

Synthesis of N-[(S)-1,2-dioxo-1-[N-[2-(3,4-methylenedioxyphenyl)ethyl]amino]- 3-heptyl]-1-[N-(morpholine-4-carbonyl)amino]cyclohexanecarboxamide

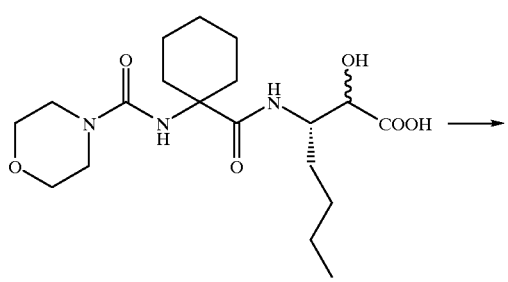

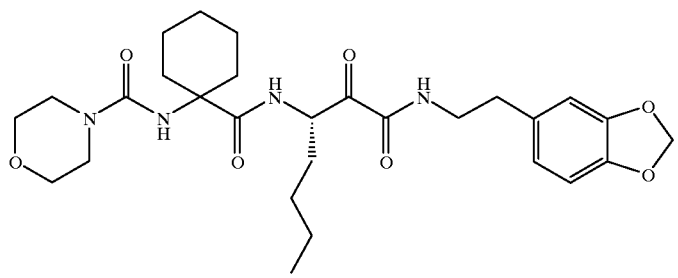

The same procedure as in Example 28 was repeated except that the 3-chlorobenzylamine was replaced by 660 mg of 3,4-methylenedioxyphenylethylamine, whereby 469 mg of the captioned N-[(S)-1,2-dioxo-1-[N-[2-(3,4-methylenedioxyphenyl)ethyl]amino]-3-heptyl]-1-[N-(morpholine-4-carbonyl)amino]cyclohexanecarboxamide was obtained in a yield of 46%.

1H-NMR (CDCl$_3$, δ): 0.88 (3H, t, J=7 Hz), 1.20–2.20 (16H, m), 2.75 (2H, td, J=7 Hz, 2 Hz), 3.37 (4H, t, J=5 Hz), 3.42–3.60 (2H, m), 3.71 (4H, t, J=5 Hz), 4.42 (1H, s), 5.17 (1H, ddd, J=12 Hz, 7 Hz, 5 Hz), 5.93 (2H, s), 6.63 (1H, dd, J=8 Hz, 2 Hz), 6.67 (1H, d, J=2 Hz), 6.74 (1H, d, J=2 Hz), 6.89 (1H, t, J=6 Hz), 7.94 (1H, d, J=7 Hz)

IR (ν, KBr, cm$^{-1}$): 3392, 2931, 2859, 1708, 1654, 1621, 1533

Rf: 0.56.

Example 141

Synthesis of N-[(S)-1,2-dioxo-1-[N-(3,4-dimethoxyphenyl)amino]-3-heptyl]-1-[N-(morpholine-4-carbonyl)amino]cyclohexanecarboxamide

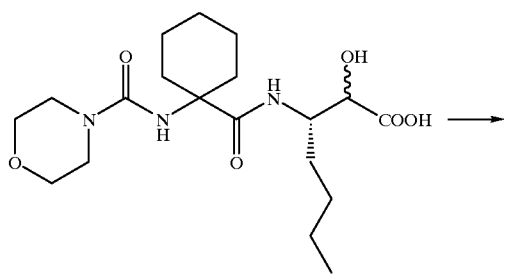

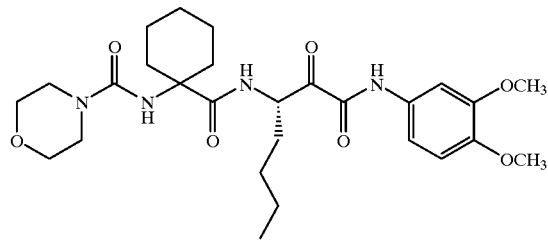

The same procedure as in Example 28 was repeated except that the 3-chlorobenzylamine was replaced by 612 mg of 3,4-dimethoxyaniline, whereby 270 mg of the captioned N-[(S)-1,2-dioxo-1-[N-(3,4-dimethoxyphenyl)amino]-3-heptyl]-1-[N-(morpholine-4-carbonyl)amino]cyclohexanecarboxamide was obtained in a yield of 25%.

1H-NMR (CDCl$_3$, δ): 0.87–0.92 (3H, m), 1.20–2.20 (16H, m), 3.36–3.83 (4H, m), 3.70 (4H, t, J=4 Hz), 3.87 (3H, s), 3.90 (3H, s), 4.46 (1H, s), 5.26 (1H, ddd, J=12 Hz, 7 Hz, 5 Hz), 6.83 (1H, d, J=8 Hz), 7.04 (1H, dd, J=8 Hz, 3 Hz), 7.42 (1H, d, 3 Hz), 8.07 (1H, d, J=7 Hz), 8.60 (1H, s)

IR (ν, KBr, cm$^{-1}$): 3374, 2931, 2857, 1725, 1662, 1608, 1515

Rf: 0.63.

Example 142

Synthesis of N-[(S)-1,2-dioxo-1-[N-[2-(3,4-dimethoxyphenyl)ethyl]amino]-3-heptyl]-1-[N-(morpholine-4-carbonyl)amino]cyclohexanecarboxamide

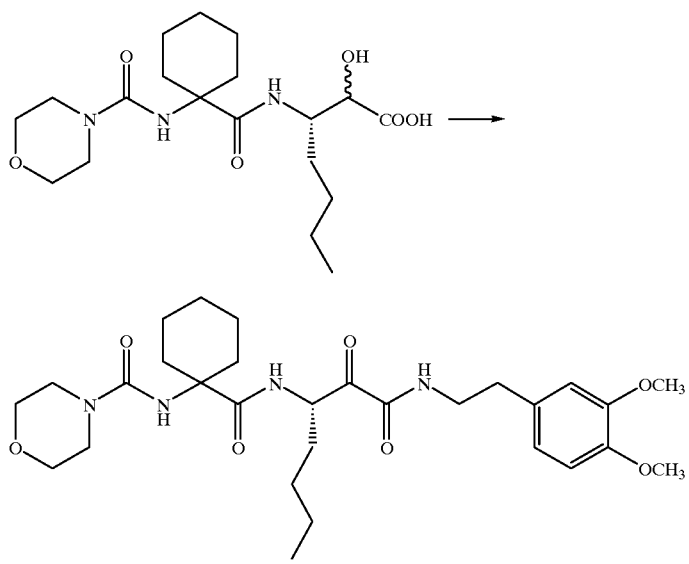

The same procedure as in Example 28 was repeated except that the 3-chlorobenzylamine was replaced by 905 mg of 3,4-dimethoxyphenyletbylamine, whereby 609 mg of the captioned N-[(S)-1,2-dioxo-1-[N-[2-(3,4-dimethoxyphenyl) ethyl]amino]-3-heptyl]-1-[N-(morpholine-4-carbonyl)amino]cyclohexanecarboxamide was obtained in a yield of 53%.

1H-NMR (CDCl$_3$, δ): 0.86–0.89 (3H, m), 1.20–2.20 (16H, m), 2.78 (2H, td, J=7 Hz, 2 Hz), 3.37 (4H, t, J=5 Hz), 3.53 (2H, td, J=7 Hz, 6 Hz), 3.71 (4H, t, J=5 Hz), 3.86 (3H, s), 3.87 (3H, s), 4.42 (1H, s), 5.17 (1H, ddd, J=11 Hz, 7 Hz, 5 Hz), 6.70 (1H, d, J=2 Hz), 6.73 (1H, dd, J=8 Hz, 2 Hz), 6.81 (1H, d, J=2 Hz), 6.92 (1H, t, J=6 Hz), 7.95 (1H, d, J=7 Hz)

IR (v, KBr, cm$^{-1}$): 3328, 2929, 2857, 1725, 1664, 1617, 1517

Rf: 0.66.

TEST EXAMPLE 1

Assay of Cathepsin K Inhibitory Activity

Cathepsin K was expressed as a secreted proenzyme using baculovirus-infected Sf 21 insect cell in a cell culture medium; and then, the proenzyme was incubated at 40° C. for 2 hours to be modified as the active-type enzyme [Tezuka et al., J. Biol. Chem., 269, 1106–1109 (1194)]. According to the method of Aibe et al. [Biol. Pharm. Bull., 1026–1031 (1996)], the activity of cathepsin K was assayed on the basis of a fluorogenic substrate Cbz-Gly-Pro-Arg-MCA. More specifically, the decomposition of 20 μM Cbz-Gly-Pro-Arg-MCA in 100 mM potassium sodium phosphate, 1 mM EDTA, 8 mM cysteine, pH 6.0 with cathepsin K was assayed. The reaction was progressed at 37° C. for 30 minutes, which was then terminated by calpeptin added at 2×10$^{-5}$ M; and then, fluorescence intensity was measured at an excitation wave length of 370 nm and an assay wave length of 460 nm. Using the reaction system described above, the compounds of Examples were assayed of cathepsin K inhibitory action. Table 1 shows the cathepsin K inhibitory activities of these compounds.

TABLE 1

Cathepsin K Inhibitory Activity

| Example | Cathepsin K Inhibitory Activity 10$^{-6}$M(%) |
|---|---|
| 1 | 53 |
| 2 | 99 |
| 3 | 99 |
| 4 | 99 |
| 5 | 99 |
| 6 | 99 |
| 7 | 99 |
| 8 | 99 |
| 9 | 99 |
| 10 | 99 |
| 11 | 98 |
| 12 | 99 |
| 13 | 97 |
| 14 | 98 |
| 15 | 98 |
| 16 | 99 |
| 17 | 98 |
| 18 | 99 |
| 19 | 97 |
| 20 | 100 |
| 21 | 99 |
| 22 | 98 |
| 23 | 99 |
| 24 | 76 |
| 25 | 99 |
| 27 | 99 |
| 28 | 99 |
| 29 | 99 |
| 30 | 99 |
| 31 | 99 |
| 32 | 98 |
| 33 | 99 |
| 34 | 98 |
| 35 | 99 |
| 36 | 99 |
| 37 | 98 |
| 38 | 99 |
| 39 | 99 |
| 40 | 99 |
| 41 | 99 |
| 42 | 69 |

TABLE 1-continued

Cathepsin K Inhibitory Activity

| Example | Cathepsin K Inhibitory Activity $10^{-6}$M(%) |
|---|---|
| 43 | 97 |
| 44 | 99 |
| 45 | 99 |
| 46 | 93 |
| 47 | 99 |
| 49 | 99 |
| 50 | 98 |
| 51 | 99 |
| 52 | 99 |
| 53 | 99 |
| 54 | 98 |
| 55 | 98 |
| 56 | 99 |
| 57 | 87 |
| 58 | 99 |
| 59 | 99 |
| 60 | 98 |
| 61 | 99 |
| 62 | 99 |
| 63 | 94 |
| 64 | 98 |
| 65 | 98 |
| 66 | 99 |
| 67 | 99 |
| 74 | 99 |
| 79 | 97 |
| 88 | 99 |
| 90 | 99 |
| 92 | 99 |
| 97 | 99 |
| 101 | 98 |
| 102 | 99 |
| 107 | 99 |
| 108 | 99 |
| 117 | 99 |
| 120 | 99 |
| 121 | 99 |
| 125 | 99 |
| 128 | 99 |
| 131 | 99 |
| 135 | 99 |
| 141 | 97 |
| 142 | 99 |

Test Example 2
Assay of Bone Resorption Inhibitory Action

For 7 days, male mice (weighed 23 to 25 g) were fed with low-calcium diet (0.1% calcium diet). After overnight starvation, the compounds of Examples as shown in Table 2 were orally given at a dose of 100 mg/kg·body weight to these animals; 4 hours after the administration, serum calcium concentration was assayed by the methylxylenol blue (MXB) method [see for example Biochem. Biophys. Res. Commun., 125, 441–447 (1984); FEBS 321, 247–250 (1993)]. The decrement ratio of serum calcium in the experimental groups compared with control groups was determined. The results are shown in Table 2.

TABLE 2

| Example | Decrement Ratio of Serum Calcium (%) |
|---|---|
| 2 | 2.91 |
| 5 | 4.71 |
| 6 | 3.46 |

TABLE 2-continued

| Example | Decrement Ratio of Serum Calcium (%) |
|---|---|
| 18 | 2.54 |
| 19 | 2.67 |
| 20 | 3.09 |
| 27 | 3.26 |
| 33 | 4.07 |
| 34 | 3.50 |
| 38 | 3.18 |
| 41 | 2.37 |
| 45 | 1.75 |
| 50 | 2.28 |
| 58 | 2.82 |
| 64 | 3.60 |
| 79 | 2.60 |
| 81 | 3.50 |
| 82 | 4.38 |
| 88 | 2.67 |
| 92 | 4.08 |
| 96 | 2.42 |
| 97 | 4.33 |
| 100 | 2.16 |
| 109 | 1.95 |
| 118 | 3.06 |
| 120 | 5.39 |
| 121 | 4.48 |
| 125 | 1.50 |
| 128 | 1.74 |
| 131 | 3.97 |
| 135 | 3.37 |
| 140 | 4.50 |
| 141 | 3.14 |

Test 3
Osteoporosis Model Test

Ovary-resected model in rat serves as an experimental model of menopausal osteoporosis. The actions of the inventive compounds were examined in the model. Female rats (age 24 weeks) were resected of their unilateral ovaries; starting from the very next day, the compounds of Examples as shown in Table 3 were orally administered at a dose of 100 mg/kg twice daily for 12 weeks. Urine was collected continuously for 24 hours in a metabolic cage. After the final administration, left femur was resected; muscle and connective tissues were removed from the femur; the volume of the resulting femur was measured. Then, the femur was dried at 180° C. for 4 hours; and the dry weight was measured. Mineral density was calculated and determined on the basis of the dry weight and the volume. The strength of femoral neck of the right femur resected in the same manner was measured with a bone strength meter (TK-252C; manufactured by Muromachi Kikai, Co.). Additionally, urine deoxypyridinoline (Dpy) was assayed by the HPLC-fluorescent method according to the method by Ruud A. et al. [J. Chromatogra. B. 703, 37–44 (1997)]. The resulting value was corrected on an urine creatinine (Cre) concentration basis. The effects of the inventive compounds on each assay item were compared in the animals administered with the compounds with in the animals with no such administration. Further, normal groups were additionally prepared.

The resultant effects of the compounds on mineral density, bone strength and bone resorption markers are shown in Table 3. The compounds of Examples decrease the bone resorption marker urine Dpy increased via ovarian resection, thereby suppressing the decrease of mineral density and bone strength. Thus, the compounds of Examples are useful for osteoporosis.

TABLE 3

| Group | Mineral Density of Femur ($\mu$g/mm$^3$) | Strength of Femoral Neck of the Femur (N) | Urine Dpy (pmol/$\mu$molCre) |
|---|---|---|---|
| Nomal Groups | 1,245 ± 10 | 148 ± 12 | 13.9 ± 1.2 |
| Control Groups | 1,183 ± 9 | 140 ± 6 | 24.8 ± 3.0 |
| Example 92 | 1,236 ± 14 | 163 ± 12 | 15.6 ± 1.4 |
| Example 97 | 1,200 ± 11 | 154 ± 6 | 18.0 ± 1.6 |
| Example 121 | 1,216 ± 8 | 147 ± 10 | 16.2 ± 1.9 |

The mean value ± Standard error

What is claimed is:

1. A cyclic amide derivative represented by to the general formula:

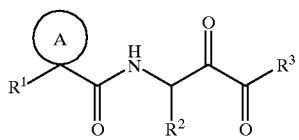

wherein $R^1$ represents a substituted alkyl group, a substituted alkenyl group, a substituted amino group, a substituted alkoxyl group, a substituted alkylthio group, a substituted carbamoyl group, a substituted sulfonamide group or a substituted amide group; the ring A represents a saturated cyclic alkyl group with 5 to 7 carbon atoms or a heteroatom-containing saturated heterocyclic group with 3 to 6 carbon atoms; $R^2$ represents a hydrogen atom, a substituted or unsubstituted alkyl group, a substituted or unsubstituted aromatic hydrocarbon group or a substituted or unsubstituted heterocyclic group; $R^3$ represents a hydrogen atom, a group represented by the general formula $R^4O$— or a group represented by the general formula $R^5(R^6)N$— wherein $R^4$ represents a hydrogen atom, a substituted or unsubstituted alkyl group, a substituted or unsubstituted aromatic hydrocarbon group or a substituted or unsubstituted heterocyclic group; $R^5$ and $R^6$ may be the same or different and each represents a hydrogen atom, a substituted or unsubstituted alkyl group, a substituted or unsubstituted aromatic hydrocarbon group or a substituted or unsubstituted heterocyclic group.

2. A cyclic amide derivative according to claim 1, wherein the ring A is a saturated cyclic alkyl group with 5 to 7 carbon atoms.

3. A cyclic amide derivative according to any of claim 1 to 2, wherein $R^1$ is a substituted amide group.

4. A cyclic amide derivative according to claim 1, wherein $R^2$ is a substituted or unsubstituted alkyl group.

5. A cyclic amide derivative according to claim 1, wherein $R^3$ is a group represented by the general formula $R^5(R^6)N$— wherein $R^5$ and $R^6$ may be the same or different and represent a hydrogen atom, a substituted or unsubstituted alkyl group, a substituted or unsubstituted aromatic hydrocarbon group or a substituted or unsubstituted heterocyclic group.

6. A pharmaceutical agent containing a cyclic amide derivative according to claim 1.

7. A method for treating a disease selected from the group consisting of arthritis, rheumatism, osteoporosis, hypercalcemia and Paget's disease which comprises administering to a patient a pharmaceutical agent comprising an effective amount of a cyclic amide derivative according to claim 1 and a carrier therefor.

8. A method according to claim 7 wherein said carrier is selected from the group consisting of organic and inorganic excipients in solid or liquid form.

9. A method for decreasing bone resorption and suppressing the decrease of mineral density and bone strength which comprises administering to a patient a pharmaceutical agent comprising an effective amount of a cyclic amide derivative according to claim 1 and a carrier therefor.

10. A method for inhibiting cathepsin K which comprises combining cathepsin K with a cyclic amide deriviative according to claim 1.

11. The method of claim 7, wherein said pharmaceutical agent is administered orally, parentally, externally, or by inhalation.

12. A method of claim 7, wherein 0.01–100 mg of said pharmaceutical agent is administered per 1 kilogram of human body weight per day.

13. A method of claim 7, wherein said pharmaceutical is a capsule, tablet, sugar-coated tablet, granule, liquid, suspension, or emulsion.

* * * * *